(12) United States Patent
Guo et al.

(10) Patent No.: US 11,964,028 B2
(45) Date of Patent: Apr. 23, 2024

(54) RNA NANOPARTICLES AND METHOD OF USE THEREOF

(71) Applicant: UNIVERSITY OF KENTUCKY RESEARCH FOUNDATION, Lexington, KY (US)

(72) Inventors: Peixuan Guo, Columbus, OH (US); Hui Li, Columbus, OH (US); Wei Luo, Lexington, KY (US)

(73) Assignee: UNIVERSITY OF KENTUCKY RESEARCH FOUNDATION, Lexington, KY (US)

( * ) Notice: Subject to any disclaimer, the term of this patent is extended or adjusted under 35 U.S.C. 154(b) by 0 days.

(21) Appl. No.: 17/093,038

(22) Filed: Nov. 9, 2020

(65) Prior Publication Data
US 2022/0047728 A1    Feb. 17, 2022

Related U.S. Application Data

(62) Division of application No. 15/566,972, filed as application No. PCT/US2016/028012 on Apr. 17, 2016, now Pat. No. 10,828,381.

(60) Provisional application No. 62/150,233, filed on Apr. 20, 2015, provisional application No. 62/149,117, filed on Apr. 17, 2015.

(51) Int. Cl.
| | | |
|---|---|---|
| C07H 21/02 | (2006.01) | |
| A61K 51/04 | (2006.01) | |
| A61K 51/12 | (2006.01) | |
| A61P 35/00 | (2006.01) | |
| C12N 15/113 | (2010.01) | |
| C12N 15/115 | (2010.01) | |
| B82Y 5/00 | (2011.01) | |

(52) U.S. Cl.
CPC .......... *A61K 51/0491* (2013.01); *A61K 51/12* (2013.01); *A61P 35/00* (2018.01); *C12N 15/113* (2013.01); *C12N 15/115* (2013.01); *B82Y 5/00* (2013.01); *C12N 2310/11* (2013.01); *C12N 2310/113* (2013.01); *C12N 2310/122* (2013.01); *C12N 2310/14* (2013.01); *C12N 2310/141* (2013.01); *C12N 2310/16* (2013.01); *C12N 2310/3517* (2013.01); *C12N 2310/3519* (2013.01); *C12N 2310/52* (2013.01)

(58) Field of Classification Search
CPC ............................ C12N 15/113; C12N 15/115
See application file for complete search history.

(56) References Cited

U.S. PATENT DOCUMENTS

| | | |
|---|---|---|
| 6,180,082 B1 | 1/2001 | Woltering et al. |
| 6,506,559 B1 | 1/2003 | Fire et al. |
| 7,655,787 B2 | 2/2010 | Guo et al. |
| 2008/0213177 A1 | 9/2008 | Rademachet et al. |
| 2008/0318340 A1 | 12/2008 | Shibasaki et al. |
| 2013/0316356 A1 | 11/2013 | Shuber et al. |
| 2014/0045709 A1 | 2/2014 | Croce et al. |
| 2014/0179758 A1 | 6/2014 | Guo |

FOREIGN PATENT DOCUMENTS

| | | |
|---|---|---|
| CN | 103403189 A | 11/2013 |
| WO | 1999007409 A1 | 2/1999 |
| WO | 1999032619 A1 | 7/1999 |
| WO | 2000001846 A2 | 1/2000 |
| WO | 2000044895 A1 | 8/2000 |
| WO | 2000044914 A1 | 8/2000 |
| WO | 2001029058 A1 | 4/2001 |
| WO | 0136646 A1 | 5/2001 |
| WO | 0216596 A2 | 2/2002 |
| WO | 2005003293 A2 | 1/2005 |
| WO | 2007016507 A2 | 2/2007 |
| WO | 2012/170372 A2 | 12/2012 |
| WO | WO2012/170372 | 12/2012 |

OTHER PUBLICATIONS

Kumar SR, et al. In vitro and in vivo evaluation of (64)Cu-radiolabeled KCCYSL peptides for targeting epidermal growth factor receptor-2 in breast carcinomas. Cancer Biother.Radiopharm. Dec. 2010; 25(6):693-703.
Laing, Christian, et al. "Predicting coaxial helical stacking in RNA junctions." Nucleic acids research 40.2 (2012): 487-498.
Laing, Christian, et al. "Predicting helical topologies in RNA junctions as tree graphs." PloS one 8.8 (2013): e71947.
Lammers T, et al. (2010) Nanotheranostics and image-guided drug delivery: current concepts and future directions. Mol Pharm. Dec. 6, 2010;7(6): 1899-912.
Lammers T, et al. (2012) Personalized nanomedicine. Clin.Cancer Res. Sep. 15, 2012;18(18):4889-94.
Lammers T, et al. Drug targeting to tumors: principles, pitfalls and (pre-) clinical progress. J.Control Release Jul. 20, 2012;161(2):175-87.
Langereis S, et al. Dendrimers and magnetic resonance imaging. New Journal of Chemistry 2007; 31(7): 1152-60.

(Continued)

*Primary Examiner* — Amy H Bowman
(74) *Attorney, Agent, or Firm* — Baker, Donelson, Bearman, Caldwell, & Berkowitz, P.C.

(57) ABSTRACT

The presently-disclosed subject matter relates to an artificial RNA nanostructure and method of use thereof. In particular, the presently-disclosed subject matter relates to RNA nanoparticles and RNA dendrimers, and methods of disease diagnosis and treatments using the RNA nanostructure and RNA dendrimers.

26 Claims, 61 Drawing Sheets
Specification includes a Sequence Listing.

(56) References Cited

OTHER PUBLICATIONS

Langereis S, et al. Evaluation of Gd(III)DTP A-terminated poly(propyleneimine) dendrimers as contrast agents for MR imaging. NMR Biomed. Feb. 2006; 19(1): 133-41.

Laurenti E, et al. Inducible gene and shRNA expression in resident hematopoietic stem cells in vivo. Stem Cells Aug. 2010;28(8): 1390-8.

Leamon CP. Preclinical antitumor activity of a novel folate-targeted dual drug conjugate. Mol Pharmacol. 2007; 4:659-67.

Lee et al. Targeted chemoimmunotherapy using drug-loaded aptamer-dendrimer bioconjugates. Journal of Controlled Release, vol. 155 , Issue 3 , Nov. 7, 2011, pp. 435-441.

Lee FT, et al. Specific localization, gamma camera imaging, and intracellular trafficking of radiolabelled chimeric anti-G (D3) ganglioside monoclonal antibody KM871 in SK-MEL-28 melanoma xenografts. Cancer Res. 61(11), 4474-4482 (2001).

Lee RC, et al. The C. elegans heterochronic gene lin-4 encodes small RNAs with antisense complementarity to lin-14. Cell Dec. 3, 1993;75(5):843-54.

Lee, H. et al. "Molecularly self-assembled nucleic acid nanoparticles for targeted in vivo siRNA delivery." Nature nanotechnology 7.6 (2012): 389.

Lee, T. J. et al. RNA nanoparticles as a vector for targeted siRNA delivery into glioblastoma mouse model. Oncotarget 2015, 6, 14766-14776.

Lee, T et al. Construction of RNA-quantum dot chimera for nanoscale resistive biomemory application. ACS Nano. Jul. 28, 2015; 9(7): 6675-6682.

Lei, Xiao-Yong, et al. "Silencing of Bcl-XL expression in human MGC-803 gastric cancer cells by siRNA." Acta biochimica et biophysica Sinica 37.8 (2005): 555-560.

Leontis NB, et al. The building blocks and motifs of RNA architecture. Curr Opin Struct Biol 2006; 16:279-87.

Leontis, N. et al. Conference Scene: Advances in RNA nanotechnology promise to transform medicine. Nanomedicine 2013, 8, 1051-1054.

Li W, et al. Lipid-based Nanoparticles for Nucleic Acid Delivery. Phann.Res Mar. 15, 2007; 24:438-49.

Li X, et al. An efficient thermally induced RNA confom1ational switch as a framework for the functionalization of RNA nanostructures. J.Am.Chem.Soc. Mar. 29, 2006; 128(12):4035-40.

Li, H. et al. "RNA as a stable polymer to build controllable and defined nanostructures for material and biomedical applications." Nano today 10.5 (2015): 631-655.

Li, Hui, et al. "RNA nanoparticles derived from three-way junction of phi29 motor pRNA are resistant to I-125 and Cs-131 radiation." nucleic acid therapeutics 25.4 (2015): 188-197.

Li, Y. et al. Controlled assembly of dendrimer-like DNA. Nat Mater. 2004, 3 (1), 38-42.

Liu J, et al. Fabrication of stable and RNase- resistant RNA nanoparticles active in gearing the nanomotors for viral DNA packaging. ACS Nano. 5(1), 237 (2011).

Liu TW, et al. Imaging of specific activation of photodynamic molecular beacons in breast cancer vertebral metastases. Bioconjug. Chem. Jun. 15, 2011; 22(6): 1021-30.

Longmire M, et al. Dendrimer-based contrast agents for molecular imaging. Curr.Top.Med.Chem. 2008; 8(14): 1180-6.

Luo W, et al. Determination of prescription dose for Cs-131 permanent implants using the BED formalism including resensitization correction. Med Phys. 41(2):024101 (2014).

Luo, W et al. "SU-E-T-338: Ultrastable Prna 3WJ Nanoparticles as Potential I-125 and C-131 Carriers for Targeted Radiation Therapy." Medical Physics 41.6, Part16 (2014): 302-302.

Luy B, et al. Measurement and application of 1H-19F dipolar couplings in the structure determination of 2'-fluorolabeled RNA. J.Biomol.NMR May 2001; 20(1):39-47.

Lyubchenko, Y. L et al. Imaging of nucleic acids with atomic force microscopy. Methods 2011, 54, 274-283.

Lyubchenko, Y.L et al. AFM for analysis of structure and dynamics of DNA and protein-DNA complexes. Methods 47.3 (2009): 206-213.

Malik N, et al. Dendrimers: relationship between structure and biocompatibility in vitro, and preliminary studies on the biodistribution of 125I-labelled polyamidoamine dendrimers in vivo. J.Control Release Mar. 1, 2000;65(1-2): 133-48.

Matsumura S, et al. Coordinated control of a designed transacting ligase ribozyme by a loop-receptor interaction. FEBS Lett. Sep. 3, 2009;583(17):2819-26.

Meigooni, Ali S., et al. "Experimental and theoretical determination of dosimetric characteristics of IsoAid ADVANTAGE™ brachytherapy source." Medical physics 29.9 (2002): 2152-2158.

Meng LJ, et al. An Ultrahigh Resolution SPECT System for 1-125 Mouse Brain Imaging Studies, Nucl Instrum Methods Phys Res A 600(1): 498-505 (2009).

Meng, H. M.; et al. DNA dendrimer: an efficient nanocarrier of functional nucleic acids for intracellular molecular sensing. ACS Nano 2014, 8 (6), 6171-6181.

Menjoge AR, et al. Dendrimer-based drug and imaging conjugates: design considerations for nanomedical applications. Drug Discov. Today Mar. 2010; 15(5-6): 171-85.

Mhlanga MM, et al. tRNA-linked molecular beacons for imaging mRNAs in the cytoplasm of living cells. Nucleic Acids Res 2005;33(6): 1902-12.

Miao Y, et al. 99mTc- and 11 Iln-labeled alpha-melanocyte-stimulating hormone peptides as imaging probes for primary and pulmonary metastatic melanoma detection. J Nucl.Med. Jan. 2007; 48(1):73-80.

Morrissey DV, et al. Potent and persistent in vivo anti-HBV activity of chemically modified siRNAs. Nat.Biotechnol. Aug. 2005; 23: 1002-7.

Murphy MK, et al. Evaluation of the new cesium-131 seed for use in low-energy x-ray brachytherapy. Med Phys. 31(6), 1529-1538 (2004).

Nagaswamy, Uma, et al. "NCIR: a database of non-canonical interactions in known RNA structures." Nucleic acids research 30.1 (2002): 395-397.

Nanjwade, B. K .; et al. Dendrimers: emerging polymers for drng-delivery systems. Eur. J Phann. Sci. 2009, 38 (3), 185-196.

Neerman MF, et al. In vitro and in vivo evaluation of a melamine dendrimer as a vehicle for drug delivery. Int.J.Pharm. Aug. 20, 2004;281(1-2): 129-32.

Nilsen, T. W .; Grayzel, J .; Prensky, W. Dendritic nucleic acid structures. J Theor. Biol 1997, 187 (2), 273-284.

Nwe K, et al. Comparison of MRI properties between derivatized DTPA and DOTA gadolinium-dendrimer conjugates. Bioorg.Med. Chem. Aug. 15, 2010; 18(16): 5925-31.

Ohno, H .; et al. Synthetic RNA-protein complex shaped like an equilateral triangle. Nat. Nanotechnol. 2011, 6 (2), 116-120.

Parker N, et al. Folate receptor expression in carcinomas and normal tissues determined by a quantitative radioligand binding assay. Anal.Biochem. Mar. 15, 2005; 338(2):284-93.

Pauwels, Ernest KJ, et al. "Nanoparticles in cancer." Current radiopharmaceuticals 1.1 (2008): 30-36.

Fire, Andrew. "RNA-triggered gene silencing." Trends in Genetics 15.9 (1999): 358-363.

Freier SM, et al. Improved free-energy parameters for predictions of RNA duplex stability. Proc.Natl.Acad.Sci.U.S.A Dec. 1986;83(24):9373-7.

Galletto R, et al. Global conformation of the *Escherichia coli* replication factor DnaC protein in absence and presence of nucleotide cofactors. Biochemistry Aug. 31, 2004;43(34): 10988-1001.

Gambini JP, et al. Evaluation of 99mTc-glucarate as a breast cancer imaging agent in a xenograft animal model. Nucl. Med.Biol Feb. 2011; 38(2):255-60.

Geary, C et al. A single-stranded architecture for cotranscriptional folding of RNA nanostructures. Science 2014, 345, 799-804.

Grabow, W.W .; et al. Self-Assembling RNA Nanorings Based on RNAI/II Inverse Kissing Complexes. Nano Lett. 2011, 11 (2), 878-887.

Griffiths-Jones et al. miRBase: microRNA sequences, targets and gene nomenclature (2006). Nucl. Acids Res. 34: D140-D144.

(56) References Cited

OTHER PUBLICATIONS

Guerrier-Takada C, Gardiner K, Marsh T, Pace N, Altman S. The RNA moiety of ribonuclease P is the catalytic subunit of the enzyme. Cell 1983; 35:849-57.
Gunnery S, et al. RNA binding and modulation of PKR activity. Methods 1998, Jul. 15(3): 189-98.
Guo P, et al. A small viral RNA is required for in vitro packaging of bacteriophage φ29 DNA. Science 1987; 236:690-4.
Guo P, et al. Biological and biochemical properties of the small viral RNA (pRNA) essential for the packaging of the double-stranded DNA of phage £29. Semin. Viral. 5, 27-37 (1994).
Guo S, et al. Construction of folate-conjugated pRNA of bacteriophage phi29 DNA packaging motor for delivery of chimeric siRNA to nasopharyngeal carcinoma cells. Gene Tuer 2006; 13( 10): 814-20.
Guo S, et al. Specific delivery of therapeutic RNAs to cancer cells via the dimerization mechanism of phi29 motor pRNA. Hum Gene Tuer. 2005; 16: 1097-109.
Guo, P, et al. RNA Nanotechnology and Therapeutics. CRC Press, Boca Raton, FL, 2013.
Guo, P et al. Inter-RNA interaction of phage phi29 pRNA to form a hexameric complex for viral DNA transportation. Mol. Cell. 2(1), 149-155 (1998).
Guo, P et al. Uniqueness, advantages, challenges, solutions, and perspectives in therapeutics applying RNA nano technology. Nucleic. Acid Ther. 22(4), 226- 245 (2012).
Guo, P. Rna Nanotechnology: Engineering, Assembly and Applications in Detection, Gene Delivery and Therapy. J. Nano. Nanotech. 5(12), 1964-1982 (2005).
Guo, P. The emerging field of RNA nano technology. Nat. Nanotechnol. 5(12), 833-842 (2010).
Hamoudeh M, et al. Radionuclides delivery systems for nuclear imaging and radiotherapy of cancer, Adv. Drug Del. Rev., 60, 1329-1346 (2008).
Hanahan, D et al. "Hallmarks of cancer: the next generation." Cell 144.5 (2011): 646-674.
Hanahan, D et al. "The hallmarks of cancer. Review." Cell, vol. 100.1 (2000): 57-70.
Haque F, et al. Ultrastable synergistic tetravalent RNA nanoparticles for targeting to cancers. Nano Today. 7(4), 245-257 (2012).
Hardy PA, et al. Convection enhanced delivery of different molecular weight tracers of gadolinium-tagged polylysine. J. Neurosci. Methods Sep. 30, 2013;219(1):169-75.
Helmling S, et al. A new class of Spiegelmers containing 2'-fluoronucleotides. Nucleosides Nucleotides Nucleic Acids May 2003;22: 1035-8.
Hendrix RW. Bacteriophage DNA packaging: RNA gears in a DNA transport machine (Minireview). Cell 1998; 94: 147-50.
Hoeprich S, et al. Bacterial virus phi29 pRNA as a hammerhead ribozyme escort to destroy hepatitis B virus. Gene Tuer. 2003;10: 1258-67.
Hong J, et al. Comprehensive analysis of sequence-specific stability of siRNA. F ASEB J. Dec. 2010 24(12): 4844-55.
Hong, C. A.; et al. Dendrimeric siRNA for Efficient Gene Silencing. Angew. Chem. Int. Ed Engl. 2015, 54 (23), 6740-6744.
Hornung V, e al. Sequence-specific potent induction of IFN[alpha] by short interfering RNA in plasmacytoid dendritic cells through TLR7. Nat Med Mar. 2005; 1(3):263-70.
Ikawa Y, et al. De novo synthesis and development of an RNA enzyme. Proc.Natl.Acad.Sci. U.S.A Sep. 21, 2004;101 (38): 13750-5.
International Search report for PCT/US16/28012 mailed Oct. 7, 2016, 6 pages.
Ishikawa F, et al.. Development of functional human blood and immune systems in NOD/SCID/IL2 receptor {gamma} chain(null) mice. Blood Sep. 1, 2005;106(5): 1565-73.
Jasinski, DL et al. Physicochemically Tunable Polyfunctionalized RNA Square Architecture with Fluorogenic and Ribozymatic Properties. ACS Nano. 8(8), 7620-7629 (2014).

Jemal, Ahmedin, et al. "Global cancer statistics." CA: a cancer journal for clinicians 61.2 (2011): 69-90.
Judge AD, et al. Sequence-dependent stimulation of the mammalian innate immune response by synthetic siRNA. Nat Biotech Apr. 2005; 23 (4): 45 7-62.
Kairemo K, et al. Nanoparticles in cancer. Cur. Radiopharm. 1(1), 30-36 (2008).
Kaminskas, L. M. et al. Dendrimer phannacokinetics: the effect of size, structure and surface characteristics on ADME properties. Nanomedicine (Land) 2011, 6 (6), 1063-1084.
Kappler, Matthias, et al. "Knockdown of survivin expression by small interfering RNA reduces the clonogenic survival of human sarcoma cell lines independently of p53." Cancer gene therapy 11.3 (2004): 186-93.
Kawasaki AM, et al. Uniformly modified 2'-deoxy-2'-fluoro phosphorothioate oligonucleotides as nuclease-resistant antisense compounds with high affinity and specificity for RNA targets. J. Med Chem. 36(7), 831-841 (1993).
Khaled A, et al. Controllable Self-Assembly of Nanoparticles for Specific Delivery of Multiple Therapeutic Molecules to Cancer Cells Using RNA Nanotechnology. Nano Letters Sep. 14, 2005;5: 1797-808.
Khisamutdinov, E.F. et al. Enhancing immunomodulation on innate immunity by shape transition among RNA triangle, square and pentagon nanovehicles. Nucleic Acids Res. 42(15), 9996-10004 (2014).
Khisamutdinov, E.F et al. RNA as a Boiling-Resistant Anionic Polymer Material to Build Robust Structures with Defined Shape and Stoichiometry. ACS Nano. 8(5), 4771-4781 (2014).
Kim DH, et al. Strategies for silencing human disease using RNA interference. Nat Rev Genet Mar. 2007; 8(3): 173-84.
Kim JK, et al. Molecular imaging of a cancer-targeting theragnostics probe using a nucleolin aptamer- and microRNA-221 molecular beacon-conjugated nanoparticle. Biomaterials Jan. 2012;33(1):207-217.
Kobayashi H, et al. Nano-sized MRI contrast agents with dendrimer cores. Adv.Drug Deliv.Rev. Dec. 14, 2005;57 (15):2271-86.
Kolb, H. C. et al. "Click chemistry: diverse chemical function from a few good reactions." Angewandte Chemie International Edition 40.11 (2001): 2004-2021.
Krol, J. et al. The widespread regulation of microRNA biogenesis, function and decay. Nat Rev. Genet. 2010, 11 (9), 597-610.
Kruger K, et al. Self-splicing RNA: autoexcision and autocyclization of the ribosomal RNA intervening sequence of Tetrahymena. Cell 1982; 31:147-57.
Kukowska-Latallo, J. F.; et al. Efficient transfer of genetic material into mammalian cells using Starburst polyamidoamine dendrimers. Proc Natl Acad Sci US A 1996, 93 (10), 4897-4902.
Kumar SR, et al. Evaluation of an 11In-radiolabeled peptide as a targeting and imaging agent for ErbB-2 receptor expressing breast carcinomas. Clin.Cancer Res. Oct. 15, 2007; 13(20):6070-9.
Thiel, Kristina W., et al. "Delivery of chemo-sensitizing siRNAs to HER2+-breast cancer cells using RNA aptamers." Nucleic acids research 40.13 (2012): 6319-6337.
Tucci P, et al. Loss of p63 and its microRNA-205 target results in enhanced cell migration and metastasis in prostate cancer. Proc. Natl.Acad.Sci.U.S.A Sep. 18, 2012; 109(38): 15312-7.
Tucker BJ, et al. Riboswitches as versatile gene control elements. Curr.Opin. Struct. Biol. Jun. 2005; 15:342-8.
Tuerk C, et al. Systematic evolution of ligands by exponential enrichment: RNA ligands to bacteriophage T4 Dna ploymerase. Science 1990; 249:505-10.
Varani, G. et al. "The G• U wobble base pair." EMBO reports 1.1 (2000): 18-23.
Wagner C, et al. Mechanism of dimerization of bicoid mRNA: initiation and stabilization. J.Biol.Chem. Feb. 6, 2004; 279:4560-9.
Wang Sh, et al. Engineered Nanopore of Phi29 DNAPackaging Motor for Real-Time Detection of Single Colon Cancer Specific Antibody in Sernm, ACS Nano Oct. 23, 2013; DOI: 10.1021/nn404435v.
Wei L, et al. Melanoma imaging using 111In, 86Y and 68Ga labeled CHX-A"-Re(Arg11)CCMSH. Nucl.Med.Biol May 2009; 36(4):345-54.

(56) References Cited

OTHER PUBLICATIONS

Went P, et al. Frequent high-level expression of the immunotherapeutic target EpCAM in colon, stomach, prostate and lung cancers. Br.J. Cancer Jan. 16, 2006; 94(1): 128-35.
Williams, L.E. et al. "Targeted radionuclide therapy." Medical physics 35.7Part1 (2008): 3062-3068.
Wooten, Charles Eric, et al. "Implementation and early clinical results utilizing Cs-131 permanent interstitial implants for gynecologic malignancies." Gynecologic oncology 133.2 (2014): 268-273.
Written Option of the ISA mailed Oct. 7, 2016.
Xin, Yurong, et al. "Annotation of tertiary interactions in RNA structures reveals variations and correlations." Rna 14.12 (2008): 2465-2477.
Xiong B, et al. MiR-21 regulates biological behavior through the PTEN/PI-3 K/Akt signaling pathway in human colorectal cancer cells. Int.J Oncol. Jan. 2013; 42(1): 219-28.
Xu W, et al. A smart magnetic resonance imaging contrast agent responsive to adenosine based on a DNA aptamer- conjugated gadolinium complex. Chem.Commun.(Camb.) May 7, 2011;47(17):4998-5000.
Yan, W., et al. "Cesium-131 brachytherapy for lung cancer: dosimetric, safety considerations and initial experience." International Journal of Radiation Oncology• Biology• Physics 78.3 (2010): S540-S541.
Ye X, et al. Targeted delivery of mutant tolerant anti-coxsackievirus artificial microRNAs using folate conjugated bacteriophage Phi29 pRNA. PLOS.One. 2011; 6(6):e21215.
Ye et al. Targeted biodegradable dendritic MRI contrast agent for enhanced tumor imaging. Journal of Controlled Release. vol. 169 (2013), pp. 239-245.
Zappulla DC, et al. Yeast telomerase RNA: a flexible scaffold for protein subunits. Proc.Natl.Acad.Sci.U.S.A Jul. 6, 2004; 101(27): 10024-9.
Zaug AJ, et al. Autocatalytic cyclization of an excised intervening sequence RNA is a cleavage-ligation reaction. Nature 1983; 301:578-83.
Zhang H, et al. Crystal Structure of 3WJ Core Revealing Divalent Ion-promoted Thermostability and Assembly of the Phi29 Hexameric Motor pRNA. RNA Aug. 20, 2013;19: 1226-37.
Zhang X, et al. Copper-62 labeled ReCCMSH peptide analogs for melanoma PET imaging. Curr.Radiopharm. Oct. 2012; 5(4):329-35.
Zhang, Longjiang, et al. "Delivery of therapeutic radioisotopes using nanoparticle platforms: potential benefit in systemic radiation therapy." Nanotechnology, science and applications 3 (2010): 159.
Zhou, T. et al. pH-responsive sizetunable self-assembled DNA dendrimers. Angew. Chem. Int. Ed Engl. 2012, 51 (45), 11271-11274.
Zhou, T. et al. Tetrahedron DNA dendrimers and their encapsulation of gold nanoparticles. Bioorg. Med. Chem. 2014, 22 (16), 4391-4394.
Zhu W, et al. PAMAM dendrimer-based contrast agents for MR imaging of Her-2/neu receptors by a three-step pretargeting approach. Magn Reson.Med. Apr. 2008; 59(4): 679-85.
Zinn KR, et al. Gamma Camera Dual Imaging with a Somatostatin Receptor and Thymidine Kinase after Gene Transfer with a Bicistronic Adenovirus in Mice, Radiology, 223(2), 417-425 (2002).
Zuker M. On finding all suboptimal foldings of an RNA molecule. Science 1989; 244:48-52.
Zuker, M. Mfold web server for nucleic acid folding and hybridization prediction. Nucleic Acid, Res. Jul. 1, 2003;31 (13):3406-15.
Luo, W et al. "SU-E-T-338: Ultrastable Prna 3WJ Nanoparticles as Potential I-125 and C-131 Carriers for Targeted Radiation Therapy." Medical Physics 41.6, Part16 (2014) (abstract).
Pieken WA, et al. Kinetic characterization of ribonucleaseresistant 2'-modified hammerhead ribozymes. Science. 253 (5017), 314-317 (1991).
Haque, F. et al. Ultrastable synergistic tetravalent RNA nanoparticles for targeting to cancers. Nano Today 2012, 7, 245-257.
Aagaard L, et al. RNAi therapeutics: Principles, prospects and challenges. Advanced Drug Delivery Reviews Mar. 30, 2007;59(2-3):75-86.

Abdelmawla S, et al. Pharmacological characterization of chemically synthesized monomeric pRNA nanoparticles for systemic delivery. Mol. Ther. 19(7), 1312-1322 (2011).
Adams KE, et al.Comparison of visible and near-infrared wavelength-excitable fluorescent dyes for molecular imaging of cancer. J.Biomed. Opt. Mar. 2007; 12:024017.
Afonin, K. A. et al. Multifunctional RNA nanoparticles. Nano Lett. 2014, 14 (10), 5662-5671.
Afonin, K. A.; et al. In vitro assembly of cubic RNA-based scaffolds designed in silico. Nat. Nanotechnol. 2010, 5 (9), 676-682.
Afonin, Kirill A., et al. "TokenRNA: a new type of sequence-specific, label-free fluorescent biosensor for folded RNA molecules." Chembiochem 9.12 (2008): 1902-1905.
Astrnc, D. Electron-transfer processes in dendrimers and their implication in biology, catalysis, sensing and nanotechnology. Nat. Chem. 2012, 4 (4), 255-267.
Bae YH, et al. Targeted drug delivery to tumors: myths, reality and possibility. J.Control Release Aug. 10, 2011;153(3): 198-205.
Bao G, et al. Multifunctional nanoparticles for drug delivery and molecular imaging. Annu.Rev.Biomed.Eng 2013;15:253-82.
Bartel DP. MicroRNAs: target recognition and regulatory functions. Cell Jan. 23, 2009; 136(2):215-33.
Baskar, Rajamanickam, et al. "Cancer and radiation therapy: current advances and future directions." International journal of medical sciences 9.3 (2012): 193.
Bass, B. The short answer. Nature 411:428-429, May 24, 2001.
Behlke MA. Chemical modification of siRNAs for in vivo use. Oligonucleotides. Dec. 2008; I8(4): 305-19.
Behlke MA. Progress towards in vivo use of siRNAs. Mol Tuer. Apr. 2006; 13: 644-70.
Bentzen, Søren M. "Preventing or reducing late side effects of radiation therapy: radiobiology meets molecular pathology." Nature Reviews Cancer 6.9 (2006): 702.
Bindewald E, et al. RNAJunction: a database of RNA junctions and kissing loops for three-dimensional structural analysis and nanodesign. Nucleic Acids Res. Jan. 2008;36:D392-D397.
Bindewald, Eckart, et al. "Multistrand RNA secondary structure prediction and nanostructure design including pseudoknots." ACS nano 5.12 (2011): 9542-9551.
Binzel, D et al. Entropy-driven one-step formation of Phi29 pRNA 3WJ from three RNA fragments. Biochemistry 2014, 53 (14), 2221-2231.
Forster AC, Altman S. External guide sequences for an RNA enzyme. Science Aug. I 7, 1990; 249(4970): 783-6.
Blount KF, et al. Riboswitches as antibacterial drug targets. Nat. Biotechnol. 2006; 24: 1558-64.
Boswell CA, et al. Synthesis, characterization, and biological evaluation of integrin alphavbeta3-targeted PAMAM dendrimers. Mol. Pharm. Jul. 2008; 5(4): 527-39.
Brannon-Peppas, L et al. "Nanoparticle and targeted systems for cancer therapy." Advanced drug delivery reviews 56.11 (2004): 1649-1659.
Bryson JM, et al. Polymer beacons for luminescence and magnetic resonance imaging of DNA delivery. Proc.Natl. Acad.Sci.U.S.A Oct. 6, 2009;106(40): 16913-8.
Cai, Weibo, et al. "Applications of gold nanoparticles in cancer nanotechnology." Nanotechnology, science and applications 1 (2008): 17.
Calzada V. et al. A potencial theranostic agent for EGF-R expression tumors: (I 77)LuDOTA-nimotuzumab. Curr. Radiopharm. Oct. 2012;5(4):318-24.
Caravan P, et al. Gadolinium(III) Chelates as MRI Contrast Agents: Structure, Dynamics, and Applications. Chem.Rev. Sep. 8, 1999; 99(9): 2293-352.
Cech TR. RNA chemistry. Ribozyme self-replication? Nature 1989; 339:507-8.
Cerchia, Laura, et al. "Cell-specific aptamers for targeted therapies." Nucleic Acid and Peptide Aptamers. Humana Press, Totowa, NJ, 2009. 59-78.
Chang KY, et al. Characterization of a "kissing" hairpin complex derived from the human immunodeficiency virus genome. Proc Natl Acad Sci U.S.A 1994;91(18):8705-9.

(56) References Cited

OTHER PUBLICATIONS

Chen AK, et al. A voiding false-positive signals with nuclease-vulnerable molecular beacons in single living cells. Nucleic Acids Res 2007; 35(16):e 105.
Chen AK, et al. Efficient cytosolic delivery of molecular beacon conjugates and flow cytometric analysis of target RNA. Nucleic Acids Res Jul. 2008; 36(12): e69, 12 pages.
Chen AK, et al. Ratiometric bimolecular beacons for the sensitive detection of RNA in single living cells. Nucleic Acids Res Aug. 2010; 38(14): e148.
Chen J, et al. Evaluation of an 111In-DOTA-rhenium cyclized alpha-MSH analog: a novel cyclic-peptide analog with improved tumor-targeting properties. J.Nucl.Med. Dec. 2001; 42(12): 1847-55.
Cheng Z, et al. Gd-conjugated dendrimer nanoclusters as a tumor-targeted T1 magnetic resonance imaging contrast agent. Angew. Chem.Int.Ed Engl. 2010; 49(2): 346-50.
Choi, Y. et al. Targeting cancer cells with DNA-assembled dendrimers: a mix and match strategy for cancer. Cell Cycle 2005, 4 (5), 669-671.
Couzin J. Breakthrough of the year. Small RNAs make big splash. Science Dec. 20, 2002; 298(5602): 2296-7.
Cui, D. et al. Regression of gastric cancer by systemic injection of RNA nanoparticles carrying both ligand and siRNA. Scientific reports 2015, 5, 10726.
Dalerba P, et al. Phenotypic characterization of human colorectal cancer stem cells. Proc.Natl.Acad.Sci.U.S.A Jun. 12, 2007; 104(24): 10158-63.
Dan M. et al. Block copolymer crosslinked nanoassemblies improve particle stability and biocompatibility of superparamagnetic iron oxide nanoparticles. Pharm.Res. Feb. 2013; 30(2): 552-61.
Das et al. Multifunctional nanoparticle-EpCAM aptamer bioconjugates: A paradigm for targeted drug delivery and imaging in cancer therapy Nanomedicine: Nanotechnology, Biology, and Medicine 11 (2015), 379-389.
Davis ME, et al. Nanoparticle therapeutics: an emerging treatment modality for cancer. Nat. Rev. Drug Discov. 7(9), 771-782 (2008).
De Fougerolles A, et al. Interfering with disease: a progress report on siRNA-based therapeutics. Nat Rev Drug Discov Jun. 2007; 6(6):443-53.
Deiters A, et al. Photocaged morpholino oligomers for the light-regulation of gene function in zebrafish and Xenopus embryos. J Am.Chem.Soc Nov. 1, 20100;132(44): 15644-50.
Dibrov, S. M. et al. Self-assembling RNA square. Proc. Natl. Acad. Sci. US. A 2011, 108 (16), 6405-6408.
Ehresmann C, et al. Probing the structure of RNAs in solution. Nucleic Acids Res. 1987; 15:9109-28.
Elbashir et al., Duplexes of 21-nucleotide RNAs mediate RNA interference in cultured mammalian cells. Nature 411:494-498, 2001.
Ellington AD, et al. In vitro selection of RNA molecules that bind specific ligands. Nature 1990; 346:818-22.
Feng L, et al. Ocular delivery ofpRNA nanoparticles: distribution and clearance after subconjunctival injection. Pharmaceutical Research (2014) 31:1046-1058, doi: 10.1007/sll095-013-1226-x.
Fire A, et al. Potent and specific genetic interference by double-stranded RNA in Caenorhabditis elegans. Nature Feb. 1998;39 I :806-11.
Peer, Dan, et al. "Nanocarriers as an emerging platform for cancer therapy." Nature nanotechnology 2.12 (2007): 751.
Peng XH, et al. Real-time detection of gene expression in cancer cells using molecular beacon imaging: new strategies for cancer research. Cancer Res Mar. 1, 2005;65(5): 1909-17.
Pleij CWA, et al. A new principle of RNA folding based on pseudonotting. Nucleic Acids Res. Mar. I 1, 1985;13(5): 1717-31.
Prestidge, B. R., et al. "Cesium-131 permanent prostate brachytherapy: an initial report." International Journal of Radiation Oncology· Biology· Physics 63 (2005): S336-S337.
Privalov PL, et al. Thermodynamic analysis of transfer RNA unfolding. J.Mol.Biol. 1978; 122:44 7-64.

Pyle AM, et al. Ribozyme recognition of RNA by tertiary interactions with specific ribose 2'-OH groups. Nature 1991; 350:628-31.
Qiu L, et al. A targeted, self-delivered, and photocontrolled molecular beacon for mRNA detection in living cells. J Am. Chem.Soc Sep. 4, 2013; 135(35): 12952-5.
Rajendran JC. Therapeutic Radioisotopes, in Nuclear Medicine Therapy. Eary, JF, and Brenner W (Ed.), Informa Healthcare USA, Inc., New York, 2007.
Rauzan, B. e al. Kinetics and Thermodynamics of Dna, Rna, and Hybrid Duplex Formation. Biochemistry 2013, 52(5), 765-772.
Ravi, A. et al. "Evaluation of the Radiation Safety of using 131Cs Seeds for Permanent Breast Seed Implantation." International Journal of Radiation Oncology Biology Physics 81.2 (2011): S720-S721.
Reddy JA, et al. Folate Receptor-Specific Antitumor Activity of EC131, a Folate-Maytansinoid Conjugate. Cancer Research Jul. 1, 2007; 67:6376-82.
Reif B, et al. Structural comparison of oligoribonucleotides and their 2'-deoxy-2'-fluoro analogs by heteronuclear NMR spectroscopy. Helvetica Chimica Acta 1997; 80(6): 1952-71.
Reif R., et al. Fluorogenic RNA Nanoparticles for Monitoring RNA Folding and Degradation in Real Time in Living Cells. Nucleic Acid Tuer. 2013;22(6):428-37.
Rhee WJ, et al. Target accessibility and signal specificity in live-cell detection of BMP-4 mRNA using molecular beacons. Nucleic Acids Res Mar. 2008;36(5):e30.
Rivard M, et al., The impact of prescription depth, dose rate, plaque size, and source loading on the central axis using Pd-103, I-125, and Cs-131. Brachytherapy, 7(4), 327-335 (2008).
Rockey WM, et al. Synthesis and radiolabeling of chelator-RNA aptamer bioconjugates with copper-64 for targeted molecular imaging. Bioorg.Med.Chem. Jul. 1, 2011; 19(13):4080-90.
Rosenbaum V, et al. Temperature-gradient gel electrophoresis: thermodynamic analysis of nucleic acids and proteins in purified form and in cellular extracts. Biophy. Chem. 26(2-3), 235-246 (1987).
Rossi S, et al. microRNAs in colon cancer: a roadmap for discovery. FEBS Lett. Sep. 21, 2012; 586(19): 3000-7.
Rozema DB, et al. Dynamic PolyConjugates for targeted in vivo delivery of siRNA to hepatocytes. Proceedings ofthe National Academy of Sciences Aug. 7, 2007; 104(32):12982-7.
Rudovsky J, et al. PAMAM dendrimeric conjugates with a Gd-DOTA phosphinate derivative and their adducts with polyaminoacids: the interplay of global motion, internal rotation, and fast water exchange. Bioconjug.Chem. Jul. 2006; 17(4):975-87.
Rychahou PG, et al. Akt2 overexpression plays a critical role in the establishment of colorectal cancer metastasis. Proc.Natl.Acad.Sci. U.S.A Dec. 23, 2008; 105(51):20315-20.
Rychahou PG, et al. Targeted molecular therapy of the PI3K pathvvay: therapeutic significance of PI3K subunit targeting in colorectal carcinoma. Ann.Surg. Jun. 2006; 243(6):833-42.
Rychahou PG, et al. Targeted RNA interference of PI3K pathway components sensitizes colon cancer cells to TNF-related apoptosis-inducing ligand (TRAIL). Surgery Aug. 2005;138(2): 391-7.
Rychahou, P. et al. Delivery of RNA nanoparticles into colorectal cancer metastases following systemic administration. ACS Nano 2015, 9 (2), 1108-1116.
Sabahi, Ali, et al. "Hybridization of 2'-ribose modified mixed-sequence oligonucleotides: thermodynamic and kinetic studies." Nucleic acids research 29.10 (2001): 2163-2170.
Schroeder KT, et al. A structural database fork-tum motifs in RNA. RNA. Aug. 2010; 16(8): 1463-8.
Searle MS, et al. On the stability of nucleic acid structures in solution: enthalpyentropy compensations, internal rotations and reversibility. Nucleic Acids Res. May I 1, 1993;21(9):2051-6.
Severcan I, et al. Square-shaped RNA particles from different RNA folds. Nano Lett. 2009, 9, 1270-1277.
Shapiro EM, et al. In vivo detection of single cells by MRI. Magn Reson.Med. Feb. 2006; 55(2):242-9.
Sharma A., et al., Controllable Self-assembly of RNA Dendrimers. Nanomedicine. Apr. 2016 ; 12(3): 835-844.

(56) References Cited

OTHER PUBLICATIONS

Shigdar S, et al. RNA aptamer against a cancer stem cell marker epithelial cell adhesion molecule. Cancer Sci. Feb. 1, 2011; 102:991-8.

Shu D, et al. Counting of six pRNAs ofphi29 DNA-packaging motor with customized single molecule dual-view system. EMBO J. 2007; 26:527-37.

Shu Y, et al. Assembly of Therapeutic pRNA-siRNA Nanoparticles Using Bipartite Approach. Molecular Therapy Apr. 5, 2011;19: 1304-11.

Shu Y, et al. Fabrication of pRNA nanoparticles to deliver therapeutic RNAs and bioactive compounds into tumor cells. Nat Protoc. Sep. 2013;8(9): 1635-59.

Shu, D. et al. "Bottom-up assembly of RNA arrays and superstructures as potential parts in nanotechnology." Nano letters 4.9 (2004): 1717-1723.

Shu, D. et al. "Systemic delivery of anti-miRNA for suppression of triple negative breast cancer utilizing RNA nanotechnology." ACS nano 9.10 (2015): 9731-9740.

Shu, D. et al. "Thermodynamically stable RNA three-way junction for constructing multifunctional nanoparticles for delivery of therapeutics." Nature nanotechnology 6.10 (2011): 658.

Shu, D. et al. Programmable folding of fusion RNA complex driven by the 3WJ motif of phi29 motor pRNA. Nucleic Acids Res. 2013.

Shu, Y. et al. "Assembly of multifunctional phi29 pRNA nanoparticles for specific delivery of siRNA and other therapeutics to targeted cells." Methods 54.2 (2011): 204-214.

Shu, Y. et al. Fabrication of 14 Different RNA Nanoparticles for Specific Tumor Targeting without Accumulation in Normal Organs. RNA 2013, 19, 766-777.

Shu, Yi, et al. Stable RNA nanoparticles as potential new generation drugs for cancer therapy. Advanced drug delivery reviews 66 (2014): 74-89.

Shukla, G. C. et al. A Boost for the Emerging Field of RNA Nanotechnology. ACS Nano 2011, 5 (5), 3405-3418.

Sofou, Stavroula. "Radionuclide carriers for targeting of cancer." International journal of nanomedicine 3.2 (2008): 181.

Spee, Bart, et al. "Specific down-regulation of XIAP with RNA interference enhances the sensitivity of canine tumor cell-lines to TRAIL and doxorubicin." Molecular Cancer 5.1 (2006): 34.

Stark BC, et al. Ribonuclease P: an enzyme with an essential RN component. Proc.Natl.Acad.Sci. U.S.A Aug. 1978; 75:3717-21.

Studnicka GM, et al. Computer method for predicting the secondary structure of single-stranded RNA. Nucleic Acids Res. 1978; 5:3365-87.

Sugimoto, N et al. Thermodynamic parameters to predict stability of RNA/DNA hybrid duplexes. Biochemistry 1995, 34 (35), 11211-11216.

Swanson SD, et al. Targeted gadolinium-loaded dendrimer nanoparticles for tumor-specific magnetic resonance contrast enhancement. Int.J.Nanomedicine. 2008; 3(2):201-10.

Tandon P, et al. NCI Image-Guided Drug Delivery Summit. Cancer Res. Jan. 15, 2011;71:314-7.

Terreno E, Uggeri F, Aime S. Image guided therapy: the advent oftheranostic agents. J.Control Release Jul. 20, 2012;161(2):328-37.

Lee et al. Journal of Controlled Release, vol. 155, Issue 3, Nov. 7, 2011, pp. 435-444.

Ye et al. Journal of Controlled Release. vol. 169 (2013), pp. 239-245.

Das et al. Nanomedicine: Nanotechnology, Biology, and Medicine 11 (2015), pp. 379-389.

International Search report mailed Oct. 7, 2016.

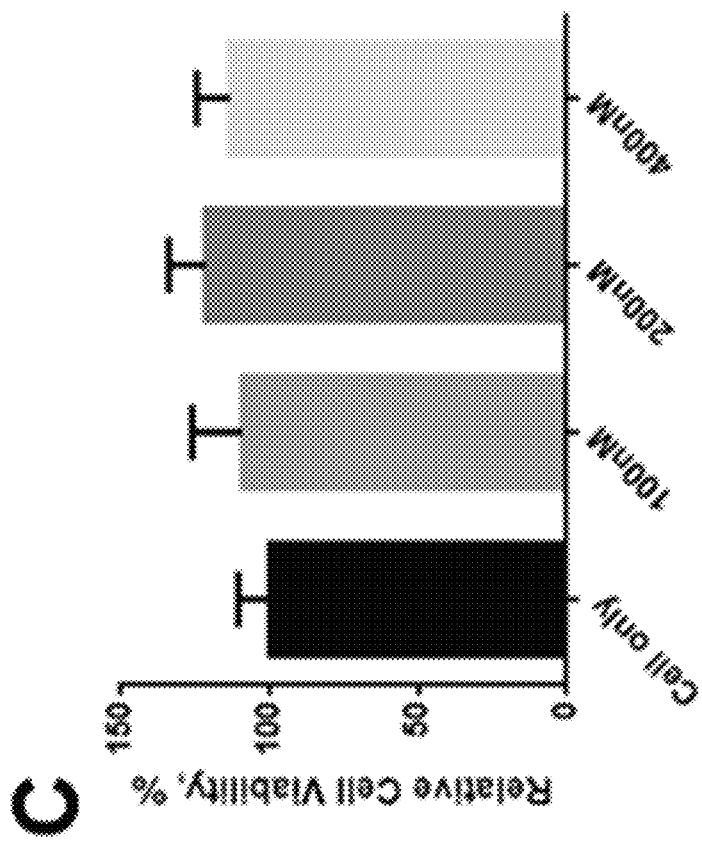
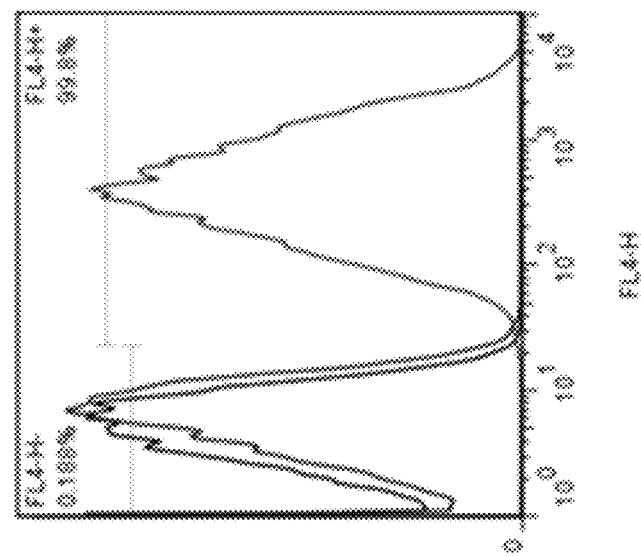
*FIG. 2 B and C*

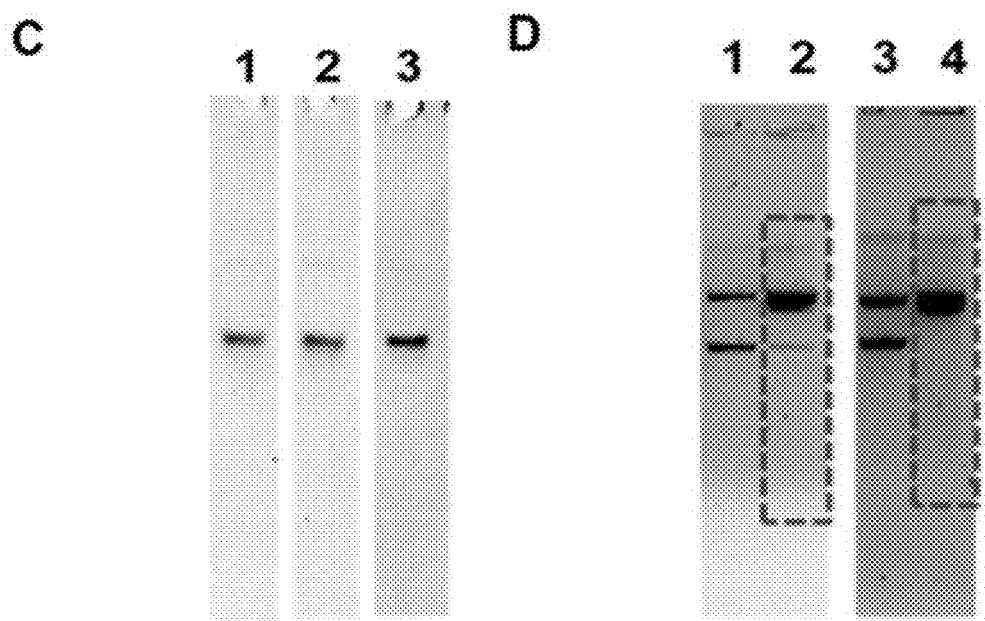
*FIG. 3C-D*

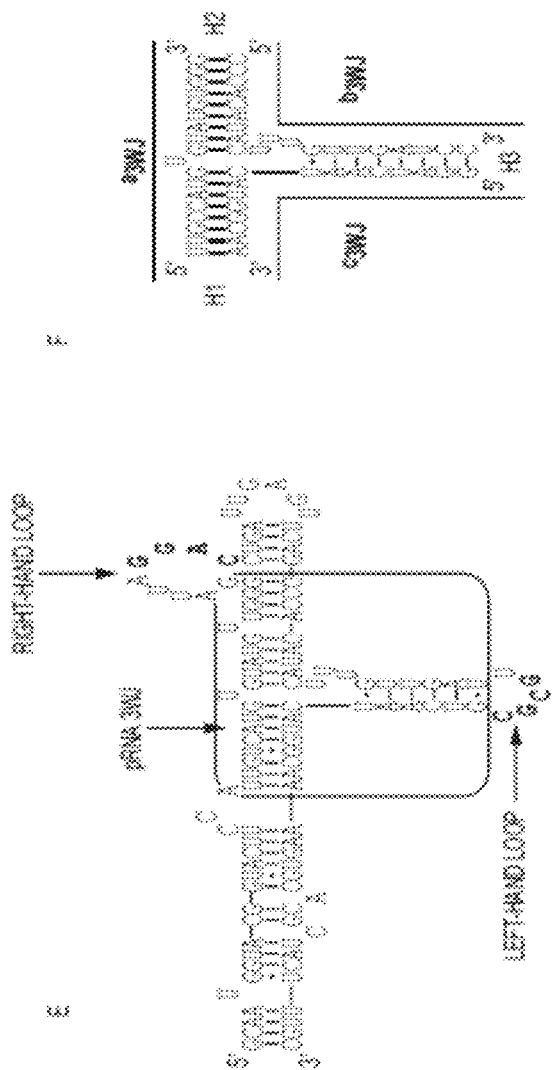
FIG. 6 E and F

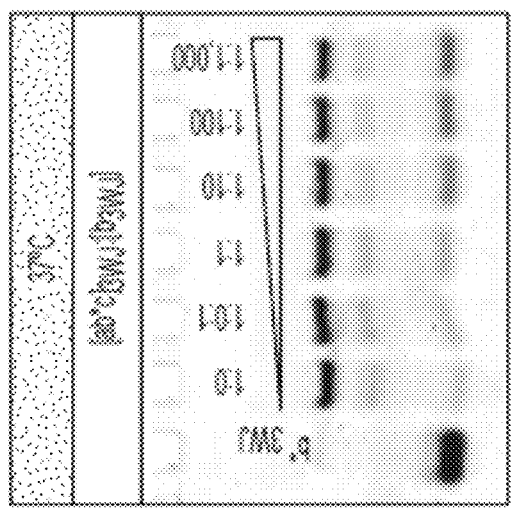
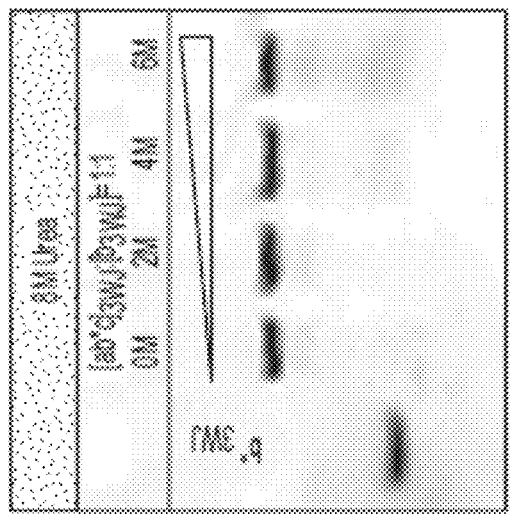
FIG. 7 A and B

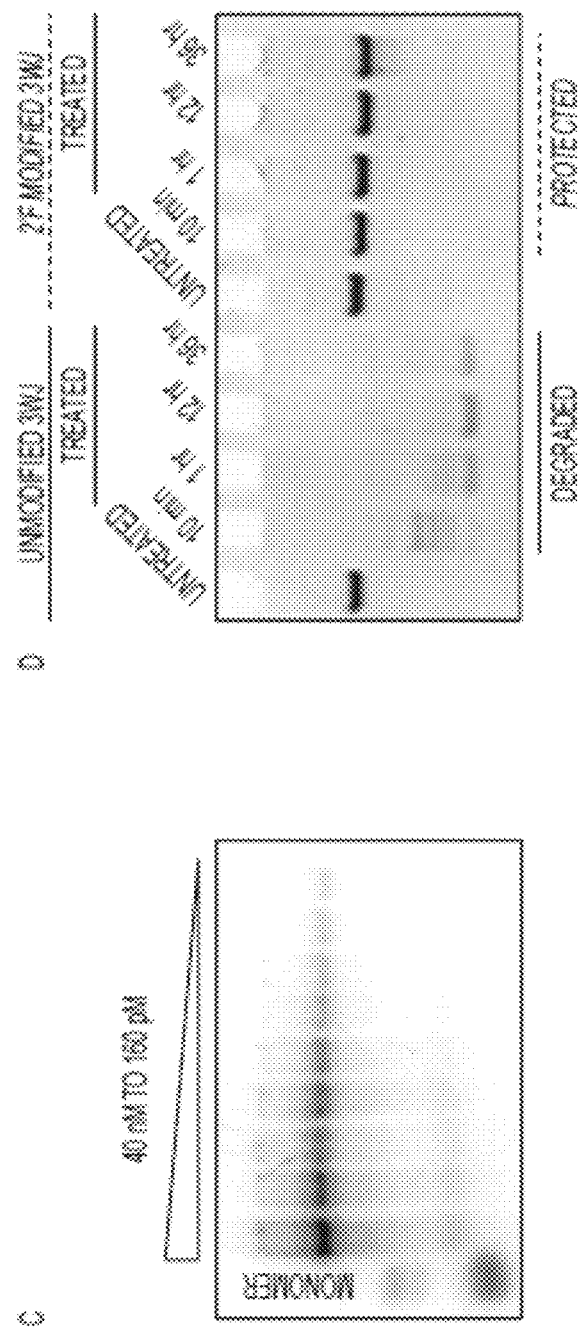
FIG. 7 C and D

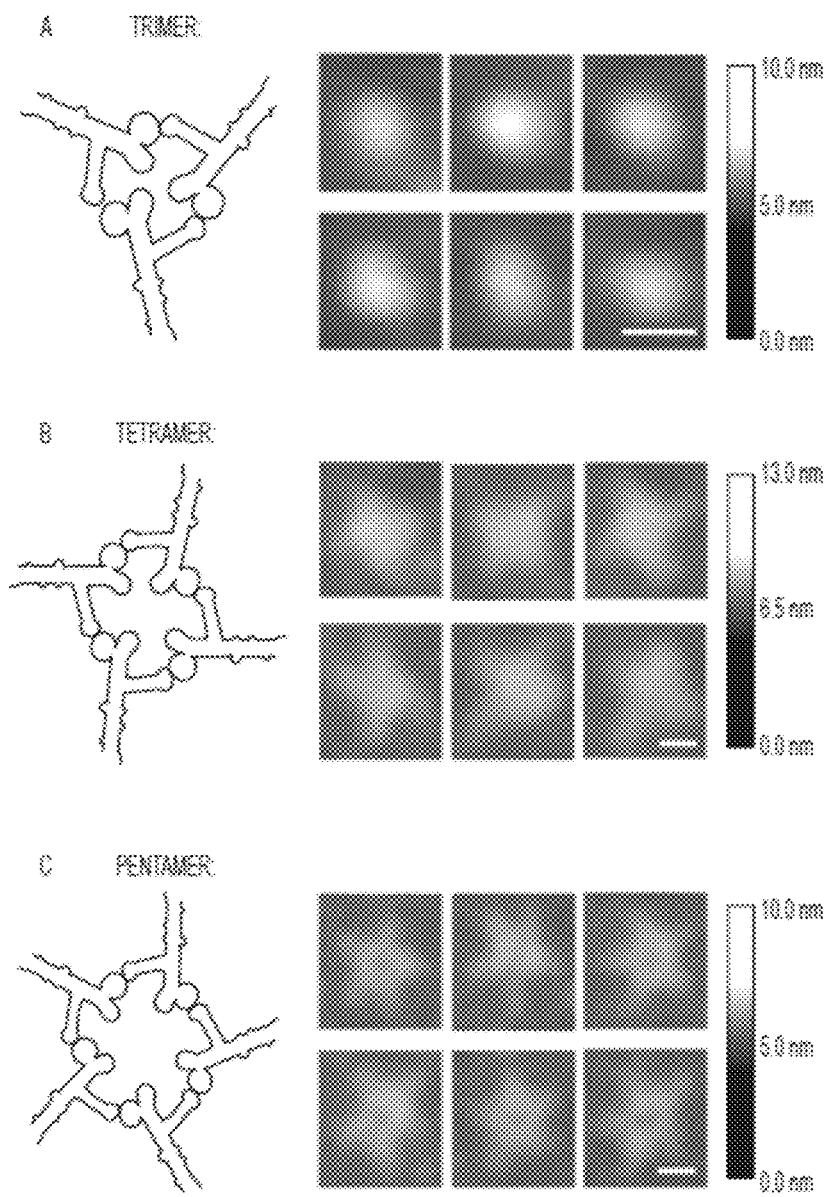
FIG. 9 A-C

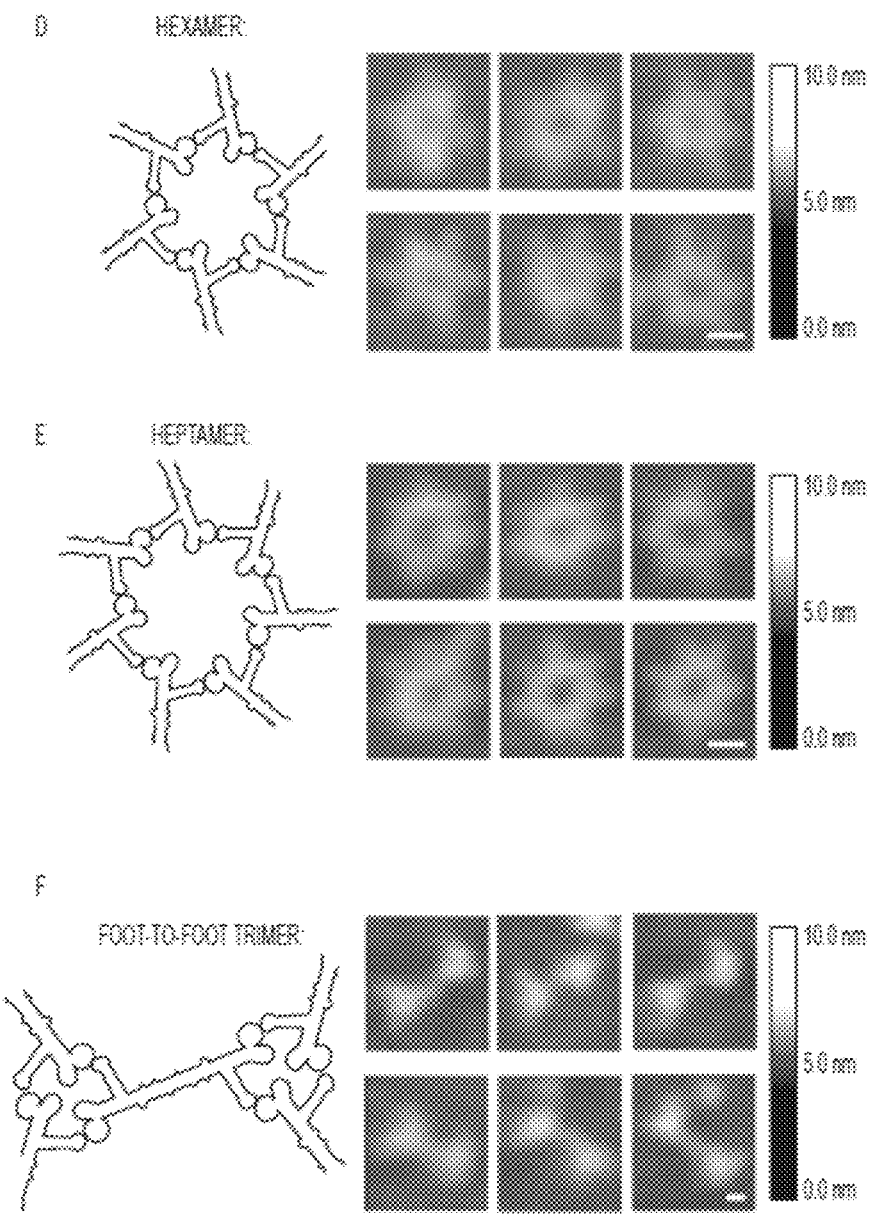
FIG. 9 D-F

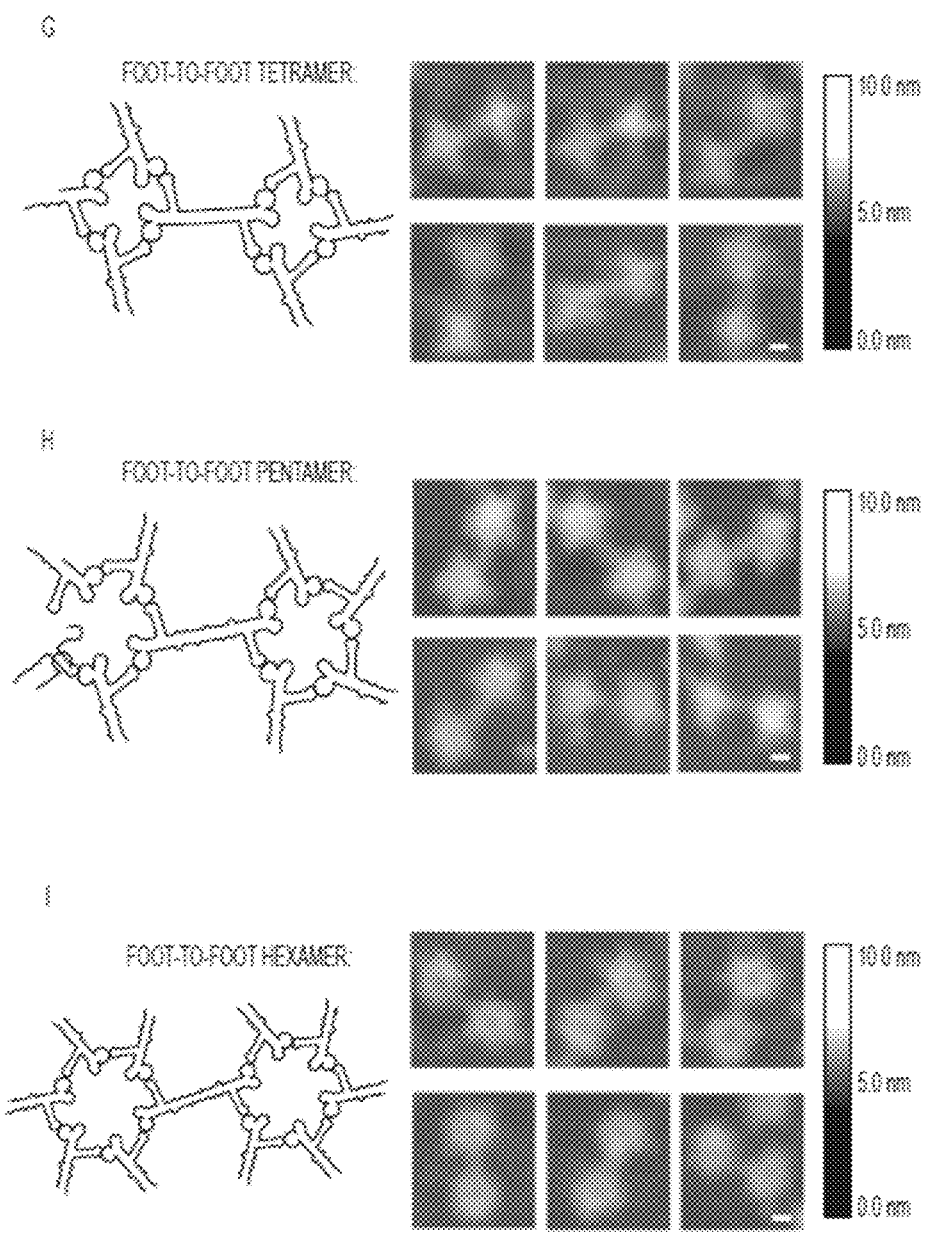
*FIG. 9 G-I*

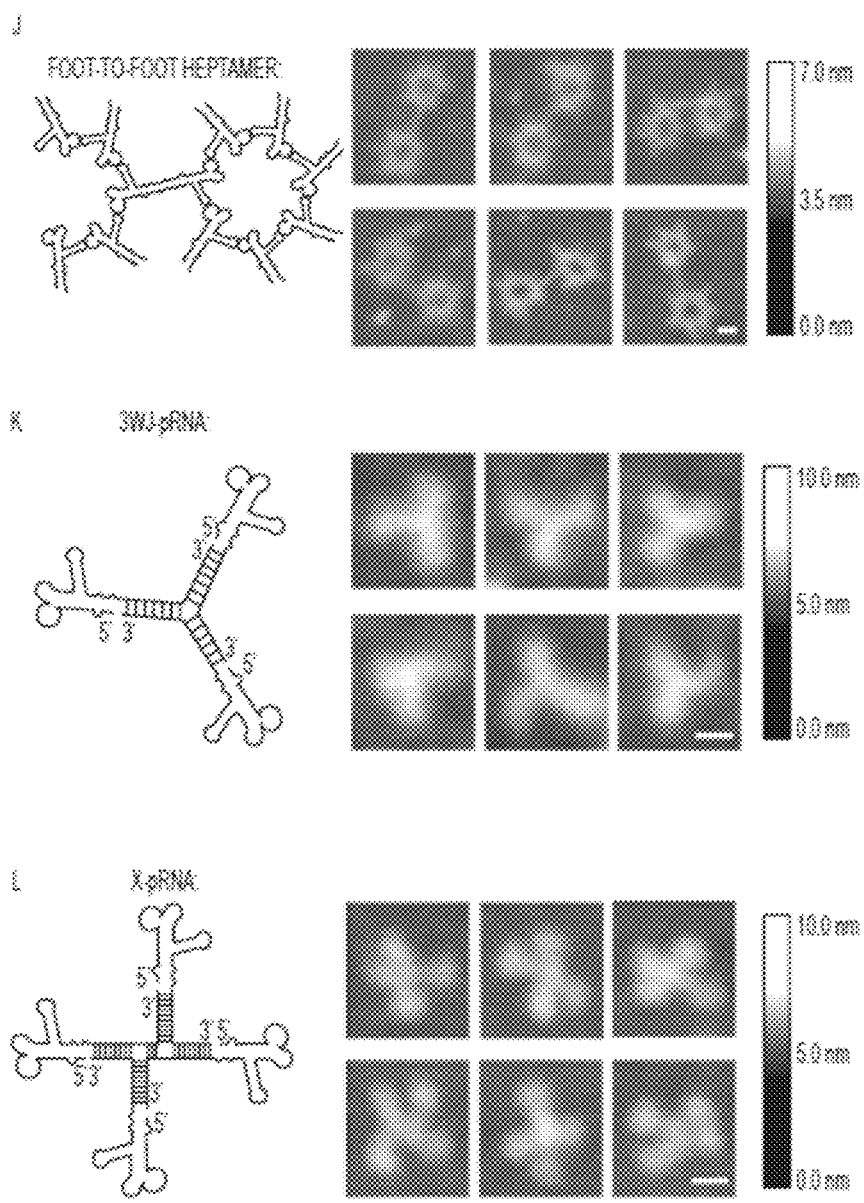
FIG. 9 J-L

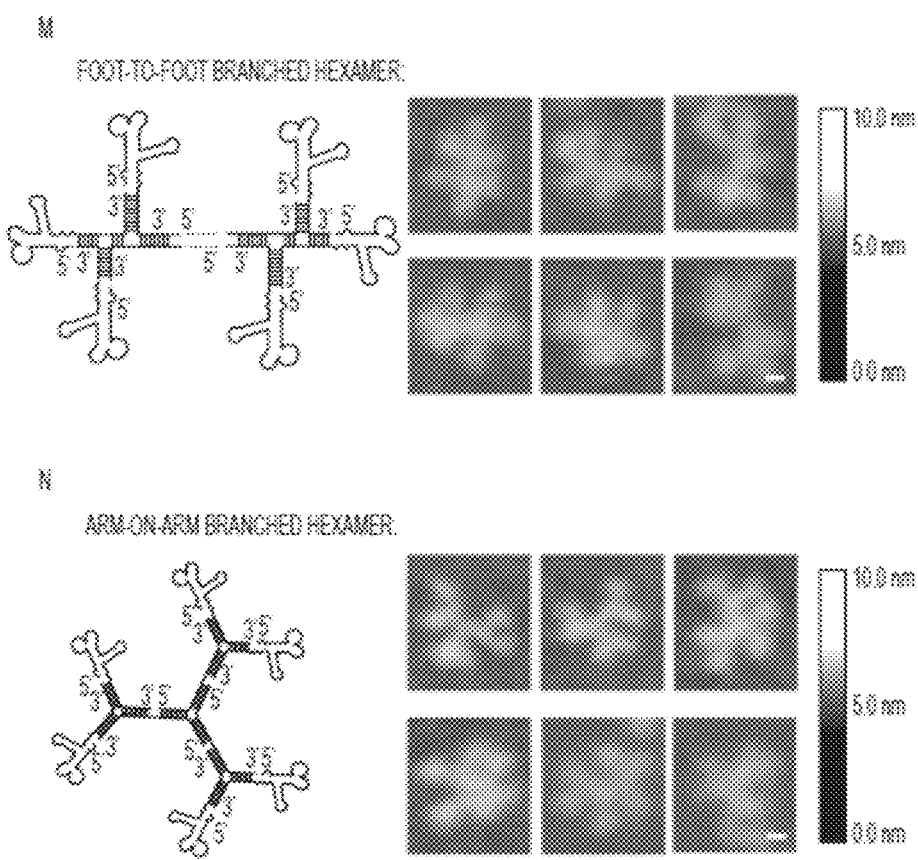
FIG. 9 M-N

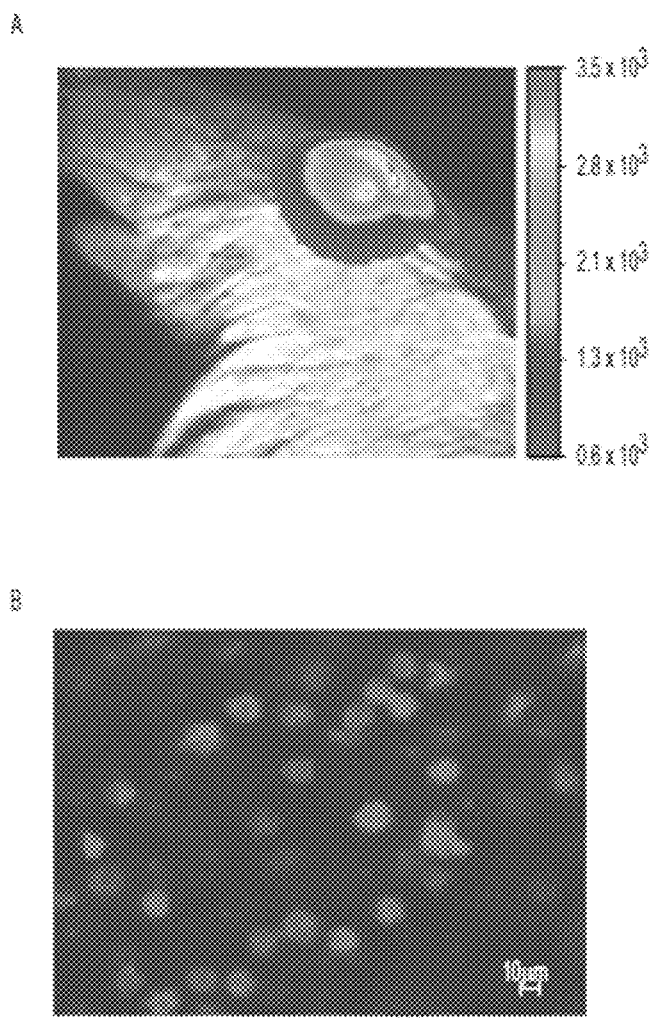
FIG. 10 A-B

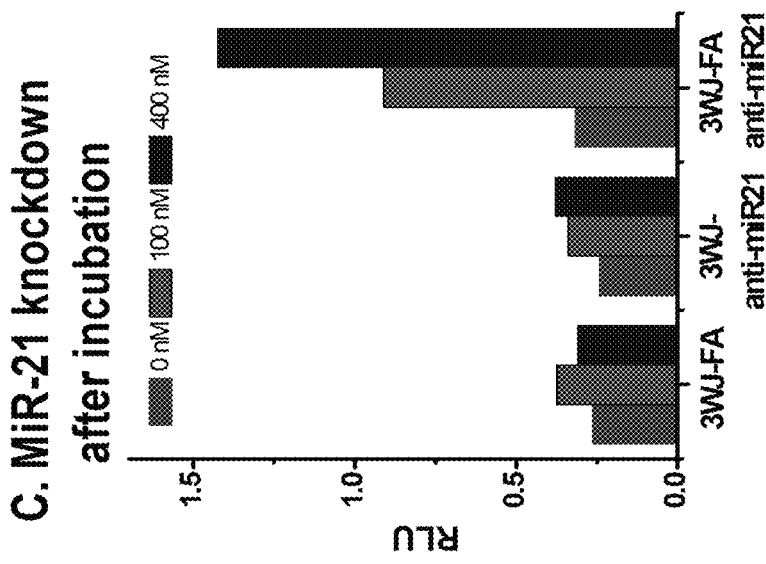
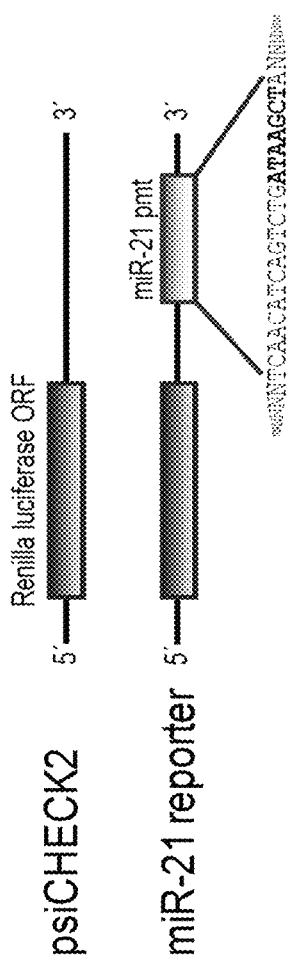
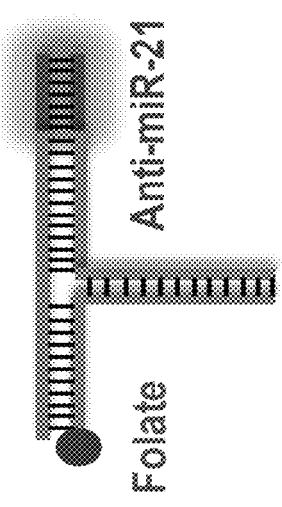
FIG. 18

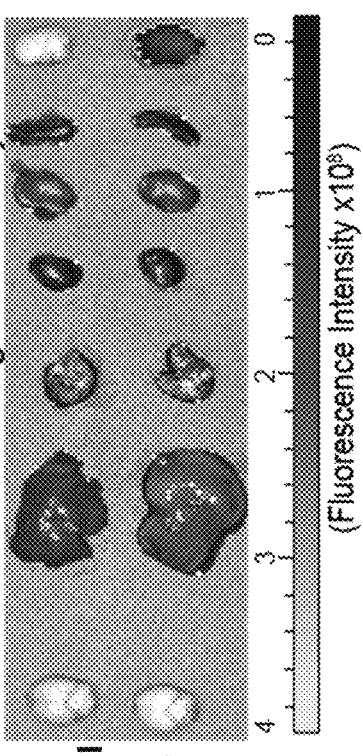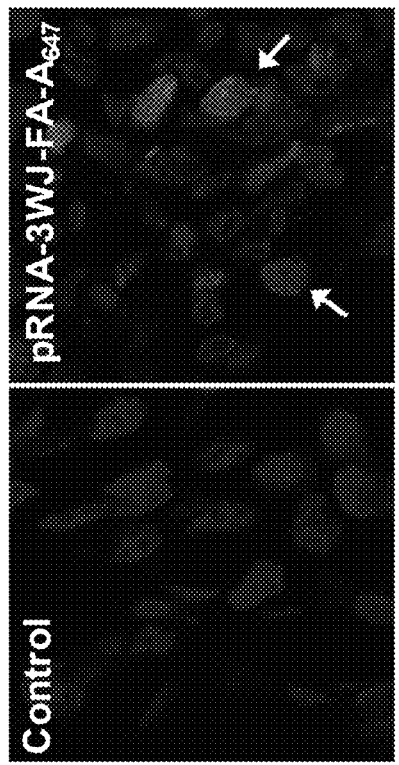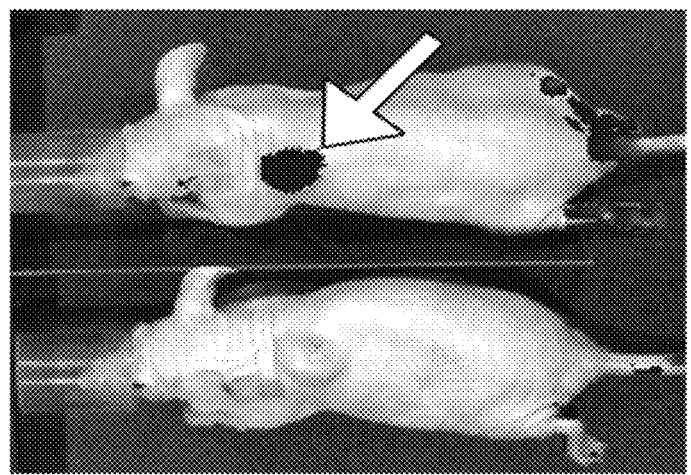
FIG. 22

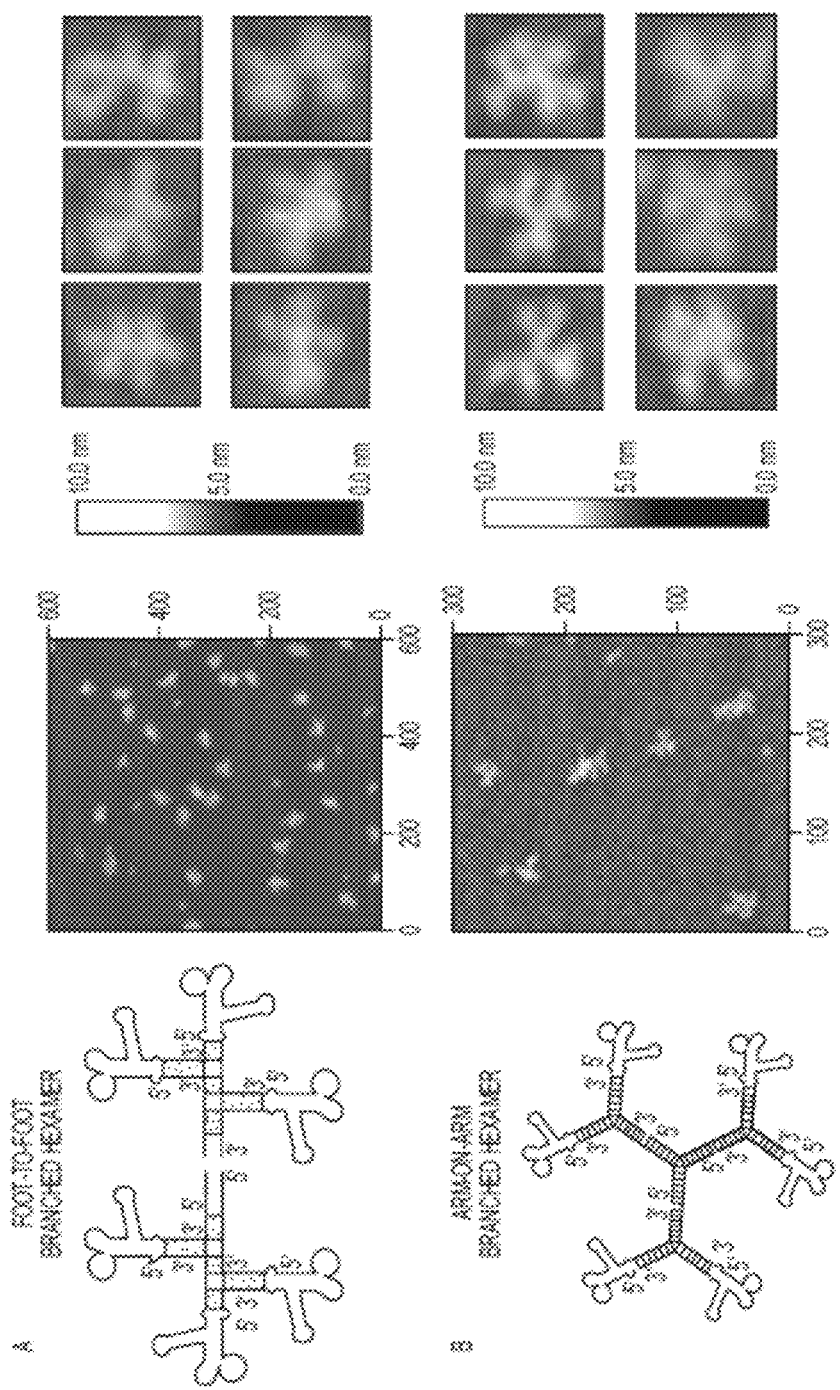
FIG. 26 A and B

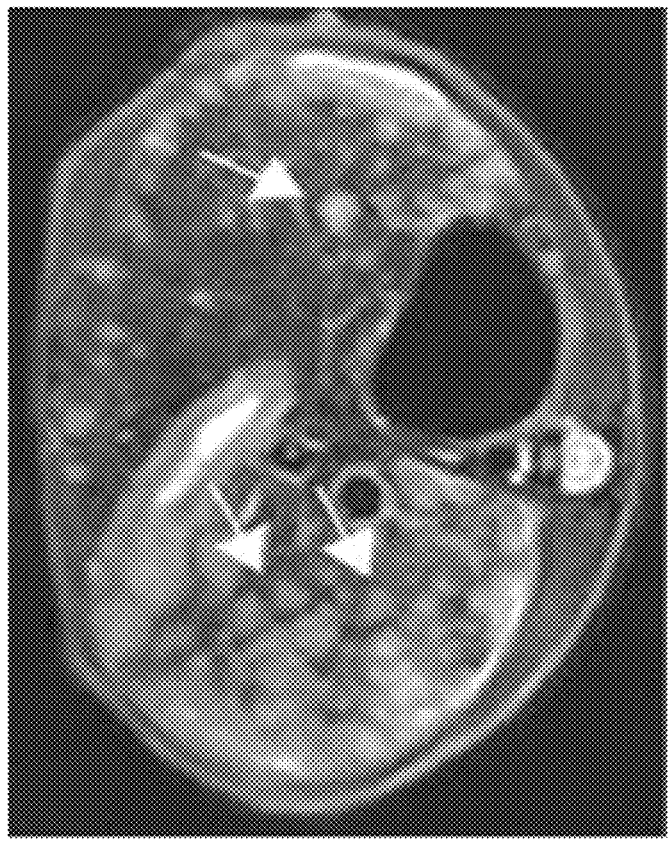
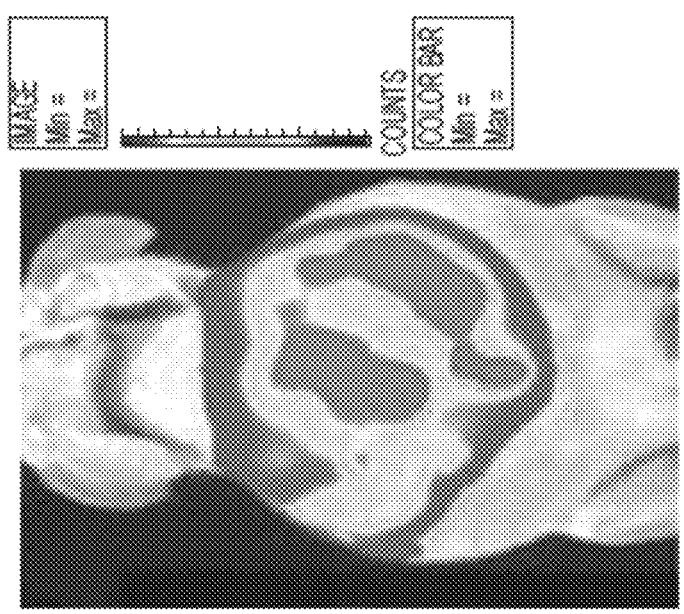
FIG. 27

A) pRNA-3WJ
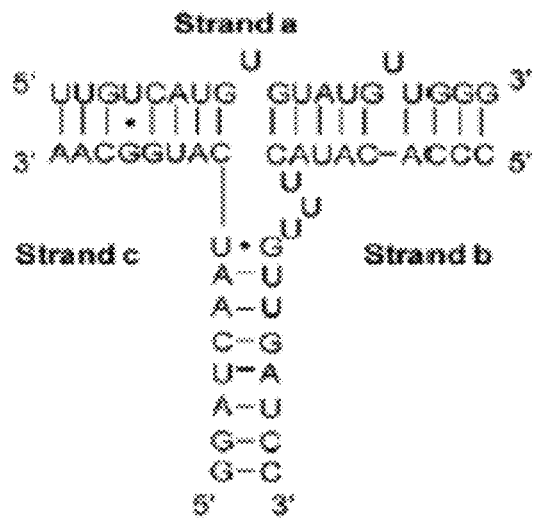
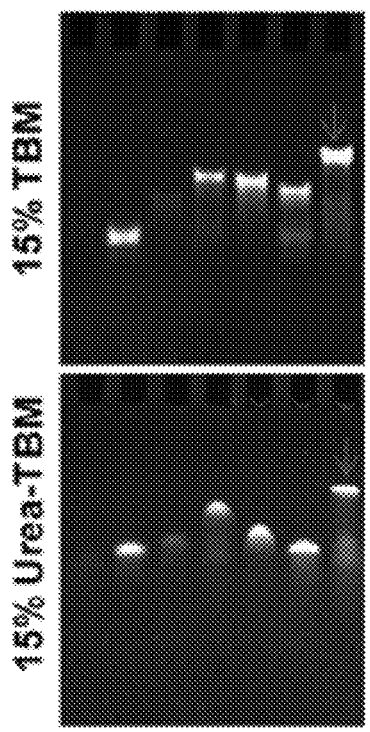
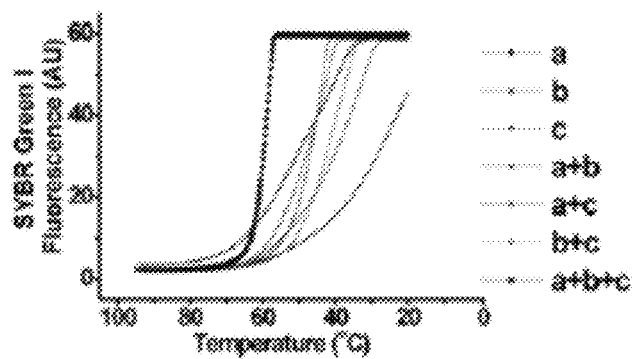
*FIG. 28A*

B) pRNA-3WJ-reverse
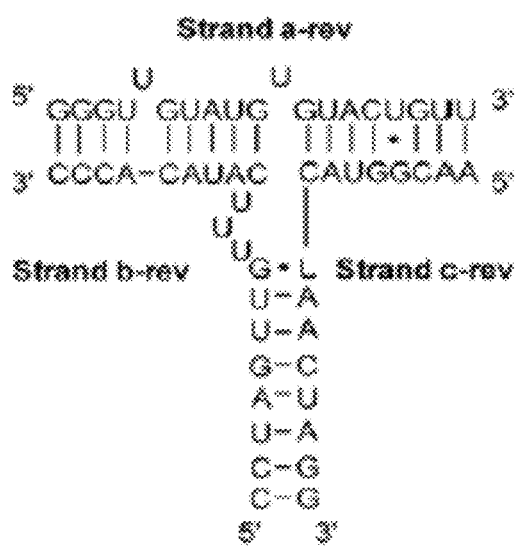
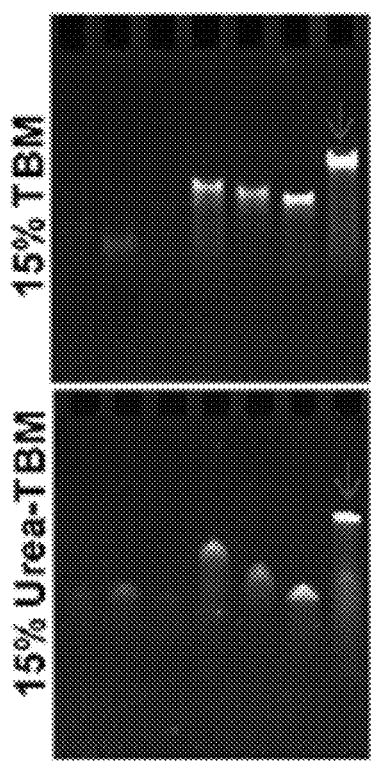
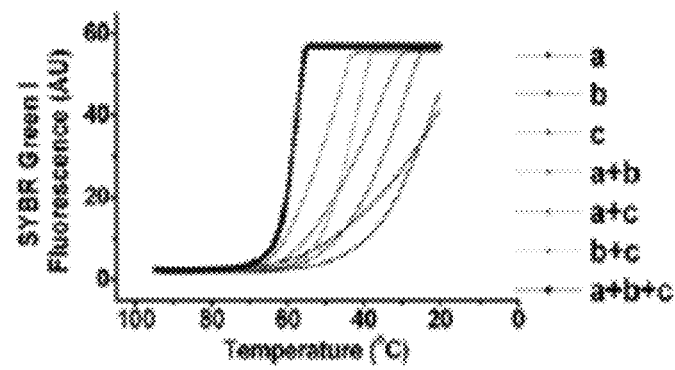
FIG. 28B

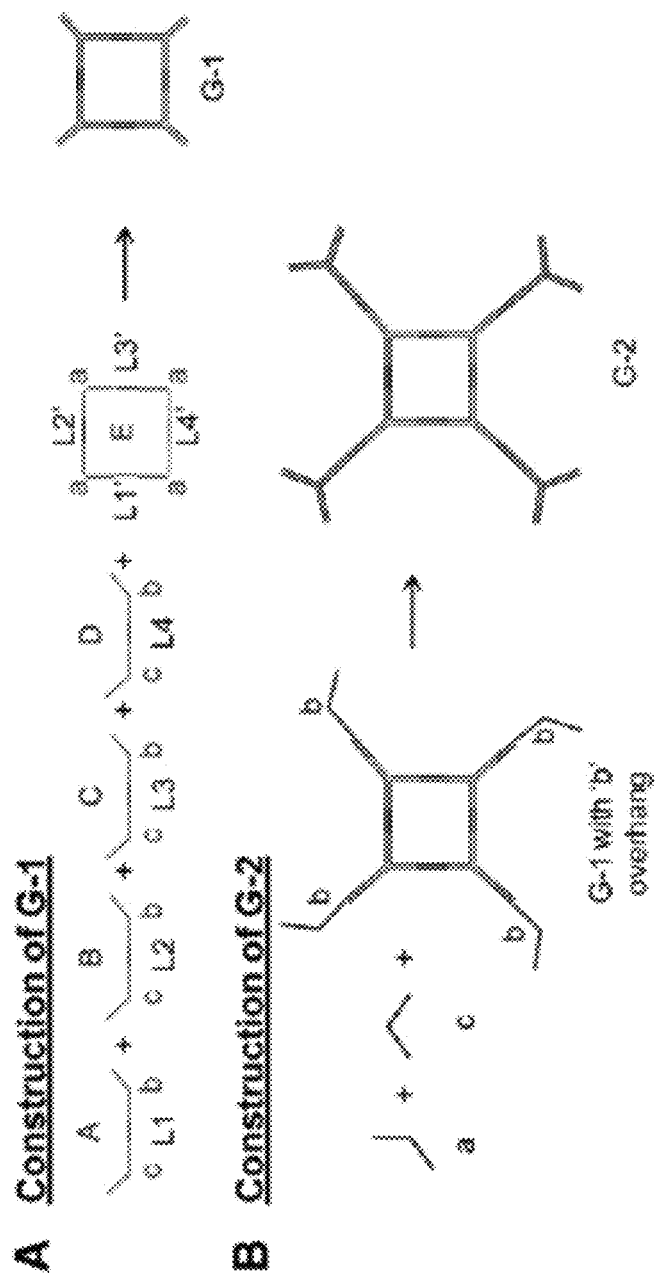
FIG. 31 A and B

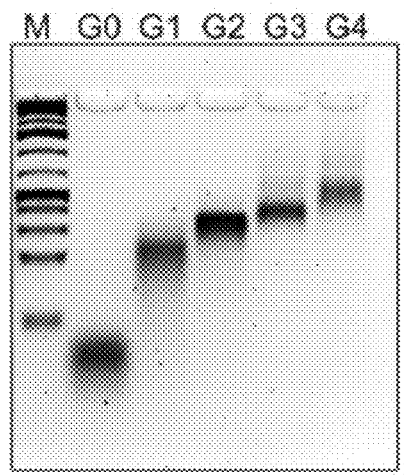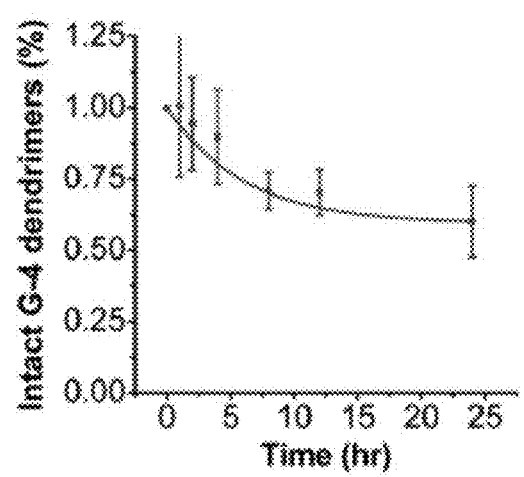
FIG. 32 B and C ially in ASCII format and is

SEQUENCE LISTING

```
<160> NUMBER OF SEQ ID NOS: 37

<210> SEQ ID NO 1
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1
uugccaugug uauguggg                                                        18

<210> SEQ ID NO 2
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 2
cccacauacu uuguugaucc                                                      20

<210> SEQ ID NO 3
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 3
```
ggaucaauca uggcaa                                                     16

<210> SEQ ID NO 4
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 4
ggguguaugu guaccguu                                                   18

<210> SEQ ID NO 5
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 5
ccuaguuguu ucauacaccc                                                 20

<210> SEQ ID NO 6
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 6
aacgguacua acuagg                                                     16

<210> SEQ ID NO 7
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 3'-folate

<400> SEQUENCE: 7
ggaucaauca uggcaa                                                     16

<210> SEQ ID NO 8
<211> LENGTH: 48
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 8
gggagccguc aaucauggca aguguccgcc auacuuuguu gcacgcac                  48

<210> SEQ ID NO 9
<211> LENGTH: 48
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 9
gggagcgugc aaucauggca agcgcaucgc auacuuuguu gcgaccua                48

<210> SEQ ID NO 10
<211> LENGTH: 48
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 10
gggaggucgc aaucauggca acgauagagc auacuuuguu ggcuggag                48

<210> SEQ ID NO 11
<211> LENGTH: 48
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 11
gggaccagcc aaucauggca auauacacgc auacuuuguu gacggcgg                48

<210> SEQ ID NO 12
<211> LENGTH: 88
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 12
ggacacuugu cauguguaug cguguauauu gucaugugua ugcucuaucg uugucaugug    60
uaugcgaugc gcuugucaug uguauggc                                      88

<210> SEQ ID NO 13
<211> LENGTH: 88
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 13
ggcccacaua cuuuguugau ccauggugcg uagggucguc aaucauggca aguguccgcc    60
auacuuuguu gcacucccuu gcucauca                                      88

<210> SEQ ID NO 14
<211> LENGTH: 88
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 14
ggcccacaua cuuuguugau ccugaugagc aagggagugc aaucauggca agcguaucgc    60
auacuuuguu gagaacccua ugugacuu                                      88

<210> SEQ ID NO 15
<211> LENGTH: 88
<212> TYPE: RNA
<213> ORGANISM: Artificial Sequence

```
<220> FEATURE:
<223> OTHER INFORMATION: Description of Artificial Sequence: Synthetic
      oligonucleotide

<400> SEQUENCE: 15
ggcccacaua cuuuguugau ccaagucaca uagggunucgc aaucauggca acgauagagc       60
auacuuuguu ggaguacccuu agaguaga                                         88

<210> SEQ ID NO 16
<211> LENGTH: 88
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 16
ggcccacaua cuuuguugau ccucuacucu aagggacucc aaucauggca auauacacgc       60
auacuuuguu gacgacccua cgcaccau                                          88

<210> SEQ ID NO 17
<211> LENGTH: 38
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 17
uugccaugug uaugugggcc uaguuguuuc auacaccc                               38

<210> SEQ ID NO 18
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 18
ggaucaauca uggcaaccua guuguuucau acaccc                                 36

<210> SEQ ID NO 19
<211> LENGTH: 38
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 19
cccacauacu uuguugaucc ggguguaugu guaccguu                               38

<210> SEQ ID NO 20
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 20
cccacauacu uuguugaucc aacgguacua acuagg                                 36

<210> SEQ ID NO 21
```

```
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 21
ggaccaccgc aucucuacat t                                                   21

<210> SEQ ID NO 22
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 22
ttccuggugg cguagagaug u                                                   21

<210> SEQ ID NO 23
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 23
aagcugucac agaggggcua c                                                   21

<210> SEQ ID NO 24
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 24 guagcccuc ugugacagcu u                                                    21

<210> SEQ ID NO 25
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 25
ccaugugcua uacagucauu acuuu                                               25

<210> SEQ ID NO 26
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 26
```

```
aaaguaauga cuguauagca caugg                                          25

<210> SEQ ID NO 27
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 27
uuggacaaug gacugguuga                                                20

<210> SEQ ID NO 28
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 28
ucaaccaguc cauuguccaa                                                20

<210> SEQ ID NO 29
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 29
ccacauaaag ggcccacua                                                 19

<210> SEQ ID NO 30
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 30
uagugggccc uuuaugugg                                                 19

<210> SEQ ID NO 31
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Gly Ser Gly Lys Cys Cys Tyr Ser Leu
1               5

<210> SEQ ID NO 32
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32
```

```
Lys Cys Cys Tyr Ser Leu
1               5
```

<210> SEQ ID NO 33
<211> LENGTH: 117
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 33
gcaaugguac gguacuucca uugucaugug uauguugggg auuaggaccu gauugaguuc    60
agcccacaua cuuuguugau ugcgcgucaa ucauggcaaa agugcacgcu acuugc       117

<210> SEQ ID NO 34
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 34
ggaucaacca uggcaa                                                    16

<210> SEQ ID NO 35
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(6)
<223> OTHER INFORMATION: a, c, t, g, unknown or other
<220> FEATURE:
<221> NAME/KEY: modified_base
<222> LOCATION: (29)..(34)
<223> OTHER INFORMATION: a, c, t, g, unknown or other

<400> SEQUENCE: 35
nnnnnntcaa catcagtctg ataagctann nnnn                                34

<210> SEQ ID NO 36
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 36
uugucaugug uauguugg                                                  18

<210> SEQ ID NO 37
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 37
ggguuguaug uguacuguu                                                 19

RNA NANOPARTICLES AND METHOD OF USE THEREOF

RELATED APPLICATIONS

This application is a divisional of U.S. patent application Ser. No. 15/566,972, filed on Oct. 16, 2017, which is a § 371 National Stage Application of PCT/US2016/028012 filed on Apr. 17, 2016, which claims the benefit of U.S. Provisional Patent Application No. 62/149,117, filed Apr. 17, 2015 and 62/150,233, filed Apr. 20, 2015, the entire disclosures of which are hereby incorporated by reference in their entireties.

GOVERNMENT INTEREST

This invention was made with government support under U01CA151648, R01EB019036 and R01EB003730 awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Apr. 11, 2018, is named 2935720-10_SL.txt and is 9,863 bytes in size.

TECHNICAL FIELD

The presently-disclosed subject matter relates to an artificial RNA nanostructure and method of use thereof. In particular, the presently-disclosed subject matter relates to RNA nanoparticles and RNA dendrimers, and methods of disease diagnosis and treatments using RNA nanostructure and RNA dendrimers.

INTRODUCTION

Cancer is a broad class of diseases featuring uncontrollable cell growth, invasion, and destruction of nearby tissues and metastasis [1, 2]. Cancer has become one of the leading causes of death in the world, accounting for about 7.6 million deaths in 2008 [3]. The economic burden of cancer is also very high, to both the person with cancer and for the whole society. According to the estimation by the National Institutes of Health (NIH), the overall annual cost of cancer in 2008 was $201.5 billion [4]. Thus, an effective, efficient, and safe treatment for cancer is urgently needed.

SUMMARY

The presently-disclosed subject matter meets some or all of the above-identified needs, as will become evident to those of ordinary skill in the art after a study of information provided in this document.

This Summary describes several embodiments of the presently-disclosed subject matter, and in many cases lists variations and permutations of these embodiments. This Summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently-disclosed subject matter, whether listed in this Summary or not. This Summary does not list or suggest all possible combinations of such features.

In some embodiments, the presently disclosed subject matter relates to an artificial RNA nanostructure molecule. The molecule includes a RNA junction motif comprising a plurality of branches and at least one imaging module, wherein a branch of the RNA junction motif comprises at least one RNA oligonucleotide. Non-limiting examples of the imaging module includes fluorescence dyes, radionuclides, and/or contrast agents. Non-limiting examples of fluorescent dye include Alexa dyes, Cy dyes or Near Infrared dyes. Further non-limiting examples of fluorescent dye include Alexa dye, Cy dyes, Near Infrared (Near IR or NIR) dyes, including but not limited to, IRdye$_{800}$, Alexa$_{647}$, Cy5, Cy5.5, Alexa680, Iowa Black RQ, QSY21, IRDyeQC, BBQ650, BHQ-3, Indocyanine green (ICG). In some embodiments, the imaging module comprises a reporter imaging module. In some embodiments, the imaging module comprises a reference imaging module. In some embodiments, the reference imaging module comprises a reference dye and a quencher. In some embodiments, the RNA molecule further includes at least one cancer targeting module coupled to the RNA junction motif. In some embodiments, the molecule further includes at least one therapeutic module coupled to the RNA junction motif In some embodiments, the imaging module is coupled to at least one branch of the RNA junction motif. In some embodiments, the imaging module is coupled to any branch of the RNA junction motif. In some embodiments, the imaging module is coupled to the cancer targeting module. In some embodiments, the imaging module is coupled to the therapeutic module. In some embodiments, the plurality of branches comprises three branches, four branches, five branches, six branches, seven branches eight or more branches. In one embodiment, the plurality of branches comprising the RNA junction motif includes a three-branched RNA junction motif. In one embodiment, the plurality of branches comprising the RNA junction motif comprises a four-branched RNA junction motif.

In some embodiment of the presently disclosed subject matter, the RNA nanostructure includes a radionuclide. In some embodiments, the term "radionuclide" includes radiolabel peptides and proteins with various isotopes. Nonlimiting examples of the radioisotopes includes $^{177}$Lu, $^{111}$In, $^{64}$Cu, $^{99m}$Tc, $^{203}$Pb, $^{188}$Re, $^{212}$Pb/$^{212}$Bi. In some embodiments, the radionuclide is coupled to more than one branch of the RNA junction motif. In some embodiment, the radionuclide is chelated by a chelating agent. In some embodiments, the chelating agent is conjugated to at least one branch of the RNA junction motif. Nonlimiting examples of the chelating agent is EDTA, DOTA, NOTA. [0058] In some embodiments, the RNA molecule includes a contrast agent. In some embodiments, the contract agent is a MRI contrast agent. In some embodiments, the MRI contract agent is gastrointestinal MRI, intravenous MRI, intravascular (blood pool) MRI tumor-specific MRI, hepatobiliary MRI and reticuloendothelial MRI. One non-limiting example of the MRI contrast agent is a gadolinium contrast agent.

In some embodiments, the nanostructure comprises at least one chemical modification at a 2' position of the RNA oligonucleotide. In some embodiments, the chemical modification comprises 2'Fluoro, 2'Amine, and 2'O-Methyl.

In some embodiments of the presently disclosed subject matter, a branch of the three-branched RNA junction motif is an a3WJ RNA module (SEQ ID NO: 1), a b3WJ RNA module (SEQ ID NO: 2), or a c3WJ RNA module (SEQ ID NO: 3). In one embodiment, the three-branched RNA junction motif comprises an a3WJ RNA module (SEQ ID NO: 1), a b3WJ RNA module (SEQ ID NO: 2), and a c3WJ RNA module (SEQ ID NO: 3). In some embodiments, SEQ ID NO: 1 has at least 90% identity to nucleotide sequence 5'-UUG CCA UGU GUA UGU GGG-3'. In one embodiment, SEQ ID NO: 1 comprises nucleotide sequence 5'-UUG CCA UGU GUA UGU GGG-3'. In some embodiments, SEQ ID NO: 2 has at least 90% identity to nucleotide sequence 5'-CCC ACA UAC UUU GUU GAUCC-3'. In one embodiment, SEQ ID NO: 2 comprises nucleotide sequence 5'-CCC ACA UAC UUU GUU GAUCC-3'. In some embodiments, SEQ ID NO: 3 has at least 90% identity to nucleotide sequence 5'-GGA UCA AUC AUG GCA A-3'. In one embodiment, SEQ ID NO: 3 comprises nucleotide sequence 5'-GGA UCA AUC AUG GCA A-3'.

In some embodiments of the presently disclosed subject matter, the RNA nanostructure includes a cancer targeting module. In some embodiments, the presently disclosed subject matter provides that the targeting module in the artificial RNA nanostructure molecule includes a ligand that binds to at least one cancer cell surface marker. In some embodiments, the cancer targeting module is a colon cancer targeting module. Non-limiting examples of folate include 5-methyltetrahydro folate, 5-formyltetrahydrofolate, dihydrofolate, tetrahydrofolate, folic acid and other folate compounds. In some embodiments, the therapeutic module comprises a siRNA, a miRNA, an anti-mRNA, a ribozyme RNA, or an antisense RNA. In some embodiments, In some embodiments, the therapeutic module comprises a chemotherapeutic drug, a riboswitch, or an endosome disrupting agent. In some embodiments, the therapeutic module is a siRNA sequence. In one embodiment, the siRNA directly binds to survivin. In some embodiments, the siRNA directly binds to PI3K, Akt, or mTOR. In some embodiments, the therapeutic module is a microRNA sequence. In some embodiments, the therapeutic module is an anti-miRNA molecule directed to a miRNA comprising miR-9, miR-10b, miR-21, or miR-26. In some embodiments, the therapeutical module is a miRNA molecule for a miRNA comprising let-7a, miR-10b, miR-25, miR-34a, miR-124, miR-145, or miR-181b. In some embodiments, the therapeutic module is a cytotoxic drug. In some embodiments, the cytotoxic drug comprises doxorubicin, paclitaxel, paclitaxel derivatives and analogues, cytochalasin D, rapamycin, rapamycin derivatives and analogues, camptothecin, dexamethasone, and 5-fluorouracil, a quinazolinone derivative, metallic silver, tranilast, everolimus and/or related compounds.

In another aspect, the presently disclosed subject matter provides an artificial RNA nanostructure molecule includes a RNA junction motif comprising a plurality of branches and a radiation-based therapeutic module coupled to the RNA junction motif, and a branch of the RNA junction motif includes at least one RNA oligonucleotide. In some embodiments, the molecule further includes a cancer targeting module coupled to the RNA junction motif. In some embodiments, the molecule further includes an imaging module coupled to the RNA junction motif. In some embodiments, the nanostructure comprises at least one chemical modification at 2' position of the RNA oligonucleotide. In some embodiments, the chemical modification comprises 2'Fluoro, 2'Amine, and 2'O-Methyl. In some embodiments, the plurality of branches comprises three branches, four branches, five branches, six branches, seven branches, eight or more branches. In some embodiments, the plurality of branches comprising the RNA junction motif includes a three-branched RNA junction motif. In some embodiments, the plurality of branches comprising the RNA junction motif comprises a four-branched RNA junction motif. In some embodiments, a branch of the three-branched RNA junction motif includes an a3WJ RNA module (SEQ ID NO: 1), a b3WJ RNA module (SEQ ID NO: 2), or a c3WJ RNA module (SEQ ID NO: 3). In some embodiments, the three-branched RNA junction motif comprises an a3WJ RNA module (SEQ ID NO: 1), a b3WJ RNA module (SEQ ID NO: 2), and a c3WJ RNA module (SEQ ID NO: 3). In some embodiments, SEQ ID NO: 1 has at least 90% identity to nucleotide sequence 5'-UUG CCA UGU GUA UGU GGG-3'. In some embodiments, SEQ ID NO: 1 comprises nucleotide sequence 5'-UUG CCA UGU GUA UGU GGG-3'. In some embodiments, SEQ ID NO: 2 has at least 90% identity to nucleotide sequence 5'-CCC ACA UAC UUU GUU GAUCC-3'. In some embodiments, SEQ ID NO: 2 comprises nucleotide sequence 5'-CCC ACA UAC UUU GUU GAUCC-3'. In some embodiments, SEQ ID NO: 3 has at least 90% identity to nucleotide sequence 5'-GGA UCA AUC AUG GCA A-3'. In some embodiments, SEQ ID NO: 3 comprises nucleotide sequence 5'-GGA UCA AUC AUG GCA A-3'. In some embodiments, the cancer-targeting module is a cancer cell-specific ligand. In some embodiments, the cancer-targeting module is folate. In some embodiments, cancer-targeting module is an RNA aptamer. In some embodiments, the radiation-based therapeutic module include a isotope. Nonlimiting examples of the isotope include 177Lu, 111In, 64Cu, 99mTc, 203Pb, 188Re, 212Pb, 212Bi, I-125, or Cs-131.

Further, in another aspect of the present subject matter, a RNA dendrimer molecule is provided. The molecule includes (a) a central core multi-branched RNA junction motif, wherein the central core motif comprises a plurality of branches, and wherein a branch comprises at least one RNA oligonucleotide; and (b) an outer surface multi-branched RNA junction motif comprising at least one repeating multi-branched RNA junction motif unit, wherein the repeating unit comprises a plurality of branches, and wherein a branch comprises at least one RNA oligonucleotide. In some embodiments, the dendrimer further includes at least one imaging module. In some embodiments, the dendrimer includes at least one targeting module. In some embodiments, the dendrimer further includes at least one therapeutic module. In some embodiments, the plurality of branches includes the central core multi-branched RNA junction motif comprises a three-branched RNA junction motif, a four-branched RNA junction motif, five-branched RNA junction motif, a six-branched RNA junction motif, seven-branched RNA junction motif, an eight or more branched RNA junction motif. In some embodiments, the plurality of branches comprising the repeating multi-branched RNA junction motif unit includes a three-branched RNA junction motif, a four-branched RNA junction motif, five-branched RNA junction motif, a six-branched RNA junction motif, seven-branched RNA junction motif, an eight or more branched RNA junction motif. In some embodiments, a branch of the three-branched RNA junction motif comprises an a3WJ RNA module (SEQ ID NO: 1); a b3WJ RNA module (SEQ ID NO: 2); or a c3WJ RNA module (SEQ ID NO: 3). In one embodiments, the three-branched RNA junction motif comprises an a3WJ RNA module (SEQ ID NO: 1); a b3WJ RNA module (SEQ ID NO: 2); and a c3WJ RNA module (SEQ ID NO: 3). In some embodiments, SEQ ID NO: 1 has at least 90% identity to nucleotide sequence 5'-UUG CCA UGU GUA UGU GGG-3'. In some embodiments, SEQ ID NO: 2 has at least 90% identity to nucleotide sequence 5'-CCC ACA UAC UUU GUU GAUCC-3'. In some embodiments, SEQ ID NO: 3 has at least 90% identity to nucleotide sequence 5'-GGA UCA AUC AUG GCA A-3'. In some embodiments, the central core multi-branched RNA junction motif is a polygon shaped architecture comprising a three-branched RNA junction motif at each corner. In some embodiments, the imaging module comprises a fluorescent dye, a radionuclide, or a contrast agent. In some embodiments, fluorescent dye is a Alexa dye, Cy dyes or Near IR dyes. Nonlimiting of fluorescent dye include IRdye800, Alexa647, Cy5, Cy5.5, Alexa680, Iowa Black RQ, QSY21, TRDyeQC, BBQ650, BHQ-3, Indocyanine green (ICG). In some embodiments, the imaging module comprises a reporter imaging module. In some embodiments, the imaging module comprises a reference imaging module. In some embodiments, the reference imaging module comprises a reference dye and a quencher. In some embodiments, the imaging module comprises at least one fluorescent dye. In some embodiments, the imaging module include a radionuclide and/or a contrast agent. A nonlimiting example of contrast agent is a MRI contrast agent. In one embodiment, the imaging module includes at least one gadolinium contrast agent. In some embodiments, the targeting module includes a cancer targeting module. In some embodiments, the cancer targeting module is a ligand that binds to at least one cancer cell surface marker. In some embodiments, the RNA dendrimer contains a targeting module comprises a chemical ligand and/or a RNA aptamer. A nonlimiting example of the ligand includes folate. In some embodiments, the cell surface markers comprises a folate receptor. In some embodiments, the ligand binds to an epithelial cell adhesion molecule (EpCAM). In some embodiments, the cell surface marker comprises an epithelial cell adhesion molecule (EpCAM). In some embodiments, the cancer targeting module comprises an aptamer. A non-limiting example of the aptamer is an EpCAM RNA aptamer. In some embodiments, the cancer targeting module is a folate. Nonlimiting examples of the folate include folic acid, 5-methyltetrahydro folate, 5-formyltetrahydrofolate, dihydrofolate, tetrahydrofolate, or a combination thereof. In some embodiments, the therapeutic module comprises a siRNA, a miRNA, an anti-mRNA, a ribozyme RNA, or an antisense RNA. In some embodiments, the therapeutic module comprises a chemotherapeutic drug, a riboswitch, or an endosome disrupting agent. In some embodiments, the therapeutic module is a cytotoxic drug. Nonlimiting examples of the cytotoxic drug include doxorubicin, paclitaxel, paclitaxel derivatives and analogues, cytochalasin D, rapamycin, rapamycin derivatives and analogues, camptothecin, dexamethasone, and 5-fluorouracil, a quinazolinone derivative, metallic silver, tranilast, everolimus and related compounds, or other agents that inhibit cell proliferation and or migration and/or inflammatory processes. In some embodiments, the plurality of branches of the multi-branched comprises at least 90% identity to nucleotide sequences of at least one of SEQ ID NOS: 1-20.

In another aspect of the presently disclosed subject matter, is a composition comprising a therapeutically effective amount of the RNA nanostructure molecule and RNA dendrimer as disclosed above and herein. In some embodiments, the composition further includes a pharmaceutically acceptable carrier.

Yet in another aspect of the presently disclosed subject matter, is a drug delivery system, the system comprising a therapeutically effective amount of the RNA nanostructure and the RNA dendrimer molecule as disclosed above and herein. In some embodiments, drug delivery system further includes a pharmaceutically acceptable carrier.

Further, in some embodiments, the presently disclosed subject matter provide a method of image-guided drug delivery of a therapeutic agent to a subject in need thereof. The method include administering a therapeutically effective amount of RNA nanostructure molecule and RNA dendrimer as disclosed above and herein, and applying an imaging detection apparatus to the subject. In some embodiments, the imaging detection apparatus is an MRI imaging system. In some embodiments, the imaging detection apparatus is an NIRF imaging system. In some embodiments, the imaging detection apparatus is an CT/PET/SPECT imaging system.

In some embodiments of the present subject matter, is a method of diagnosing and/or treating a disease in a subject having or at risk of having the disease. The method comprising administering to the subject a therapeutically effective amount of a composition comprising a RNA nanostructure and/or RNA dendrimer as disclosed herein. In some embodiments, the composition further comprises a pharmaceutically acceptable carrier. In some embodiments, the subject is a mammal or a non-mammal vertebrate. In some embodiments, the subject is a human. In some embodiments, the disease includes but not limited to ovarian cancer, brain cancer, bone cancer, lung cancer, colorectal cancer.

BRIEF DESCRIPTION OF THE DRAWINGS

The features of the presently disclosed subject matter are set forth with particularity in the appended claims. A better understanding of the features and advantages of the presently disclosed subject matter will be obtained by reference to the following detailed description that sets forth illustrative embodiments, in which the principles of the subject matter are used, and the accompanying drawings of which. The drawings were originally published in color, incorporated by reference in their entireties (Li H, et al., *Nucleic Acid Ther.* 2015 August; 25(4):188-97; Sharma A., et al., *Nanomedicine.* 2016 April; 12(3):835-44. doi: 10.1016/j.nano.2015.11.008). The black and white drawings of the instant application correspond to the color ones published.

FIGS. 2A-2D shows targeting, uptake, and cytotoxicity of RNA 3WJ nanoparticles. A. Confocal images showing the uptake comparison of the folate-3WJ RNA nanoparticles and 3WJ only RNA nanoparticles to colon cancer HT29 cells by colocalization of nucleus (blue), actin (green) and Alexa647-labeled RNA nanoparticles (red) signals. B. Flow cytometry analysis showing the binding of folate labeled 3WJ 2'F RNA nanoparticles to folate receptor over-expressed KB cells. Black curve: cell only control; blue curve: 3WJ RNA nanoparticles without folate; red curve: 3WJ RNA nanoparticles with folate. C. Effect of the folate-3WJ RNA nanoparticles on HT29 cells viability. The cells were incubate with three different concentration (100 nM, 200 nM and 400 nM) of the folate-3WJ RNA nanoparticles. D. The folate-3WJ-Alexa647 were injected intravenously into nude mice with HT29 subcutaneous xenografts. Accumulation of fluorescently labeled folate-3WJ nanoparticles in tumor, liver and lung was evaluated by IVIS Spectrum station.

FIGS. 3A-3D show stability assay of RNA 3WJ nanoparticles for urea, serum and irradiation. A. 12% native PAGE demonstrates the stability of RNA 3WJ nanoparticles against 2 M-8 M Urea denaturation. The gel was stained by ethidium bromide. Lane: 1: $3WJ_a$ (SEQ ID NO: 1); 2: $3WJ_b$ (SEQ ID NO: 2); 3: $3WJ_c$ (SEQ ID NO: 3); 4: $3WJ_a$+$3WJ_b$ (SEQ ID NO: 1, SEQ ID NO: 2); 5: $3WJ_a$+$3WJ_c$ (SEQ ID NO: 1, SEQ ID NO: 3); 6: $3WJ_b$+$3WJ_c$ (SEQ ID NO: 2, SEQ ID NO: 3); 7: $3WJ_a$+$3WJ_b$+$3WJ_c$ (SEQ ID NO: 1, SEQ ID NO: 2, SEQ ID NO: 3). B. Nanoparticle stability in serum was compared between 2'F modified and non-modified RNA 3WJ nanoparticles for up to 36 hr. Black square: RNA nanoparticle; red sphere: 2'F RNA nanoparticle. C. RNA 3WJ nanoparticles were resistant to radiation. 2'F-modified RNA 3WJ nanoparticles were examined by 12% native PAGE with TBM running buffer after 7-day irradiation with Cs-131 or 18-day irradiation with I-125. A dose of 30 Gy was given by both Cs-131 and I-125. No obvious change was detected after 7-day or 18-day irradiation. Lane: 1: RNA nanoparticles without irradiation; 2: RNA nanoparticles after 7-day irradiation (30 Gy) with Cs-131; 3: RNA nanoparticles after 18-day irradiation (30 Gy) with I-125. D. Plasmid DNA was damaged by radiation. Plasmid DNA was examined by 0.7% agarose gel with TAE running buffer after 7-day irradiation (30 Gy) with Cs-131 or 18-day irradiation (30 Gy) with I-125. Plasmid DNA was damaged after both 7-day and 18-day irradiation. Lane: 1 & 3: Plasmid DNA without irradiation; 2: Plasmid DNA after 7-day irradiation (30 Gy) with Cs-131; 4: Plasmid DNA after 18-day irradiation (30 Gy) with I-125.

FIG. 4B discloses SEQ ID NOS 1, 3 and 2, respectively, in order of appearance.

FIGS. 6A-6F includes (A) phi29 DNA packaging motor. (B) pRNA hexamer derived from the crystal in (D)14. (C) Hexameric pRNA nanoparticles. (D) pRNA-3WJ crystals and X-ray diffraction pattern14. (E) pRNA monomer (SEQ ID NO: 33). Box: 3WJ domain. (F) 3WJ domain9 composed of three fragments a3wJ, b3wJ, and c3wJ. H1-3: helical segments (FIG. 6F discloses SEQ ID NOS 1, 3 and 2, respectively, in order of appearance).

FIGS. 7A-7D includes competition and dissociation assays of pRNA-3WJ nanoparticles [G9] (A) Temperature effects: Fixed concentration of Cy3-pRNA-3WJ core [ab*c]$_{3WJ}$ was incubated with varying concentrations of unlabeled b3wJ at 37° C. (B) Urea denaturing effects: A fixed concentration of Cy3-[ab*c]$_{3WJ}$ was incubated with unlabeled b3wJ at a 1:1 ratio in the presence of 0-6 M urea at 25° C. (C) Serial dilution assay: The [$^{32}$P]pRNA-3WJ complex remains intact even at 160 pM. (D) After 2'-F modification, RNA nanoparticles are chemically stable [G13].

FIG. 9A-9N shows RNA nanotechnology approach for constructing polyvalent RNA nanoparticles with various shapes and sizes [G9-G1 1].

FIGS. 10A-10B includes (A-B) Ocular delivery of pRNA nanoparticles to cornea and retina following subconjunctival injection [G18]: (A) whole body (B) confocal images of the retina showing RNA accumulation after 4 hrs.

FIGS. 18A-18C (A) shows construction of miR-21-luciferase reporter system. (B) Schematic of pRNA-3WJ-FA-anti-miR21 nanoparticles (FIG. 18A discloses SEQ ID NO: 35). (C) Upon incubation, specific knock-down miR-21 in KB cells was observed, compared to controls (without FA or anti-miR21).

FIGS. 22A-22C shows (A) Whole body and (B) Internal organ images showing that upon systemic injection, pRNA-3WJ-FA nanoparticles specifically targeted Folate receptor+ HT29 colon cancer subcutaneous xenografts and were not detected in any vital organs in the body, after 8 hrs. (C) Confocal imaging of fixed frozen tumor xenografts sections confirmed binding and accumulation of pRNA nanoparticles in vivo. Control: PBS.

FIGS. 26A-26C shows (A-B) Schematic and AFM images of RNA dendrimers composed mainly of RNA by branch extension[11]. (C) 2D structure of Generation-3 RNA Dendrimers using pRNA-3WJ as scaffold for harboring DOTA-chelated Gd$^{3+}$, radionuclides and/or folate.

FIGS. 27A-27B shows In vivo assessment of liver metastases. (A) HT29-Luc cells were injected into the spleen to induce liver metastases. Representative bioluminescence images of mice with Luc-expressing liver metastases (B) T2 weighted images acquired on the University of Kentucky small animal Clinscan MRI scanner depicting multiple liver metastases (arrows).

FIGS. 28A-28B shows (A-B) 2D sequence; assembly in 15% native PAGE and stability in 8 M urea 15% PAGE; and thermodynamic properties of pRNA-3WJ (A) and pRNA-3WJ-rev (B) scaffold. (FIG. 28A-B disclose SEQ ID NOS 36, 3, 2, 37, 5 and 6, respectively, in order of appearance).

FIGS. 31A-D shows assembly of G-1 to G-4 RNA dendrimers from component strands. G-0 assembles for three strands: 3WJ-a, 3WJ-b, and 3WJ-c, as shown in FIG. 2A module 1. (A) G-1 assembles from five strands: A, B, C, D and E with complementary linkers (black) and 3WJ strands (red). (B) G-2 assembles from G-1 harboring four 3WJ-b sticky ends, and 3WJ-a and 3WJ-c strands. (C) G-3 assembles from G-2 harboring eight 3WJ-b_rev sticky ends, and 3WJ-a_rev and 3WJ-c_rev strands. (D) G-4 assembles from G-2 harboring eight 3WJ-b_rev sticky ends, and a dimer module harboring 3WJ-a_rev and 3WJ-c_rev strands. Please refer to Table 4 for defining characteristics.

FIGS. 32A-32C shows (A) 2D structure (left), AFM images (middle), and 3D model (right) (using Pymol and Swiss PDB viewer) of G-0 to G-4 RNA dendrimers. (B) 2% agarose gel showing assembly of G-0 to G-4 RNA dendrimers. (C) Serum stability assay of G-4 RNA dendrimers assayed in 2% agarose gel and quantified by ImageJ.

DESCRIPTION OF EXEMPLARY EMBODIMENTS

Figure 1A:
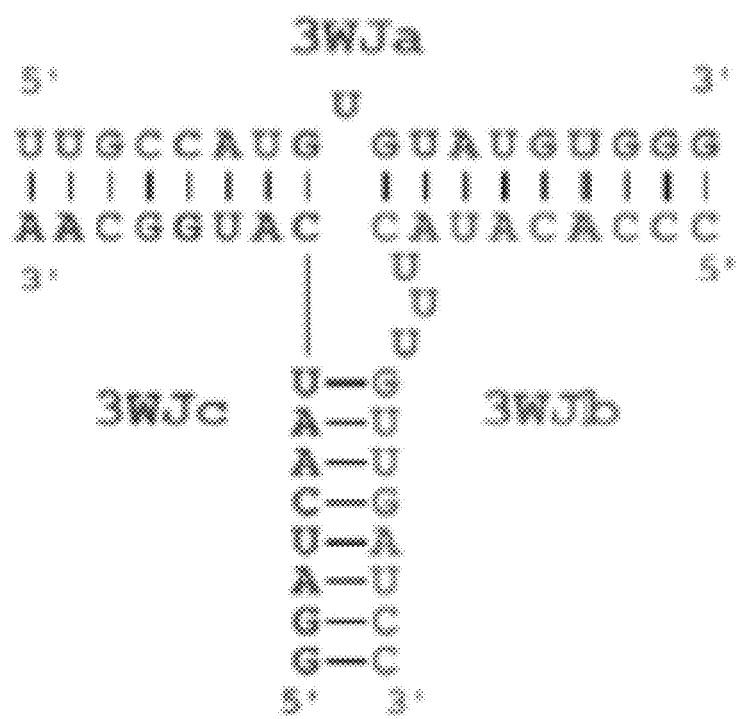
FIGS. 1A to 1D shows structure, assembly and characterization of RNA 3WJ nanoparticles. A. Secondary structure of the pRNA 3WJ (FIG. 1A discloses SEQ ID NOS 1, 3 and 2, respectively, in order of appearance). B. Eight representative images of RNA 3WJ-pRNA nanoparticles are shown in magnified view and the images reveal a three-branch shape of the RNA nanoparticles. The AFM images of the RNA nanoparticles were obtained on APS-modified mica surface by a Veeco MultiMode AFM NanoScope IV system. (Scale bar: 10 nm). C. 12% native PAGE demonstrates the step-wise assembly of RNA 3WJ nanoparticles, stained by ethidium bromide (upper) and SYBR Green II (lower). Lane: 1: $3WJ_a$ (SEQ ID NO: 1); 2: $3WJ_b$ (SEQ ID NO: 2); 3: $3WJ_c$ (SEQ ID NO: 3); 4: $3WJ_a+3WJ_b$ (SEQ ID NO: 1, SEQ ID NO: 2); 5: $3WJ_a+3WJ_c$ (SEQ ID NO: 1, SEQ ID NO: 3); 6: $3WJ_b+3WJ_c$ (SEQ ID NO: 2, SEQ ID NO: 3); 7: $3WJ_a+3WJ_b+3WJ_c$ (SEQ ID NO: 1, SEQ ID NO: 2, SEQ ID NO: 3). D. The thermodynamic stability of assembled RNA 3WJ nanoparticles was revealed by using the TGGE system. The temperature gradient was set from 36 to 80° C., and the direction was set as perpendicular to the electric field. The left two lanes are the 3WJ fragments and the 3WJ complex starts at the third lane.

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom.

In certain instances, nucleotides and polypeptides disclosed herein are included in publicly-available databases, such as GENBANK® and SWISSPROT. Information including sequences and other information related to such nucleotides and polypeptides included in such publicly-available databases are expressly incorporated by reference. Unless otherwise indicated or apparent the references to such publicly-available databases are references to the most recent version of the database as of the filing date of this Application.

While the terms used herein are believed to be well understood by one of ordinary skill in the art, definitions are set forth to facilitate explanation of the presently-disclosed subject matter.

Unless defined otherwise, all technical and scientific terms used herein have the same meaning as commonly understood by one of ordinary skill in the art to which the presently-disclosed subject matter belongs. Although any methods, devices, and materials similar or equivalent to those described herein can be used in the practice or testing of the presently-disclosed subject matter, representative methods, devices, and materials are now described.

Following long-standing patent law convention, the terms "a", "an", and "the" refer to "one or more" when used in this application, including the claims. Thus, for example, reference to "a cell" includes a plurality of such cells, and so forth.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, the abbreviations for any protective groups, amino acids and other compounds, are, unless indicated otherwise, in accord with their common usage, recognized abbreviations, or the IUPAC-IUB Commission on Biochemical Nomenclature (see, Biochem. (1972) 11(9): 1726-1732).

The presently-disclosed subject matter includes an artificial RNA nanostructures and RNA dendrimers and methods of use thereof.

Figure 6A:
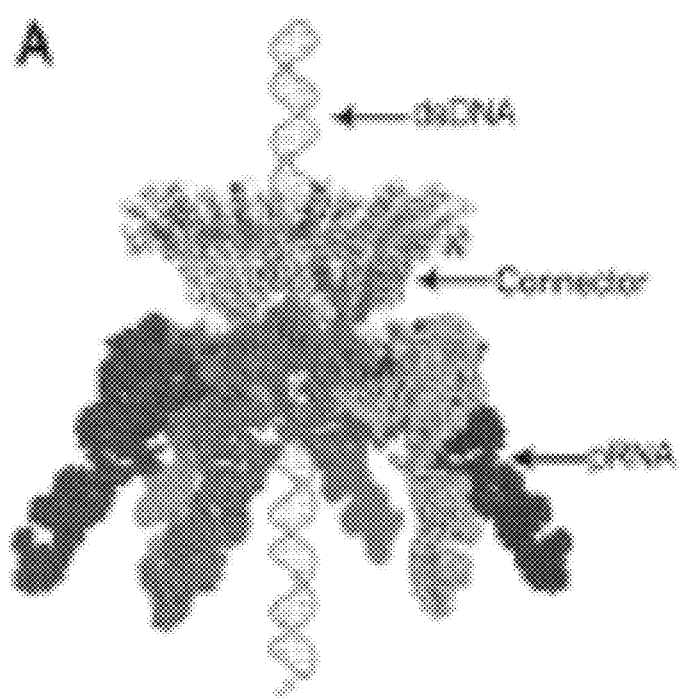
Figure 6B:
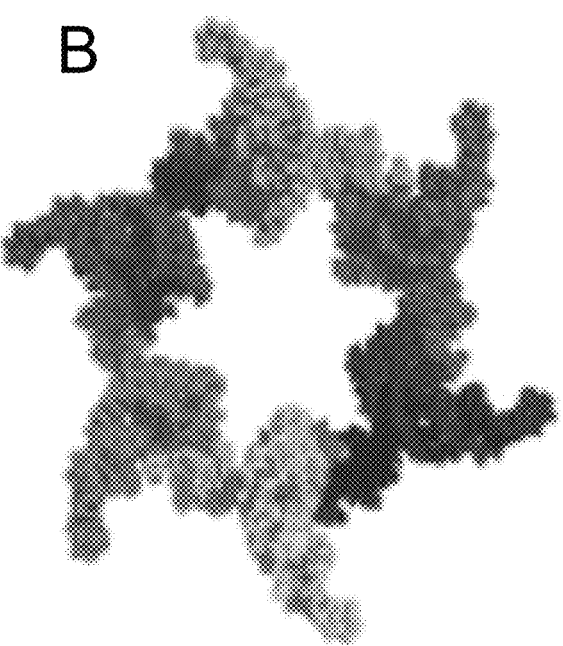
Figure 6C:
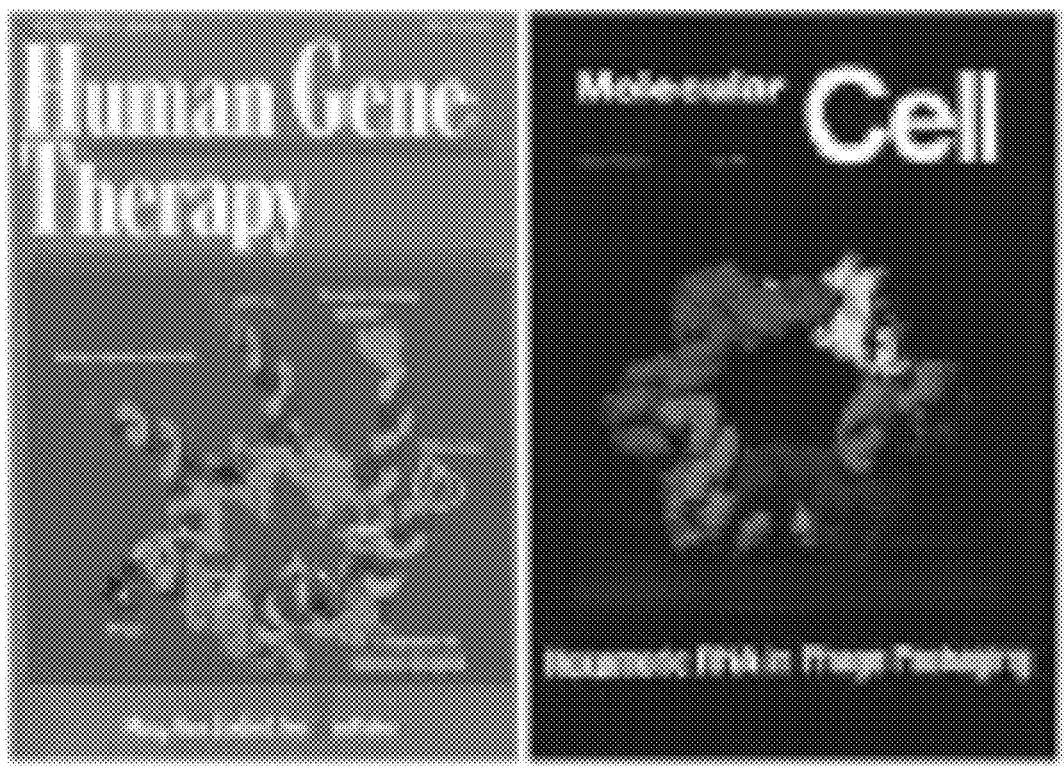
Figure 6D:
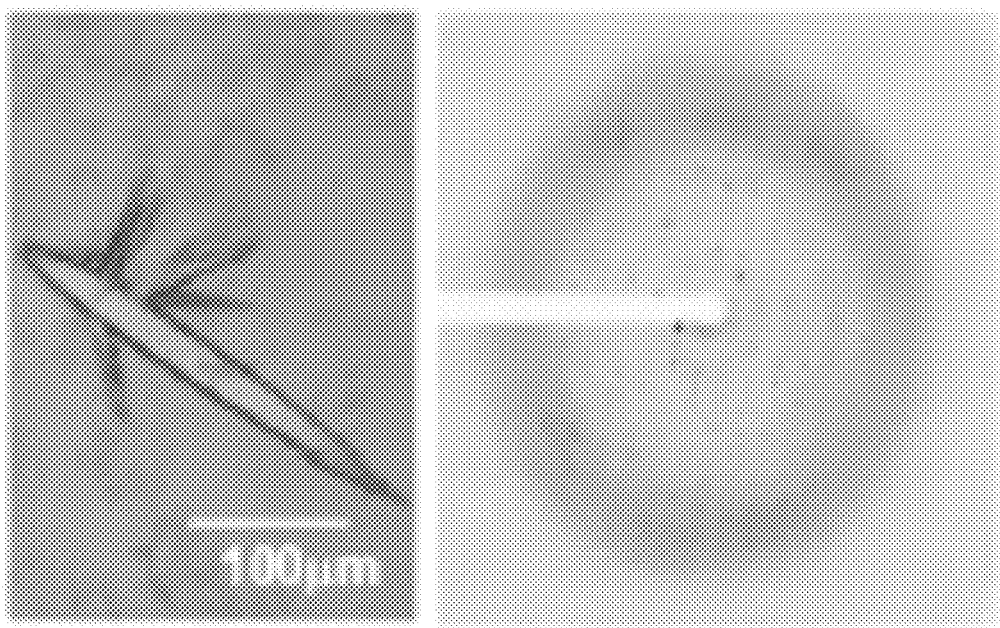

RNA nanotechnology is an unique field [G8,G24], distinct from the classical studies of RNA structure and folding [G25-31]. In 1998, the feasibility of constructing RNA nanoparticles by bottom-up self-assembly was first demonstrated. RNA dimer, trimer, and hexamer nanoparticles were assembled using re-engineered RNA fragments from the pRNA, a viral component gearing the phi29 DNA packaging motor (FIG. 6A-C [G32]). This finding (published in *Molecular Cell*, and featured in *Cell* (G32-33)) was the proof-of-concept for RNA nanotechnology. Generally speaking, RNA is unique in several aspects: (1) RNA contains varieties of motifs such as helices, loops, stems, hairpins, and pseudo-knots to specify rich 3D architectures; (2) RNA possesses both canonical, noncanonical base pairings(G34-38), as well as base stacking capabilities for inter- or intra-molecular interactions(G39-40); (3) RNA is thermodynamically more stable than DNA [G9,G10,G39,G40]; (4) RNA displays unique features in transcription, termination, splicing, and self-processing producing RNA fragments that are able to self-assemble into nanoparticles in vitro and in vivo [G32,G41-45]; and (5) RNA exhibits functional entities, such as siRNA [G46,G47], ribozyme [G48,G49], riboswitch [G50-51], and miRNA [G52-53]. As disclosed herein, RNA nanotechnology is an important field due to finding of its high thermodynamic stability, favorable and distinctive in vivo attributes (US 2014/0179758, hereby incorporate by reference in its entirety). In some embodiments of the present disclosure, as disclosed in US2014/0179758, the RNA molecules form dimers, trimers, hexamers, and patterned superstructures.

Figure 8:
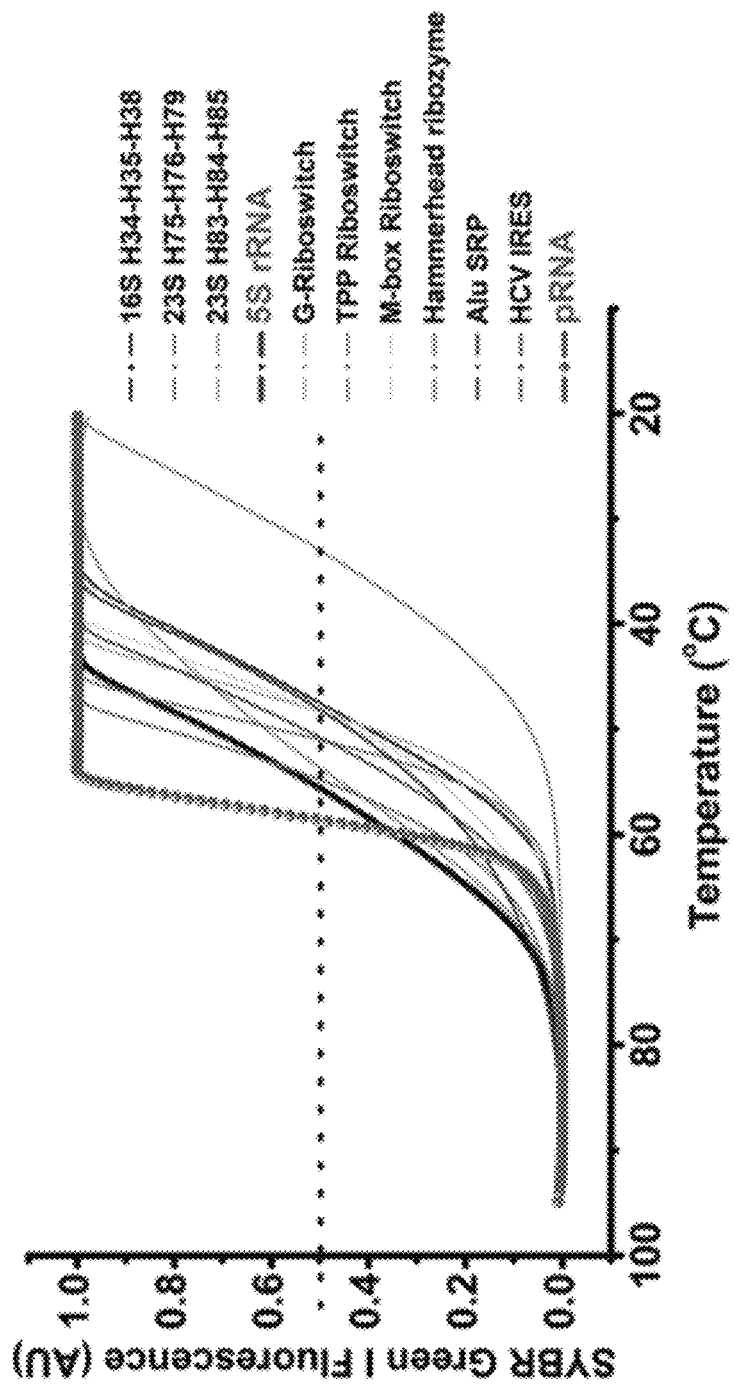
FIG. 8 shows that, compared to 11 different RNA 3WJ core motifs, the 3WJ-pRNA motif displayed the highest $T_m$ with the steepest slope [G9].
Figure 11A:
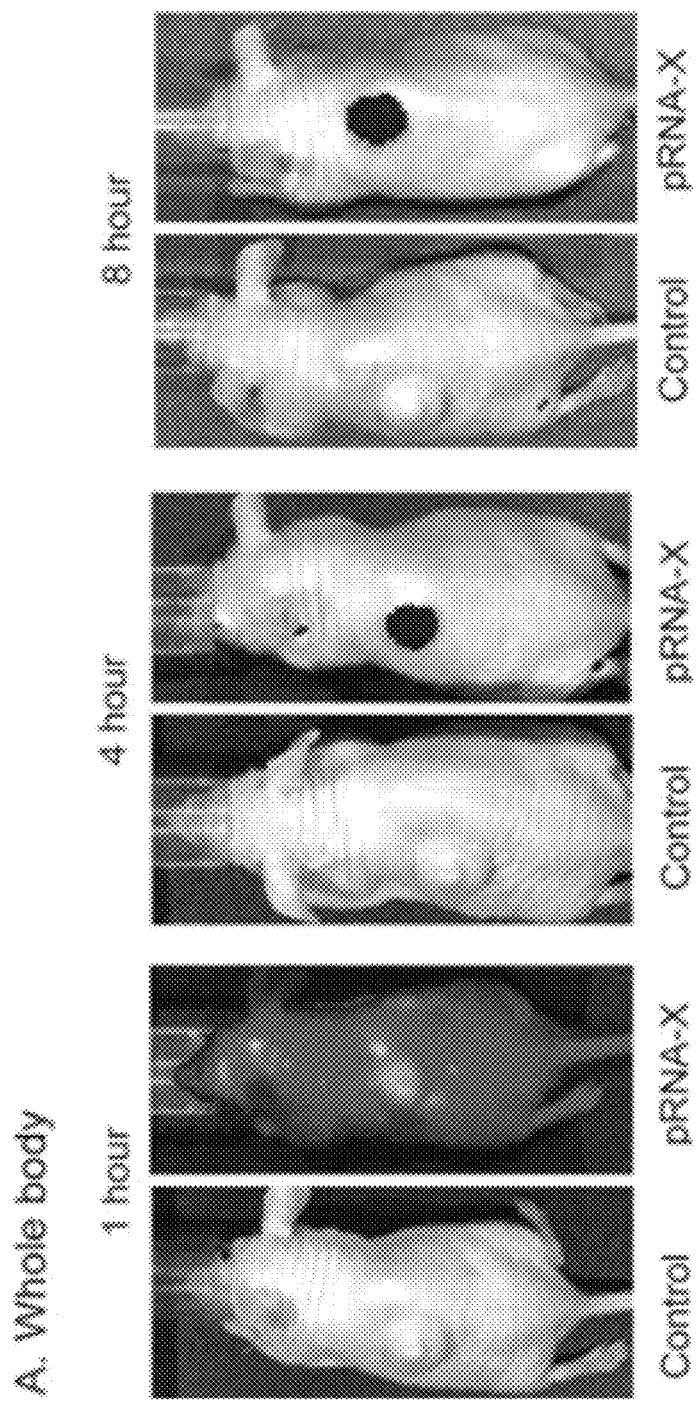
FIGS. 11A-11B includes (A-B) Upon systemic injection, pRNA-3WJ nanoparticles were located specifically at the cancer xenografts expressing the cancer receptors and were not detected in any vital organs in the body [G9-11].
Figure 11:
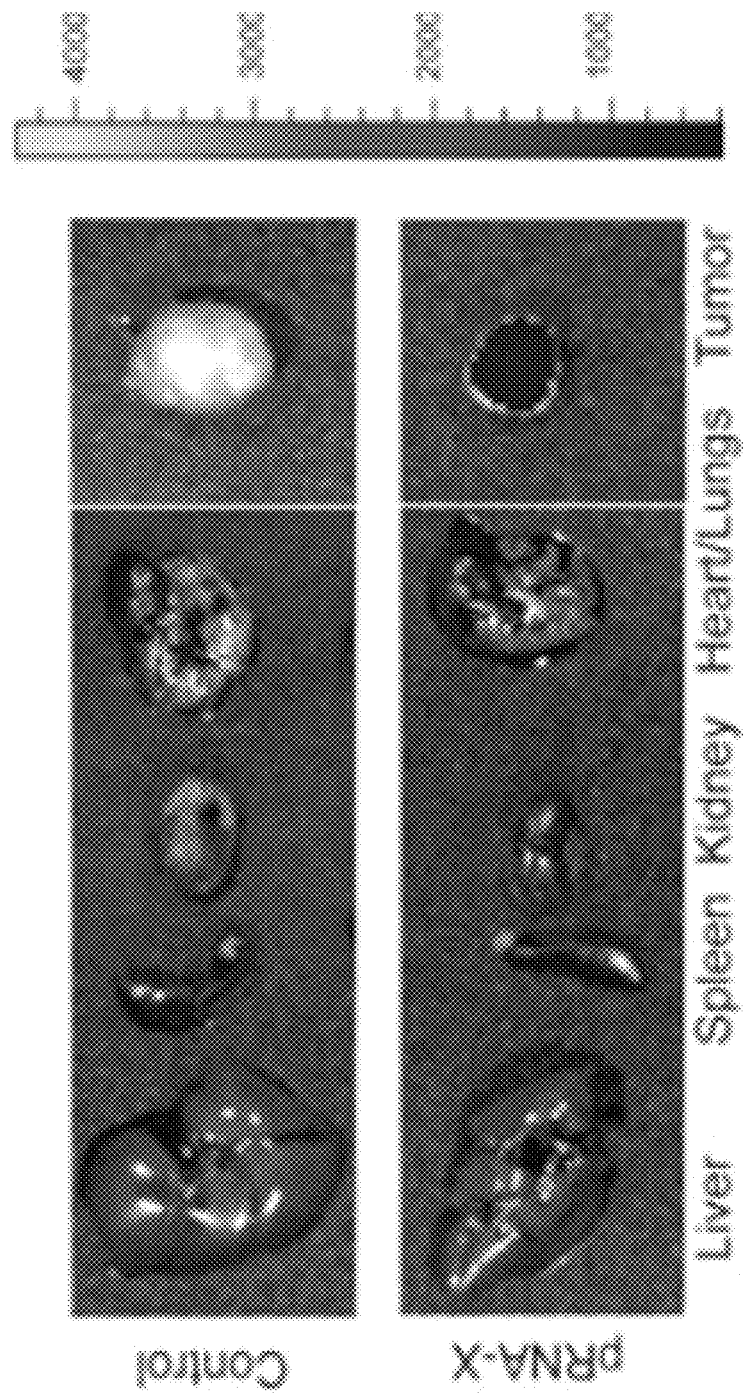
Figure 25A:
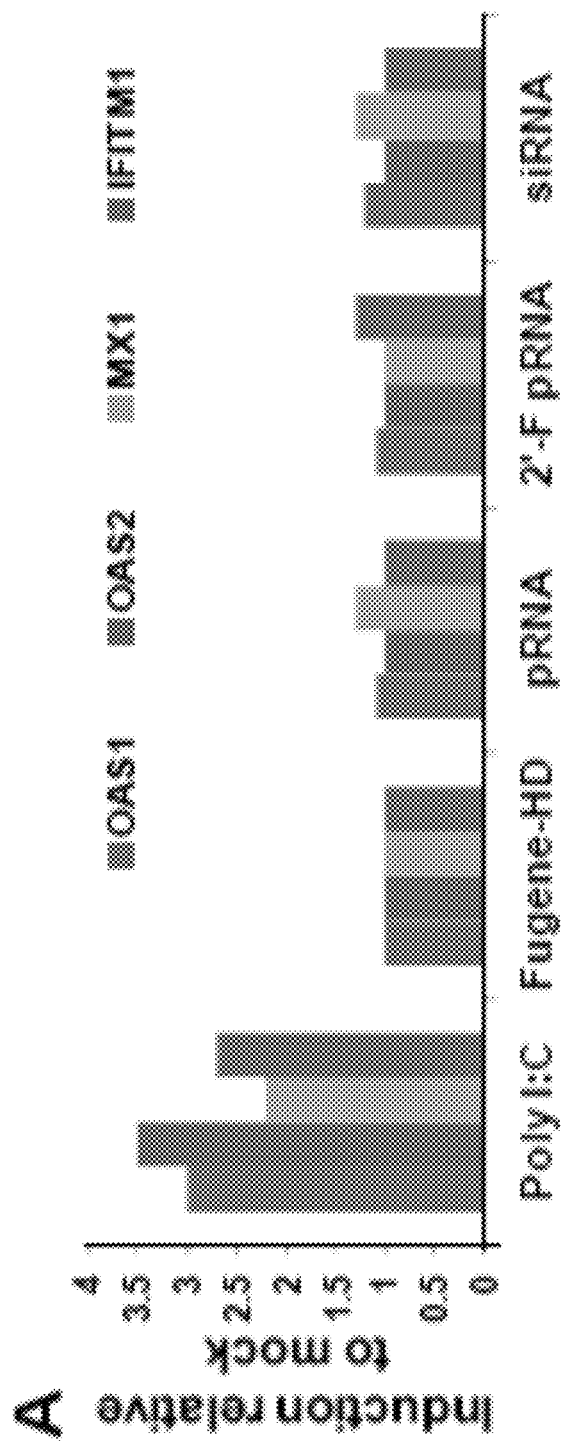
FIGS. 25A-25C shows pRNA nanoparticles did not induce interferon response[12], as assayed by (A) IFN of KB cells; (B) TLR-3, 7 and 9 gene for human blood mononuclear cells; (C) TLR-3 pathway of HEK-Blue-hTLR3 reporter cells.
Figure 25B:
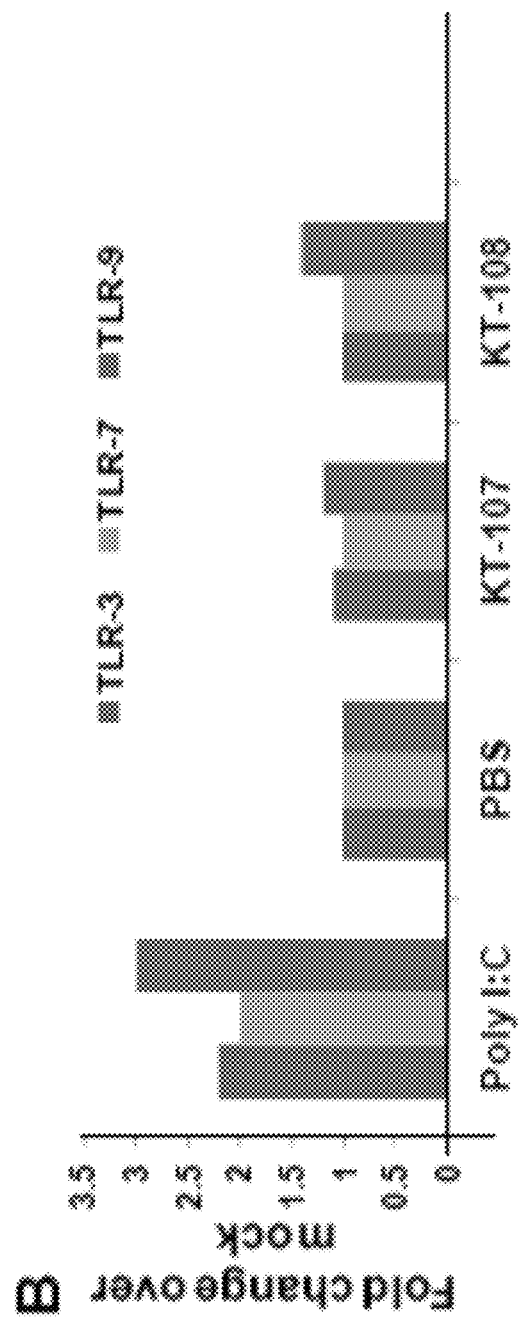
Figure 25C:
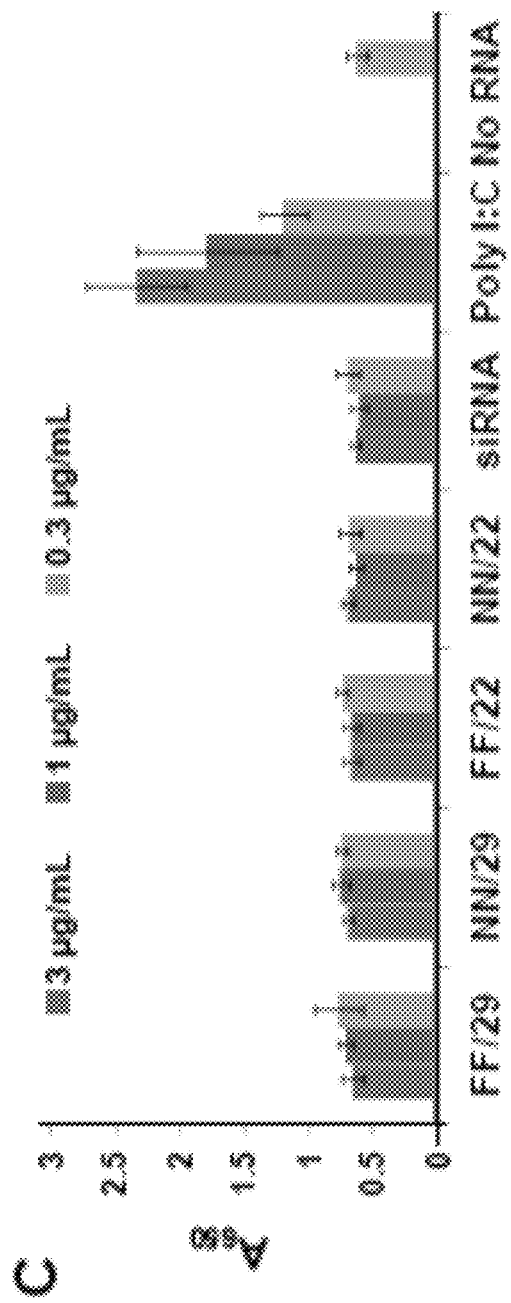

In nature, several RNA molecules form unique multimers with diverse functions. In one embodiment, bacteriophage phi29 pRNA forms dimers and hexamers, via hand-in-hand interactions, between right- and left-interlocking loops [G20,G32,G54,G55] (FIG. 6A-C). Unusual properties of an ultra-stable pRNA 3-way junction (3WJ) motif was recently discovered (FIG. 6E-F) (*Nature Nanotechnology,* 2011; *Nano Today,* 2012) [G9-10]. The 3WJ assembles from three RNA oligos with unusually high affinity in the absence of metal salts; is resistant to denaturation by 8 M urea; displays thermodynamically stable properties; and does not dissociate at ultra-low concentrations (FIG. 7) [G9-12]. Without being bound by theory, a melting curve with a slope close to 900 indicates an extremely low free energy (ΔG) and cooperative assembly of the three component strands (FIG. 8). 2'-Fluoro (2'-F) modification [G9,G13,G56-58] resulted in RNA nanoparticles resistant to RNase degradation, while retaining authentic folding and biological activities [G9, G10,G13] (FIG. 7D). Varieties of RNA nanoparticles were constructed using the pRNA-3WJ as a scaffold and demonstrated that each functional module retained their folding and independent functionalities for specific cell binding and entry, gene silencing, and catalytic function in vitro and in animal trials [G9-12] (FIG. 9-11). The pRNA-3WJ nanoparticles displayed favorable biodistribution and pharmacokinetic profiles, and avoided interferon responses and cytokine production in mice [G12] (FIG. 25). The in vivo half-life of our 2'-F functional RNAs is 6-12 hr, compared to 0.25-0.75 hr of 2'-F bare siRNA [G12,G59,G60]. Recently the crystal structure of the pRNA-3WJ core was obtained [G14], which will facilitate the design of multifunctional RNA nanoparticles.

RNA nanoparticles can be fabricated with a level of simplicity characteristic of DNA, while possessing versatile tertiary structures and catalytic functions that mimic some proteins [G8,G49,G61-66]. RNA nanotechnology refers to the design, fabrication, and application of RNA architectures primarily made up of RNA via bottom-up self-assembly (FIG. 9), in contrast to other widely studied drug delivery systems conjugating functional RNA modules to polymer, lipid, dendrimer, gold, or other nanomaterial based nanoparticles. Properties of the RNA nanoparticles created in the presently disclosed subject matter include: (1) the body treats RNA particles as its own, avoids phagocytosis by macrophages and minimizes accumulation in normal organs; (2) the polyanionic nature of RNA can avoid non-specific cell entry since it is unfavorable for it to cross the negatively charged cell membranes [G67-70]; (3) RNA is a polymer (polynucleic acid). RNA nanoparticles have defined size, structure, and stoichiometry (FIG. 9). Unpredictable side effects from heterogeneous particles can thus be avoided (FIG. 9) [G8-10, G20,G24]; (4) RNA nanoparticles was designed that are 10-60 nm in size and sufficient to harbor siRNAs, ribozymes, miRNAs, and aptamers (FIG. 9). The nanoparticles are large enough to avoid renal excretion (as is the case for bare siRNA), yet small enough to enter cells by receptor-mediated endocytosis [71] and avoid entrapment by liver Kupffer cells and lung macrophages [G3,G8]; (5) the branched ratchet shape of our RNA nanoparticle design (FIG. 9) facilitates tumor penetration and EPR (Enhanced Permeability and Retention) effects [G3, G8]; (6) economic large scale production is possible in a cell-free system; (7) RNA is highly soluble, not prone to aggregation, and do not require linkage to PEG or serum albumins [G8,G24], typically used for a wide range of nanoparticles; (8) the multivalent nature of RNA nanoparticles allows integration of targeting, imaging and therapeutic modules for achieving synergistic effects without using any cross-linking approaches (FIG. 9) [G8,G9] Modular design allows self-assembly of engineered RNA fragments [G8,G24]; (9) It has been demonstrated that 2'-F chemically modified RNA is resistant to RNase degradation while retaining authentic folding and biological functions [G9, G10,G13]; (10) pRNA-3WJ nanoparticles are thermodynamically stable, and therefore will remain intact in vivo at ultra-low concentrations (FIG. 7-8) [G9,G10]; (11) the pRNA-3WJ based nanoparticles has favorable pharmacokinetic and pharmacodynamic profiles in vivo; is non-toxic and does not induce interferon (FIG. 25) or cytokine production in mice [G9,G10,G12]; (12) systemic injection of the stable RNA nanoparticles into mice has revealed that RNA nanoparticles strongly and specifically bind to cancers with little accumulation in vital organs or tissues [G9,G10, G12] (FIG. 11); (13) RNA nanoparticles do not induce host-antibody responses, which will allow for repeated treatment of cancer. This is particularly applicable to patients who develop neutralizing antibodies in response to protein-based reagents; (14) RNA is a chemical reagent. Therefore, the regulatory processes are expected to be more favorable compared to protein-based clinical reagents [G8,G24].

In some embodiments, the presently disclosed subject matter relates to an artificial RNA nanostructure molecule. The molecule includes a RNA junction motif and at least one imaging module. The RNA junction motif includes a plurality of branches, and a branch of the RNA junction motif comprises at least one RNA oligonucleotide. In some embodiments, the plurality of branches includes three branches, four branches, five branches, six branches, seven branches, eight or more branches (US 2014/0179758, herein incorporated by reference by its entirety).

Nonlimiting examples of the imaging module includes fluorescence dyes, radionuclides, and/or contrast agents. Non-limiting examples of fluorescent dye include Alexa dyes, Cy dyes or Near Infrared dyes. Further nonlimiting examples of fluorescent dye include Alexa dye, Cy dyes, Near Infrared (Near IR or NIR) dyes, including but not limited to, IRdye$_{800}$, Alexa$_{647}$, Cy5, Cy5.5, Alexa680, Iowa Black RQ, QSY21, TRDyeQC, BBQ650, BHQ-3, Indocyanine green (ICG). In some embodiments, the imaging module comprises a reporter imaging module. In some embodiments, the imaging module comprises a reference imaging module. In some embodiments, the reference imaging module comprises a reference dye and a quencher. In some embodiments, the RNA molecule further includes at least one cancer targeting module coupled to the RNA junction motif In some embodiments, the molecule further includes at least one therapeutic module coupled to the RNA junction motif. In some embodiments, the imaging module is coupled to at least one branch of the RNA junction motif In some embodiments, the imaging module is coupled to any branch of the RNA junction motif In some embodiments, the imaging module is coupled to the cancer targeting module. In some embodiments, the imaging module is coupled to the therapeutic module. In one embodiment, the plurality of branches comprising the RNA junction motif includes a three-branched RNA junction motif. In one embodiment, the plurality of branches comprising the RNA junction motif comprises a four-branched RNA junction motif.

Also, as used herein, the term "couple," as used herein, refers to the joining of two molecules together. Non-limiting examples include a covalent attachment between an RNA nanoparticle a ligand moieties such as folate, or of labeling moieties, or of therapeutic agents, or by incorporation of nuclease-resistant nucleotides (WO/2002/016596; U.S. Pat. No. 7,655,787; WO/2005/003293; WO/2007/016507, which are expressly incorporated by reference herein.)

NIR dyes or fluorophores are particularly attractive since they can penetrate deep into tissues and more importantly, auto-fluorescence from tissues is greatly reduced. without being bound by theory, a robust RNA nanotechnology will be developed utilizing the pRNA-3WJ motif for monitoring the in vivo delivery of therapeutics non-invasively by NIRF and PET/SPECT imaging. In some embodiments, the RNA nanostructure molecule is used for in vivo imaging, In some embodiment of the presently disclosed subject matter, the RNA nanostructure includes a radionuclide. In some embodiments, the term "radionuclide" includes radiolabel peptides and proteins with various isotopes. Nonlimiting examples of the radioisotopes includes $^{17}$Lu, $^{111}$In, $^{64}$Cu, $^{99m}$Tc, $^{203}$Pb, $^{188}$Re, $^{212}$Pb/$^{212}$Bi. In some embodiments, the radionuclide is coupled to more than one branch of the RNA junction motif. In some embodiment, the radionuclide is chelated by a chelating agent. In some embodiments, the chelating agent is conjugated to at least one branch of the RNA junction motif. Nonlimiting examples of the chelating agent is EDTA, DOTA, NOTA.

In some embodiments, the RNA molecule includes a contrast agent. The term "contrast agent," as used herein, refers to a compound employed to improve the visibility of internal body structures in an image, including but not limited to, an X-ray image or a scanning image (e.g., CAT (Computerized Axial Tomography) scan, MRI (Magnetic Resonance Imaging) scan). The term contrast agent is also referred to herein as a radiocontrast agent. Contrast agents are employed in various diagnostic (e.g., cardiac catheterization) and therapeutic (e.g., vascular shunt placement) procedures. Magnetic resonance imaging (MRI) is a powerful noninvasive technique that provides high quality three dimensional images of tissues, including information on anatomy, function, and metabolism of tissue in vivo. Gadolinium is a common $T_1$-weighted MRI contrast agent. In some embodiments, the contract agent is a MRI contrast agent. In some embodiments, the MRI contract agent is gastrointestinal MRI, intravenous MRI, intravascular (blood pool) MRI tumor-specific MRI, hepatobiliary MRI and reticuloendothelial MRI. One non-limiting example of the MRI contrast agent is a gadolinium contrast agent.

Biological macromolecules, as natural building blocks, are critical for the functioning of living organisms. RNA is one of the five most important biological macromolecules in addition to DNA, proteins, lipids and carbohydrates. With some aspects similar to DNA, RNA, composed of four nucleotides including adenosine (A), cytosine (C), guanosine (G) and uridine (U), is special in its homogeneity. RNA is a homopolymer of nucleotide, but is also a heteropolymer of A, U, G, and C. Each nucleotide contains a ribose sugar, a nucleobase, and a phosphate group. The nucleotides are covalently linked together through 3'→5' phosphodiester bonds between adjacent ribose units, giving the directionality to the sugar-phosphate backbone that defines RNA as a polynucleic acid. The phosphate moieties in the backbone are negatively charged, making RNA a polyanionic macromolecule at physiological pH. RNA molecules are typically single-stranded; however, Watson-Crick (canonical) base-pair interactions (A:U and G:C), wobble base pairing (such as G:U) [G. Varani, W. H. McClain, *EMBO Rep.*, 1 (2000), pp. 18-23] or other non-canonical base pairing such as twelve basic geometric families of edge-to-edge interaction (Watson-Crick, Hoogsteen/CH or sugar edge) with the orientation of glycosidic bonds relative to the hydrogen bonds (cis or trans) [U. Nagaswamy, et., al., *Nucleic Acids Res.,* 30 (2002), pp. 395-397], all together give rise to various structural conformations exhibiting loops, hairpins, bulges, stems, pseudoknots, junctions, etc., which are essential elements to guide and drive RNA molecules to assemble into desired structures [Y. Xin, et al., *RNA,* 14 (2008), pp. 2465-2477; Y. Xin, et al., *RNA,* 14 (2008), pp. 2465-2477; C. Laing, et al., *PLoS ONE,* 8 (2013), p. e71947; and C. Laing, et al., *Nucleic Acids Res.,* 40 (2012), pp. 487-498].

The characteristic of RNA that defines and differentiates it from DNA is the 2'-hydroxyl on each ribose sugar of the backbone. The 2'-OH group offers RNA a special property, which can be either an advantage or a disadvantage. From a structural point of view, the advantage of this additional hydroxyl group is that it locks the ribose sugar into a 3'-endo chair conformation. As a result, it is structurally favorable for the RNA double helix to adopt the A-form which is ~20% shorter and wider rather than the B-form that is typically present in the DNA double helix. Moreover, the 2'-OH group in RNA is chemically active and is able to initiate a nucleophilic attack on the adjacent 3' phosphodiester bond in an SN2 reaction. This cleaves the RNA sugar-phosphate backbone and this chemical mechanism underlies the basis of catalytic self-cleavage observed in ribozymes. The disadvantage is that the 2'-OH group makes the RNA susceptible to nuclease digestion since many RNases recognize the structure of RNAs including the 2'-OH group as specific binding sites. However, such enzymatic instability has been overcome by applying chemical modification of the 2'-OH group. For example, the substitution of the 2' hydroxyl group with a Fluorine (2'-F), O-methyl (2'-O-Me) or Amine (2'-N12) dramatically increases the stability of RNA in vivo by preventing degradation by RNases [48] [49 and [51]. Recent studies also showed that the stability of siRNA in serum is also highly depended on the specific RNA sequences and the degradation of both short and long RNA duplexes mostly occurred at UA/UA or CA/UG sites [G112] [Hui Li et al., Nanotoday, volume 10, Issue 5, October 2015, pp 631-655, herein incorporated by reference in its entirety].

In some embodiments, the nanostructure comprises at least one chemical modification at a 2' position of the RNA oligonucleotide. In some embodiments, the chemical modification comprises 2'Fluoro, 2'Amine, and 2'O-Methyl.

In some embodiments of the presently disclosed subject matter, a branch of the three-branched RNA junction motif is an a3WJ RNA module (SEQ ID NO: 1), a b3WJ RNA module (SEQ ID NO: 2), or a c3WJ RNA module (SEQ ID NO: 3). In one embodiment, the three-branched RNA junction motif comprises an a3WJ RNA module (SEQ ID NO: 1), a b3WJ RNA module (SEQ ID NO: 2), and a c3WJ RNA module (SEQ ID NO: 3). In some embodiments, SEQ ID NO: 1 has at least 90% identity to nucleotide sequence 5'-UUG CCA UGU GUA UGU GGG-3'. In one embodiment, SEQ ID NO: 1 comprises nucleotide sequence 5'-UUG CCA UGU GUA UGU GGG-3'. In some embodiments, SEQ ID NO: 2 has at least 90% identity to nucleotide sequence 5'-CCC ACA UAC UUU GUU GAUCC-3'. In one embodiment, SEQ ID NO: 2 comprises nucleotide sequence 5'-CCC ACA UAC UUU GUU GAUCC-3'. In some embodiments, SEQ ID NO: 3 has at least 90% identity to nucleotide sequence 5'-GGA UCA AUC AUG GCA A-3'. In one embodiment, SEQ ID NO: 3 comprises nucleotide sequence 5'-GGA UCA AUC AUG GCA A-3'. In some embodiments, the imaging module attaches to any one of the a, b, and c module disclosed above. In some embodiments, the targeting module attached to any one of the a, b, and c module disclosed above. In some embodiments, the therapeutic module any one of the a, b, and c module disclosed above.

In some embodiments of the presently disclosed subject matter, the RNA nanostructure includes a cancer targeting module. In some embodiments, the presently disclosed subject matter provides that the targeting module in the artificial RNA nanostructure molecule includes a ligand that binds to at least one cancer cell surface marker. In some embodiments, the cancer targeting module is a colon cancer targeting module.

As used herein, cell surface markers include any cellular component that may be detected within or on the surface of a cell, or a macromolecule bound or aggregated to the surface of the cell. As such, cell surface markers are not limited to markers physically on the surface of a cell. For example, cell surface markers may include, but are not limited to, surface antigens, transmembrane receptors or coreceptors, macromolecules bound to the surface, such as bound or aggregated proteins or carbohydrates, internal cellular components, and the like. Non-limiting examples of the surface marker includes folate receptor, epithelial cell adhesion molecule (EpCAM), EGFR, transferrin receptor, and an RGD. In some embodiments, the ligand includes an aptamer. In some embodiments, the aptamers binds against EpCAM, EGFR (EGFR protein [*Homo sapiens*] GenBank: AAI18666.1), PDGFR (platelet-derived growth factor receptor beta precursor [*Homo sapiens*] NCBI Reference Sequence: NP_002600.1), or folate receptor (folate receptor [*Homo sapiens*] GenBank: AAB05827.1). In some embodiments, the targeting module is a folate.

The term "folate" as used herein can comprise a genus of well-defined B-vitamin compounds, including but not limited to, 5-methyltetrahydro folate, 5-formyltetrahydrofolate, dihydrofolate, tetrahydrofolate, folic acid and other folate compounds. As disclosed herein, the targeted delivery systems call for a ligand-receptor pair that is specifically found in cancer cells. Many cancer cells, including but not limited to, stomach, ovary, lung, breast, kidney, endometrium, colon and hematopoietic cells, over-expressed folate receptors (FRs) than normal cells for high uptake of folate, since folate is essential component during DNA replication and methylation in highly proliferating cells. Folic acid (FA), a synthetic oxidized form of folate, has been widely used as a ligand conjugate in various cancer targeting materials.

In some embodiments, the therapeutic module comprises a siRNA, a miRNA, an anti-mRNA, a ribozyme RNA, or an antisense RNA. In some embodiments, In some embodiments, the therapeutic module comprises a chemotherapeutic drug, a riboswitch, or an endosome disrupting agent. In some embodiments, the therapeutic module is a siRNA sequence. Non-limiting examples of the siRNA are siRNA is directed to Survivin, Bcl-2, XIAP, BCL-XL, or BRCAA1. In some embodiments, the siRNA directly binds to PI3K, Akt, or mTOR. In some embodiments, the therapeutic module is a microRNA sequence.

The terms "small interfering RNA", "short interfering RNA", "small hairpin RNA", "siRNA", and shRNA are used interchangeably and refer to any nucleic acid molecule capable of mediating RNA interference (RNAi) or gene silencing. See e.g., Bass, Nature 411:428-429, 2001; Elbashir et al., Nature 411:494-498, 2001a; and PCT International Publication Nos. WO 00/44895, WO 01/36646, WO 99/32619, WO 00/01846, WO 01/29058, WO 99/07409, and WO 00/44914. In one embodiment, the siRNA comprises a double stranded polynucleotide molecule comprising complementary sense and antisense regions, wherein the antisense region comprises a sequence complementary to a region of a target nucleic acid molecule (for example, a nucleic acid molecule encoding Survivin). In another embodiment, the siRNA comprises a single stranded polynucleotide having self-complementary sense and antisense regions, wherein the antisense region comprises a sequence complementary to a region of a target nucleic acid molecule. In another embodiment, the siRNA comprises a single stranded polynucleotide having one or more loop structures and a stem comprising self-complementary sense and antisense regions, wherein the antisense region comprises a sequence complementary to a region of a target nucleic acid molecule, and wherein the polynucleotide can be processed either in vivo or in vitro to generate an active siRNA capable of mediating RNAi. As used herein, siRNA molecules need not be limited to those molecules containing only RNA, but further encompass chemically modified nucleotides and non-nucleotides.

In some embodiments, the presently disclosed subject matter takes advantage of the ability of short, double stranded RNA molecules to cause the down regulation of cellular genes, a process referred to as RNA interference. As used herein, "RNA interference" (RNAi) refers to a process of sequence-specific post-transcriptional gene silencing mediated by a small interfering RNA (siRNA). See Fire et al., Nature 391:806-811, 1998 and U.S. Pat. No. 6,506,559, each of which is incorporated by reference herein in its entirety. The process of post-transcriptional gene silencing is thought to be an evolutionarily conserved cellular defense mechanism that has evolved to prevent the expression of foreign genes (Fire, Trends Genet 15:358-363, 1999).

Disclosed herein are non-limiting examples of siRNA including Survivin-specific, Bcl-2, XIAP, and BCL-XL siRNA sequences. The Survivin-specific siRNA includes sense sequence: 5' GGACCACCGCAUCUCUACAdTdT 3' (SEQ ID NO: 21) and antisense sequence: 5' dTdTCCUG-GUGGCGUAGAGAUGU 3' (SEQ ID NO: 22) (See, e.g., *Cancer Gene Ther.* 2004 March; 11(3):186-93. Knockdown of survivin expression by small interfering RNA reduces the clonogenic survival of human sarcoma cell lines independently of p53.); the Bcl-2 siRNA includes sense sequence: 5'-AAGCUGuCACAGAGGGGCUAC-3' (SEQ ID NO: 23), and antisense sequence: 5'-GUAGCCCCUCU-GUGACAGCUU-3 (SEQ ID NO: 24) (See, e.g., *Nucleic Acids Res.* 2012 July; 40(13):6319-37. doi: 10.1093/nar/gks294. Epub 2012 Mar. 30. Delivery of chemo-sensitizing siRNAs to HER2+-breast cancer cells using RNA aptamers.); XIAP siRNA includes sense sequence: 5'-CCAU-GUGCUAUACAGUCAUUACUUU-3 (SEQ ID NO: 25), and antisense sequence: 5'-AAAGUAAUGACU-GUAUAGCACAUGG-3 (SEQ ID NO: 26) (See, e.g., *Mol Cancer.* 2006 Sep. 5; 5:34. Specific down-regulation of XIAP with RNA interference enhances the sensitivity of canine tumor cell-lines to TRAIL and doxorubicin); and BCL-XL siRNA includes sense sequence: 5'-UUGGACAAUGGACUGGUUGA-3 (SEQ ID NO: 27), antisense sequence: 5'-UCAACCAGUCCAUUGUCCAA-3 (SEQ ID NO: 28) (See, e.g., *Acta Biochim Biophys Sin* (Shanghai). 2005 August; 37(8):555-60. Silencing of Bcl-XL expression in human MGC-803 gastric cancer cells by siRNA.) Further, in one embodiment, siRNA is a BRCAA1 siRNA. A non-limiting example is a siRNA sequence 5'-CCACAUAAAGGGCCCACUA-3' (SEQ ID NO: 29). Another non-limiting example is a siRNA sequence 5'-UAGUGGGCCCUUUAUGUGG-3' (SEQ ID NO: 30).

In some embodiments, the bioactive agent is a microRNA sequence. The term "MicroRNAs (miRNAs)" as used herein are single-stranded, or double stranded non-coding RNAs, at least about 6 nucleotide in length that can regulate gene expression at the post-transcriptional level by either degrading their target mRNAs or inhibiting their translation(1,2). MiRNAs play important roles in regulating cell cycle, proliferation, differentiation, metabolism, and apoptosis(1). A compendium of microRNA and respective microRNA binding sequences is available at the miRNA registry. (See, e.g., Griffiths-Jones et al. (2006) Nucl. Acids Res. 34:D140-D144; US20140045709, herein incorporate by reference in their entireties.) In particular embodiments, the microRNA and microRNA binding sequence employed in the present assay are associated with a disease or condition, wherein an antagonist or agonist to the microRNA would be useful in preventing or treating the disease or condition.

In some embodiments, the present disclosure provides inhibitors of miRNAs (e.g., anti-miR-21). Compositions comprising such inhibitors and methods for inhibiting miR-21 using such inhibitors are also disclosed herein. Any miRNA inhibitor may be used alone, or with other miRNA inhibitor(s) known in the art. In some embodiments, the miRNA inhibitor comprises an antisense molecule. In some embodiments, the antisense molecule could be a single or a double stranded sequence. Examples of antisense molecule include, but are not limited to, siRNAs, triple-helix-forming agents, ribozymes, RNAi, synthetic peptide nucleic acids (PNAs), antigens (agRNAs), LNA/DNA copolymers, small molecule chemical compounds, and antisense oligonucleotides.

In some embodiments, the microRNA sequence is at least 6 nucleotide in length. In some embodiments, the miRNA molecule or an equivalent, or a mimic thereof is from about 6 to about 30 nucleotides in length. In some embodiments, the miRNA is about 12 to about 30 nucleotides in length. In some embodiments, the miRNA is from about 15 to about 28 nucleotides in length. In some embodiments, the miRNA is about 19 to about 25 nucleotides in length. In some embodiments, the miRNA molecule has a length of at least about 6, 7, 8, 9, 10, 11, 12, 13, 14, 15, 16, 17, 18, 19, 20, 21, 22, 23, 24, 25, 26, 27, 28, 29, about 30 nucleotides or more. In some embodiments, an antagomir of a miRNA molecule is from about 6 to about 30 nucleotides in length, from about 10 to about 30 nucleotides in length, from about 12 to about 28 nucleotides in length. In some embodiments, the antagomir of a miRNA molecule has a length of at least about 6, 7, 8, 9, 10, 11, 12, 13, 14, 15, 16, 17, 18, 19, 20, 21, 22, 23, 24, 25, 26, 27, 28, 29, about 30 nucleotides or more.

In some embodiments, the miRNA interferes oncogenic miRNA to regress cancer growth. The RNA nanostructure molecule contains anti-miRNA that silences oncogenic miR-NAs, including but not limited to, miR-9, miR-10b, miR-21, miR-17, and miR-26. In some embodiments, the miRNA rescues down-regulated cancer suppressive miRNAs, where the RNA nanostructure introduces cancer suppressive miR-NAs, including but not limited to, let-7a, miR-10b, miR-25, miR-34a, miR-124, miR-145, and miR-181b. Further examples is disclosed in US20140045709, which herein incorporate by reference in its entirety.

In some embodiments, the therapeutic module is a cytotoxic drug. The terms "cytotoxic drug" used herein refers to agents that have the property of inhibiting the growth or proliferation (e.g., a cytostatic agent), or inducing the killing, of hyper proliferative cells. Non-limiting examples include doxorubicin, paclitaxel, paclitaxel derivatives and analogues, cytochalasin D, rapamycin, rapamycin derivatives and analogues, camptothecin, dexamethasone, and 5-fluorouracil, a quinazolinone derivative, metallic silver, tranilast, everolimus and related compounds, or other agents that inhibit cell proliferation and or migration and/or inflammatory processes.

In another aspect, the presently disclosed subject matter provides an artificial RNA nanostructure molecule includes a RNA junction motif comprising a plurality of branches and a radiation-based therapeutic module coupled to the RNA junction motif, and a branch of the RNA junction motif includes at least one RNA oligonucleotide. In some embodiments, the molecule further includes a cancer targeting module coupled to the RNA junction motif In some embodiments, the molecule further includes an imaging module coupled to the RNA junction motif. In some embodiments, the nanostructure comprises at least one chemical modification at 2' position of the RNA oligonucleotide. In some embodiments, the chemical modification comprises 2'Fluoro, 2'Amine, and 2'O-Methyl. In some embodiments, the plurality of branches comprises three branches, four branches, five branches, six branches, seven branches, eight or more branches. In some embodiments, the plurality of branches comprising the RNA junction motif includes a three-branched RNA junction motif. In some embodiments, the plurality of branches comprising the RNA junction motif comprises a four-branched RNA junction motif. In some embodiments, a branch of the three-branched RNA junction motif includes an a3WJ RNA module (SEQ ID NO: 1), a b3WJ RNA module (SEQ ID NO: 2), or a c3WJ RNA module (SEQ ID NO: 3). In some embodiments, the three-branched RNA junction motif comprises an a3WJ RNA module (SEQ ID NO: 1), a b3WJ RNA module (SEQ ID NO: 2), and a c3WJ RNA module (SEQ ID NO: 3). In some embodiments, SEQ ID NO: 1 has at least 90% identity to nucleotide sequence 5'-UUG CCA UGU GUA UGU GGG-3'. In some embodiments, SEQ ID NO: 1 comprises nucleotide sequence 5'-UUG CCA UGU GUA UGU GGG-3'. In some embodiments, SEQ ID NO: 2 has at least 90% identity to nucleotide sequence 5'-CCC ACA UAC UUU GUU GAUCC-3'. In some embodiments, SEQ ID NO: 2 comprises nucleotide sequence 5'-CCC ACA UAC UUU GUU GAUCC-3'. In some embodiments, SEQ ID NO: 3 has at least 90% identity to nucleotide sequence 5'-GGA UCA AUC AUG GCA A-3'. In some embodiments, SEQ ID NO: 3 comprises nucleotide sequence 5'-GGA UCA AUC AUG GCA A-3'. In some embodiments, the cancer-targeting module is a cancer cell-specific ligand. In some embodiments, the cancer-targeting module is folate. In some embodiments, cancer-targeting module is an RNA aptamer. In some embodiments, the radiation-based therapeutic module include a isotope. Nonlimiting examples of the isotope include 177Lu, 111In, 64Cu, 99mTc, 203Pb, 188Re, 212Pb, 212Bi, I-125, or Cs-131. In some embodiments, the RNA nanoparticles derived from the pRNA 3WJ are substantially stable under irradiation with clinically relevant doses ranging from about 1 Gy, 5 Gy, 10 Gy, 15 Gy, 20 Gy, 25 Gy, 30 Gy, 35 Gy, 40 Gy, 45 Gy, 50 Gy, 55 Gy, 60 Gy, 65 Gy, 70 Gy, 75 Gy, 80 Gy, 85 Gy, to about 90 Gy.

Cancer is a broad class of diseases featuring uncontrollable cell growth, invasion, and destruction of nearby tissues and metastasis. An effective, efficient, and safe treatment for cancer is urgently needed. Radiation therapy represents a major modality for anticancer therapy, which utilizes ionizing radiation produced by linear accelerators (external beam therapy) or radioactive isotopes (brachytherapy and nuclear medicine) to kill cancer cells, inhibit tumor growth, and prevent recurrence of the tumor [5]. However, radiation not only kills cancer cells, but also damages healthy cells. The side effects associated with current radiation therapy significantly limit the doses delivered to the patients [6, 7]. The goal of radiation therapy is to deliver a high dose of radiation to the target to kill cancer cells while sparing the surrounding healthy tissues. But, this is not easy to achieve using current techniques. Medical imaging including CT and MRI is used to accurately identify and locate or track tumor before, during and even after treatment. Since such imaging can only recognize balky lesions, it is very difficult to find and locate all the cancer cells especially microscopic disease. In addition to that, it is also very difficult to avoid normal tissue damages during dose delivery. External beam therapy uses ionization particles that may have to pass through the normal tissue before reaching the target. Brachytherapy handles radiation sources mechanically and has significant uncertainty in localizing the radioactive sources. Although certain ionizing radiopharmaceuticals, such as I-131 and Y-90 used in nuclear medicine, can target certain organs and tumors, variation in biodistribution caused by metabolism and excretion of the pharmaceuticals and localization errors produce uncertainties and limitations in targeting tumor and dosimetry, and thus increase damages to normal tissues [8].

The RNA nanoparticle-based nano-carrier platform can overcome aforementioned limitations for conventional radiation therapy and diagnosis and opens new opportunities for specific delivering radiation to cancer without damaging healthy organs and tissues, reducing the toxicity and side effect, improving the therapeutic effect, and exhibiting great potential in clinical cancer therapy and diagnosis.

Recently, nanoparticles have been found to be able to accurately target cancer cells and thus, can be used for cancer targeting and treatment [9-14]. Nanoparticles are typically within several hundred nanometers in size, and comparable to large biological molecules such as enzymes, receptors, and antibodies. Because of small size, nanoparticles can interact with biomolecules both on the surface of and inside the cells, participate in molecular, biochemical, and biological processes, and thus, can be used as agents for medical imaging and targeted cancer treatment [15]. The most common well-studied nanoparticles include quantum dots, carbon nanotubes, paramagnetic nanoparticles, liposomes, gold nanoparticles, and many others. However, there are concerns regarding the biocompatibility of these nanoparticles especially when they are exposed to radiation and their ability to escape the reticuloendothelial system, which could lead to short- and long-term toxicity [16, 17].

A new discovery in nanotechnology has led to the development of novel RNA nanoparticles that are mainly composed of RNA that are capable of strongly binding to tumors without accumulation in other vital organs or tissues [18-20]. Since the first proof-of-concept in 1998 [21], RNA nanotechnology has emerged as a popular and rapidly-growing field that is at the interface of nanotechnology, molecular biology, medicine, and biomedical engineering [13, 20, 22-26]. RNA nanotechnology holds significant translational potential in medicine and features that could make RNA nanoparticles desired pharmaceutical agents and radioisotope carriers. First of all, RNA nanoparticles can be produced with a known stoichiometry with a high reproducibility [21, 26, 27]. The simplicity of RNA, being composed of only four nucleic acid bases, allows for predictable and addressable formation of various nanostructures harboring different functional groups by bottom-up self-assembly. Secondly, RNA nanoparticles can target specific cell groups by targeting cell surface receptors through the use of RNA aptamers that function like protein or chemical ligands [18, 28, 29]. These structures do not induce antibody production, allowing for repeated delivery and therapy [28]. Thirdly, RNA nanoparticles that have been produced have a size range of 10-50 nm, which is the perfect size not only to be retained within the body by avoiding rapid renal excretion, but also to pass through leaky blood vessels in cancer tumors, as well as cell membranes, by cell surface receptor-mediated endocytosis [18-20].

To have clinical applications, RNA nanoparticles and those properties must remain stable and unchanged under the clinical conditions. The bacteriophage phi29 packaging RNA (pRNA) represents an attractive platform for bottom-up assembly of RNA nanoparticles [18-20, which are incorporated by reference by their entirety]. The molecular structure of pRNA contains a helix domain, a central domain containing right and left-hand loops, and a three-way junction (3WJ) core [30]. A recent study has indicated that the pRNA 3WJ has thermodynamical stability, and RNA nanoparticles constructed based on the pRNA 3WJ core are also thermodynamically and chemically stable [27]. In addition, a receptor-binding ligand, an aptamer, a short interfering RNA and a ribozyme can be incorporated in the pRNA 3WJ nanoparticle and retain their correct folding and function. The pRNA nanoparticles also display a favorable pharmacokinetics profile for in vivo target delivery (half-life of 5-10 hr compared to 0.25-0.75 hr of 2'F siRNA counterparts) [28, which is incorporated by reference in its entirety]. To be used as radioisotope carriers, the stability of RNA nanoparticles will be further tested under irradiation with clinically relevant doses.

In some embodiments, the molecule is substantially stable under radiation treatment. As used herein, the term "substantially stable" can refer to physical and/or chemical stability. As will be recognized by those of ordinary skill in the art, the term "substantially stable" can refer to stability of the composition under certain conditions, relative to an initial composition (i.e., when a particular batch of the composition is initially prepared). In this regard, as will be recognized by those of ordinary skill in the art, one manner in which stability of a particular embodiment of the composition can be determined is as follows: preparing a batch of the embodiment of the composition, making an initial assessment of a sample of the composition (control sample), subjecting a sample of the composition to conditions of interest (e.g., storage at a particular temperature for a particular time period) (test sample), making an assessment of the test sample, and comparing the assessment of the control sample to the assessment of the test sample. Calculations can be made to determine whether the amounts present in the test sample are 100%±20, 19, 18, 17, 16, 15, 14, 13, 12, 11, 10, 9, 8, 7, 6, 5, 4, 3, 2, 1, 0.5, or 0.1% of the amount that is in the control sample.

In one embodiment, the present disclosure proposes to use the 3WJ RNA nanoparticles to carry radioisotope. In one embodiment, the present disclosure proposes to use a four-way junction (4WJ) RNA nanoparticles to carry radioisotope. Non limiting examples of the radioisotope are I-125 or Cs-131. Using such RNA nanoparticles, cancer cells can be targeted and treated by I-125 or Cs-131 [31]. In nuclear medicine, several radioactive isotopes, such as I-131, P-32, and Y-90, have been used for targeted radionuclide therapy, but those isotopes are only applied to very limited types of cancer [32-36]. Also, most of isotopes used for nuclear medicine therapy are beta emitters and not suitable for imaging. Accurate dose estimation is almost impossible without accurate imaging. On the other hand, I-125 and Cs-131 have been widely used in permanent implant brachytherapy and successfully treated various types of cancer. The idea of using I-125 or Cs-131 with 3WJ RNA nanoparticles is to increase the accuracy of tumor targeting and enhance the effectiveness in treating a broad range of tumors and sparing normal tissues. Also, both I-125 and Cs-131 emit photons that will help with in vivo nuclear imaging and studying the biodistribution of those isotopes for estimation of patient-specific dose. The stabilities of the pRNA 3WJ nanoparticles that are essential for in vivo cancer targeting and treatment are investigated in this study.

This study further investigates whether chemically modified RNA nanoparticles derived from pRNA Three-Way Junction (3WJ) of phi29 DNA-packaging motor are resistant to potent I-125 and Cs-131 radiation, which is a required perquisite for utilizing these RNA nanoparticles as carriers for targeted radiation therapy. pRNA 3WJ nanoparticles were constructed and characterized and the stability of these nanoparticles under I-125 and Cs-131 irradiation with clinically relevant doses was examined. RNA nanoparticles derived from the pRNA 3WJ targeted tumors specifically and they were stable under irradiation of I-125 and Cs-131 with clinically relevant doses ranging from about 1 Gy to about 90 Gy over a significantly long time up to 20 days, while control plasmid DNA was damaged at 20 Gy or higher.

The RNA nanoparticle-based nano-carrier platform for radiation therapy and diagnosis is expected to outperform current radiation systems or other strategies in several aspects: (1) RNA nanoparticles have defined size, structure and stoichiometry; unpredictable side effects arising from heterogeneous particles can thus be avoided; (2) nanoscale size of the RNA nanoparticles will facilitate tissue penetration and target to tumor; (3) RNA nanoparticles are easy to construct by self-assembly, highly soluble and not prone to aggregation; (4) the RNA nanoparticles are thermodynamically stable and, therefore, the entire construct will remain intact at ultra-low concentrations in the body; (5) the polyvalent nature of the RNA nanoparticle allows for easy integration of targeting modules, imaging modules and therapeutic modules into a single form; (6) RNA nanoparticles display low or no immunogenicity and/or toxicity even at high doses. The 3WJ-pRNA scaffold displays favorable pharmacokinetic and pharmacodynamic profiles in vivo (half-life of 5-10 hours compared to 0.25-0.75 hours of the most stable 2'F modified siRNA counterparts); non-toxic; and no induction of interferon or cytokines; (7) systemic injection of the thermodynamically and chemically stable RNA nanoparticles into the tail-vein of mice revealed that the RNA nanoparticles remain intact. They strongly and specifically bind to cancers without entering liver, lung, or any other vital organs or tissues. This is particularly an advantage for targeting solid tumors previously inaccessible due to penetration problems through the vasculature and dispersion against an interstitial pressure; (8) RNA nanoparticles derived from the pRNA 3WJ are stable under irradiation of 1-125 and Cs-131 with clinically relevant doses ranging from 1 Gy to 90 Gy over a significantly long time up to 20 days.

Further, in another aspect of the present subject matter, a RNA dendrimer molecule is provided. The molecule includes (a) a central core multi-branched RNA junction motif, wherein the central core motif comprises a plurality of branches, and wherein a branch comprises at least one RNA oligonucleotide; and (b) an outer surface multi-branched RNA junction motif comprising at least one repeating multi-branched RNA junction motif unit, wherein the repeating unit comprises a plurality of branches, and wherein a branch comprises at least one RNA oligonucleotide. In some embodiments, the dendrimer further includes at least one imaging module. In some embodiments, the dendrimer includes at least one targeting module. In some embodiments, the dendrimer further includes at least one therapeutic module. In some embodiments, the plurality of branches includes the central core multi-branched RNA junction motif comprises a three-branched RNA junction motif, a four-branched RNA junction motif, a five-branched RNA junction motif, a six-branched RNA junction motif, a seven-branched RNA junction motif, an eight or more branched RNA junction motif. In some embodiments, the plurality of branches comprising the repeating multi-branched RNA junction motif unit includes a three-branched RNA junction motif, a four-branched RNA junction motif, a five-branched RNA junction motif, a six-branched RNA junction motif, a seven-branched RNA junction motif, an eight or more branched RNA junction motif. In some embodiments, a branch of the three-branched RNA junction motif comprises an a3WJ RNA module (SEQ ID NO: 1); a b3WJ RNA module (SEQ ID NO: 2); or a c3WJ RNA module (SEQ ID NO: 3). In one embodiments, the three-branched RNA junction motif comprises an a3WJ RNA module (SEQ ID NO: 1); a b3WJ RNA module (SEQ ID NO: 2); and a c3WJ RNA module (SEQ ID NO: 3). In some embodiments, SEQ ID NO: 1 has at least 90% identity to nucleotide sequence 5'-UUG CCA UGU GUA UGU GGG-3'. In some embodiments, SEQ ID NO: 2 has at least 90% identity to nucleotide sequence 5'-CCC ACA UAC UUU GUU GAUCC-3'. In some embodiments, SEQ ID NO: 3 has at least 90% identity to nucleotide sequence 5'-GGA UCA AUC AUG GCA A-3'. In some embodiments, the central core multi-branched RNA junction motif is a polygon shaped architecture comprising a three-branched RNA junction motif at each corner. In some embodiments, the imaging module comprises a fluorescent dye, a radionuclide, or a contrast agent. In some embodiments, fluorescent dye is a Alexa dye, Cy dyes or Near IR dyes. Nonlimiting of fluorescent dye include IRdye800, Alexa647, Cy5, Cy5.5, Alexa680, Iowa Black RQ, QSY21, IRDyeQC, BBQ650, BHQ-3, Indocyanine green (ICG). In some embodiments, the imaging module comprises a reporter imaging module. In some embodiments, the imaging module comprises a reference imaging module. In some embodiments, the reference imaging module comprises a reference dye and a quencher. In some embodiments, the imaging module comprises at least one fluorescent dye. In some embodiments, the imaging module include a radionuclide and/or a contrast agent. A nonlimiting example of contrast agent is a MRI contrast agent. In one embodiment, the imaging module includes at least one gadolinium contrast agent. In some embodiments, the targeting module includes a cancer targeting module. In some embodiments, the cancer targeting module is a ligand that binds to at least one cancer cell surface marker. In some embodiments, the RNA dendrimer contains a targeting module comprises a chemical ligand and/or a RNA aptamer. A nonlimiting example of the ligand includes folate. In some embodiments, the cell surface markers comprises a folate receptor. In some embodiments, the ligand binds to an epithelial cell adhesion molecule (EpCAM). In some embodiments, the cell surface marker comprises an epithelial cell adhesion molecule (EpCAM). In some embodiments, the cancer targeting module comprises an aptamer. A non-limiting example of the aptamer is an EpCAM RNA aptamer. In some embodiments, the cancer targeting module is a folate. Nonlimiting examples of the folate include folic acid, 5-methyltetrahydro folate, 5-formyltetrahydrofolate, dihydrofolate, tetrahydrofolate, or a combination thereof. In some embodiments, the therapeutic module comprises a siRNA, a miRNA, an anti-mRNA, a ribozyme RNA, or an antisense RNA. In some embodiments, the therapeutic module comprises a chemotherapeutic drug, a riboswitch, or an endosome disrupting agent. In some embodiments, the therapeutic module is a cytotoxic drug. Nonlimiting examples of the cytotoxic drug include doxorubicin, paclitaxel, paclitaxel derivatives and analogues, cytochalasin D, rapamycin, rapamycin derivatives and analogues, camptothecin, dexamethasone, and 5-fluorouracil, a quinazolinone derivative, metallic silver, tranilast, everolimus and related compounds, or other agents that inhibit cell proliferation and or migration and/or inflammatory processes. In some embodiments, the plurality of branches of the multi-branched comprises at least 90% identity to nucleotide sequences of at least one of SEQ ID NOS: 1-20.

In recent years, extensively branched 3D structures called dendrimers[D1-3] have become an attractive platform for building multifunctional macromolecular nanomaterials as diagnostic and therapeutic agents[D4-8]. This is primarily because of the polyvalent nature, nanoscale size, highly branched, and void-space containing framework of dendrimers, which offers high loading capacity of desired functionalities. The attractive and intriguing dendrimers were conceptualized over four decades ago[G1]; however, improvements are desirable for realizing their commercial availability in clinical settings. For example, the multi-step synthetic reactions necessary to generate defect-free dendrimer that impact product yield and purity. Incorporation of different functional modules to generate a multifunctional framework often requires series of protection-deprotection steps that affects synthetic yield, water solubility and even functionality. Traditional small molecule building blocks, such as high molecular weight carrier poly(amidoamine) (PAMAM) and poly (propyleneimine) (PPI) dendrimers are mostly smaller than 10 nm with angstrom level size differences within successive generations, make it desirable to seek alternate building blocks to enhance their size in order to avoid rapid renal clearance for in vivo applications.

Larger building blocks such as nucleic acids can overcome the size limitation. The self-assembly properties of nucleic acids can prevail over the complex synthetic routes to generate precisely assembled dendrimers under control. It has been proposed that DNA can serve as building blocks [D3], and the construction of DNA dendrimers by enzymatic ligation[D9], and recently, by hybridization using sticky end segments[D6,D10-13] have been reported. RNA dendrimers have not been realized to date due to challenges in predicting intra- and inter-molecular RNA folding involving canonical and non-canonical base pairing, base stacking, and tertiary interactions[D14,D15], as well as concerns regarding the chemical stability of RNA[D16-18].

Recent progress in RNA nanotechnology has enabled construction of varieties of RNA nanostructures with precise control of size, shape and stoichiometry[D16-21]. Several structural RNA motifs have been used as scaffold to construct varieties of 2D and 3D architectures including, branched RNA nanoparticles[D22-24], packaging RNA (pRNA) hexamers[D24,D25], nanorings[D26,D27], triangles[D28,D29], square[D30-32], pentagons[D33]; cube [D34], and origami structures[D35]. Recently we discovered a robust 3WJ (three-way junction) motif derived from pRNA[D36] of the phi29 bacteriophage DNA packaging motor[D22] that can serve as a scaffold for fabricating RNA nanoparticles. The pRNA-3WJ assembles from three pieces of RNA oligonucleotides, is unusually thermodynamically stable ($T_m$ of 59° C.; $\Delta G°_{37° C.}$ of −28 kcal/mol), is resistant to denaturation even in presence of 8 M urea, and remains intact at ultra-low concentrations in vivo[D22,23,37]. We have functionalized the pRNA-3WJ with targeting, imaging and therapeutic modules, and the resulting RNA nanoparticles have been used for cancer targeting[D22-24,D38-40] and therapy[D41,D42], as well as for resistive biomemory applications [D43]. More recently, we solved the crystal structure of the pRNA-3WJ scaffold[D44], which has facilitated the designs of multifunctional RNA nanoparticles. RNA has also been reported as a boiling-resistant anionic polymer material to build robust structures with defined shape and stoichiometry[D28,D45].

As disclosed herein, the presently disclosed subject matter provides the construction of RNA dendrimers utilizing the highly stable pRNA-3WJ motif as core scaffold. Each of the component strands were synthesized by transcription or chemically using phosphoramidite chemistry and then self-assembled sequentially to construct 3D globular Generation-0-4 (G-0-G-4) RNA dendrimers. The assembly of RNA dendrimers employs modular design principles and is highly controllable. Functional groups can be introduced with relative ease both internally as well as at the peripheral ends of the component strands prior to the assembly process, thus resulting in homogenous (monodisperse) RNA dendrimers with high yield and purity.

As disclosed herein, RNA dendrimers have the following features: (1) monodisperse; (2) polyanionic nature; (3) tunable shape with defined 3D structure (G0-G3); (4) tunable nanoscale size (5-100 nm) (G0-G3); (5) polyvalent nature that allows conjugation of multiple therapeutic payloads and detection modules without any cross-linking; (6) large number of readily accessible terminal functional groups; (7) modular design that allows self-assembly of engineered RNA fragments; (8) biocompatible; (9) thermodynamic stable; hence, the entire construct will remain intact at ultra-low concentrations in the body; (10) chemically stable, after 2'-F modifications and therefore resistant to RNase degradation while retaining correct folding and biological functions; (11) longer plasma half-life using chemically modified RNA; (12) reproducible manufacturing framework for generating homogenous RNA nanoparticles, which avoids immune responses and non-specific side effects; (13) economic industrial scale production is possible in a cell-free system; (14) highly soluble and not prone to aggregation. They do not require any additional steps, such as linkage to PEG or serum albumins; (15) display low or no immunogenicity and/or toxicity even at high doses; (16) displays favorable pharmacokinetic and pharmacodynamic profiles in vivo (half-life of 5-10 hrs compared to 0.25-0.75 hrs of 2'F siRNA counterparts) in mice; (17) systemic injection of the thermodynamically and chemically stable RNA nanoparticles into mice revealed that the RNA nanoparticles strongly and specifically bind to cancers without accumulating in liver, lung, or any other vital organs or tissues; (18) minimal induction of antibody production will allow for repeated treatment of cancer. This is particularly applicable to patients who develop neutralizing antibodies to the protein-based reagents following repeated administrations.

As disclosed herein, RNA as construction material for fabricating G0, G1, G2 and G3 dendrimers. In some embodiments, RNA dendrimers harbor cytotoxic drugs (hydrophilic and hydrophobic) to kill tumors in a controlled and sustained manner. In some embodiments, RNA dendrimers harbor siRNA to knockdown genes involved in disease progression. In some embodiments, RNA dendrimers harbor anti-miRNA to knock-down oncogenic genes. In some embodiments, RNA dendrimers harbor miRNA to increase the endogenous tumor-suppressor miRNA. In some embodiments, RNA dendrimers harbors aptamers or chemical ligands for binding to cell surface receptors. In some embodiments, RNA dendrimers harbor aptamers or chemical ligands for internalization of RNA dendrimers into target cells via endocytosis. In some embodiments, RNA dendrimers harbor ribozymes for cleaving target substrates. In some embodiments, RNA dendrimers harbor riboswitch for modulating cellular pathways in response to stimuli. In some embodiments, RNA dendrimers harbor multiple MRI contrast agents. In some embodiments, RNA dendrimers harbor multiple CT contrast agents, multiple PET tracers, multiple NIR imaging agents. In some embodiments, RNA dendrimers harboring radioactive isotopes for disease detection. In some embodiments, RNA dendrimers carry electropositive proton sponge reagents such as imidazoles or amines for endosome escape, and electronegative therapeutic RNA such as siRNA, miRNA, riboswitch, and ribozyme for therapy of cancers and other diseases including disease diagnosis including, but not limited to cancer, immunology, respiratory, central nervous system, inflammatory, and infectious diseases. In some embodiments, RNA dendrimer is used for transdermal drug delivery, oral drug delivery, ocular drug delivery, pulmonary drug delivery, tissue engineering and organ scaffolding. In some embodiments, RNA dendrimer is used for disease treatment, including, but not limited to cancer, immunology, respiratory, central nervous system, inflammatory, and infectious diseases. In some embodiments, RNA dendrimers are used for disease diagnosis including, but not limited to cancer, immunology, respiratory, central nervous system, inflammatory, and infectious diseases.

In another aspect of the presently disclosed subject matter, is a composition comprising a therapeutically effective amount of the RNA nanostructure molecule and RNA dendrimer as disclosed above and herein. In some embodiments, the composition further includes a pharmaceutically acceptable carrier.

Yet in another aspect of the presently disclosed subject matter, is a drug delivery system, the system comprising a therapeutically effective amount of the RNA nanostructure and the RNA dendrimer molecule as disclosed above and herein. In some embodiments, drug delivery system further includes a pharmaceutically acceptable carrier.

Further, in some embodiments, the presently disclosed subject matter provide a method of image-guided drug delivery of a therapeutic agent to a subject in need thereof. The method include administering a therapeutically effective amount of RNA nanostructure molecule and RNA dendrimer as disclosed above and herein, and applying an imaging detection apparatus to the subject. In some embodiments, the imaging detection apparatus is an MRI imaging system. In some embodiments, the imaging detection apparatus is an NIRF imaging system. In some embodiments, the imaging detection apparatus is an CT/PET/SPECT imaging system.

Development of image-guided drug delivery systems for real-time monitoring, and validating the effect of delivery and response is very important for research and clinical applications[G1]. In the last decade, multifunctional nanoparticles of varying materials and physiochemical properties have been pursued as imaging and therapeutic platforms; however, effective strategies to quantitatively evaluate delivery of therapeutic payloads to tumors and metastatic cancer cells are challenging due to low efficiency in specific cancer targeting, non-specific accumulation in vital organs such as, liver and lungs, particle heterogeneity, dissociation after systemic injection due to dilution, and unfavorable pharmacokinetic and pharmacodynamic profiles [G1-7]. The goal is to adopt an innovative RNA nanotechnology approach (The Emerging Field of RNA Nanotechnology, *Nature Nanotechnology* 2010, 5:833)[G8] to construct ultrastable multifunctional RNA Beacons and RNA Dendrimers for quantitative assessment of tumor and metastatic cancer targeted therapeutic delivery, distribution, uptake and response. As reported in recent publications [G9-23], the RNA constructs are non-toxic, non-immunogenic and capable of penetrating across heterogeneous biological barriers to deliver high doses of therapeutics to solid tumors and metastatic cells in mice with little accumulation in normal organs and tissues [G9-23]. This provides an ideal system to non-invasively image delivery of cancer therapeutics in vivo.

The presently disclosed subject matter will employ multimodal imaging techniques (NIRF, PET/SPECT and/or MRI) that provide anatomic and quantitative functional measures of the drug delivery process at various spatial and temporal resolutions in real-time. This approach is based on the consideration that each of these three modalities has advantages, and an integrated approach will lead to synergistic imaging benefits. For instance, MRI using contrast agents harbored in RNA Dendrimers and RNA Beacons (FIG. 4-5) offers a high spatial resolution and can provide a better description of the particle distribution pattern than either PET or NIRF. PET provides a better signal-to-noise ratio because of the use of radiotracers. NIRF, on the other hand, can be visualized both in vivo by an IVIS system and ex vivo, by fluorescence microscopy, playing a unique role of bridging the in vivo and histological observations.

In some embodiments, the presently disclosed subject matter provides a kit for detecting, determining and/or localizing a biological substances of interest. The kit includes a RNA nanostructure and/or a RNA dendrimer as disclosed herein. In some embodiments, the kit further included a suitable means of detection. In some embodiments, the kit includes the RNA-3WJ-Beacon as disclosed herein. Non-limiting examples of suitable means of detection include MRI, nuclear imaging (e.g. PET or SPECT), optical imaging, sonoluminence imaging or photoacoustic imaging (ultrasound). The skilled in the art will appreciate that the particular imaging module of the present disclosure should be compatible with the particular imaging modality being used.

In some embodiments, the presently disclosed subject matter provides a method of diagnosing and/or treating a disease in a subject having or at risk of having the disease, the method comprising administering to the subject a therapeutically effective amount of a composition comprising a RNA nanostructure molecule and RNA dendrimer as disclosed above and herein. In some embodiments, the composition further comprises a pharmaceutically acceptable carrier. In some embodiments, the subject is a mammal or a non-mammal vertebrate. In some embodiments, the subject is a human. In some embodiments, the disease is a cancer. In some embodiments, the cancer is a colon cancer. Non-limiting examples of the disease include cancer, immunology, respiratory, central nervous system, inflammatory, and infectious diseases. Non-limiting examples of a cancer include but not limited to ovarian cancer, brain cancer, bone cancer, lung cancer, colorectal cancer.

The term "pharmaceutically acceptable carrier" as used herein refers to a diluent, adjuvant, excipient, or vehicle with which a heterodimeric probe of the disclosure is administered and which is approved by a regulatory agency of the federal or a state government or listed in the U.S. Pharmacopeia or other generally recognized pharmacopeia for use in animals, and more particularly in humans. Such pharmaceutical carriers can be liquids, such as water and oils, including those of petroleum, animal, vegetable, or synthetic origin, such as peanut oil, soybean oil, mineral oil, sesame oil, and the like. The pharmaceutical carriers can be saline, gum acacia, gelatin, starch paste, talc, keratin, colloidal silica, urea, and the like. When administered to a patient, the heterodimeric probe and pharmaceutically acceptable carriers can be sterile. Water is a useful carrier when the heterodimeric probe is administered intravenously. Saline solutions and aqueous dextrose and glycerol solutions can also be employed as liquid carriers, particularly for injectable solutions. Suitable pharmaceutical carriers also include excipients such as glucose, lactose, sucrose, glycerol monostearate, sodium chloride, glycerol, propylene, glycol, water, ethanol, and the like. The present compositions, if desired, can also contain minor amounts of wetting or emulsifying agents, or pH buffering agents. The present compositions advantageously may take the form of solutions, emulsion, sustained release formulations, or any other form suitable for use.

The term "therapeutically effective amount," as used herein, refers to the amount of a composition containing administered to a patient already suffering from a disease, condition, or disorder, sufficient to cure or at least partially arrest, or relieve to some extent one or more of the symptoms of the disease, disorder, or condition being treated. The effectiveness of such compositions depend upon conditions including, but not limited to, the severity and course of the disease, disorder, or condition, previous therapy, the patient's health status and response to the drugs, and the judgment of the treating physician. By way of example only, therapeutically effective amounts may be determined by routine experimentation, including but not limited to a dose escalation clinical trial.

The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In further various aspects, a preparation can be administered in a "prophylactically effective amount"; that is, an amount effective for prevention of a disease or condition.

Suitable methods for administering to a subject an effective amount of the composition in accordance with the methods of the present disclosure include but are not limited to systemic administration, parenteral administration (including intravascular, intramuscular, intraarterial administration), oral delivery, buccal delivery, subcutaneous administration, inhalation, intratracheal installation, surgical implantation, transdermal delivery, local injection, and hyper-velocity injection/bombardment. Where applicable, continuous infusion can enhance drug accumulation at a target site (see, e.g., U.S. Pat. No. 6,180,082).

As used herein, the term "subject" refers to a target of administration of the pharmaceutical composition. The subject of the herein disclosed methods can be a vertebrate, such as a mammal, a fish, a bird, a reptile, or an amphibian. Thus, the subject of the herein disclosed methods can be a human or non-human. Thus, veterinary therapeutic uses are provided in accordance with the presently disclosed subject matter. As such, the presently disclosed subject matter provides for administration to mammals such as humans and non-human primates, as well as those mammals of importance due to being endangered, such as Siberian tigers; of economic importance, such as animals raised on farms for consumption by humans; and/or animals of social importance to humans, such as animals kept as pets or in zoos. Examples of such animals include but are not limited to: carnivores such as cats and dogs; swine, including pigs, hogs, and wild boars; ruminants and/or ungulates such as cattle, oxen, sheep, giraffes, deer, goats, bison, and camels; rabbits, guinea pigs, and rodents. Also provided is the treatment of birds, including the treatment of those kinds of birds that are endangered and/or kept in zoos, as well as fowl, and more particularly domesticated fowl, i.e., poultry, such as turkeys, chickens, ducks, geese, guinea fowl, and the like, as they are also of economic importance to humans. Thus, also provided is the treatment of livestock, including, but not limited to, domesticated swine, ruminants, ungulates, horses (including race horses), poultry, and the like. The term does not denote a particular age or sex.

The presently-disclosed subject matter is further illustrated by the following specific but non-limiting examples. The following examples may include compilations of data that are representative of data gathered at various times during the course of development and experimentation related to the present invention.

Example 1

Radiation reagents that specifically target tumors are in high demand for the treatment of cancer. The field of RNA nanotechnology can provide new opportunities for targeted radiation therapy. We recently found that chemically modified RNA nanoparticles derived from pRNA Three-Way Junction (3WJ) of phi29 DNA-packaging motor are resistant to potent 1-125 and Cs-131 radiation, which is a required perquisite for utilizing these RNA nanoparticles as carriers for targeted radiation therapy. Specifically, RNA nanoparticles derived from the pRNA 3WJ targeted tumors in vivo and they were stable under irradiation of 1-125 and Cs-131 with clinically relevant doses ranging from 1 Gy to 90 Gy over a significantly long time up to 20 days. These studies demonstrated that the RNA nanoparticles could be used as carriers for radiation therapy and diagnosis.

Materials and Methods

Oligonucleotides and Assembly of RNA 3WJ Nanoparticles

The RNA oligonucleotides used in this study for constructing the RNA 3WJ nanoparticles were ordered from TriLink BioTechnologies (San Diego, Calif.). Assembly of RNA 3WJ nanoparticles was performed by mixing equal molar concentrations of corresponding strands (3WJa: UUGCCAUGUGUAUGUGGG (SEQ ID NO: 1); 3WJb: CCCACAUACUUUGUUGAUCC (SEQ ID NO: 2) and 3WJc: GGAUCAAUCAUGGCAA (SEQ ID NO: 3)) in TMS (50 mM TRIS pH=8.0, 100 mM NaCl, 10 mM $MgCl_2$) buffer. The 3WJ formations were confirmed on a 12% native PAGE (polyacrylamide gel electrophoresis) with running buffer (89 mM Tris, 200 mM Borate acid, and 5 mM $MgCl_2$), according to published procedure [27]. Gels were stained with ethidium bromide (EB) or SYBR Green II and imaged by Typhoon FLA 7000 (GE Healthcare). The assembled RNA 3WJ nanoparticles were stored in −20° C. freezer prior to further characterization.

Atomic Force Microscopy (AFM) Imaging

Atomic force microscopy (AFM) was used to study the shape and size of 3WJ-pRNA nanoparticles harboring three monomeric pRNA [27]. AFM images were obtained by imaging the nanoparticles using specially modified mica surfaces (APS mica) [37] with a Veeco MultiMode AFM NanoScope IV system (Veeco/Digital Instruments, Santa Barbara, Calif.), operating in tapping mode, according to the method previously reported [27].

Temperature Gradient Gel Electrophoresis (TGGE)

The thermodynamic stability of 2'F U/C modified RNA 3WJ nanoparticles was studied using the TGGE system (Biometra GmbH, Germany). The 2'F U/C modified RNA oligonucleotides used in this study for constructing the RNA 3WJ nanoparticles were ordered from TriLink BioTechnologies (San Diego, Calif.). The 3WJb strand was 5'-end γ-32P ATP (Perkin-Elmer, MA) labeled prior assembly. Assembly of RNA 3WJ nanoparticle was achieved by mixing 10 uM total RNA strands in TMS buffer, heating to 80° C. and cooling it down to 4° C. over 1 hour. RNA nanoparticles were subjected to a 15% native PAGE (2.5 uL of RNA per well) and allowed to run for 10 minutes at ambient temperature at constant 100 V. After RNA entered into the gel matrix, the gel was transferred into TGGE apparatus and a linear temperature gradient was set up from 36° to 80° C. perpendicular to electrical current. The gel was ran at 100 V for 1 h, and then was dried under vacuum and imaged using a phosphor storage screen with Typhoon FLA 7000 (GE Healthcare).

Confocal Microscopy of HT29 Colon Cancer Cells Incubated with RNA Nanoparticles

Colon cancer HT29 cells were plated on coverslips (Fisher Scientific) with folate free medium in a 24-well plate and cultured at 37° C. in humidified air containing 5% CO2 overnight. The cells were washed with folate free medium twice to remove dead cells. The Alexa-647 labeled folate-3WJ and folate free 3WJ 2'F RNA nanoparticles were diluted in folate free medium and incubated with the cells at 37° C. for 2 hours. After washing with PBS, the cells were fixed with 4% paraformaldehyde, stained with Alexa Flour® 488 Phalloidin (Life technologies Corporation, Carlsbad, Calif., USA) for actin and ProLong® Gold Antifade Reagent with DAPI (Life technologies) for nucleus. The images were taken on an Olympus FV1000 confocal microscope (Olympus Corporation, Tokyo, Japan).

Flow Cytometry Analysis of Cellular Binding of RNA Nanoparticles

KB cells were cultured in folate free RPM1-1640 medium (Gibco), then digested with trypsin and rinsed with folate free medium. 3 nM of Alexa647 labeled 3WJ-Folate and 3WJ 2'F RNA were incubated with $2\times10^5$ KB cells at 37° C. for 1 hr. After washing with PBS twice, the cells were re-suspended in 200 μL of PBS buffer for flow cytometry analysis. Fluorescence intensity was determined with a FACS Calibur flow cytometer (BD Biosciences) by counting 20 000 events each sample.

Cytotoxicity Assay

The cytotoxicity of RNA nanoparticles were evaluated with an MTT assay kit (Promega, Madison, Wis.) following manufacture's instruction. Briefly, HT29 cells were plated in a 96-well plate and cultured at 37° C. in humidified air containing 5% CO2 overnight. The folate-3WJ 2'F RNA nanoparticles were suspended in fresh McCoy's 5A with 10% FBS medium at the indicated concentrations and added to the cells for incubation at 37° C. for 24 hrs. Then, 15 ul of dye solution was added to each well and incubated at 37° C. for 4 hrs; 100 ul of solubilization/stop solution was added to each well and incubated at room temperature for 2 hrs for color development. The absorbance at 570 nm was recorded using a microplate reader (Synergy 4, Bio Tek Instruments, Inc, USA). The cell viability was calculated relative to the absorbance of cells only control (viability of cells only control=100%).

Animal Trial: In Vivo Cancer Targeting of RNA 3WJ Nanoparticles

In order to evaluate the cancer targeting property of RNA 3WJ nanoparticles, an animal trial was conducted. All experiments involving animals are approved by the University of Kentucky Institutional Animal Care and Use Committee (IACUC). Male athymic nude nu/nu (6-8 week old) mice were obtained from Taconic (Hudson, N.Y.) and housed in clean, pathogen-free rooms in an environment with controlled temperature (27° C.), humidity, and a 12 hour light/dark cycle. The mice were fed standard chow and tap water ad libitum and allowed to acclimate for one week. HT29 colon cancer tumor cells were injected subcutaneously ($5\times10^6$ cells in 100 ul 1× phosphate buffered saline (PBS)). RNA nanoparticles were administered intravenously 3 weeks after tumor cells injection. The folate and Alexa647 labeled 2'F U/C modified RNA oligo strands for assembling the RNA 3WJ nanoparticles were custom ordered from TriLink BioTechnologies, Inc (San Diego, Calif.). Mice were fed a folate-free diet (Harlan Laboratories; Indianapolis, Ind.) for a total of 2 weeks before the folate-pRNA 3WJ nanoparticles were injected. For intravenous injection mice were anesthetized using isoflurane gas (2% in oxygen at 0.6 L/min flow rate) and injected with 100 μg (4 mg/kg) of 2'F U/C modified folate-Alexa647-labeled pRNA 3WJ nanoparticles in 300 μl of PBS. Whole-body imaging (Alexa Fluor 647, Ex=640 nm, Em=680 nm;) was carried out on IVIS Spectrum station (Caliper Life Sciences; Hopkinton, Mass.) 15 min, 1 hour, 2 hour and 3 hour post injection. Composite images obtained were comprised of black and white digital photos with an overlay of images reflecting fluorescent activity. The density map, measured as photons/second/cm2/steradian (p/s/cm2/sr), was created using the Living Image 3.1 (Caliper Life Sciences; Hopkinton, Mass.) software and represented as a color gradient centered at the maximal spot. CO2 asphyxiation was performed by 3 h and 15 minute post injection. Following CO2 asphyxiation, the tumors of the mice were dissected.

Confocal Microscopy of Tissue Samples

For in vivo samples, collected tissues were fixed in 4% paraformaldehyde (Polysciences; 18814) with 10% sucrose (Sigma-Aldrich; St. Louis, Mo.) for 12 h at 4° C. and embedded into Tissue-Tek® O.C.T. compound on dry ice (Tissue-Tek; Andwin Scientific, Schaumburg, Ill.) for frozen sectioning (10 μm section thickness). Sectioned tissues were dried overnight in the dark, washed in room temperature PBS, stained and mounted by ProLong® Gold Antifade Reagent with DAPI (Life Technologies Corporation, Carlsbad, Calif.) overnight. The Olympus FV1000 confocal microscope (Olympus Corporation, Tokyo, Japan) was used to obtain the images.

Urea Stability Assay

Urea is a denaturing agent that is widely used in biochemistry to denature RNAs or proteins. Urea stability assays were performed to assay the stability of RNA 3WJ nanoparticles in the presence of urea. Urea stability was tested by mixing assembled RNA 3WJ nanoparticles with different concentrations of urea (2 M, 4 M, 6 M and 8 M). The samples were assayed on a 12% native PAGE, stained with EB, and imaged by Typhoon FLA 7000 (GE Healthcare).

Fetal Bovine Serum (FBS) Degradation Assay

Stability of nanoparticles in the body is critical for its in vivo application, as many enzymes could degrade nanoparticles rapidly and hinder their application. In the blood, the instability of RNA is mainly the result of enzymatic degradation by ribonucleases (RNases). RNases can be divided into two major categories: endoribonucleases and exoribonucleases. Endoribonucleases cleave phosphodiester bonds within the RNA backbone, while exoribonucleases cleave phosphodiester bonds at either the 5' end or the 3' end of an RNA chain. RNA is indeed very sensitive to degradation by RNases, which confers a very short half-life and thus, a poor pharmacokinetic profile for most RNA molecules. This limits the in vivo usage of RNA molecules as therapeutics. However, chemical modifications of RNA can overcome this shortcoming. For example, the substitution of the 2' hydroxyl group with a 2' fluorine (2'F) atom dramatically increases the stability of RNA in vivo by preventing degradation by RNases [48-51]. To test the stability of RNA 3WJ nanoparticles with FBS treatment, assembled RNA 3WJ nanoparticles were incubated with 10% FBS in 1640 cell culture medium in a 37° C. water bath for different time up to 36 hr. Samples were then assayed on a 12% native PAGE, stained with EB, and imaged by Typhoon FLA 7000 (GE Healthcare). ImageJ software was used to integrate the intensities of the assembled RNA 3WJ nanoparticles in the gel. Integration areas for each time point were compared to the integration area for the 0 min time point to construct a serum degradation comparison between the RNA and 2'F RNA nanoparticles. Origin 8.6 software were used to generate the plots.

Irradiation of RNA 3WJ Nanoparticles with I-125 and Cs-131

Two brachytherapy sources were used in this study. I-125 is an isotope that is commonly used to treat prostate cancer and tumors in various sites. It decays into Te-125 with electron capture emitting photons with a broad spectrum whose mean energy is 28 KeV; the half-life is 59.4 days. I-125 brachytherapy sources used in this study for prostate implants were produced by IsoAid (Port Richey, Fla.) as a cylindrical shape with a physical length of 4.5 mm and outer diameter of 0.8 mm; the I-125 material was coated onto a silver rod encapsulated with a thin Titanium shielding [38].

Isotope Cs-131 is relatively new to brachytherapy, but has already been used for the treatment of various types of cancer such as prostate, breast, and eye, and recent gynecological malignancies [39-44]. It is similar to I-125 in many aspects. It also decays in electron capture and emits photons with a mean energy of 30 KeV, but the half-life of Cs-131 is only 9.7 days [45]. The Cs-131 source was provided by IsoRay Medical, Inc., Richland, Wash. as a small cylinder 4.5 mm in length and 0.8 mm in diameter.

I-125 or Cs-131 radioactive sources were immersed in the sample liquid (1 cc) contained in a small vial. The irradiation of the 2'F U/C modified RNA samples was performed for different time periods and doses. The purpose was to distinguish the effects of radiation on DNA and RNA structures. Un-irradiated samples were maintained in the same buffer and temperature and used as control. After irradiation, the integrity of the RNA 3WJ nanoparticles and plasmid control were assayed by 12% native PAGE with TBM running buffer or 0.7% agarose gel with TAE running buffer, respectively.

Results

RNA 3WJ Nanoparticles Form by One-Pot Self-Assembly

Figure 1B:
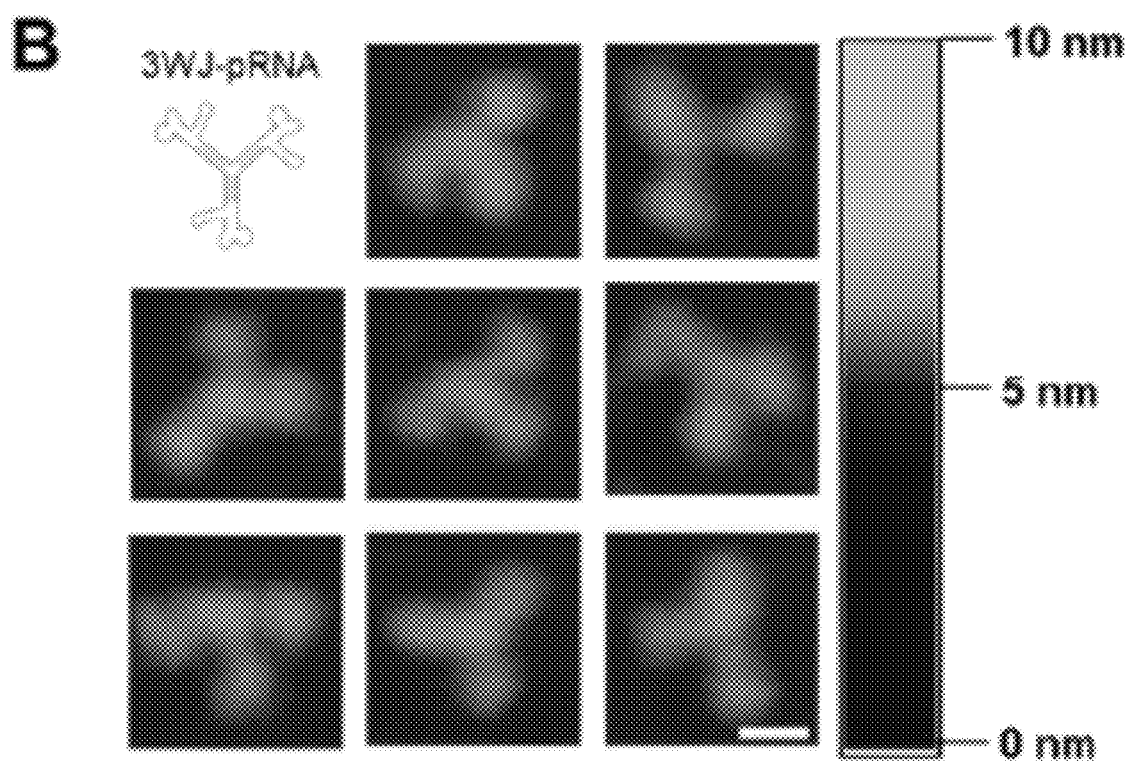
Figure 1C:
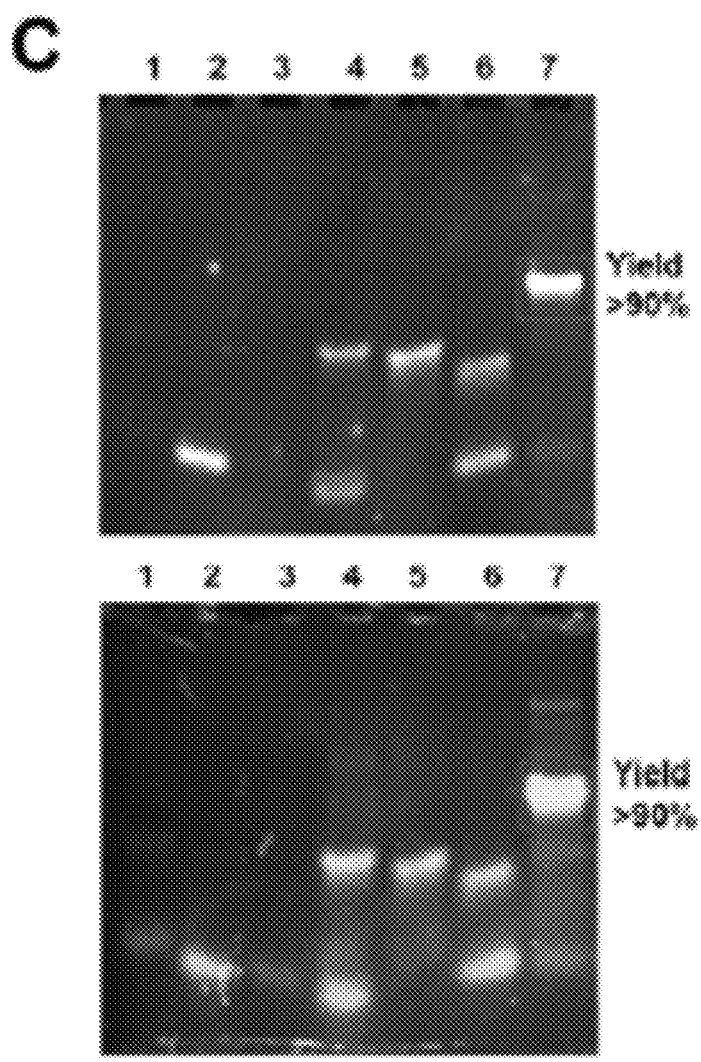

RNA 3WJ consists of three fragments: $3WJ_a$, $3WJ_b$, and $3WJ_c$. RNA nanoparticles were formed by mixing three pieces of chemically synthesized oligos, $3WJ_a$, $3WJ_b$, and $3WJ_c$ at 1:1:1 molar ratio (FIG. 1). The three pieces were assembled into nanoparticles very efficiently by simple mixing (FIG. 1C, lane 7), indicating the thermodynamically stable properties of the pRNA 3WJ. Notably, with the 1:1:1 ratio of 3WJa, 3WJb, and 3WJc, almost more than 90% or close to 100% of the three RNA fragments assembled efficiently into the 3WJ complex. This feature of efficient self-assembly [27] suggests that pRNA 3WJ nanoparticles can be fabricated very simply and easily, which is advantageous for therapeutics development and clinical translation. AFM imaging also confirmed the formation of 3WJ-pRNA nanoparticles harboring three monomeric pRNA and revealed the triangular branched structure of the nanoparticle with the size of 10-15 nm (FIG. 1B).

Figure 1D:
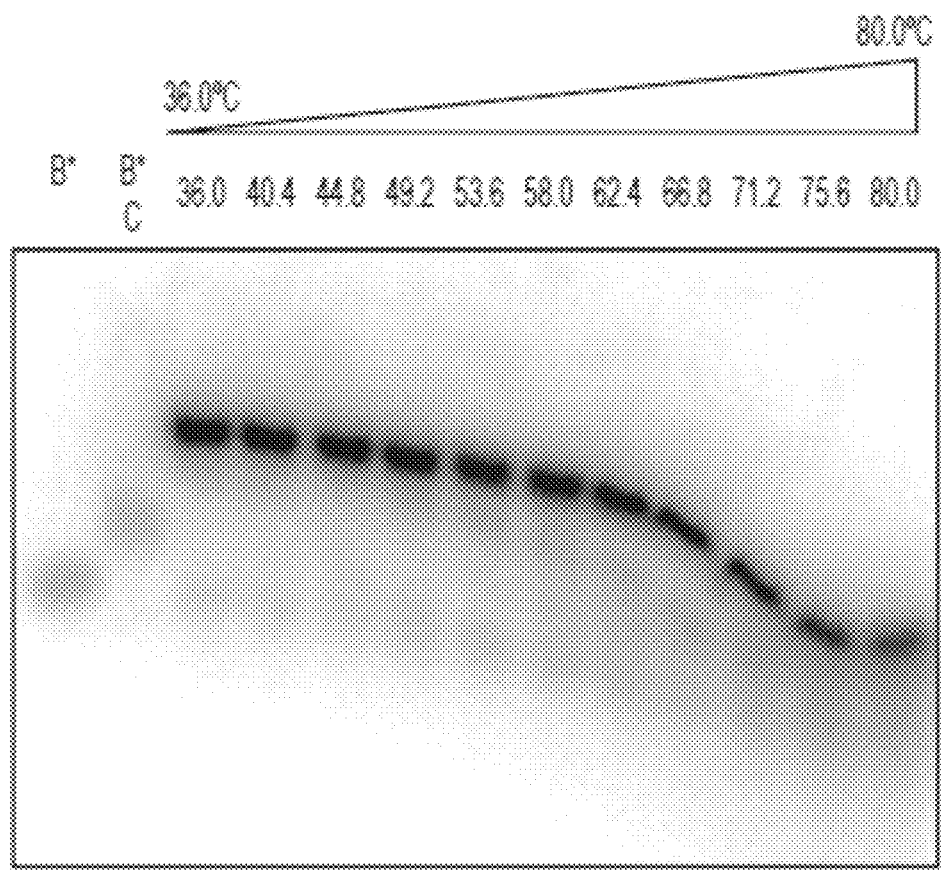

Chemically Modified RNA 3WJ Nanoparticles are Chemically and Thermodynamically Stable In addition, we measured thermodynamic stability of the RNA 3WJ nanoparticles by temperature gradient electrophoresis gel (TGGE) (FIG. 1D). This technique allows the determination of melting temperatures of nucleic acids by means of decreasing fraction of a nanoparticle with increasing temperature on PAGE [46,47] (FIG. 1D). The 2'F modified 3WJ nanoparticles remained stable at temperatures as high as 66.8±2° C., which is above the temperature of normal human body.

Figure 3A:
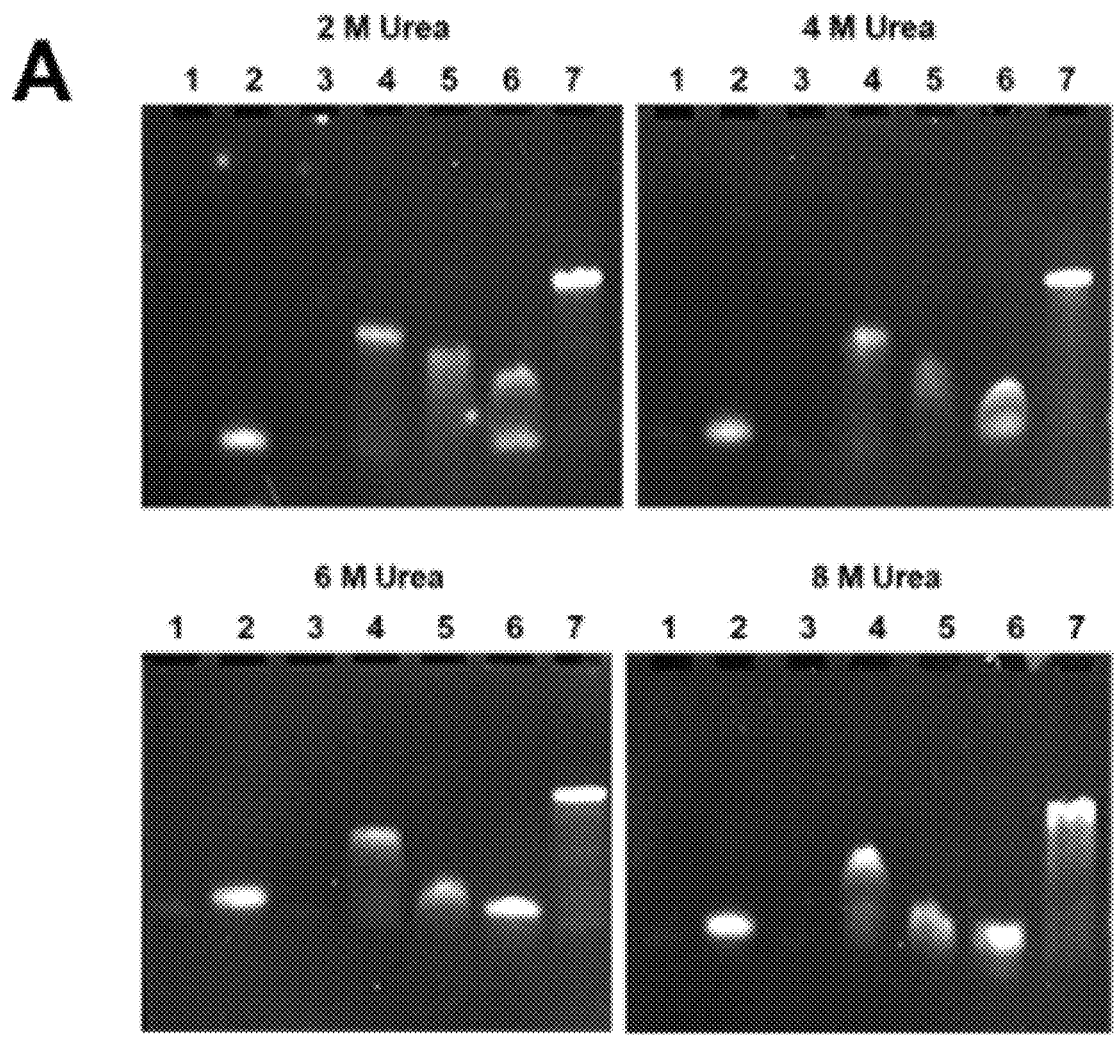

RNA 3WJ nanoparticles were mixed with 2 M, 4 M, 6 M, and 8 M urea and loaded into TBM gel (FIG. 3A). In the presence of 8 M urea, assembled RNA 3WJ nanoparticles still showed little dissociation, which is in agreement with previously published results [27].

Figure 3B:
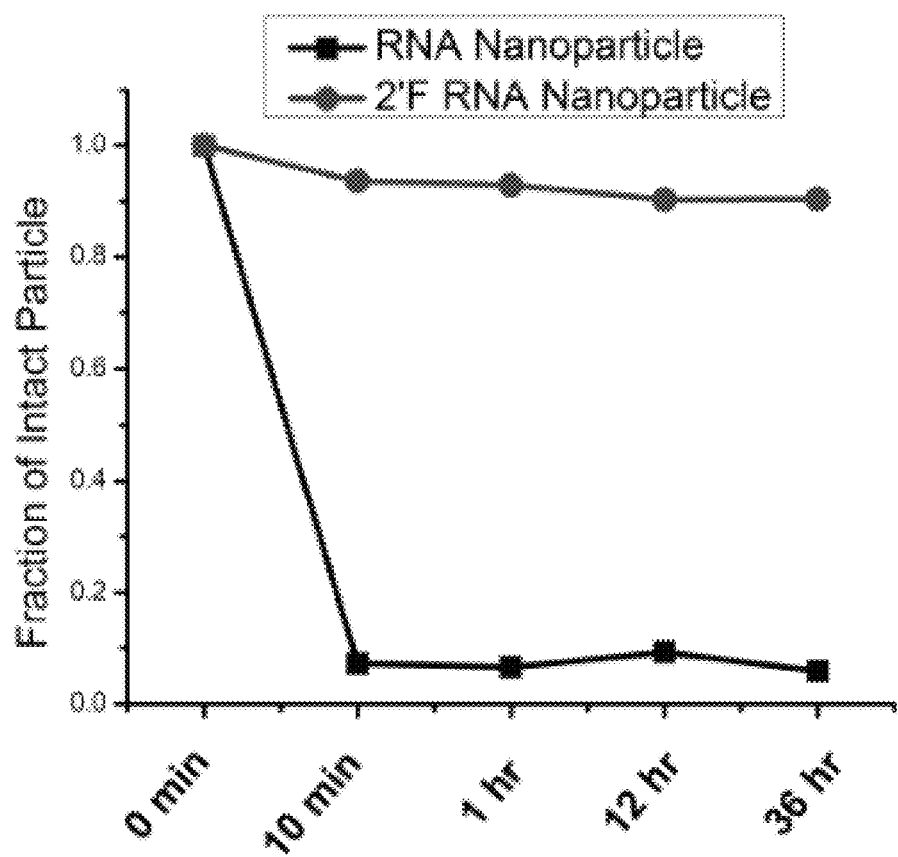

The stability of RNA 3WJ nanoparticles was tested with up to 36 hr serum treatment (FIG. 3B). Previously published reports by Pieken et al. [48], Kawasaki et al. [49], Sabahi A et al. [50] and Liu et al. [51] have demonstrated that 2'F-modified RNA has increased resistance to ribonuclease as well as enhanced thermodynamic stability. Our results showed the similar results for the RNA 3WJ nanoparticles. Specifically, unmodified RNA 3WJ nanoparticles were degraded in serum which was revealed by the disappearance of the non-modified RNA 3WJ nanoparticles after serum treatment, indicating the majority of the unmodified RNAs were degraded. However, 2'F-modified RNA 3WJ nanoparticles were resistant to serum-induced degradation. In contrast to unmodified RNA nanoparticles, more than 90% of 2'F-modified RNA 3WJ nanoparticles remained intact after 36 hours serum treatment, which is in agreement with published reports [27].

Folate-Conjugated RNA Nanoparticles Bind to Cancer Cells Specifically In Vitro

Figure 2A:
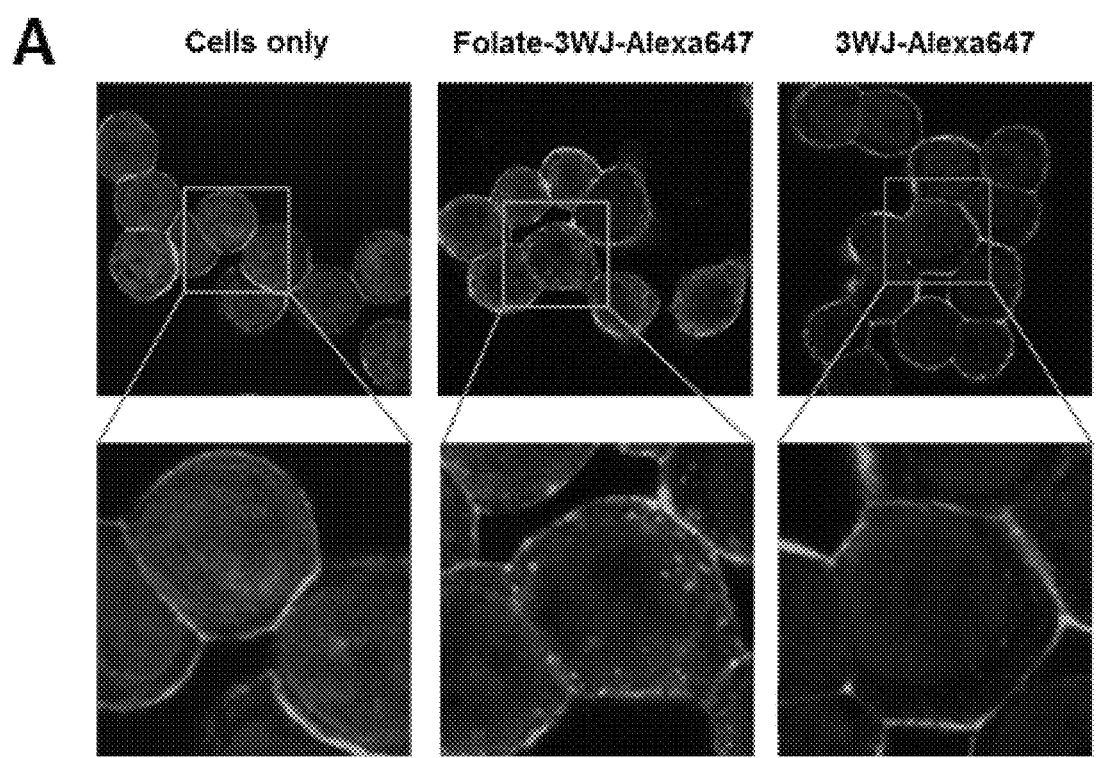

In one embodiment, the 2'F modified 3WJ RNA nanoparticles conjugated with folate were tested for specific binding and entry to colon cancer HT29 cells by confocal microscopy. In the folate-conjugated 3WJ RNA nanoparticles, 3WJb strand was labelled with folate and 3WJc strand was labeled with Alexa647. 3WJ RNA nanoparticles without folate were used as a negative control. Confocal imaging indicated strong binding and entry of the folate-conjugated 3WJ nanoparticles to colon cancer HT29 cells, as demonstrated by colocalization of nucleus (blue), actin (green) and Alexa647-labeled RNA nanoparticles (red) signals. (FIG. 2A). Flow cytometry analysis indicated that folate labeled 3WJ 2'F RNA nanoparticles can also bind to folate receptor over-expressed KB cells (FIG. 2B).

RNA 3WJ Nanoparticles Holds Low Cytotoxicity Revealed in Cell Assay

The cytotoxicity of folate-3WJ 2'F RNA nanoparticles on colon cancer HT29 cells was evaluated with a standard colorimetric MTT assay that assesses the cell proliferation. We found that folate 3WJ 2'F RNA nanoparticles did not induce measurable cell viability loss on colon cancer HT29 cells even at a high concentration of 0.4 µM (FIG. 2C), indicating the RNA nanoparticles are biocompatible and not toxic.

RNA 3WJ Nanoparticles Targeting Xenograft Cancer by Systemic Injection

Systemic injection of RNA 3WJ nanoparticles was used to confirm the chemical and thermodynamical stability and cancer targeting of these nanoparticles. Moreover, as a preliminary study to evaluate the feasibility of RNA nanoparticles to carry radioisotopes for cancer targeting in vivo, we used fluorescent dye instead of a radioisotope in a pilot experiment. RNA nanoparticles was constructed with one RNA fragment carrying folate as a cancer-targeting ligand and another RNA fragment carrying the Alexa647 fluorescent probe instead of a radioisotope. The 3WJ RNA nanoparticles were systemically injected into mice via tail vein. Whole body imaging of treated mice revealed a fluorescence signal located specifically at the cancer xenograft, which expressed the folate-receptor. Fluorescent signal was not detected in healthy tissue or normal organs in the mice body (FIG. 2D), indicating that the particles did not accumulate or become trapped in liver, lungs, or other organs after systemic delivery. Further confocal microscope analysis (FIG. 2E) also confirmed that the Alexa647 labeled RNA nanoparticles could enter into the tumor and bind to cancer cells.

RNA 3WJ Nanoparticles are Stable Under Irradiation with I-125 and Cs-131

The stability of 2'-F modified RNA 3WJ nanoparticles under irradiation with clinically relevant doses was crucial for the development of targeted radiation therapy. The stability tests were performed with I-125 and Cs-131 irradiation. DNA plasmids were included as control. The plasmid DNA we used was in the circular form. Cleavage of the circular plasmid at a random site will result in a linear DNA that migrates to different location in the gel. Multiple cleavage of the DNA will result in random sizes that form a smear in the gel and many individual bands with low concentration were not visible since each DNA will have several thousand random cleavage sites. The test with I-125 was first performed for a low dose of 1 Gy to both RNA and DNA samples, but no change was observed. When the dose was increased to 30 Gy, a typical therapeutic dose, RNA 3WJ nanoparticles still remained unchanged (FIG. 3C) while DNA smear was formed as shown in FIG. 3D, which provided evidence of the cleavage of the plasmid DNA by radiation. The upper band and lower bands in lane 1 represent linear and supercoiled plasmid DNA, respectively. These results are summarized in Table 1.

TABLE 1

Results of I-125 irradiation.

| Test | Dose (Gy) | $S_k$ (U) | Time (day) | RNA change | DNA change |
|---|---|---|---|---|---|
| 1 | 1 | 1.4 | 1 | N | N |
| 2 | 30 | 1.7 | 18 | N | Y |

Y = Yes,
N = No.

Four tests were also conducted with Cs-131 for 7 Gy, 20 Gy, 30 Gy, and 90 Gy, and the irradiation lasted up to 20 days (longer than 2 half-life of 9.7 days). Both DNA and RNA structures were intact for 7 Gy, but DNA was broken while RNA 3WJ nanoparticles remained intact for 20 Gy or higher. The results are summarized in Table 2, and the result for 30 Gy is shown in FIG. 3D.

TABLE 2

Results of Cs-131 irradiation.

| Test | Dose (Gy) | $S_k$ (U) | Time (day) | RNA change | DNA change |
|---|---|---|---|---|---|
| 1 | 7 | 0.98 | 7 | N | N |
| 2 | 20 | 1.47 | 20 | N | Y |
| 3 | 30 | 4.03 | 7 | N | Y |
| 4 | 90 | 8.57 | 11 | N | Y |

Y = Yes,
N = No.

The results showed that RNA 3WJ nanoparticles were stable under irradiation of I-125 and Cs-131 with doses ranging from 1 Gy to 90 Gy. However, the DNA plasmids were damaged with a dose of 20 Gy or higher, the therapeutic doses prescribed for cancer treatment, while the RNA 3WJ nanoparticles remained intact. This result has indicated that RNA 3WJ nanoparticles may be able to carry therapeutic doses of I-125 and Cs-131 for cancer treatment.

Discussion

Figure 2D:
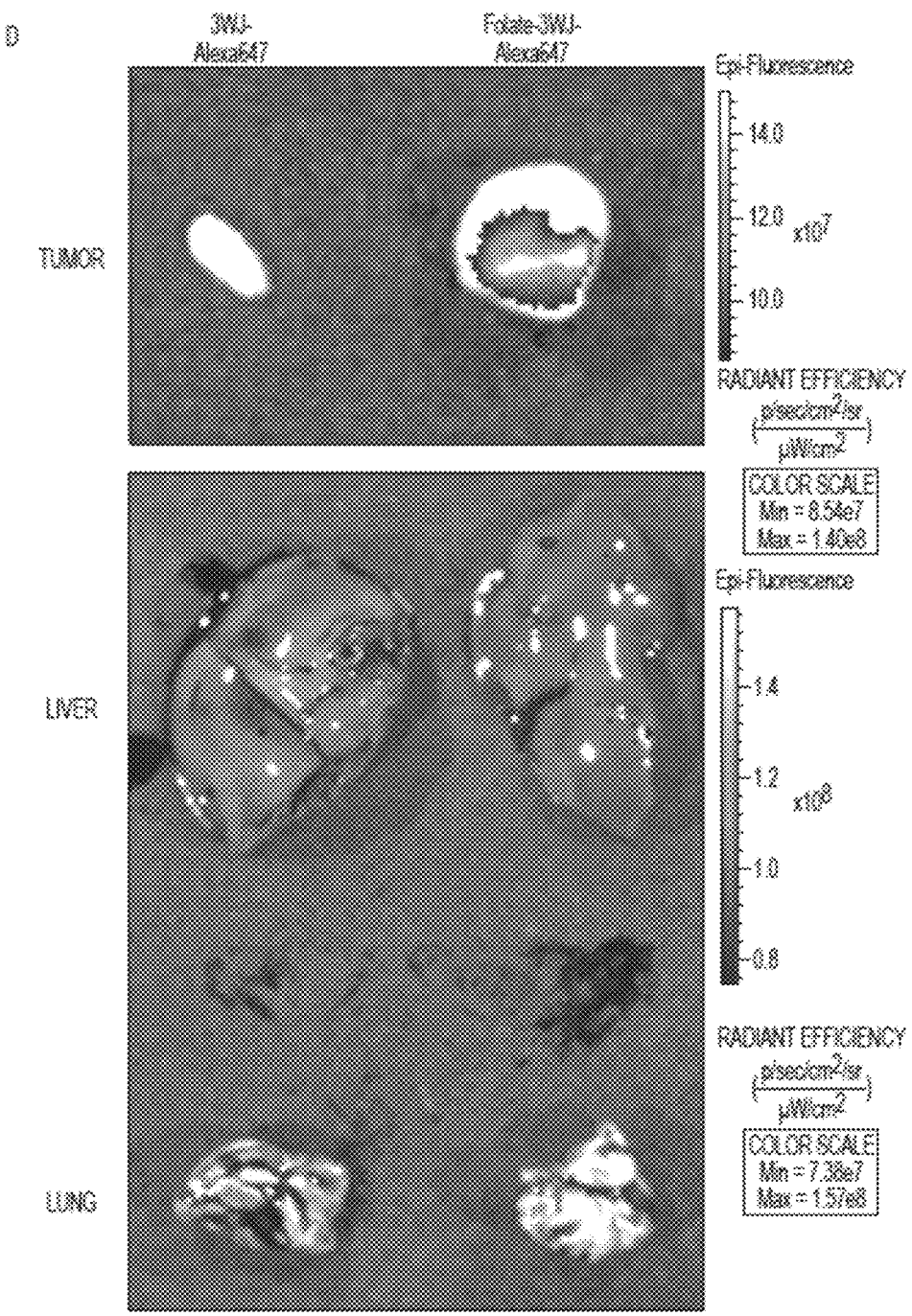

RNA nanotechnology is an field with increasing popularity among the scientific community [13, 21, 52-56]. RNA 3WJ-based nanoparticles have been successfully fabricated (FIG. 1) and share the advantages of a targeted drug delivery system of specific delivery and longer retention time, which reduce the dosage required and the side effects. The specific delivery can be achieved through EPR (enhanced permeability and retention) effect or active targeting through conjugation with ligands such as aptamer, folate, and RGD. Systemic injection of thermodynamically and chemically stable RNA nanoparticles into mice revealed that RNA nanoparticles strongly and specifically bound to cancers without accumulating in liver, lung, or any other vital organs or tissues (FIGS. 2D and 2E).

The high stability of RNA 3WJ nanoparticles in the presence of high concentration of denaturing agents (FIG. 3A) is a remarkable advantage for in vivo applications, including radiation therapy, because remaining intact in vivo and being resistant to various denaturing factors will be crucial for fulfilling the nanoparticle's designated function after injection into the body. Moreover, the determined melting temperature of the 3WJ RNA nanoparticles (FIG. 1D) is approximately two times higher than the normal human body temperature (37° C.), which also indicates that this physical property of the RNA 3WJ nanoparticles is favorable for in vivo applications including radiation therapy, because these RNA nanoparticles should not disassociate within the normal human body temperature range. Furthermore, the property of resistance to serum-induced degradation (FIG. 3B) suggests that these 2'F modified RNA nanoparticles will also stay intact within the human body, and, again, should be favorable as a targeted delivery system for in vivo cancer therapy.

The principle of radiation therapy is to use radiation to break DNA helical structures in the cancer cells. However, RNA has similar structures. To be able to carry radioisotopes, RNA structures should keep intact with the radiation. The study has shown that, unlike DNA, RNA nanoparticles were resistant to the radiation of I-125 or Cs-131 and remained stable under irradiation with therapeutic doses (FIGS. 3C and 3D, Table I and II). This indicates that RNA nanoparticles are feasible to carry radioisotope to kill cancer cells while remaining intact. The stability of the RNA nanoparticles under irradiation over a long time is important since the chemical conjugation of radioactive isotopes to RNA might be a time-consuming process depending on the rate and efficiency of the conjugation reaction. In the future experiments, we will also study the stability of RNA nanoparticles inside tumor tissues and try to develop the method to control the degradation of RNA nanoparticles as well as the release of radioisotope inside the tumor. In addition, I-125 and Cs-131 are gamma emitters and presence of gamma emission is helpful in imaging and studying the biodistribution of the radiopharmaceutical for estimation of patient-specific dose distribution [57]. This is an advantage that gamma emitters have over the pure beta emitters like Y-90. In the absence of gamma emission, surrogate isotopes like In-111 have to be used for internal dosimetry for pure alpha or beta emitters such as Y-90. Compared to I-131 that also emits photons, I-125 and Cs-131 have much lower energies and easy for radiation protection. Although image quality for I-125 or Cs-131 will be affected by the low energies of photons, good quality I-125 image have been obtained using Gamma camera [58, 59]. Therefore, RNA nanoparticles carrying I-125 or Cs-131 have the potential to be used for accurate targeted radiation therapy. As disclosed herein, in some embodiments, beta emitters include but not limited to Strontium-90, Tritium, Carbon-14, Phosphorus-32, Nickel-63. In some embodiments, gamma-emitting isotopes include but not limited to Caesium-137, Iodine-131, Lanthanum-140, cobalt-60, iridium-192.

It should be noted, however, that the sealed I-125 and Cs-131 sources used in this study were not carried by RNA nanoparticles. To be carried by RNA nanoparticles, unsealed I-125 or Cs-131 should be used to label RNA nanoparticles. The I-125 or Cs-131 labeled RNA nanoparticles will be injected into the patient body to target the tumor, and the radiation from I-125 or Cs-131 can thus kill the cancer cells guided by the nanoparticles. The I-125/Cs-131 labeled RNA particles will stay inside the tumor cells to deposit almost all the dose produced by I-125/Cs-131. Considering that the blood circulation time for humans is about one minute compared to the half-life of I-125/Cs-131 of about 60 days/10 days, the dose lost during circulation is negligible. Detailed discussion of I-125/Cs-131 labeled RNA particles will be addressed in our future study. Based on the biodistribution study of pRNA nanoparticles published by Abdelmawla et al. [28], we expected that 3WJ nanoparticles labelled with radioisotope will also have favorable biodistribution profile with similar tumor-targeting efficiency as the previously reported pRNA nanoparticles. In the future experiments, we will radioactively label 3WJ RNA nanoparticles and use the radioactive signal to quantify the doses delivered in individual organs and tumor. We will also compare the delivered dose to that provided by brachytherapy implanted sources.

Conclusions

Chemically modified RNA nanoparticles derived from pRNA three-way junction (3WJ) of phi29 DNA-packaging were resistant to the radiation of I-125 or Cs-131 and remained stable under irradiation with therapeutic doses over a significantly long time up to 20 days. Therefore, RNA 3WJ nanoparticles have the potential to carry I-125 or Cs-131 for targeted radiation therapy.

Example 2

This study will utilize pRNA-3WJ as a platform for constructing RNA-3WJ-Beacons and RNA Dendrimers as multifunctional systems harboring multimodal imaging agents, cancer targeting ligands, and therapeutic siRNA/miRNA, all in one nanoconstruct that will allow the delivery of therapeutics to be visualized at various spatial and temporal resolutions in vivo. Example 2 focuses on the construction of multifunctional pRNA-3WJ nanoparticles harboring (1) imaging modules: NIR fluorophores, such as Alexa$_{647}$ and IRdye$_{800}$ for in vivo fluorescence imaging; Radionuclides, such as $^{177}$Lu, $^{111}$In or $^{64}$Cu for PET/SPECT imaging; and Contrast agents, such as gadolinium (Gd$^{3+}$) for MRI; (2) targeting modules: such as RNA aptamer or chemical ligand for binding to cancer specific cell surface receptors resulting in internalization of RNA nanoparticles into cancer cells; and (3) therapeutic modules: siRNAs or anti-miRNAs to down-regulate oncogenic genes.

Construction of Multifunctional RNA Nanoparticles Harboring Multimodal Imaging Agents, Targeting Aptamers and Therapeutic Modules Using pRNA-3WJ Platform Multifunctional RNA nanoparticles will be constructed using the pRNA-3WJ motif as a scaffold to harbor: (1) Imaging modules: NIR fluorophores for in vivo fluorescence imaging; Radionuclides for PET/SPECT imaging; and gadolinium contrast agents for MRI; (2) Targeting modules: RNA aptamers or chemical ligands for binding to cancer specific cell surface receptors resulting in internalization of RNA nanoparticles into cancer cells; and (3) Therapeutic modules: siRNAs and anti-miRNAs to down-regulate oncogenic genes.

Figure 12:
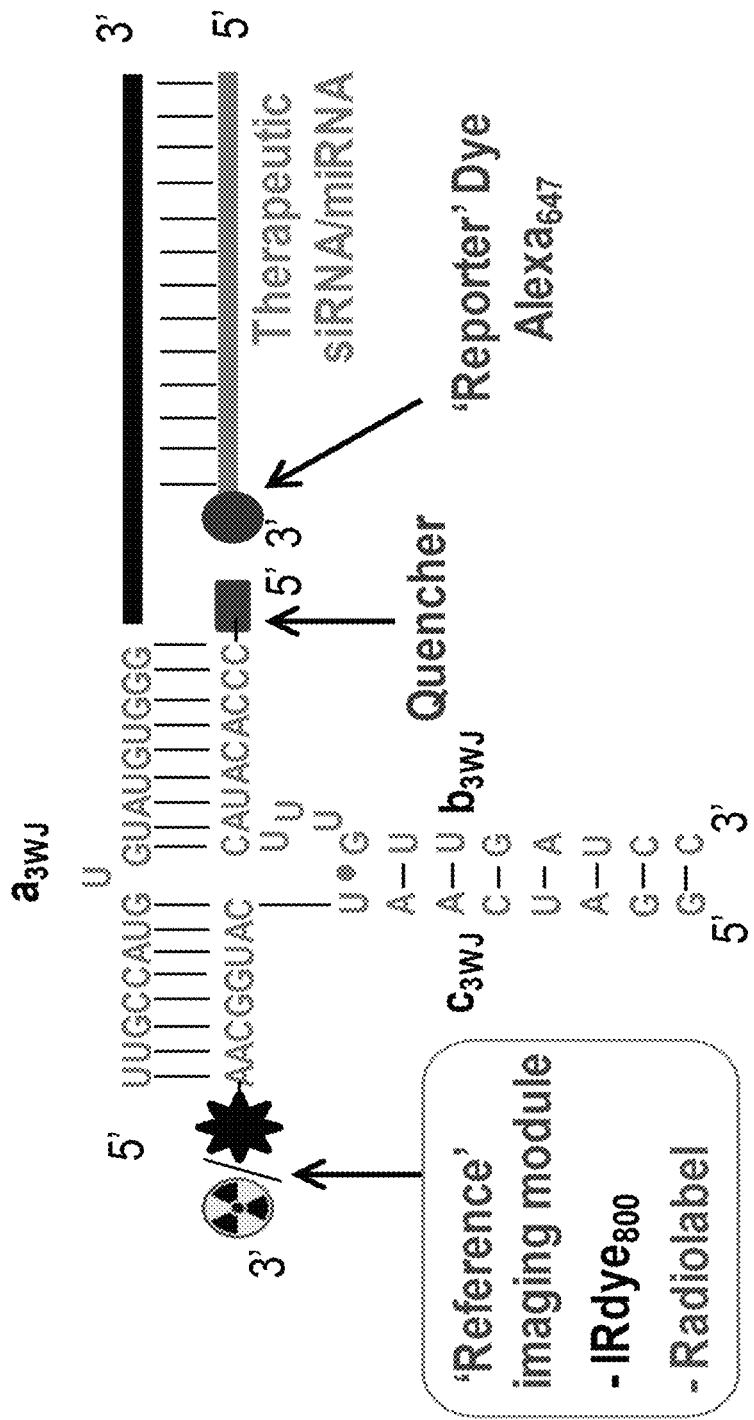
FIG. 12 includes conjugation of 'reference' dye IRdye$_{800}$, quencher Iowa Black, and 'reporter' dye Alexa$_{647}$ to pRNA-3WJ scaffold for fluorescence imaging. Alternatively, radionuclides will be incorporated as 'reference' module for simultaneous PET/SPECT and fluorescence imaging. Figure discloses SEQ ID NOS 1, 3 and 2, respectively, in order of appearance.

1.1 Conjugation of Imaging Modules to RNA Constructs 1.1.1 NIR fluorophores: For in vivo imaging, NIR dyes are particularly attractive since they can penetrate deep into tissues and more importantly, auto-fluorescence from tissues is greatly reduced. without being bound by theory, a robust RNA nanotechnology will be developed utilizing the pRNA-3WJ motif for monitoring the in vivo delivery of therapeutics non-invasively by NIRF and PET/SPECT imaging (FIG. 12). The RNA-3WJ-Beacon contains a 'reporter' fluorophore darkened by a quencher in close proximity and will only elicit a fluorescence signal upon cleavage of the incorporated siRNA/anti-miRNA by Dicer in the cell (see Section 2.1, described herein in Example 3). The RNA-3WJ-Beacon also contains a 'reference' probe (either NIR dye or radiolabel), which remains active at all times and allows tracking of the entire RNA-3WJ-Beacon construct in the cell (FIG. 12).

The pRNA-3WJ motif utilizes a modular design composed of three individual fragments (FIG. 6F, 12). One of the fragments ($c_{3WJ}$) will be end-labeled with 'reference' dye IRdye$_{800}$ while another fragment ($b_{3WJ}$) will be end-labeled with a quencher, Iowa Black for the 'reporter' dye Alexa$_{647}$. The 'reporter' dye will be end-labeled on therapeutic RNA fragments (siRNA/miRNA). All these 2'-F modified RNA fragments will be custom-designed and purchased from IDT, TriLink or IBA, as described in our publications [G9-11, which are incorporated by reference in their entities.] Upon mixing the chemically synthesized individual strands in stoichiometric ratio, the RNA fragments will assemble into an ultrastable 3WJ nanoparticle with high efficiency, as shown in our publications [G9-11].

Figure 13:
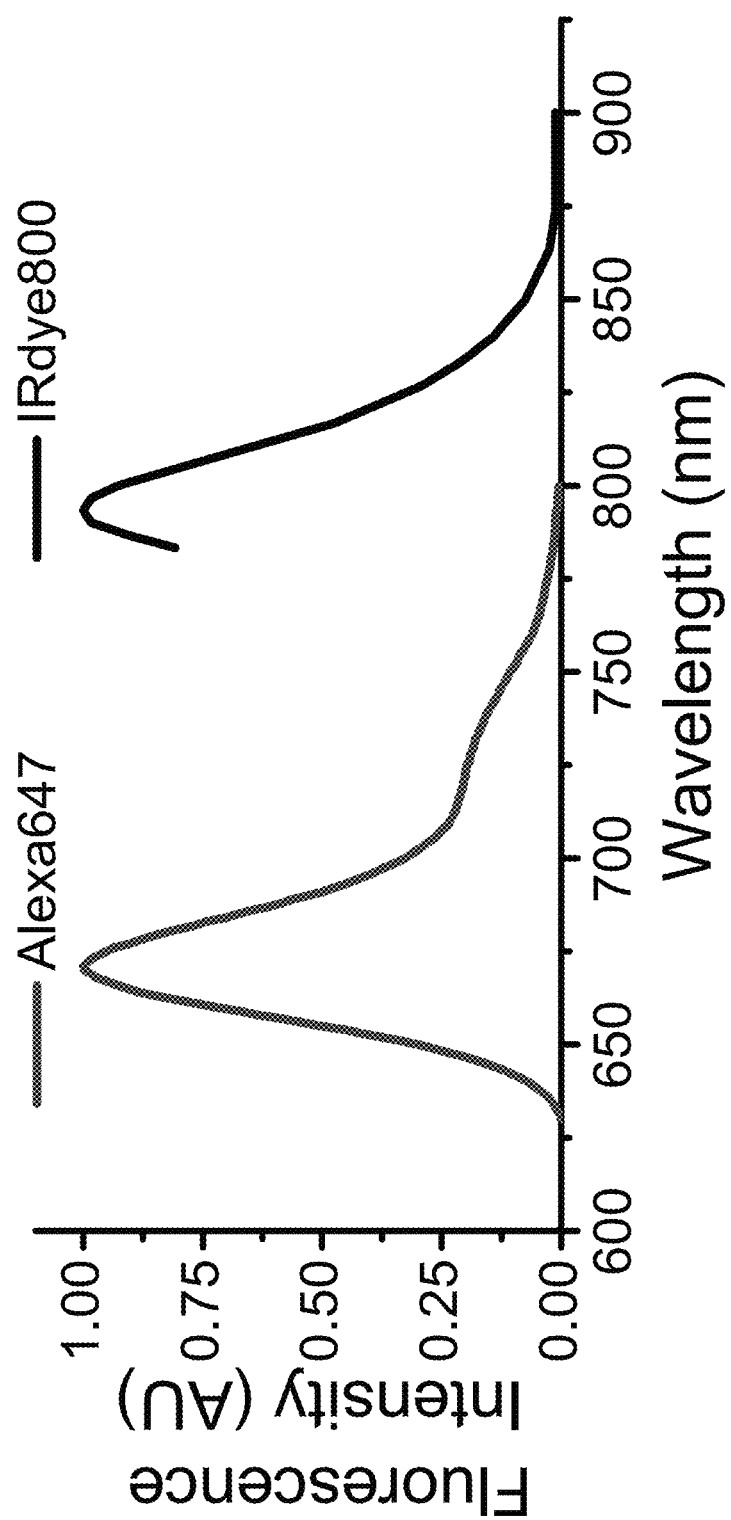
FIG. 13 shows emission spectra of the 'reporter' dye Alexa$_{647}$, and 'reference' dye IRdye$_{800}$, showing no spectral overlaps.

It is important to note that the NIR fluorophores and quenchers used herein are highly soluble in physiological buffers, display very low nonspecific binding to cellular components and have high signal-to-noise ratio [G72]. In our RNA-Beacon constructs, the fluorescence spectrum of the 'reference' and 'reporter' dyes are designed such that there are no potential spectrum overlaps or quenching through FRET (FIG. 13). As alternatives, other available quencher/emitter pairs (Table 3) will be investigated.

TABLE 3

Emitter-quencher pairs for designing RNA molecular beacons (as alternatives)

| Emitter | Quencher |
|---|---|
| Alexa647/Cy5 | Iowa Black RQ/QSY21 |
| IRDye 800CW | IRDyeQC |
| Cy5.5/Alexa-680 | BBQ650/BHQ-3 |

Source: Trilink, IDT, Invitrogen; Li-COR 1.1.2 Radionuclide: radiolabel peptides and proteins with various isotopes ($^{177}$Lu, $^{111}$In, $^{64}$Cu, $^{99m}$Tc, $^{203}$Pb, $^{188}$Re, $^{212}$Pb/$^{212}$Bi) have been developed as tumor specific diagnostic and therapeutic agents [G73-77]. Similar methodologies will be applied to label RNA constructs used in this study.

Radionuclide selection: $^{177}$Lu, $^{111}$In or $^{64}$Cu (as alternatives) will be used to label the RNA nanoparticles. High specific activity of these radionuclides are commercially available. Metals are highly toxic in their free form and thus have to be chelated to minimize their toxicity. We will use DOTA(1,4,7,10-tetraazacyclododecane-N,N',N'',N'''-tetraacetic acid) or NOTA (1,4,7-triazacyclononane-N,N',N''-1,4,7-triacetic acid) as chelating agents for our radionuclides.

Lutetium-177 ($t_{1/2}$=6.71 days, β0.497 MeV, $γ_{avg}$ 175 keV) is an attractive radioisotope for targeted radionuclide therapy, imaged by SPECT. The DOTA macrocyclic chelator can stably coordinate Lutetium-177 at 37° C. to 75° C. [G73].

Indium-111 ($t_{1/2}$=2.8 days, EC 100%, γ 171 keV, γ 245 keV) is a gamma emitter that is routinely used in diagnostic SPECT nuclear medicine imaging. The DOTA macrocyclic chelator can stably coordinate $^{111}$In at 37° C. to 75° C. [G78].

Copper-64 ($t_{1/2}$=12.7 hrs, 17.4% β$^+$, 41% EC, 40% β$^-$, $E_{avg}$ 278 keV) is a positron and beta emitter. The NOTA macrocyclic chelator can efficiently and stably coordinate $^{64}$Cu from 25° C. to 50° C.$^{76,79}$. The 12.7 hr half-life is sufficiently long to radiolabel the RNA nanoparticle and perform biodistribution and imaging studies using PET.

Figure 14:
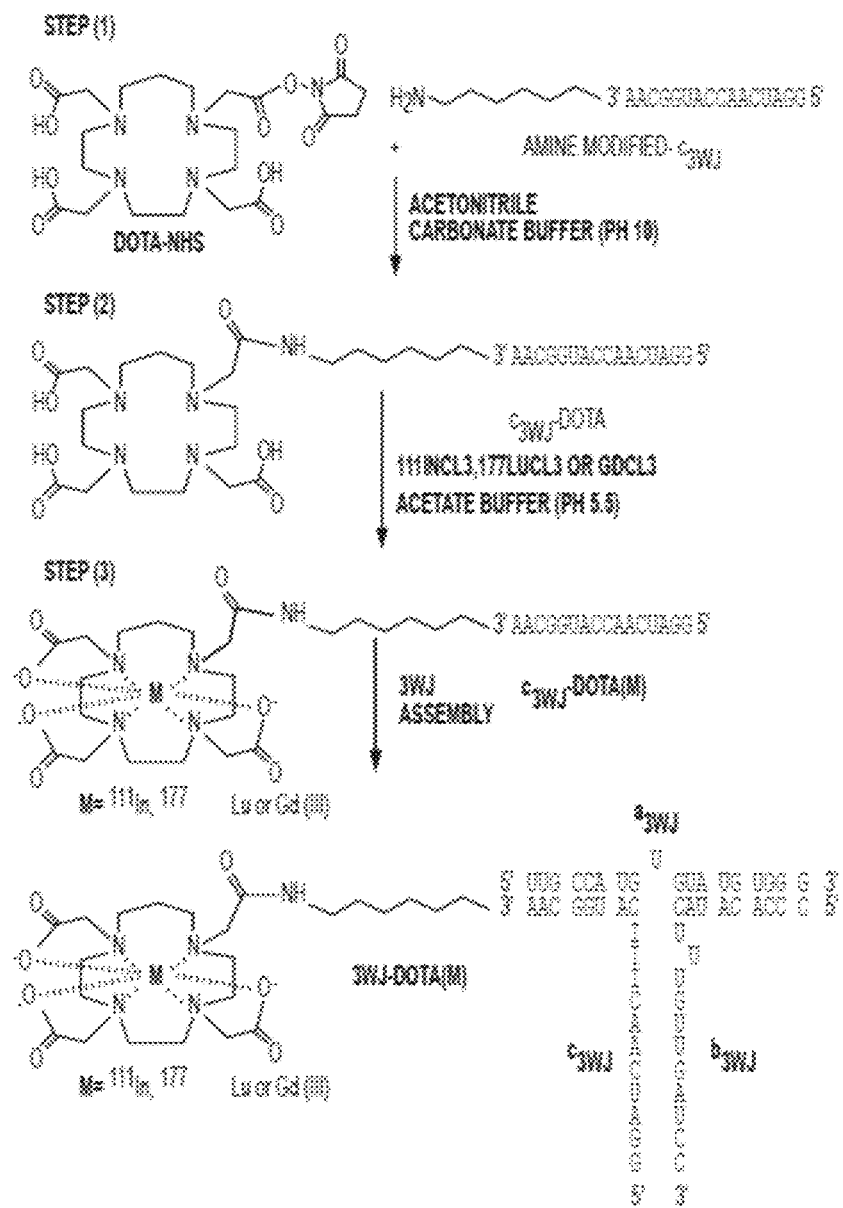
FIG. 14 shows step-wise preparative scheme for labeling DOTA conjugated RNA nanoparticles with a radionuclide ($^{177}$Lu or $^{111}$In) or contrast agent Gd$^{3+}$. For $^{64}$Cu, NOTA-SCN will be used instead. The radiolabeled strand will then be mixed with the other 3WJ component strands to assemble the 3WJ nanoparticles. Figure discloses SEQ ID NOS 34, 34, 34, 1, 34 and 2, respectively, in order of appearance.

Conjugation of DOTA or NOTA to amine modified nanoparticles: One of the fragments ($c_{3WJ}$) of the pRNA-3WJ will be 2'-F modified and end-labeled with amine ($NH_2$) (custom ordered from Trilink). The $c_{3WJ}$-$NH_2$ RNA will be reacted with a 50 equivalent excess of DOTA-NHS (for $^{177}$Lu, $^{111}$In) or NOTA-SCN (for $^{64}$Cu) (Macrocyclics Inc.) (FIG. 14). The DOTA-NHS chelator will conjugated to the RNA in acetonitrile carbonate buffer (pH 10); NOTA-SCN will be conjugated to the RNA in sodium bicarbonate buffer (pH 8). The reactions will be monitored by reverse phase high performance liquid chromatography (RP-HPLC). Unreacted DOTA-NHS and NOTA-SCN will be removed from solution using a 7 kDa weight cutoff spin column pre-equilibrated in sterile water. The chelator modified nanoparticles will be lyophilized and stored at −80° C.

Radiolabeling DOTA and NOTA conjugated RNA: The chelator conjugated RNA fragment will be radiolabeled in acetate buffer (pH 7) over a concentration range of 0.1-1 nM (20-200 µg) to maximize radiolabeling efficiency[G80]. DOTA conjugated nanoparticles will be radiolabeled with 40 MBq of $^{177}$LuCl$_3$ or $^{111}$InCl$_3$ (>50 mCi/µg; Mallinckrodt Pharmaceuticals) at 60° C. for 40 min [G78]. NOTA conjugated nanoparticles will be radiolabeled with 75 MBq of $^{64}$CuCl$_2$ (>100 mCi/g; Essential Isotopes Inc.) at 50° C. for 30 min[G76,G80]. Based on the published work[G76,G78, G79], it is expected to achieve >95% radiolabeling efficiency. Any free radionuclide will be removed using 7 KDa cutoff spin columns pre-equilibrated with buffered saline. The radiolabeled strand will then be mixed with the other 3WJ component strands to assemble the 3WJ nanoparticles (FIGS. 12, 14).

1.1.3 Gadolinium contrast agent: Gadolinium is a common $T_1$-weighted MRI contrast agent. A similar approach using standard NHS chemistry will be used to couple $Gd^{3+}$ to RNA using DOTA-NHS (FIG. 14). GdCl$_3$ and RNA-DOTA solutions will be mixed slowly to avoid any precipitation. The solution will be kept at 75° C. for 1 hr, which will result in ~100% incorporation yield[81]. The chelated RNA strand will be purified by size exclusion chromatography and then mixed with the other 3WJ component strands to assemble the 3WJ nanoparticles (FIG. 12,14)) (See Section 3.1 described in Example 4 for constructing RNA dendrimers with gadolinium).

Without bound by theory, the entire synthesis is kept free from any metal contamination as DOTA is a strong chelator for almost all metal cations. If the contamination of metal cations, such as $Zn^{2+}$, $Cu^{2+}$ and $Fe^{2+}$ occurs, it is difficult to incorporate $Gd^{3+}$ due to both kinetic and thermodynamic issues.

1.2 Construct RNA Nanoparticles Harboring Targeting Ligands

Colon cancer will be used as a model system to evaluate our multifunctional RNA constructs in vitro and in our established subcutaneous, orthotopic, and metastatic mouse models (see Section 2.2 described in Example 3).

Figure 15:
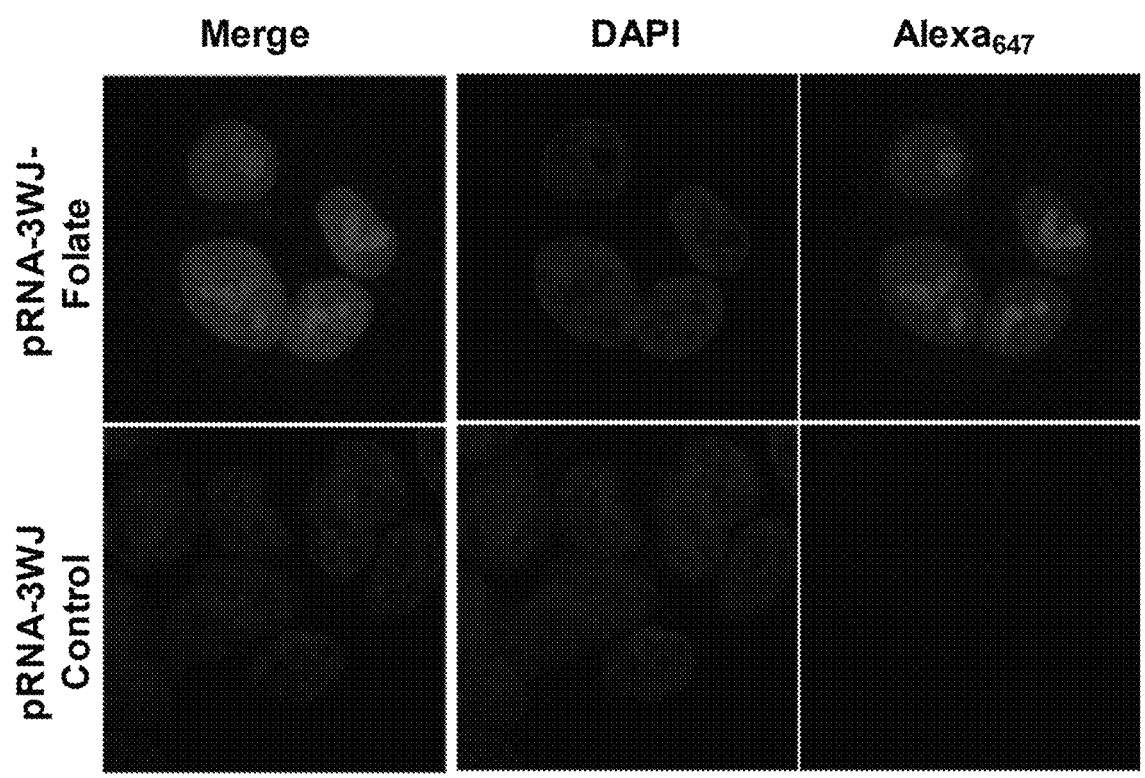
FIG. 15 shows confocal images showing strong binding and entry of pRNA-3WJ-FA nanoparticles into HT29 colon cancer cells. Magnification: 180×.

1.2.1 Folate ligand: Many cancer cells, especially from the epithelial origin overexpress the folate receptor (FR) on the surface elevated by 1000-fold including colon cancer. Folate receptor density increases as the stage or grade of the cancer worsenss[82]. We demonstrated that Alexa$_{647}$-FA-pRNA-3WJ constructs efficiently and specifically bound and internalized to FR+ HT29 and KM20 colon cancer cells in vitro (FIG. 15). More importantly, the RNA constructs specifically and dose-dependently targeted FR+ HT29 colon cancer subcutaneous xenografts in mice with little accumulation in normal organs and tissues (FIG. 22). However, targeting the folate receptor is expected to be successful only in ~one-third of all colon cancers [G83,G84].

Figure 16:
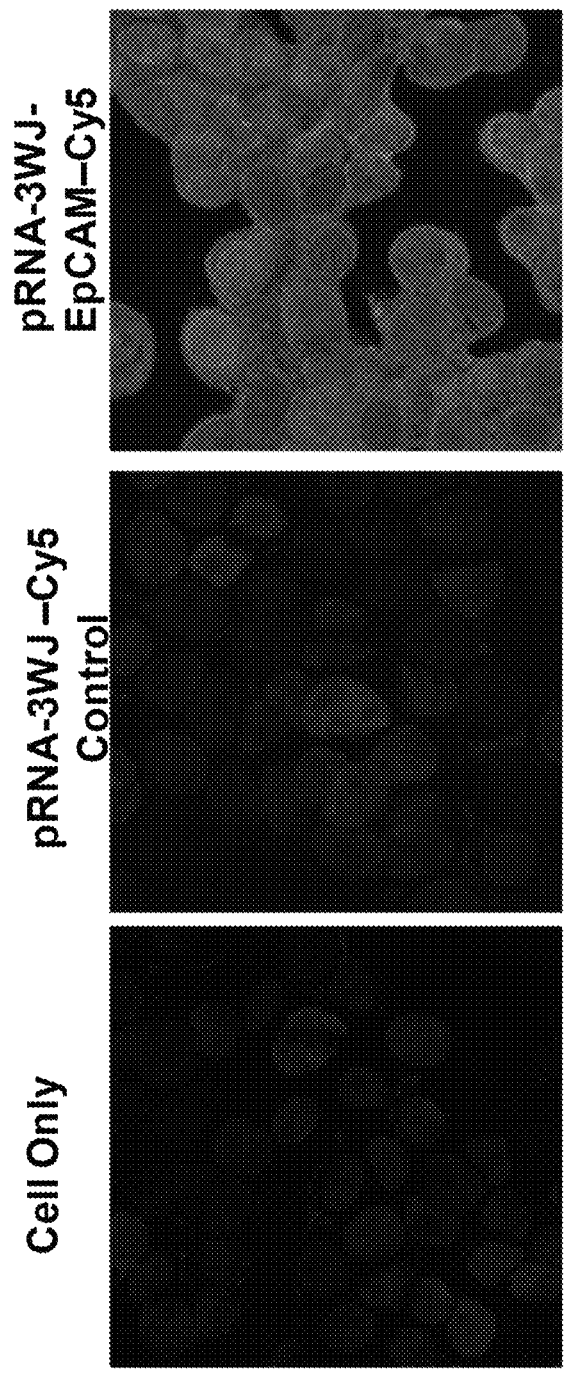
FIG. 16 shows confocal images showing strong binding and entry of Cy5 labeled pRNA-3WJ-EpCAM aptamer constructs into HT29 colon cancer cells. The aptamer was selected from our novel 2'-F 3WJ library based on RNA nanotechnology.

1.2.2 2'-F EpCAM RNA aptamer: As an alternative to folate, we identified EpCAM (Epithelial cell adhesion molecule [*Homo sapiens*] GenBank: AAH14785.1), which is over expressed in primary and metastatic colon cancers, including stem cells [G85-87]. We have developed a novel 2'-F 3WJ library system based on RNA nanotechnology to select 2'-F RNA aptamers using SELEX[G88-89]. We used this library and successfully isolated RNA aptamers with an unusually strong binding affinity for colon cancer EpCAM receptor (FIG. 16).

1.3 Design RNA Constructs Harboring Therapeutic Modules siRNA/Anti-miRNA

Figure 17:
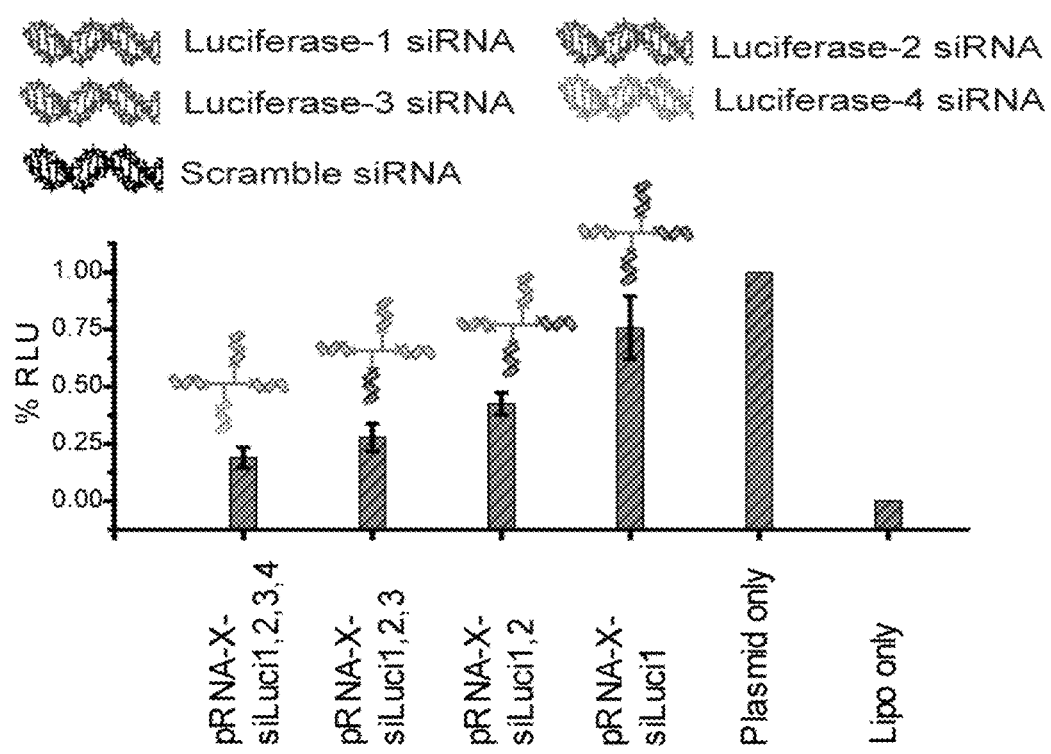
FIG. 17 shows enhanced gene silencing effects of tetravalent pRNA-X nanoparticles harboring different siRNAs targeting different loci on the same gene[10]. RLU: Relative Luciferase Units.

For proof-of-concept of our image-guided drug delivery system, we will incorporate siRNAs targeting luciferase and evaluate the effects in HT29 or KM20 colon cancer cells expressing luciferase. To enhance apoptosis of cancer cells, several groups have tried repeated transfection of siRNA into cells [G90]. However, repeated administrations or high doses of siRNA can lead to high cytotoxicity. We have used the pRNA-X motif as a scaffold to conjugate multiple copies of luciferase siRNA targeting the same gene locus or different loci in one gene. Gene knock-down effects were progressively enhanced by increasing the number of siRNA in the complex [G10] (FIG. 17). Furthermore, 1 nM of pRNA-X nanoparticles with four siRNA modules can achieve the same silencing effects as 100 nM unformulated siRNA[G10].

Alternative 1: siRNA targets: As therapeutic siRNAs, we will induce apoptosis of the colon cancer cells by inhibiting anti-apoptotic protein survivin using siRNAs, as described in our previous publications[G9,G10,G22]. siRNAs is directed to PI3K (a ubiquitous lipid kinase) and its downstream effector proteins (Akt and mTOR) can effectively inhibit CRC cell viability [G91-93, herein incorporated by reference in their entirety]. These siRNAs will be used as alternatives to survivin (UniProtKB/Swiss-Prot: O15392.3).

Alternative 2: anti-miRNA targets: MicroRNAs are small non-coding RNAs (19-25 nt) that display two classes of function, either as oncogenes or tumor suppressors[G94-95]. The pRNA-3WJ motif was shown to be an effective carrier of suppressor miRNA to silence viral genes by targeting the 3'-UTR of coxsackievirus genome [G96-97]. Following a similar delivery principle, we will deliver anti-miRNAs to kill tumors by down-regulating oncogenic miR-21. MiR-21 regulates biological behavior through the PI3K/Akt signaling pathway[G98], and downregulating miR-21 will serve as an alternative to our siRNA strategy. We have constructed a miR-21-luciferase reporter system and found that pRNA-3WJ-Folate-anti-miR-21 nanoparticles can effectively knockdown miR-21 expression after incubation (as opposed to transfection) in KB cells (FIG. 18) (Dan Shu, et al., Systemic Delivery of Anti-miRNA for Suppression of Triple Negative Breast Cancer Utilizing RNA Nanotechnology, ACS NANO, (2015) Vol. 9, No. 10, pp 9731-9740, hereby incorporated by reference in its entirety)

Figure 19:
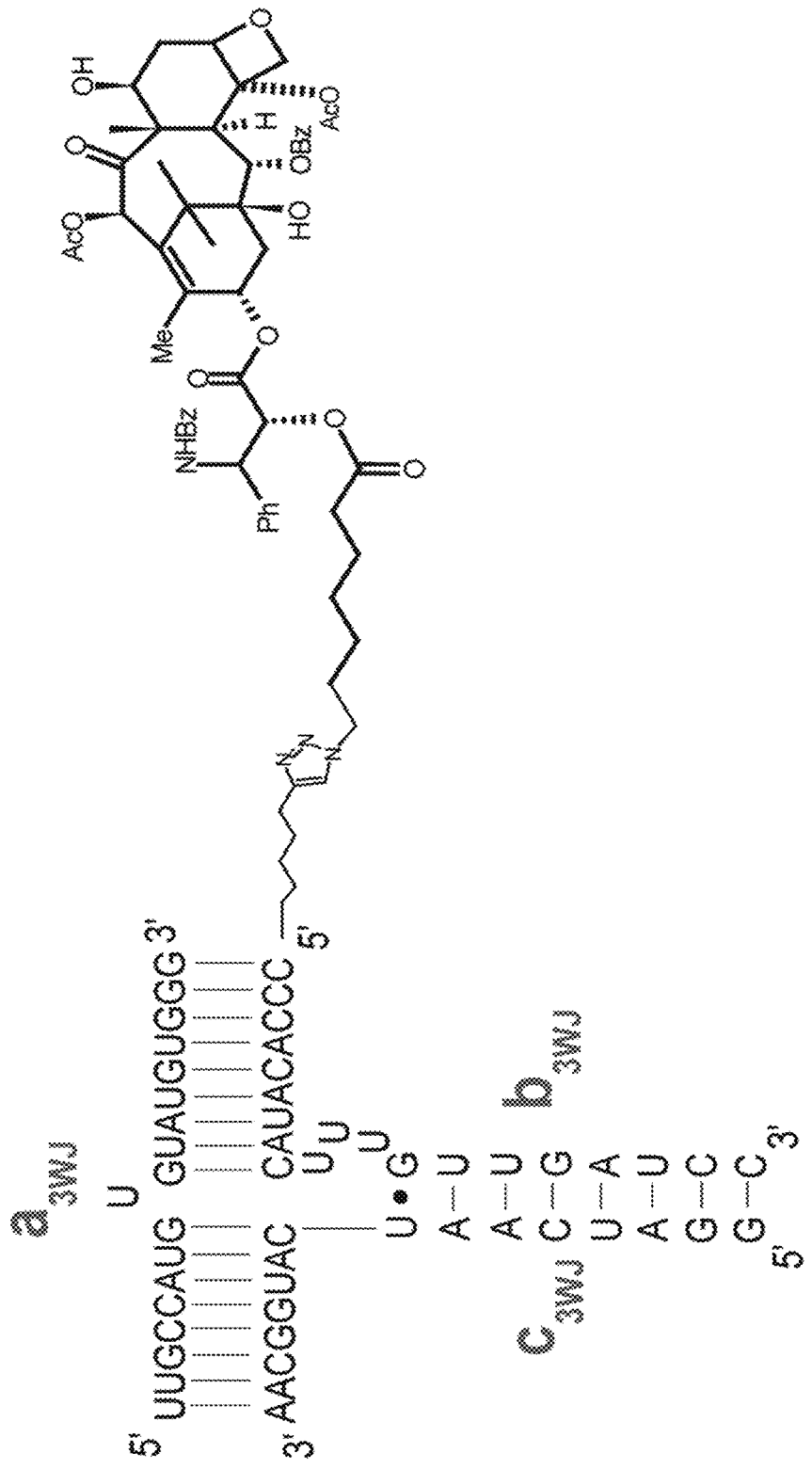
FIG. 19 shows conjugation of Paclitaxel to pRNA-3WJ using 'click chemistry' approach and acid-labile bonds. Figure discloses SEQ ID NOS 1, 3 and 2 respectively, in order of appearance.
Figure 20:
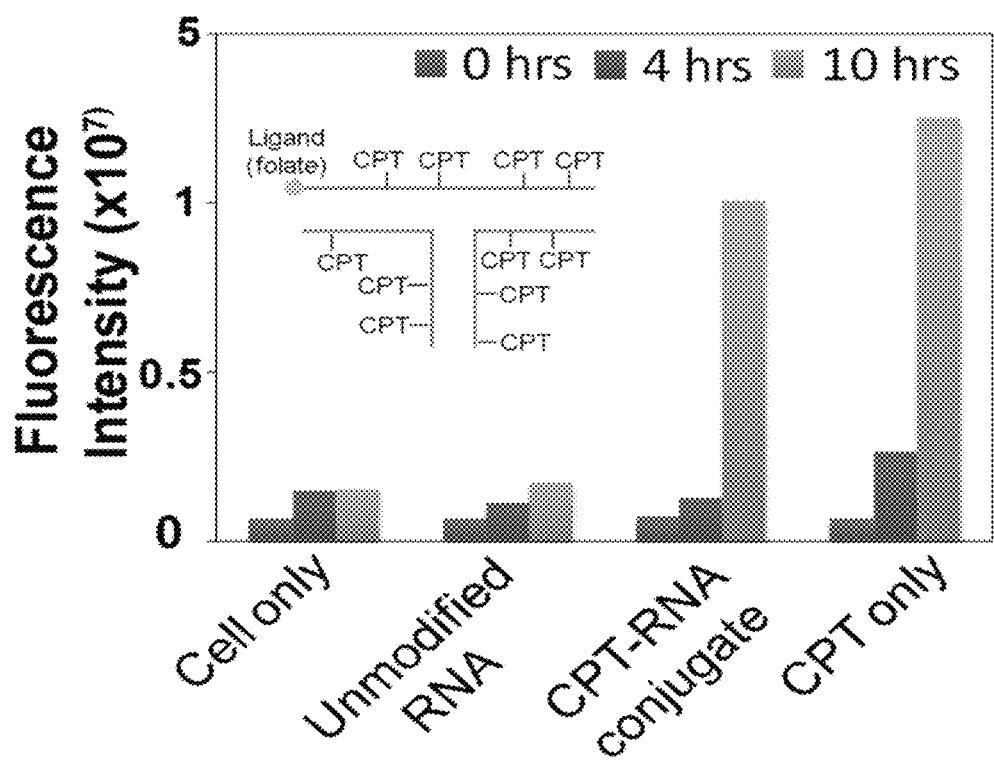
FIG. 20 shows preliminary data of Caspase 3 assay demonstrating cell apoptosis induced by the CPT-RNA strand. Inset: Design of pRNA-3WJ constructs carrying Camptothecin (CPT).

Alternative 3: cytotoxic drugs: We have conjugated Paclitaxel (PTX) and Camptothecin (CPT) to the pRNA-3WJ scaffold using 'click chemistry' approach and acid-labile bonds (FIG. 19) [US 20130116419; Kolb, Hartmuth C., M. G. Finn, and K. Barry Sharpless. "Click chemistry: diverse chemical function from a few good reactions." Angewandte Chemie International Edition 40.11 (2001): 2004-2021, hereby incorporated by reference in there entirety]. The RNA-drug-folate complex can effectively induce cell apoptosis in KB cells (FIG. 20).

1.4: Characterize Biochemical and Biophysical Properties of RNA Nanoparticles

The pRNA-3WJ scaffold harboring different functional modules retain their folding and independent functionalities of all incorporated modules[9,10]. Nevertheless, we will characterize biochemical and biophysical properties of RNA constructs from Section 1.1-1.3 using well-established methods: (1) assay RNA nanoparticle folding and assembly using native gels[G9,G10]; (2) assessment of $T_m$ by quantitative PCR with SYBR Green, temperature gradient gels, or UV absorbance [G9,G10]; (3) assessment of $K_D$ by competition assays using radiolabeled/fluorescent labeled RNA[G9] or SPR; (4) evaluate chemical stability (after 2'-F modifications) by incubating RNA with RNase or 10% FBS [G9,G13]; (5) examine resistance to denaturation by 2-8 M urea in denaturing gels[G9,G10]; (6) structural characterization by AFM imaging[G9-11]; secondary structure prediction by "m-fold" algorithm [G99]; (7) radiochemical stability assays. Briefly, RNA nanoparticles will be initially examined in PBS (pH 7.4), PBS with 1 mM EDTA and in serum at 37° C. Samples of the radiolabeled nanoparticle solution will be removed at various time points over a 24 hr period and examined by HPLC for evidence of degradation or transchelation of the radiometal by the competitive metal chelator EDTA.

Example 3

Evaluation of pRNA-3WJ-Beacon Constructs by NIRF and PET/SPECT Imaging in Colon Cancer Model System This study focuses on construction of the RNA-3WJ-Beacon harboring targeting ligands, therapeutic siRNA/anti-miRNA, and imaging agents to track the delivery and image therapeutic responses non-invasively by NIRF and PET/SPECT in colon cancer mouse models. Detailed histological assays of tumors will be carried out to verify the in vivo non-invasive imaging evaluation. RNA-3WJ-Beacons will be constructed, combining the robust features of the pRNA-3WJ delivery platform with the functional components of molecular beacons and therapeutic siRNA/anti-miRNA as well as cancer targeting ligands, all in one nanoconstruct (FIG. 4). Upon target recognition, the RNA-3WJ-Beacon will generate a 'reporter' imaging signal, which in combination with a 'reference' imaging module will enable us to track the distribution and transport of RNA therapeutics in vivo. We have successfully generated orthotopic and metastatic colon cancer mouse models to evaluate the RNA constructs in vivo.

Significant challenges exist in detecting endogenous gene expression and silencing in vivo, including probe design, in vivo delivery, specific targeting, and probe sensitivity. Molecular beacons to image intracellular RNA expression in vitro by competitive hybridization method have been reported[G100-108], but they were done in solutions with defined molecular beacon-target conditions. Although these studies showed the feasibility of detecting mRNAs and monitoring the transportation of RNAs in cells, the procedure for delivery of the molecular beacons through microinjection or by liposome delivery has made it difficult to apply this promising technology into broad research areas or into a routine clinical procedure. Challenges include: (1) nuclease degradation of RNA or DNA in vivo; (2) low signal-to-background ratio; (3) inefficient competitive hybridization due to steric hindrances; and (4) lack of cell specificity; and (5) inefficient delivery due to non-specific accumulation in liver and lungs. To overcome these problems, we have developed an innovative RNA-3WJ-Beacon platform (FIG. 4B) that incorporates the functionality of molecular beacons into the robust pRNA-3WJ delivery system that displays highly efficient cancer targeting capabilities with little accumulation in normal organs such as, liver, lungs, and kidneys. Upon target recognition, the RNA-3WJ-Beacon will generate a 'reporter' imaging signal, which in combination with 'reference' imaging module will enable us to track the distribution and transport of the therapeutics RNA nanoparticles in vitro and in vivo using our well-established colon cancer model system. Our RNA constructs are polyanionic in nature and can therefore avoid nonspecific cell entry across the negatively charged cell membranes[G67-70]. In addition, they can deliver therapeutics to cells after incubation as opposed to transfection and microporation, typically used in other systems [G101,G103, G105,G106,G109,G110].

Figure 4A:
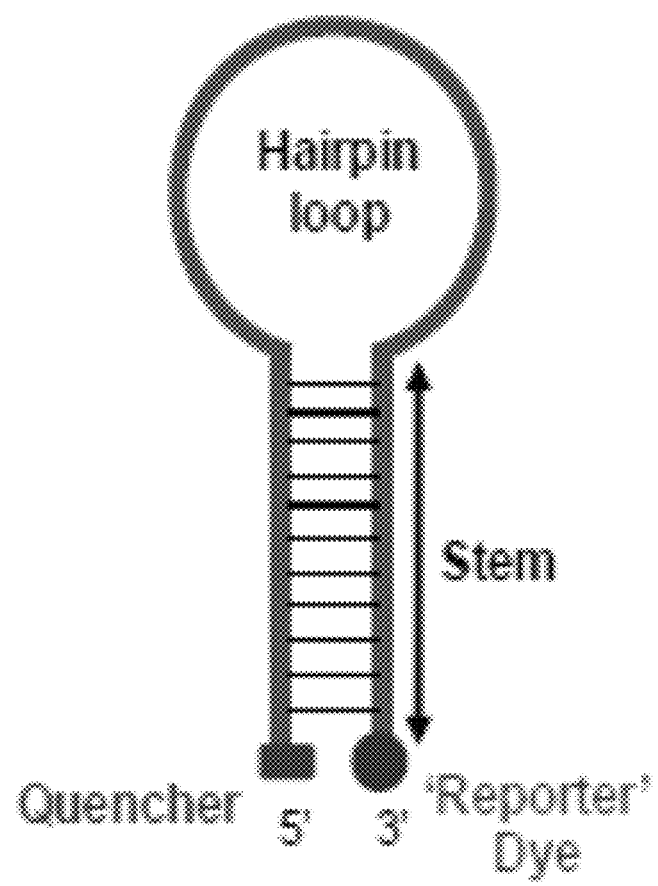
FIGS. 4A-4B includes diagrams illustrating comparison of (A) conventional molecular beacon and (B) RNA nanotechnology-based 3WJ-Beacons.
Figure 4B:
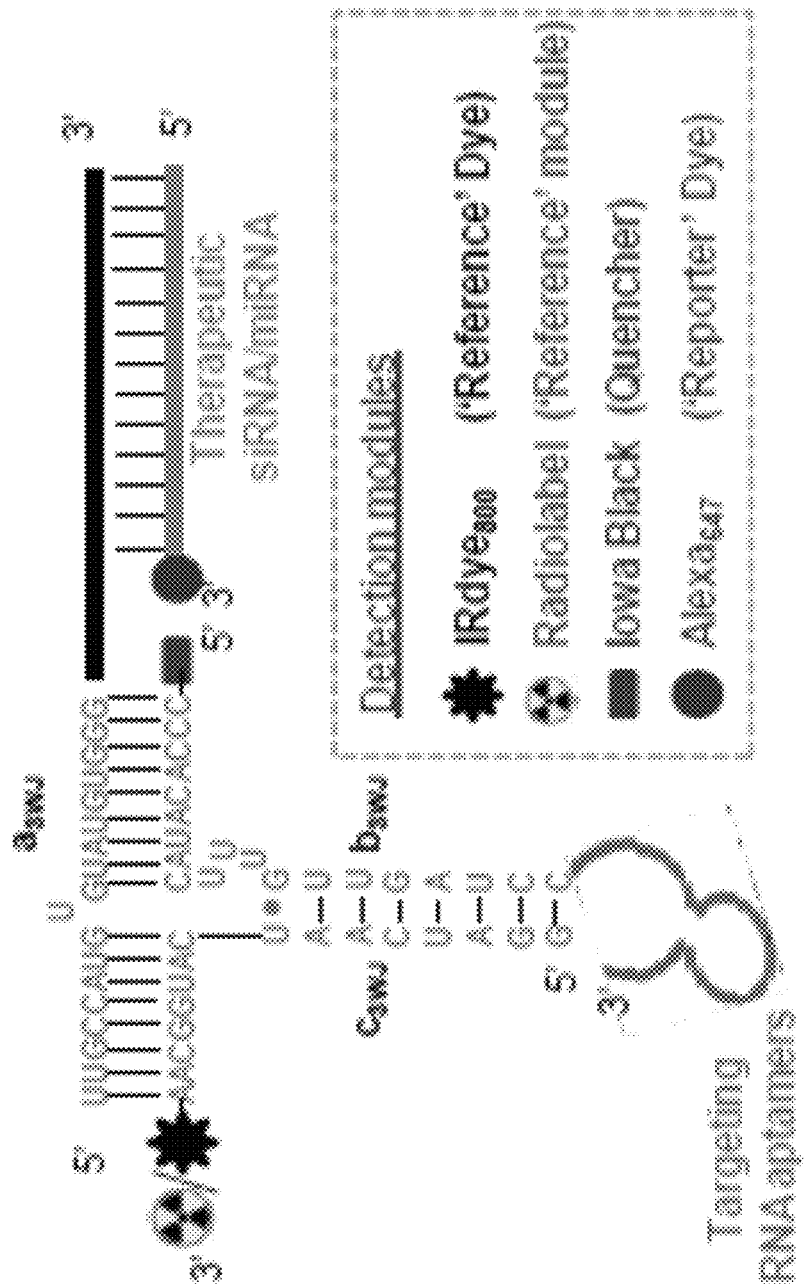
Figure 5:
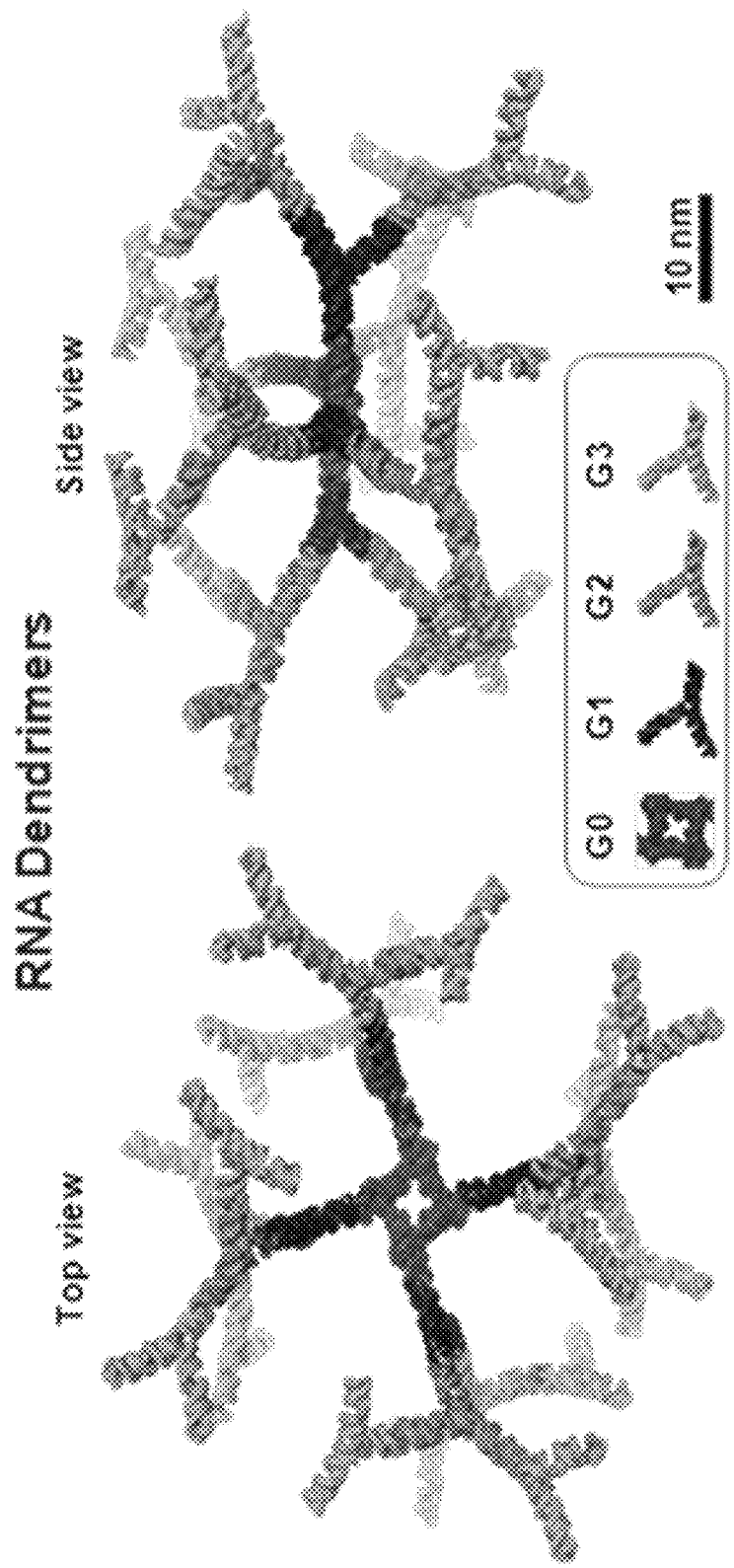
FIG. 5 includes construction of pRNA-3WJ based RNA Dendrimers (G0-G3) for harboring multiple gadolinium contrast agents for MRI Imaging and radionuclides for PET/SPECT imaging.
Figure 21:
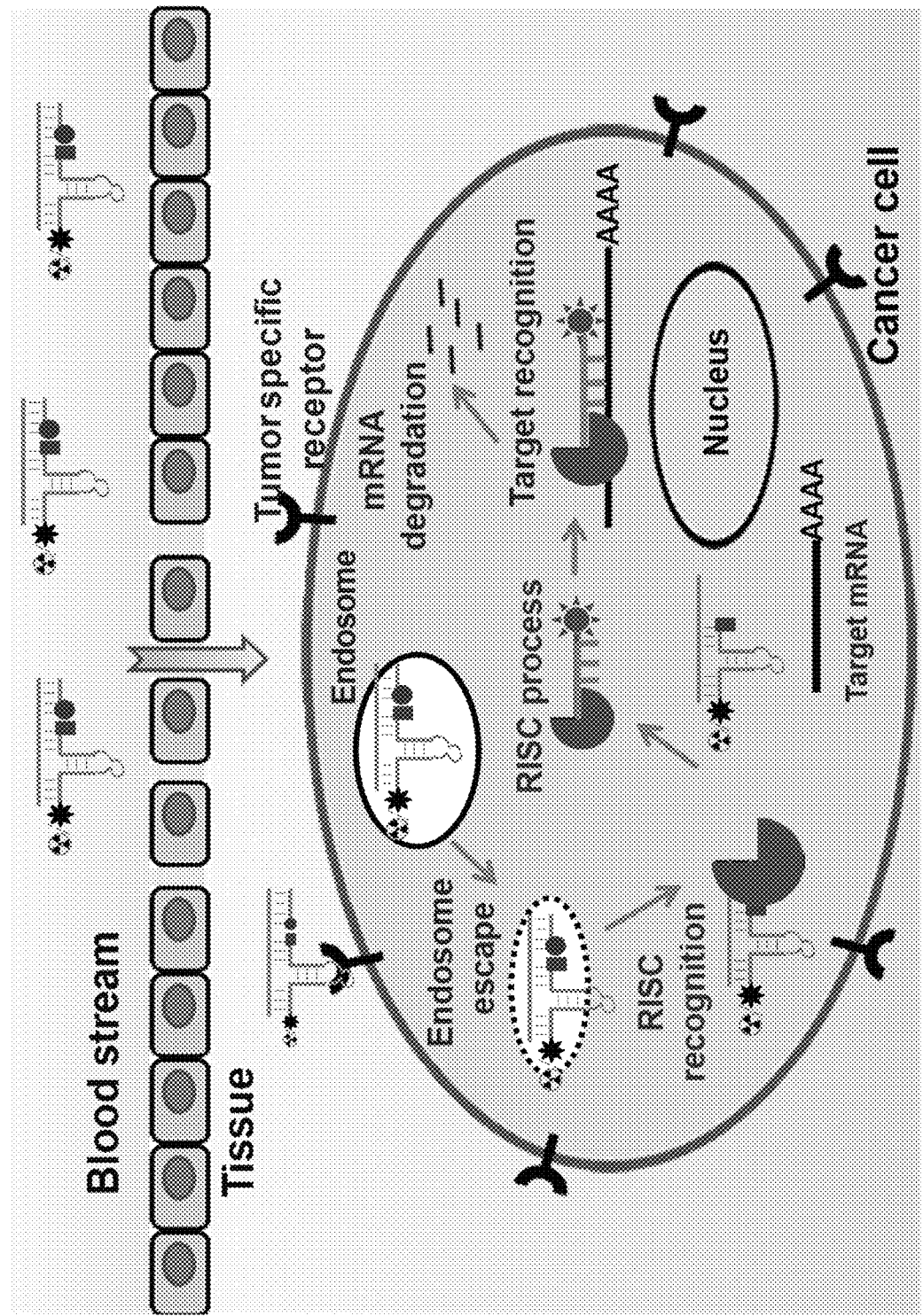
FIG. 21 shows working principle of pRNA-3WJ-Beacon. Once internalized into the cells and released from the endosome, the RNA-3WJ-Beacon is processed by RISC and the siRNA component will be released from the 3WJ complex and away from the quencher, thereby restoring the fluorescence of 'reporter' dye Alexa647 for real-time imaging

Conventional molecular beacons are stem-loop (hairpin) structures of oligonucleotide dual-labeled with a fluorophore on one end and quencher on the other (FIG. 4A). The fluorophore and the quencher are held in close proximity resulting in none or low fluorescence signal. Upon hybridization with a perfectly matching complementary RNA target, the 'reporter' fluorophore and quencher separate and fluorescence is restored. Our RNA-3WJ-Beacon that contains a 'reporter' fluorophore darkened by a quencher in close proximity will elicit a fluorescence signal upon cleavage of the incorporated siRNA/miRNA by Dicer in the cell (FIG. 21). The 'reference' probe (either fluorescent dye or radiolabel) is present on another strand of the 3WJ complex and remains active regardless of the conformation of the RNA nanoparticles.

2.1: In Vitro Characterization of RNA-3WJ-Beacon-(FA or EpCAM Aptamer)-(siRNA or Anti-miRNA) in Colon Cancer Cells 2.1.1 Assay specific cell recognition and entry of multifunctional RNA-3WJ-Beacon: The RNA-3WJ-Beacon carrying FA (or EpCAM aptamer) will recognize HT29 colon cancer cells specifically and internalize into the cells through receptor mediated endocytosis. The binding and internalization of RNA-3WJ-Beacon will be examined by flow cytometry, and confocal microscopy, with appropriate controls (FIG. 15-16). These assays are well established in [G9-11, G22,G23]. IRdye 800 has excitation/emission maxima at 774 nm/789 nm, while Alexa$_{647}$ has excitation/emission maxima at 647 nm/668 nm. $^{177}$Lu, $^{111}$In or $^{64}$Cu radionuclides will serve as alternative 'reference' imaging modules to track the RNA-3WJ-Beacons in vivo.

2.1.2 Assay the gene silencing effects of multifunctional RNA-3WJ-Beacons: The RNA-3WJ-Beacon-(FA or EpCAM aptamer)-(siRNA or anti-miRNA, from Section 1.3 describe in Example 2) with appropriate scramble controls will be incubated with colon cancer cells without transfection reagents. Once internalized into the cells and released from the endosome, the RNAi Induced Silencing Complex (RISC) will bind to the branch of pRNA-3WJ-Beacon containing the siRNA or anti-miRNA. If the siRNA/anti-miRNA is processed correctly, it will be released from the 3WJ complex and away from the quencher, thereby restoring the fluorescence of 'reporter' dye Alexa$_{647}$ (FIG. 21). The released siRNA/anti-miRNA will trigger knockdown of the target gene in a dose-dependent manner, which can be tracked in real-time by monitoring the fluorescence of 'reporter' dye Alexa$_{647}$, following published procedures

[G101,G102,G105,G109]. The gene knock-down effects will be validated by functional assays:

For quantification of luciferase siRNA silencing effects, we will use HT29-Luciferase expressing cells and image the cells using IVIS Spectrum system. The luminescence intensity, photon counts per second from each well will be recorded and plotted. Cell numbers will be quantified by staining with sulforhodamine B (SRB) assay, as described in our publications[G10,G11] The relative luciferase activity will be used to reflect the expression level of firefly luciferase gene by normalizing the firefly luciferase activity with SRB readouts. For survivin siRNA, we will use RT-PCR and Western blot to determine gene expression at mRNA and protein levels, respectively, similar to our previous publications [G9,G10,G21-23]. The effects of RNA nanoparticles on cell growth and apoptosis will be assayed by routine assays [G9,G10,G21-23], such as WST-1, TUNEL, in situ caspase activity, DNA fragmentation, and Annexin V/PI staining.

For evaluating miR-21 knockdown, at different time points, the incubation efficiency will be monitored by fluorescence microscopy or in situ hybridization with miR-CURY™ LNA detection probes, following established protocols[G111]. We will isolate and analyze the total RNA for miR-21 levels using real-time PCR. The functionality of miR-21 on its validated targets (ex. PTEN, PDCD4, RECK) will be assayed by RT-PCR at the mRNA level and Western blot at the protein level or immunostaining.

Without being bound by theory, the $Alex_{647}$ dye that is attached to the 3'-end of siRNA or anti-miRNA (FIG. 12) may interfere with the siRNA or miRNA function. This can be solved by alternating the sense or antisense strand of the siRNA. It has been shown that modification of sense or antisense strands on the siRNA made a difference on the efficiency of gene silencing[G112]. (2) To account for non-specific RNA-3WJ-Beacon effects, we will implement published procedures used to determine the extent of non-specific opening using ratiometric analysis [G113]. Briefly, the fluorescence ratio (total integrated 'reporter' fluorescence/total integrated 'reference' fluorescence) will be compared with same RNA-3WJ-Beacon samples prior to intracellular delivery. (3) The extent of conventional molecular beacon binding to target mRNA is highly dependent on the selection of target sequences and their accessibility[G103]. Our RNA-3WJ-Beacon construct design does not utilize a hairpin with extended sequences. Once Dicer processes the siRNA off the 3WJ, the siRNA retains its authentic size and shape (~21 nt dsRNA) for optimum function.

Alternative approaches: (1) In one embodiment, a disulfide linkage between the siRNA strand and 3WJ core complex will be incorporated. In presence of a reductive environment in cytoplasm, the disulfide bond will cleave and trigger activation of the siRNA and conjugated 'reporter' fluorescence[G104]. (2) We will employ a photo-decaging strategy using photo-cleavable linkers, whereby the molecular activity of the molecular beacon is masked by a photo-responsive caging group and then recovered by specific light irradiation at a designated time and location[G114]. In another embodiments, Acid-labile linkers will be used between the siRNA strand and 3WJ core complex.

2.1.3 Determine the toxicity profiles of RNA-3WJ-Beacon harboring FA (or EpCAM aptamer), siRNA, (or anti-miRNA) in vitro: An issue concern regarding the evaluation of RNA interference is the activation of innate immune responses[G115-117]. We have shown that our pRNA nanoparticles display favorable pharmacological profiles[G12]. We will use RT-PCR analysis, ELISA, and flow cytometry to scout for the activation of protein kinase R (PKR), toll-like receptor (TLR) and interferon (INF) pathways in human peripheral blood mononuclear cells (PBMC)[G12, G118] (FIG. 25). Cell proliferation (MTT) and apoptosis assays (TUNEL) will also be performed to assay for cytotoxic effects.

2.2 Validation of Our Multivalent RNA Nanoparticles In Vivo Using Mouse Models 2.2.1 Subcutaneous xenograft model: Subcutaneous xenograft are good model systems since they mimic the tumor-extracellular matrix interactions, inflammation and angiogenesis. We will establish subcutaneous xenografts first by injecting $1\times10^6$ HT29 tumor cells directly into the flank and then intravenously inject the multifunctional RNA constructs. Preliminary data demonstrated that $Alexa_{647}$ labeled pRNA-3WJ-Folate constructs can efficiently target subcutaneous HT29 colon cancer xenografts in mice after systemic injection without accumulating in normal organs and tissues (FIG. 22). The experimental designs will include: (1) pRNA-3WJ-Beacon-(FA or EpCAM aptamer)-(siRNA/anti-miRNA); (2) pRNA-3WJ-Beacon-(w/o targeting ligands); and (3) pRNA-3WJ-Beacon-(FA or EpCAM aptamer)-(scrambled siRNA/anti-miRNA). The frequency of dosing required to achieve tumor growth inhibition will be determined empirically and will be monitored over time by whole body NIRF and PET/SPECT imaging before sacrificing the mice.

Figure 23:
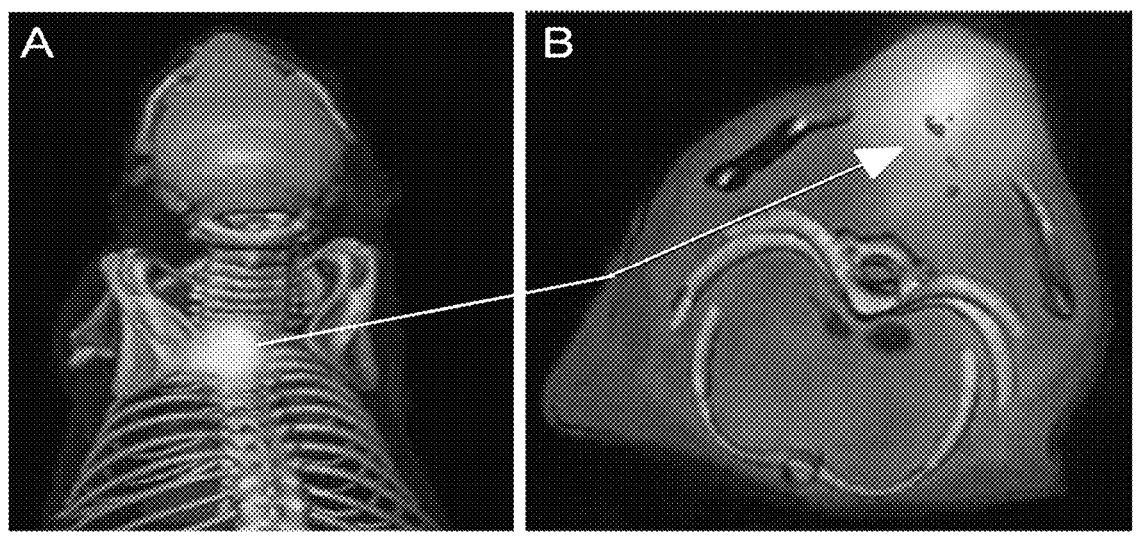
FIGS. 23A-23B shows Micro-SPECT/CT imaging of MDA-MB-435 breast cancer subcutaneous xenograft bearing mice[119]. (A) The whole body SPECT images were fused with conventional micro-CT images to validate regions of increased uptake of radiolabeled [11]In-DOTA(GSG)-KCCYSL peptide (SEQ ID NO: 31). (B) The trans-axial SPECT/CT image focusing on tumor uptake in the xenograft. (Kumar S R, et al., Clin. Cancer Res. 2007 Oct. 15; 13(20):6070-9).

Based on previous radionuclide experiences, we will inject ~0.5-1.5 mCi of radiolabeled ($^{177}$Lu, $^{111}$In or $^{64}$Cu) RNA-3WJ-Beacon into the tail vein of each mouse[G73, G74,G76,G119,G120]. Imaging time points and duration of acquisitions will be dependent on radionuclide half-life and biodistribution data. Whole body small animal SPECT and PET images will be obtained on a Siemens INVEON multimodality SPECT/CT system combined with a docking Siemens INVEON PET system (FIG. 23). Anatomical imaging and X-ray computed tomography (CT) will be performed immediately prior to the PET study.

Organ and tumor imaging, full necropsy, and histological profiles will be conducted to evaluate tumor regression, tumor growth delay, survival time extension, and tumor-free cures. Detailed target gene expression profiles for siRNA and anti-miRNA mediated therapies will be determined on both mRNA and protein levels (see Section 2.1.2).

Figure 24A:
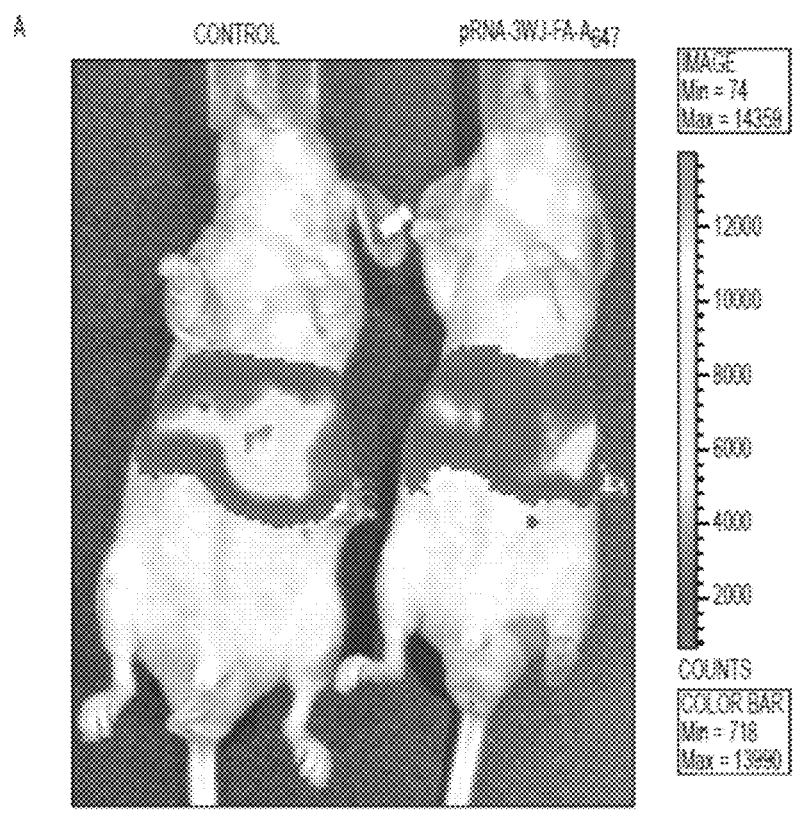
FIGS. 24A-24C shows targeting of metastatic liver cancer by pRNA-3WJ-Folate nanoparticles. (A) Bio-luminescence images confirming liver metastasis. The pRNA-3WJ-FA-Alexa$_{647}$ nanoparticles specifically targeted HT29 liver metastatic cells, but not the normal liver parenchyma cells after systemic injection, as shown by macroscopic (B) and histological (C) assays. Control: PBS treated mice. Green: cancer cells; blue: DAPI for nucleus; magenta: Alexa$_{647}$ RNA; White arrows: Folate-pRNA-Alexa$_{647}$ accumulation and binding; Yellow arrows: normal liver parenchyma.

2.2.2 Orthotopic model: Orthotopic models more closely mimic the microenvironment of the tumor, since cancer cells grow in their natural location and therefore replicate colon cancer with high fidelity. We will generate several orthotopic xenografts in nude mice by injecting $1\times10^6$ HT29 cells expressing luciferase directly into the cecum of nude mice after surgical procedures (laparotomy for exposure of the cecum). The tumor growth will be monitored by bioluminescence imaging (FIG. 24A). The promising RNA constructs from subcutaneous xenograft assays will then systemically injected in mice monitored over time by whole body fluorescence and PET/SPECT imaging before sacrificing the mice, as described in Section 2.2.1.

Alternative approach: Xenografts derived directly from patients have better retention of the morphological features, such as human stroma and are more heterogeneous than tumors derived from established cell lines, and, therefore, represent important in vivo models. We will generate orthotopic xenografts using these heterogeneous patient-derived tumor cells and evaluate the therapeutic effects of our RNA nanoparticles.

Figure 24B:
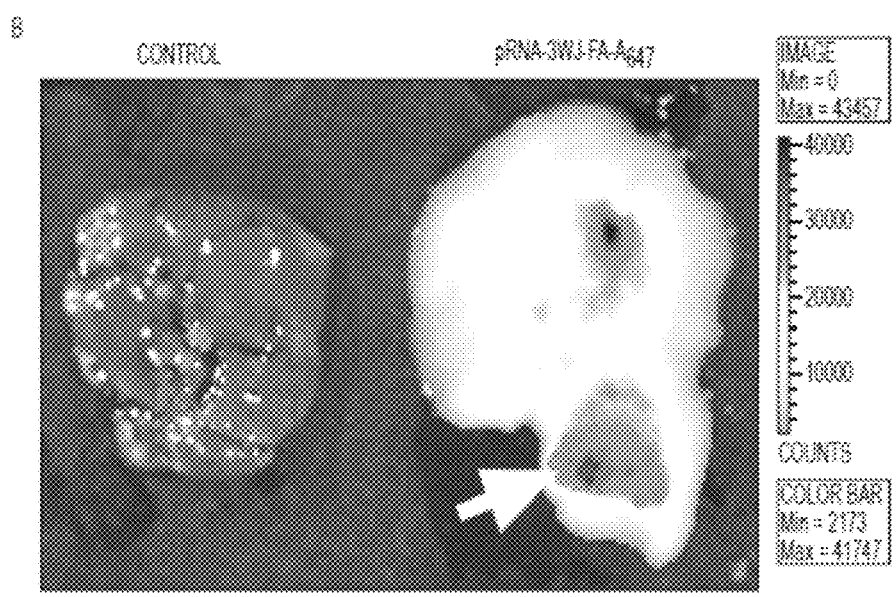
Figure 24C:
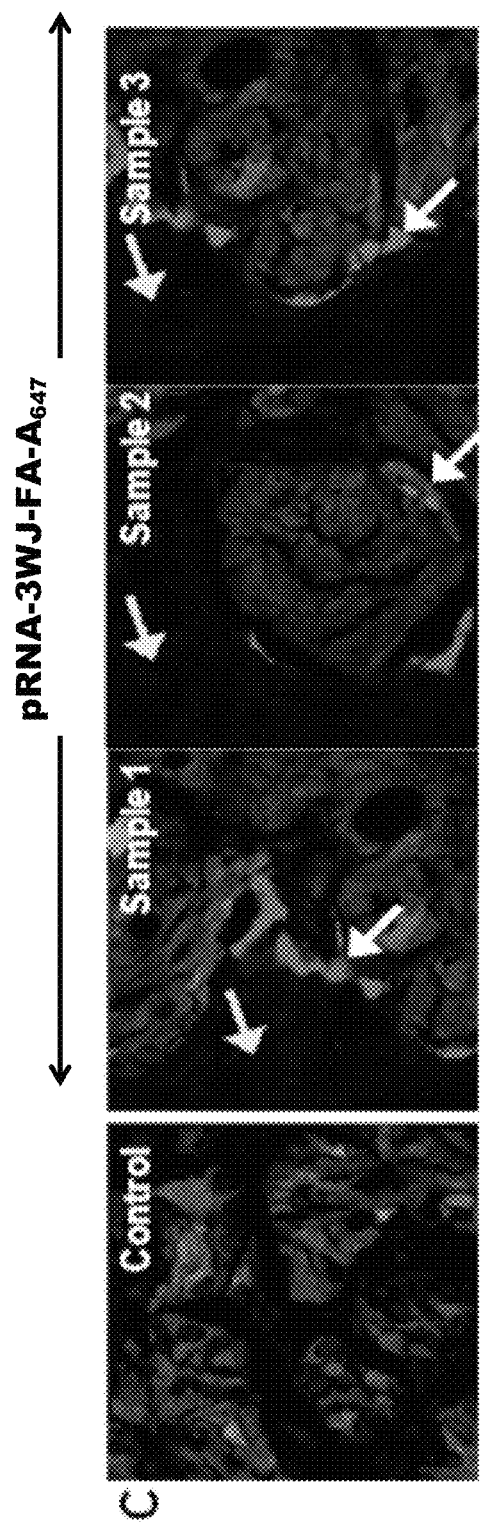

2.2.3 Metastasis model: We will test whether our new RNA constructs can be used to track down colon cancer metastasis. Liver metastasis will be established by injecting HT29 cells expressing luciferase directly into the spleen or the wall of the cecum and monitored by bioluminescence imaging (FIG. 21A). Preliminary data demonstrated that after systemic injection in mice, $Alexa_{647}$-labeled pRNA-3WJ nanoparticles efficiently targeted HT29 liver metastatic cells, but not the normal liver parenchyma cells (FIG. 24). The RNA-3WJ-Beacon will be injected intravenously and monitored over time by whole body NIRF and PET/SPECT imaging before sacrificing the mice, as described in Section 2.2.1., described here in Example 3.

Without being bound by theory, targeting a single pathway, such as anti-apoptotic machinery may not result in significant tumor regression in vivo. We will therefore evaluate cocktail treatment strategies using multifunctional RNA constructs harboring siRNA/anti-miRNA. (2) For in vivo delivery of RNA therapeutics, an important consideration is endosome escape. We are currently developing a 'click chemistry' approach to incorporate endosome disrupting agents (for proton sponge effect) to our 3WJ scaffold. (3) Lack of an immune system in SCID mice can profoundly affect tumor development and progression. We will use $IL2rg^{-/-}$ NOG (NOD-SCID $IL2rg^{-/-}$) mice, which can be readily humanized using hemopoietic stem cells. After establishing orthotopic xenografts in mice, we will inject human PBMCs, and bone marrow to develop functional blood and immune systems[G121]. We can then systemically inject the RNA constructs and assay the therapeutic effects.

2.2.4 Assessment of biodistribution and pharmacokinetic profiles in mice: Our pRNA scaffold display favorable pharmacological profiles: 10-fold (5-10 hrs) enhancement in half-life compared to regular siRNA counterparts (0.25-0.75 hrs); CL of <0.13 L/kg/hour; Va of 1.2 L/kg; non-induction of interferon-I or cytokine production in mice. Repeated intravenous administrations in mice, up to 30 mg/kg, did not result in any toxicity (FIG. 25) [G12]. Previous studies were done using $Alexa_{647}$ labeled RNA nanoparticles, and due to quenching by the blood, the overall uptake by tumors and organs can be underestimated. We will add an additional radiolabel component ($^{17}Lu$, $^{111}In$ or $^{64}Cu$) to quantitatively assess the biodistribution (organ and tumor accumulation), PK/PD, and toxicity profiles of RNA constructs, following our previous publications [G12,G76,G77]. The percent injected dose per gram (% ID/g) and percent injected dose (% ID) will be calculated for each tissue.

Example 4

Design pRNA-3WJ Dendrimers to Carry MRI Contrast Agent and Radionuclides for Imaging in Colon Cancer Mouse Models This study focuses on construction of RNA Dendrimers harboring targeting ligands, contrast agents for MRI, and radioisotopes for PET/SPECT imaging and evaluate their functionalities non-invasively in colon cancer mouse models.

MRI is a powerful imaging modality owing to its non-invasive nature, superb spatial resolution at the sub-millimeter range, and excellent potential for longitudinal studies[109,122]. Contrast agents have been employed to enhance the sensitivity of the MRI scan. Clinically used FDA-approved low molecular weight contrast agents, such as Gd(DTPA) (Magnevist®) or Gd(DOTA) (Dotarem®) suffer from non-specificity; relative low signal enhancing effects; rapid extravasation from the blood vessels; and fast elimination from the circulatory system. Therefore they often require repeated administrations and high dosages, which in turn induces false-positive contrast enhancements and Gd-mediated toxicity (Nephrogenic Systemic Fibrosis)[G123].

In recent years, extensively branched 3D structures called dendrimers have become an attractive platform for building multifunctional macromolecular nanomaterials as diagnostic and therapeutic agents[G124-131]. MRI contrast agents composed of multiple Gd(III) chelates assembled on a dendrimer platform are much more efficient and effective in modulating the longitudinal relaxation rate and time of water protons, as compared to a single chelate unit analogue [G109]. This was demonstrated with Gd(III) chelates to high molecular weight carrier poly(amidoamine) (PAMAM) and poly(propyleneimine) (PPI) dendrimers [G125,G127,G129, G131-133] that prolonged intravascular retention and circulation time, slowed down molecular rotation which resulted in a short relaxation time, and increase in relaxivity, and this in turn improved resolution and sensitivity.

Without being bound by theory, if the negatively charged RNA polymer can replace PAMAM and PPI to build dendrimers, it will avoid the interaction with negatively charged cell membrane and will not trigger non-specific cell entry and associated toxicity [G134,G135]. The body treats RNA as a material of its own and will reduce liver/lung accumulation due to phagocytosis. Compared to other chemical polymers, the degradation of RNA can be timely controlled by adjusting the percent and location of chemically modified stable nucleotides [G13,G56-58]. Furthermore, our RNA-based Dendrimer-Gd(III)-chelate complex will retain the reported favorable attributes of the pRNA-3WJ nanoparticles[G9-12], such as thermodynamic stability, desirable pharmacokinetic profiles including free of normal organ accumulation and strong cancer targeting, non-toxic nature, and well-defined structure (monodisperse), while providing additional high relaxivity properties of MRI contrast agents.

Figure 26C:
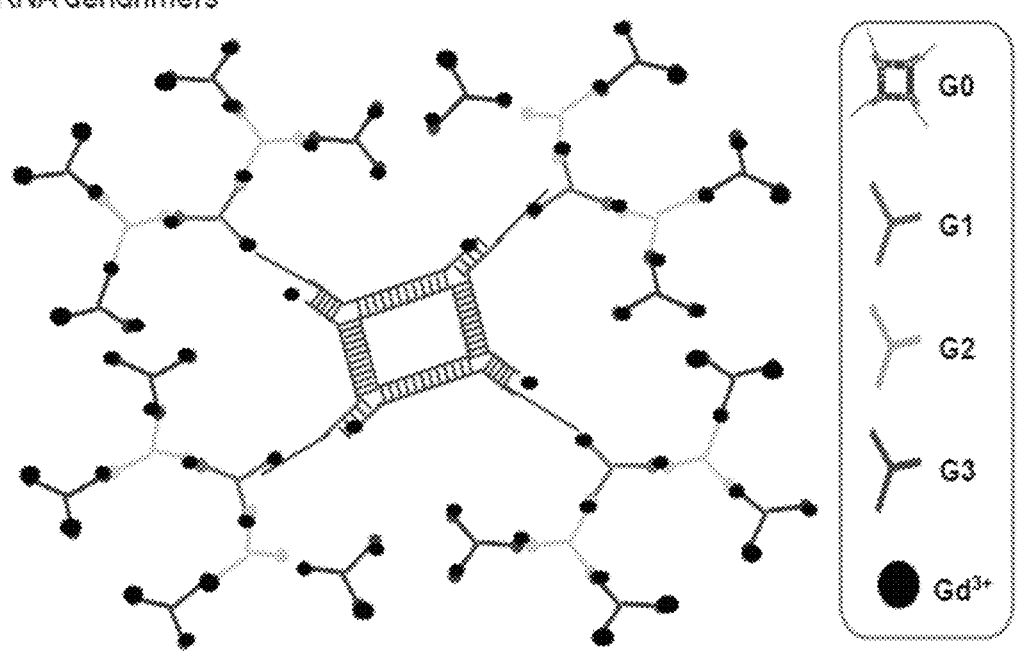

3.1 Construction of RNA Dendrimers Using pRNA-3WJ Motif Harboring Gadolinium Contrast Agents, Radionuclides and Targeting Ligands We previously applied a RNA nanotechnology based bottom-up approach to construct large macromolecular assemblies of RNA nanoparticles by branch extension of pRNA-3WJ motif (FIG. 26)[G11]. More recently, we solved the crystal structure of the pRNA-3WJ scaffold[14], which will facilitate the design of RNA Dendrimers. The 3WJ motif is a highly programmable building block and can be used to generate square shaped architectures (consisting of 3WJ motifs at each corner) to serve as G0 core. The square shape will eliminate any steric hindrances that may arise in the course of building higher-ordered structures. A step-wise iterative assembly approach will then be applied via intramolecular interactions between pRNA-3WJ motifs to construct highly branched Generation-3 (G3) RNA Dendrimers with precise control of size (~60 nm), shape (3D globular) and stoichiometry (FIG. 26). From Section 1.1-1.2 of Example 2 we will have constructed pRNA-3WJ harboring NIR fluorophores, radionuclides, galodinium contrast agents and folate targeting ligand. These functionalized pRNA-3WJ units will be placed with control at any desired location within the G3 construct to generate multifunctional G3 RNA Dendrimers harboring gadolinium for MRI, radionuclides for PET/SPECT imaging and folate, as a targeting ligand (FIG. 26).

Our approach does not require any linkers, such as PEG which has been used in higher-ordered Dendrimers to increase Gd-payload, but with modest increase in relaxivity (due to large amount of internal motion caused by PEG linkers within Dendrimers)[G124]. In addition, our construct can be labeled with Gd-chelates on the outer surface as well as inner core (which is readily accessible to water), thereby ensuring higher Gd payloads without any cross-linking, such as those recently used to generate Dendrimer porous nanoclusters[G124]. This in turn will reduce the dose (lower than 0.2 mmol/kg that is clinically used for Magnevist™) employed for in vivo imaging and associated metal toxicities. Finally, RNA Dendrimer constructs allow integration of targeting and imaging modules leading to the new design of targeted contrast agents.

We will conjugate Gd(DOTA) to our RNA Dendrimers (see Section 1.1.3 of Example 2 for conjugation), which is known to be a better contrast agent in terms of chemical stability (dissociation of the metal ion was exceedingly slow even at low pH (2-4), on the order of days) and thus potentially less toxic as compared to Gd(DTPA)[G136]. The assembly of RNA Dendrimers will be verified by gel assays and AFM (see Section 1.4 of Example 2). Transmission Electron Microscopy (TEM) will then be used to confirm the labeling of RNA Dendrimers with Gd. Since Gd ions are electron dense, RNA-Gd Dendrimers can be directly imaged on a carbon-coated copper grid without any additional staining reagents.

3.2 In Vitro Characterization of RNA Dendrimers 3.2.1. Molar relaxivity measurements: Relaxivity expresses the ability of a paramagnetic material to perform as a MRI contrast agent. The water proton relaxation enhancement by the Gd compound is dependent on the concentration. It is quantitatively described by the equation $(1/T_1)=(1/T_{1o})+r1[Gd]$, where $T_1$ is the relaxation time of the water proton' $T_{1o}$ is the water proton relaxation time of pure water, [Gd] is the concentration of the gadolinium compound, and r1 is defined as the compound's relaxivity. The relaxivity of a gadolinium compound can be quantitatively described by the Solomon-Bloembergen-Morgan theory[137]. The simplified model is represented by the equation $r1=qP_m/(T1_m+\tau_m)$, where $P_m$ is the concentration of water proton, which is constant, q is the hydration number (the number of water molecules bound to each Gd cation), and $\tau_m$ is the lifetime of the bound water molecule. Finally, $T1_m$ is a fitted parameter (the bound water proton relaxation time), and is decided by factors such as the strength of the magnetic field and the size of the Gd compound. The Solomon-Bloembergen-Morgan theory precisely predicts the performance of the Gd-based MRI contrast agents and aids the design of contrast agents with high relaxivity and 'smart' characteristics. The relaxivity and relaxation rate constants of the RNA-Gd Dendrimers will be compared to commercial contrast agent Dotarem® at different magnetic field strengths and solution conditions.

3.2.2. Assay cell binding and uptake: To confirm the folate receptor targeting capabilities of the multifunctional RNA Dendrimers, HT29 colon cancer cells will be incubated with RNA Dendrimer-Gd-FA-Alexa$_{647}$ constructs, with appropriate controls and subsequently analyzed by flow cytometry and confocal fluorescence microscopy (FIG. 15-16), as described in Example 3 at Section 2.1. Cell proliferation (MTT) and apoptosis (TUNEL) assays will also be performed to assay for specific cytotoxic effects.

To further investigate the MRI contrast capabilities, HT29 cells will be incubated with RNA Dendrimer-Gd-FA-Alexa$_{647}$ constructs and assessed by acquiring T1-weighted magnetic resonance images of HT29 cells that pelleted in PCR tubes. HT29 cells in presence of Gd will exhibit a significant enhancement in MR signal intensity compared with control cells.

3.3 Characterization of RNA Dendrimers in Colon Cancer Mouse Models

An advanced 3T Siemens Magnetom Trio scanner with high performance gradients, echo-planar whole body imaging and hydrogen spectroscopic capabilities for both human and animal studies. For dedicated animal studies, a modern Bruker/Siemens 7T MR scanner will be used [G138,G139] (FIG. 27) to evaluate our RNA Dendrimers.

We will generate subcutaneous, orthotopic and metastatic colon cancer mouse models (see Section 2.2, described in Example 3) to evaluate the multifunctional RNA Dendrimer-Gd-Folate-radiolabel constructs, with appropriate controls. Axial MR images of mice harboring tumors will be acquired pre-contrast and at various time-points after intravenous injection of RNA Dendrimers. In the pre-contrast images, there will be little intrinsic contrast between the tumors and surrounding muscle. Over time, specific signal enhancement will be observed from the tumors compared to surrounding tissues. Blood clearance rates will be determined from intensity measurements of the jugular vein. Alternatively, blood samples will be collected at various time points and analyzed for Gd content. Detailed biodistribution and pharmacokinetic properties will be evaluated, following our publication[G12] and as described in Example 3 at Section 2.2.4.

Due to the multimodal nature of the RNA Dendrimers, the targeting of tumors and metastatic cells can be further verified by fluorescence (using Alexa$_{647}$) and SPECT/PET (using $^{177}$Lu, $^{111}$In or $^{64}$Cu) imaging. There is a critical need in medical imaging to co-register functional PET images with MRI that offers detailed anatomical structures. PET offers highest tumor detection sensitivity because of the use of radiotracers. However, tumor sites with high radioactivity cannot be accurately located in the abdomen or near the boundary of a moving organ owing to a lack of anatomical structure in PET images. MRI offers excellent soft-tissue contrast and thus facilitates tumor localization in co-registered MRI and PET images.

Example 5

This study relates to programmable self-assembly of branched, 3D globular, monodisperse and nanoscale sized dendrimers using RNA as building blocks. The central core and repeating units of the RNA dendrimer are derivatives of the ultrastable three-way junction (3WJ) motif from the bacteriophage phi29 motor pRNA. RNA dendrimers were constructed by step-wise self-assembly of modular 3WJ building blocks initiating with a single 3WJ core (Generation-0) with overhanging sticky-end and proceeding in a radial manner in layers up to Generation-4. The final constructs were generated under control without any structural defects in high yield and purity, as demonstrated by gel electrophoresis and AFM imaging. Upon incorporation of folate on the peripheral branches of the RNA dendrimers, the resulting constructs showed high binding and internalization into cancer cells. RNA dendrimers are envisioned to have a major impact in targeting, disease therapy, molecular diagnostics and bioelectronics in the near future.

Methods

RNA synthesis and purification: RNA oligonucleotides were prepared by chemical synthesis using a oligo synthesizer, custom ordered from Trilink Biotechnologies, Inc. (San Diego, Calif., USA) or generated by in vitro transcription of respective PCR amplified dsDNA containing the T7 promoter[46]. RNA strands were purified by HPLC or by 8%

Urea-PAGE. Single-stranded DNA templates and primers were purchased from Integrated DNA Technologies (Coralville, Iowa, USA).

Construction of G-0 to G-4 dendrimers: Dendrimers structure G-0, G-1, G-2 and G-3 were constructed using one-pot self-assembly of component strands (see sequences below). For G-0, the three component strands (3WJ-a):(3WJ-b):(3WJ-c)=1:1:1 molar ratio; For G-1, the five component strands (SquareA):(SquareB):(SquareC):(SquareD):(SquareE)=1:1:1:1:1 molar ratio. For G-2, the seven component strands (b-SquareA):(b-SquareB):(b-SquareC):(b-SquareD):(SquareE):(3WJ-a):(3WJ-c)=1:1:1:1:1:4:4 molar ratio. For G-3, the nine component strands (b-SquareA):(b-SquareB):(b-SquareC):(b-SquareD):(SquareE):(3WJ-c-b_rev):(3WJ-a-b_rev):(3WJ-a_rev):(3WJ-c_rev)=1:1:1:1:1:4:4:8:8 molar ratio. The required dendrimer RNA strands were mixed together in stoichiometric ratio in TMS buffer (25 mM Tris, 50 mM NaCl, 5 mM $MgCl_2$) and the mixture was heated to 95° C. for 5 min and then slowly cooled to 4° C. at a rate of 2° C./min on an Eppendorf thermocycler. The assembly efficiency was verified using 8% native PAGE or 2% agarose gel.

For the construction of G-4 dendrimer, a two-step approach was used. First, the dendrimer nanostructure G-2 with sticky ends was constructed by mixing together required RNA strands with appropriate stoichiometry in TMS buffer. The mixture was heated to 95° C. for 5 min and then slowly cooled as described above for the construction of G-1, G-2 and G-3 dendrimer generations. The free strands were removed by passing the mixture through Amicon Ultracentrifugal spin filters with 100 KDa cut off following manufacturer protocol and washed twice with TMS buffer. The pure G-2 with sticky ends was collected from column. In second step, the G-2 with sticky ends was mixed in stoichiometric ratio with other RNA strands needed to form G-4. The final molar ratio of the 11 G-4 component strands are (b-SquareA):(b-SquareB):(b-SquareC):(b-SquareD):(SquareE):(3WJ-c-b_rev):(3WJ-a-b_rev):(3WJ-b-a_rev):(3WJ-b-c_rev):(3WJ-a):(3WJ-c)=1:1:1:1:1:4:4:8:8:16:16. The mixture was incubated at room temperature for 1 hour. Then, an agarose gel was run to check assembly efficiency. G-4 was constructed with a maximum final concentration of 1 µM in TMS buffer.

The sequences of all the strands of the RNA dendrimers are as follows (Sequence 5'→3'):
(1) 3WJ-a: UUG CCA UGU GUA UGU GGG (SEQ ID NO: 1)
(2) 3WJ-b: CCC ACA UAC UUU GUU GAU CC (SEQ ID NO: 2)
(3) 3WJ-c: GGA UCA AUC AUG GCA A (SEQ ID NO: 3)
(4) 3WJ-a_rev: GGG UGU AUG UGU ACC GUU (SEQ ID NO: 4)
(5) 3WJ-b_rev: CCU AGU GUU UUC AUA CAC CC (SEQ ID NO: 5)
(6) 3WJ-c_rev: AAC GGU ACU AAC UAG G (SEQ ID NO: 6)
(7) 3WJ-c-folate: GGA UCA AUC AUG GCA A—folate (SEQ ID NO: 7)
(8) SquareA: GGG AGC CGU CAA UCA UGG CAA GUG UCC GCC AUA CUU UGU UGC ACG CAC (SEQ ID NO: 8)
(9) SquareB: GGG AGC GUG CAA UCA UGG CAA GCG CAU CGC AUA CUU UGU UGC GAC CUA (SEQ ID NO: 9)
(10) SquareC: GGG AGG UCG CAA UCA UGG CAA CGA UAG AGC AUA CUU UGU UGG CUG GAG (SEQ ID NO: 10)
(11) SquareD: GGG ACC AGC CAA UCA UGG CAA UAU ACA CGC AUA CUU UGU UGA CGG CGG (SEQ ID NO: 11)
(12) SquareE: GGA CAC UUG UCA UGU GUA UGC GUG UAU AUU GUC AUG UGU AUG CUC UAU CGU UGU CAU GUG UAU GCG AUG CGC UUG UCA UGU GUA UGG C (SEQ ID NO: 12)
(13) b-SquareA: GGC CCA CAU ACU UUG UUG AUC CAU GGU GCG UAG GGU CGU CAA UCA UGG CAA GUG UCC GCC AUA CUU UGU UGC ACU CCC UUG CUC AUC A (SEQ ID NO: 13)
(14) b-SquareB: GGC CCA CAU ACU UUG UUG AUC CUG AUG AGC AAG GGA GUG CAA UCA UGG CAA GCG UAU CGC AUA CUU UGU UGA GAA CCC UAU GUG ACU U (SEQ ID NO: 14)
(15) b-SquareC: GGC CCA CAU ACU UUG UUG AUC CAA GUC ACA UAG GGU UCG CAA UCA UGG CAA CGA UAG AGC AUA CUU UGU UGG AGU CCC UUA GAG UAG A (SEQ ID NO: 15)
(16) b-SquareD: GGC CCA CAU ACU UUG UUG AUC CUC UAC UCU AAG GGA CUC CAA UCA UGG CAA UAU ACA CGC AUA CUU UGU UGA CGA CCC UAC GCA CCA U (SEQ ID NO: 16)
(17) 3WJ-a-b_rev: UUG CCA UGU GUA UGU GGG CCU AGU UGU UUC AUA CAC CC (SEQ ID NO: 17)
(18) 3WJ-c-b_rev: GGA UCA AUC AUG GCA A CCU AGU UGU UUC AUA CAC CC (SEQ ID NO: 18)
(19) 3WJ-b-a_rev: CCC ACA UAC UUU GUU GAU CC GGG UGU AUG UGU ACC GUU (SEQ ID NO: 19)
(20) 3WJ-b-c_rev: CCC ACA UAC UUU GUU GAU CC AAC GGU ACU AAC UAG G (SEQ ID NO: 20)

Gel Analysis: RNA dendrimers were analyzed using 2% agarose gel and 6-8% PAGE. The gels were prepared and ran in TMS buffer at 90 V for 1 hr. The gels were stained with ethidium bromide and scanned using Typhoon FLA 7000 (GE Healthcare, Cincinnati, Ohio, USA).

AFM Imaging: Dendrimer structures were imaged using APS modified mica surfaces with a Multi-Mode AFM Nano-Scope IV system (Veeco/Digital Instruments, Town of Oyster Bay, N.Y., USA), operating in tapping mode, as described previously[47].

Serum stability assay: The chemical stability of RNA dendrimers was studied by incubating the dendrimers with 50% Fetal Bovine Serum (FBS) at 37° C. at final concentration of 1 µM. 10 µL of samples were collected at each time point (0, 0.16 hr, 1 hr, 3 hr, 6 hr, 18 hr, and 24 hr) and were subjected to a 2% agarose gel assay with TBM running buffer. The gel was run at 120 V for 120 minutes, imaged by Typhoon FLA 7000 (GE Healthcare, Cincinnati, Ohio, USA), and gel bands quantified by Image J.

Flow cytometry analysis: Folate receptor (+) KB Cells were cultured in T75 flask and harvested at a density of $1 \times 10^6$ cells/ml with 0.25% trypsin. Cells were washed with Opti-MEM medium once and then incubated with different concentration of Cy5 labeled 2'-F RNA dendrimers in Opti-MEM medium for 1 hr at 37° C., protected from light. Cells were then washed three times and suspended in PBS (137 mM NaCl, 2.7 mM KCl, 100 mM $Na_2HPO_4$, 2 mM $KH_2PO_4$, pH 7.4) for analysis.

Confocal Imaging: KB cells were grown in cover glass (Thermo Fisher Scientific, Waltham, Mass., USA) in 24 well bottom culture dishes in its complete medium overnight. Cells were seeded at a density of $2 \times 10^5$ cells/ml in a volume of 500 μl. On the day of testing, cells were washed with Opti-MEM medium twice, and RNA dendrimer (with whole chain Cy5 labeled SquareE-strand) were suspended in 200 l of Opti-MEM medium and incubated with cells at 37° C. for 1 hr. Cells were washed with PBS twice, fixed with 4% paraformaldehyde solution (Microscopy Sciences, Hatfeld, Pa., USA) in PBS at room temperature for 20 min, then washed with PBS and permeabilized with 0.05% Triton-X 100 in PBS at room temperature for 3 min. The cells were then stained with Alexa488 phallodin (Thermo Fisher Scientific, Waltham, Mass., USA) at room temperature for 20 min, the wells washed with PBS and air dried. The cells were stained with gold antifade (Thermo Fisher Scientific, Waltham, Mass., USA) for DAPI staining for confocal microscopy imaging with Zeiss LSM 510 laser scanning system.

Results

Design and Assembly of Parts and Intermediates for RNA Dendrimers

We developed three modules as building blocks for construction of RNA dendrimers. Module-1 is the 3WJ motif composed of three individual strands (3WJ-a, 3WJ-b and 3WJ-c) with three terminal ends (FIG. 28A). In order to build higher order structures, we need to interconnect the 3WJ motifs in a radial manner, and this requires using two different 3WJs with near identical folding properties to avoid cross-talk between layers. Otherwise, misfolding and aggregation can occur. We generated a reverse pRNA-3WJ, denoted pRNA-3WJ-rev, which is a mirror image of the pRNA-3WJ with the 5'- and 3'-ends switched (FIG. 28B). The pRNA-3WJ-rev has identical properties as the conventional pRNA-3WJ with regards to thermodynamic stability, as well as assembly in native and 8 M denaturing PAGE.

Figure 29:
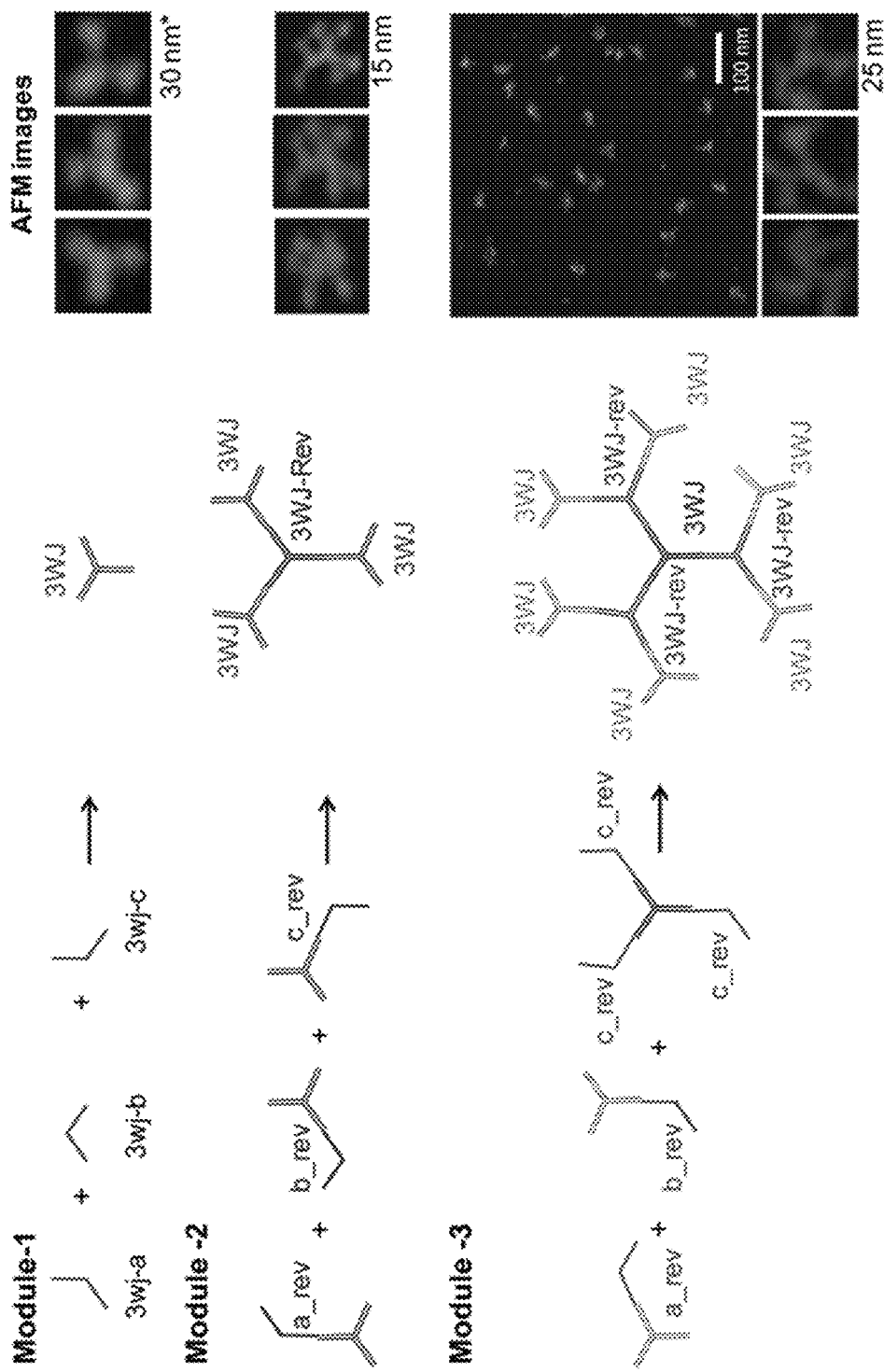
FIG. 29 shows step-wise assembly of three modules used as building blocks for RNA dendrimer construction. Module-1 assembles for three strands: 3WJ-a, 3WJ-b, and 3WJ-c. Module-2 assembles from three units: pRNA-3WJ harboring a_rev, pRNA-3WJ harboring b_rev, and pRNA-3WJ harboring c_rev sticky-ends. Module-3 assembles from three units: pRNA-3WJ harboring a_rev, pRNA-3WJ harboring b_rev, and pRNA-3WJ harboring three c_rev sticky ends. Right panel: AFM images of the modular building blocks. For module-1, the AFM image is for 3WJ with three pRNA subunits at the three branches.

Module-2 consists of three sets of pRNA-3WJ building blocks, each harboring one of the component strands of the pRNA-3WJ-rev serving as sticky ends (3WJ-a_rev, 3WJ-b_rev and 3WJ-c_rev). The use of 3WJ core strands as sticky ends ensures near spontaneous 3WJ assembly with minimal non-specific hybridization, which can otherwise lead to misfolding, and also eliminates the need for additional linking sequences between 3WJs. Upon mixing the three building blocks in stoichiometric ratio, the pRNA-3WJ-rev assembles from the three sticky-ends thereby generating module-2 with high efficiency (FIG. 29). Module-2 is composed of 5 component strands and has 6 terminal ends.

Similarly, module-3 was constructed from iterative stepwise assembly on top of module-2 complexes by branch extension using one of the 3WJ component strands as sticky ends. The final complex is composed of 7 strands and 12 terminal ends with alternating pRNA-3WJ core and pRNA-3WJ-rev cores (FIG. 29).

Figure 30:
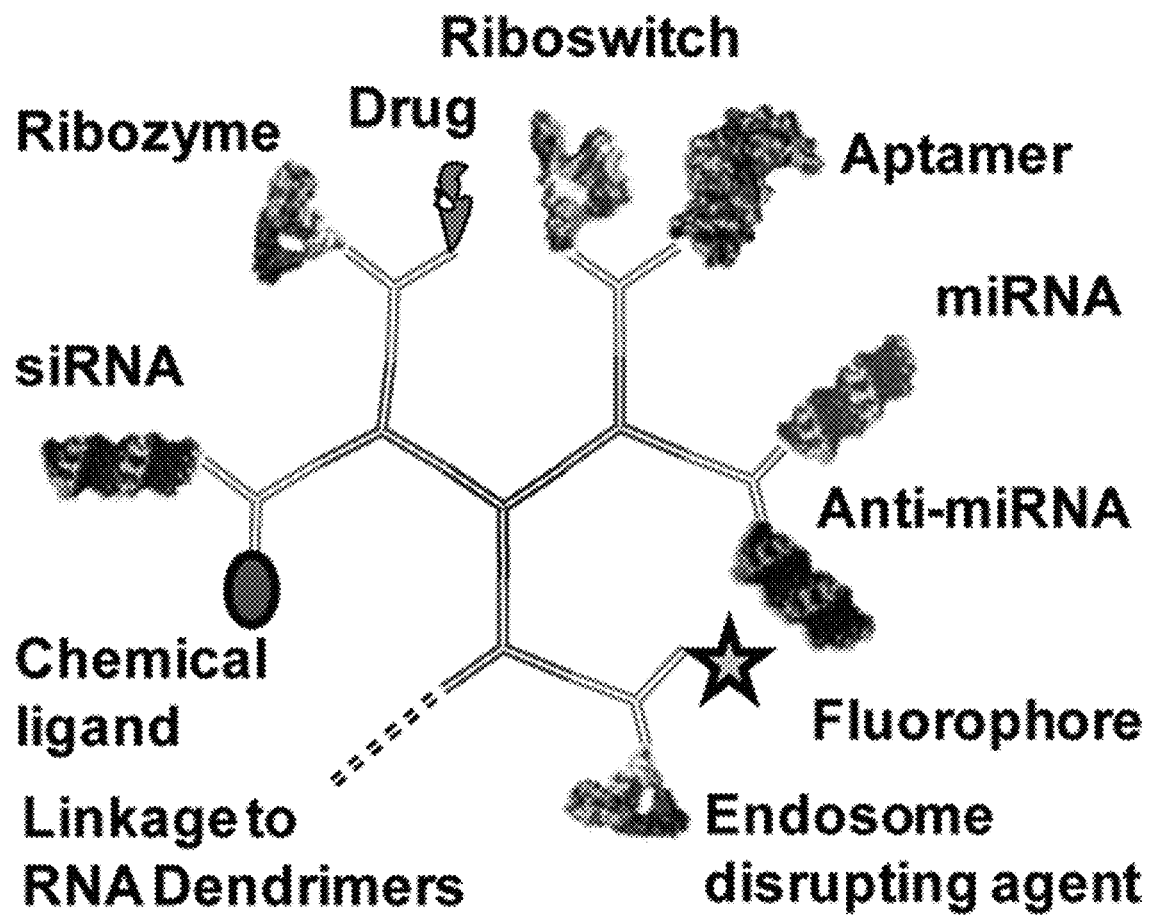
FIG. 30 shows construction of multifunctional RNA dendrimers. Functionalization of module-3 with varieties of moieties for targeting (chemical ligand or RNA aptamer), imaging (fluorophore or radiolabel), and therapeutic (siRNA, miRNA, anti-miRNA, chemotherapeutic drugs, ribozyme, riboswitch, endosome disrupting agents) units.

All three modules can be assembled either in one step or step-wise by simply mixing the strands at room temperature in TMS buffer (40 mM Tris, 10 mM MgCl2, 100 mM NaCl) or by annealing (heating to 95° C. and cooling to room temperature over the course of 1 hour). The use of these modules will enable construction of RNA dendrimers with desired functional moieties, such as RNAi reagents siRNA, miRNA, anti-miRNA; chemotherapeutic drug; receptor targeting RNA aptamer or chemical ligand; riboswitch; ribozyme; endosome disrupting agents; and imaging fluorophores or radiolabels (FIG. 30).

Design and Assembly of RNA Dendrimers G-0 to G-4

Figure 31C:
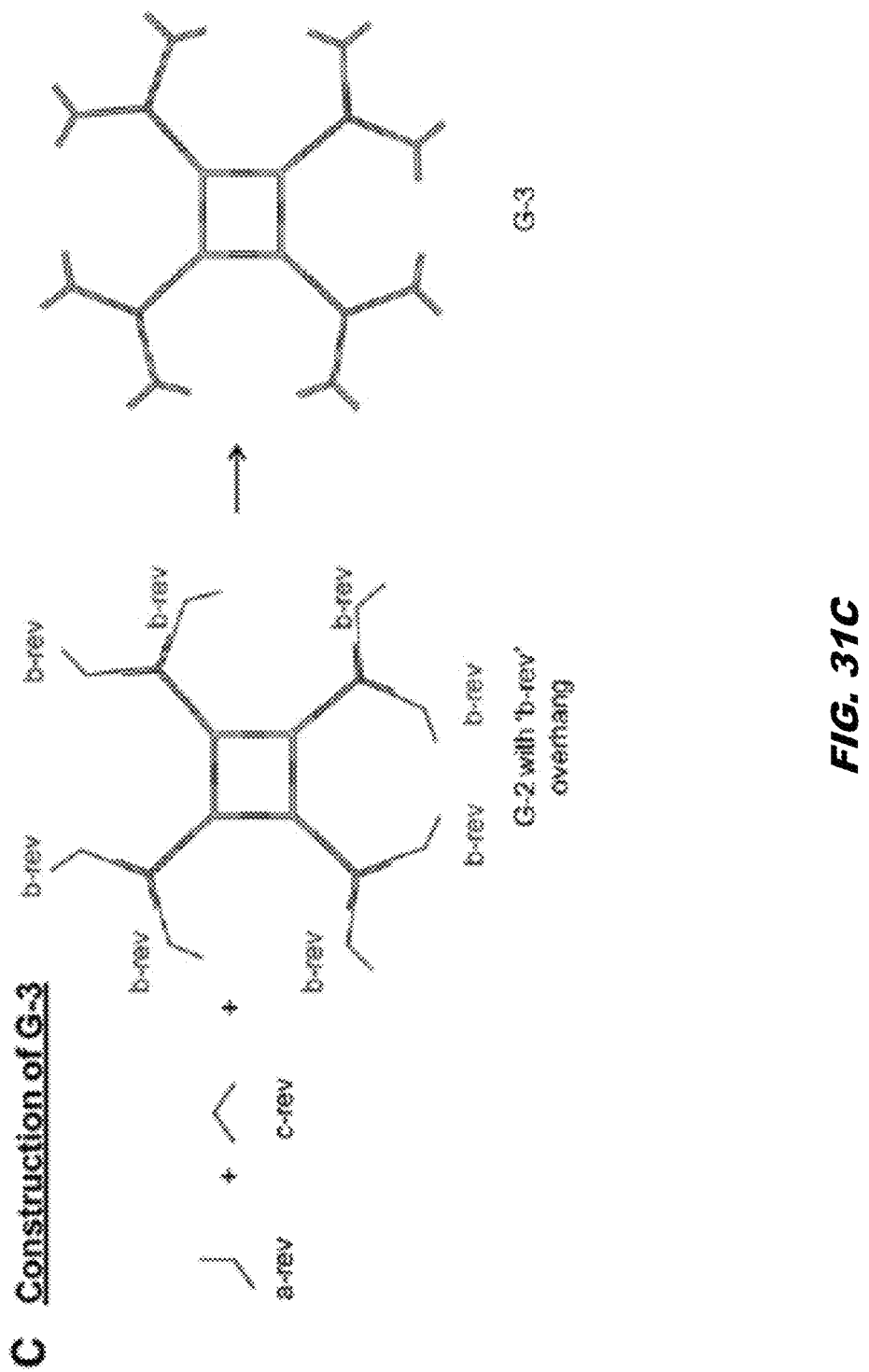
Figure 31D:
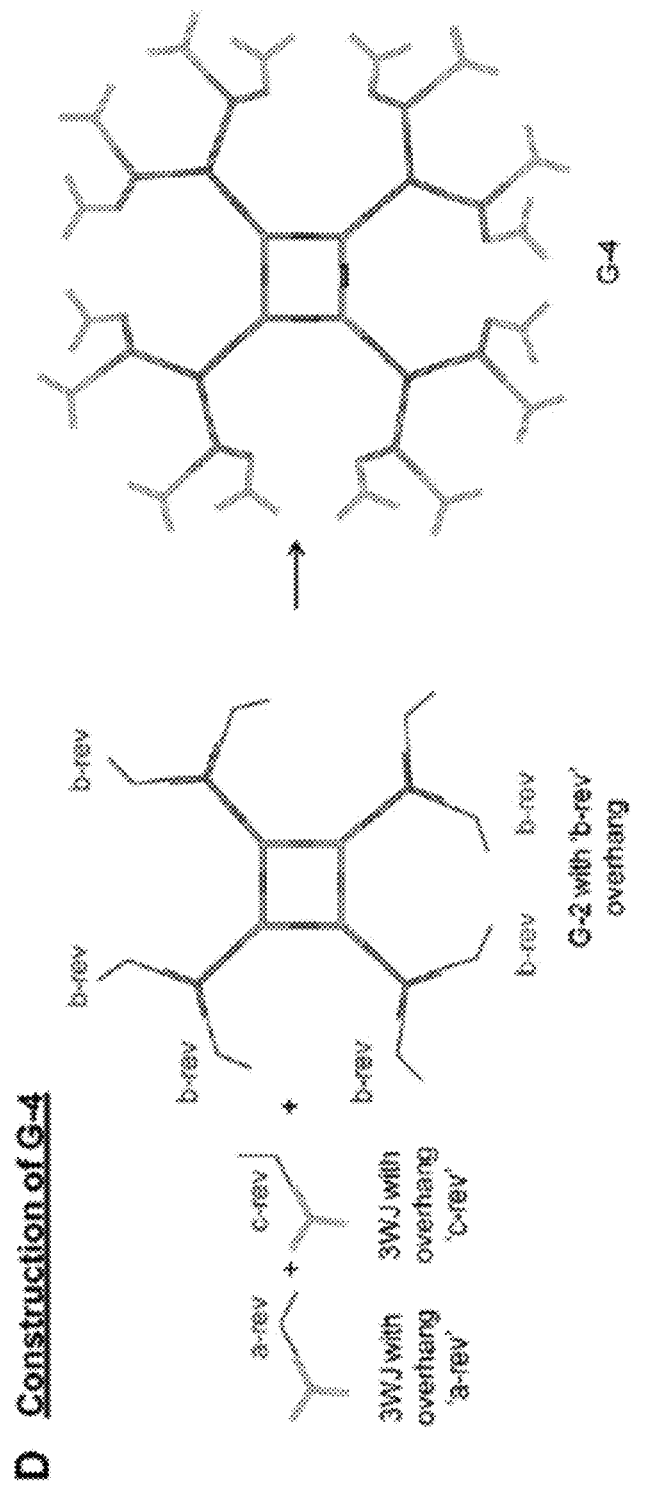
Figure 32A:
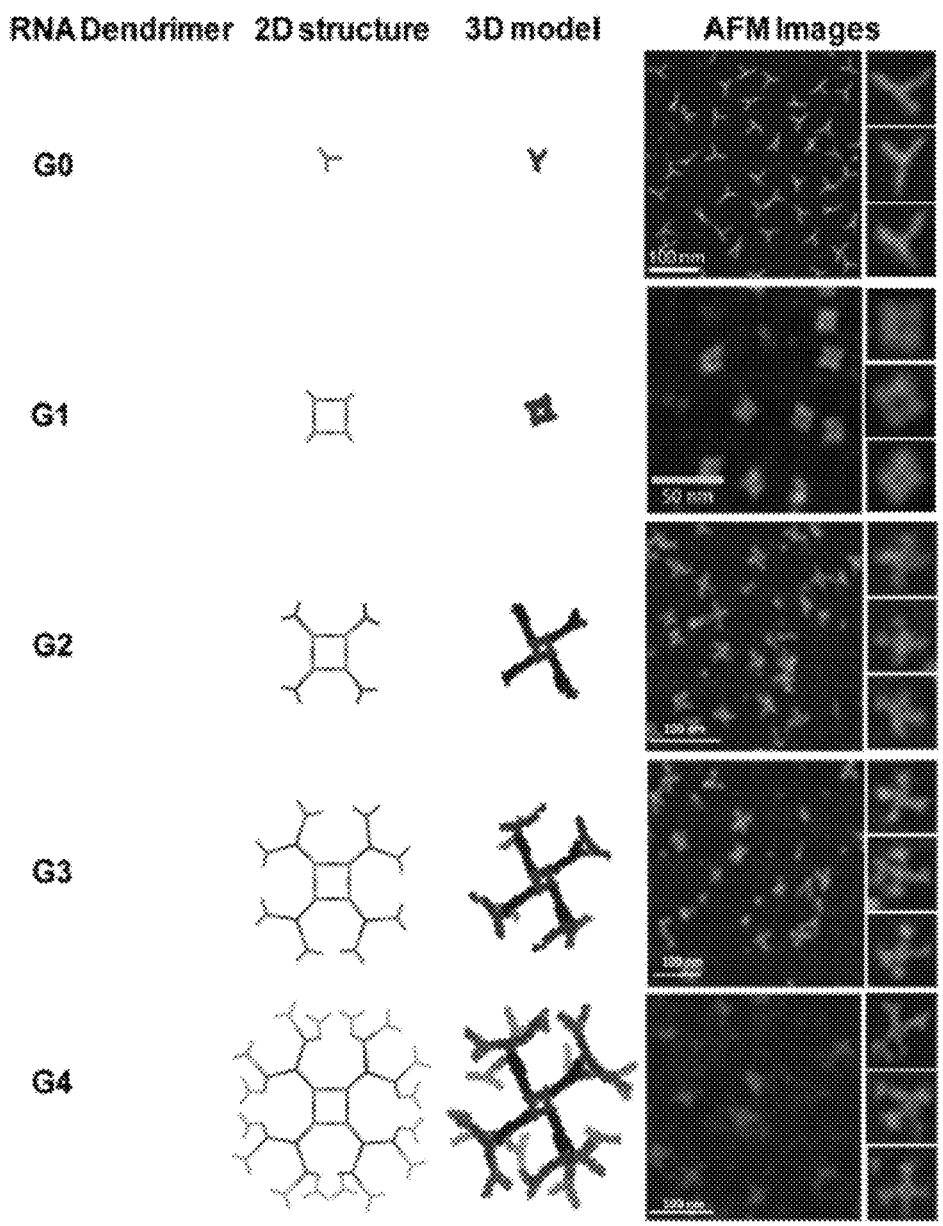

RNA dendrimers have similar architectures as small molecule based dendrimers consisting of an initiating core, interior layer of repeating units, and terminal units at the peripheral ends of the outermost generation. In the traditional sense, we adopted a 'divergent growth' method, whereby the dendrimer initiates from a core site and grows in a radial manner layer by layer. We used the pRNA-3WJ as G-0 initiating core (FIGS. 29A, 32A-B) and then constructed a planar square nanoparticle to serve as G-1 (FIGS. 31A, 32A-B). The pRNA-3WJ scaffold is highly tunable and the internal angle can be stretched from native 60° to 90° in the square configuration, as demonstrated previously[30]. The pRNA-3WJ cores at each vertex is linked by double stranded RNA sequences, with the entire square construct (G-1) composed of 5 strands and 4 terminal ends (MW ~83 KDa) (FIG. 31A). The square pattern ensures equal spacing between the protruding corner branches and minimizes steric hindrances for addition of building blocks. We then adopted a similar strategy as aforementioned using one of the 3WJ component strands as sticky ends to sequentially construct G-2 (7 unique strands; 8 terminal ends; MW~187 kDa) (FIGS. 31B, 32A-B), G-3 (9 unique strands; 16 terminal ends; MW~328 kDa) (FIGS. 31C, 32A-B) and finally G-4 (11 unique strands; 32 terminal ends; MW~610 kDa) (FIGS. 31D, 32A-B) (Table 4). G-0 through G-3 dendrimers can be assembled with high yield by mixing the component strands in equimolar ratio followed by annealing, except for G-4, which requires an additional incubation step with module-2 (FIG. 29, 31D). Our design does not require any enzymatic ligation step and simply relies on self-assembly of individual blocks for the construction of higher order dendrimers. All the sequences for dendrimer generations were optimized to avoid any nonspecific interactions using the Mfold algorithm [D48].

TABLE 4

Characteristics of RNA dendrimers

| RNA Dendrimer | Predicted Size (nm) | Molecular Weight (kDa) | # of strands | # of nucleotides | Terminal units |
|---|---|---|---|---|---|
| G-0 | 6 | 17784 | 3 unique 3 total | 54 | 3 |
| G-1 | 12 | 82843 | 5 unique 5 total | 440 | 4 |
| G-2 | 37 | 186675 | 7 unique 13 total | 576 | 8 |
| G-3 | 50 | 327675 | 9 unique 29 total | 1008 | 16 |
| G-4 | 65 | 609675 | 11 unique 61 total | 1872 | 32 |

Characterization of RNA Dendrimers for Thermodynamic Stability and Serum Stability The thermodynamic stability of individual building blocks is of paramount importance to ensure that the RNA dendrimers remain intact without dissociating in vivo. Both the pRNA-3WJ and pRNA-3WJ-rev scaffold assemble with high efficiency, as shown in native PAGE (FIG. 28A-B; top gel). Both 3WJs remain stable in presence of strongly denaturing 8 M urea, thereby demonstrating the robust attributes (FIG. 28A-B; bottom gel). Melting experiments indicated that the three component strands have a much higher affinity to interact with one another than any of the one or two component strands. The slope of the melting curve is very steep indicating cooperative assembly of the three strands with very low free energy ($\Delta G°_{37° C.}$ of −28 kcal/mol), as calculated previously[37]. The $T_m$ values are near identical for pRNA-3WJ and pRNA-3WJ-rev scaffolds with 59±0.5° C. and 58.5±0.5° C., respectively (FIG. 28A-B). $T_m$ analysis of RNA dendrimers is challenging involving multiple strands and multi-step folding intermediates.

For successful clinical application of RNA dendrimers, a major hurdle is their stability in biological media, such as serum. Unmodified RNAs are intrinsically sensitive to degradation because of presence of nucleases in serum or in cells with a half-life varying from a few minutes to several hours[D40,D49,D50]. Chemical modifications, such as 2'-Fluoro (2'-F) modification on the ribose sugar of the RNA, have been shown to be nuclease resistant [D22,D51, D52] and also enhance the thermodynamic stability of RNA nanoparticles [D37]. Within the dendrimer RNA sequences, the U and C nucleotides were replaced by 2'-F modified U and C nucleotides during solid state synthesis or in vitro transcription. The 2'-F modified G-4 RNA dendrimers were assembled and showed similar assembly efficiency as unmodified G-4 RNA dendrimers in native gel assays. To test the serum stability, 2'-F modified G-4 dendrimers were incubated with 10% Fetal Bovine Serum (FBS) at 37° C. At specific time points, aliquots were extracted and snap frozen. Gel assays demonstrated that the 2'-F G-4 RNA dendrimers are resistant to nuclease degradation for more than 24 hours (FIG. 32C), while unmodified constructs are degraded within 10-15 minutes.

Characterization of RNA Dendrimer Assembly by Atomic Force Microscopy (AFM) and Gel Electrophoresis The assembly of dendrimers was tested by native gel electrophoresis (FIG. 32B). G-0, G-1, G-2, G-3 and G-4 dendrimers all display a single band in the gels without any smears indicating high efficiency of the adopted assembly strategy. No significant change in assembly efficiency was observed by going from lower to higher generations. The free RNA strands were removed after dendrimer assembly using centrifugal membrane filter columns. The slow migration of the gel band from G-0 to G-4 clearly indicates the increasing size of the constructs, as expected.

To further confirm the results, all constructed dendrimer generations from G-0 to G-4 were examined by AFM imaging, which strongly support the formation of all dendrimers with branched conformations (FIG. 32A). For G-4 dendrimers, the bifurcation in the arms of outer layer can be easily observed and the central square is visible in most of the structures from G-1 to G-4. The dendrimer structures are indeed three dimensional as designed in silico utilizing the crystal structure of the planer 3WJ structural motif[D44]. Swiss PDB Viewer (www.spdbv.vital-it.ch) and Pymol (https://www.pymol.org/) were used to align 3WJ building blocks into three dimensional structure models (FIG. 32A), based on the available crystal structure of pRNA-3WJ (PDB ID: 4KZ2)[D44]. The three dimensional nature of dendrimer make the structures to appear in different orientations on the surface for AFM imaging thus bringing dendrimer arms appear close or farther away from each other in different images. RNA dendrimers are highly negatively charged and do not aggregate in solution. This anionic nature and aggregation-free physical property will minimize non-specific cell entry, and entrapment by lung and spleen macrophages and liver Kupffer cells[D53].

Characterization of RNA Dendrimers for Cell Receptor Targeting

Figure 33A:
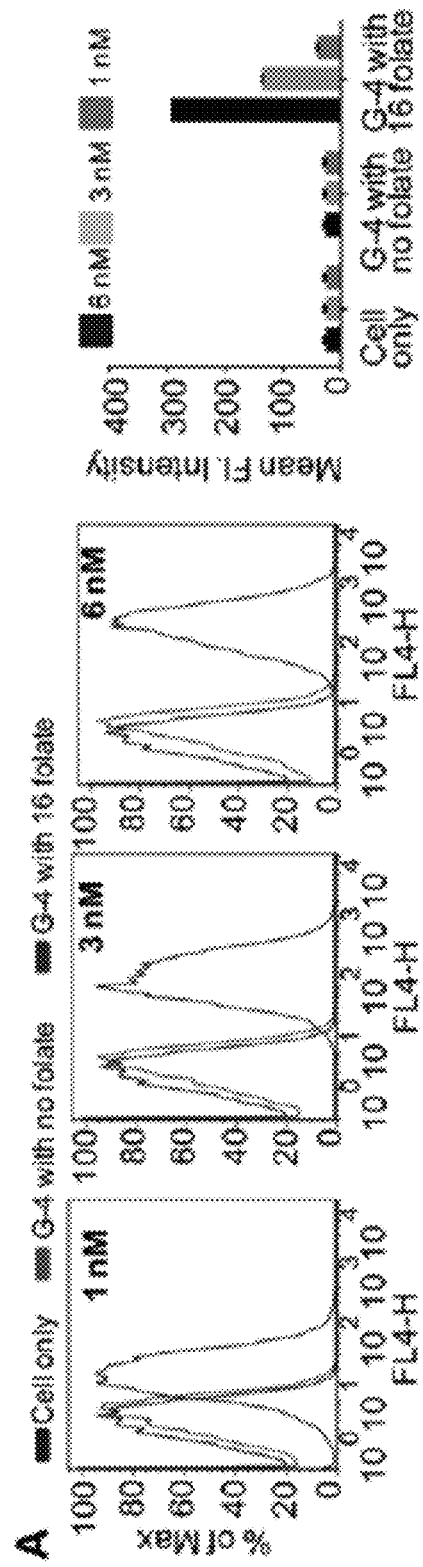
FIGS. 33A-33B shows (A) Flow cytometry data of G-4 RNA dendrimers at different concentrations (1 nM, 3 nM and 6 nM) with KB cells. Cell only (black), G-4 dendrimer with no folate (red); and G-4 with 16 folates (blue). Right: Summary of binding results. (B) Confocal microscope images of G-4 RNA dendrimers incubated with KB cells, nuclear staining by DAPI (blue), cell membrane staining by phalloidin Alexa488 (green), Cy5-labeled folate-G4 dendrimer (red) and a overlay of three panels. Bottom: Magnified view of overlayed image section boxed in red.
Figure 33B:
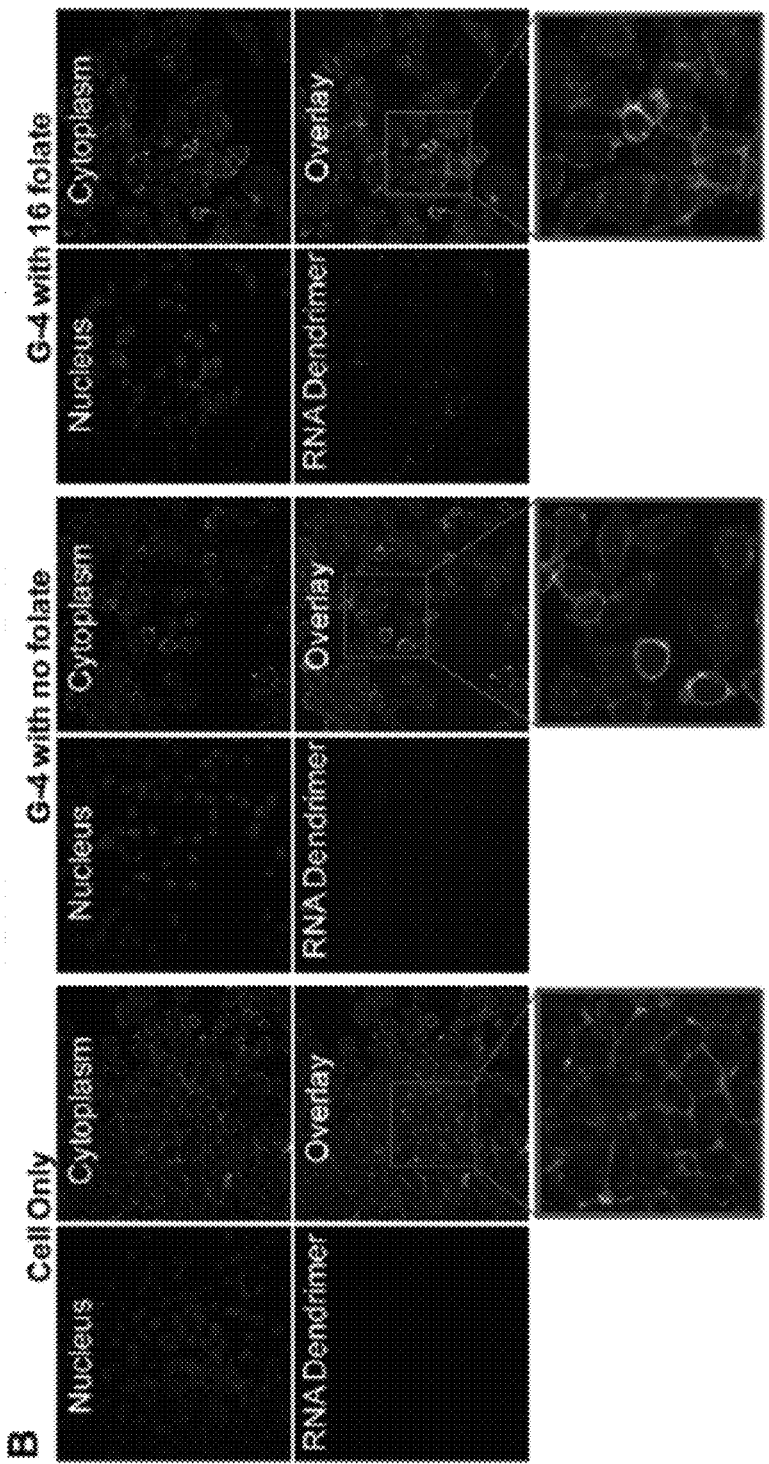

To study the potential applications of RNA dendrimers in targeting specific cells, 2'-F modified RNA dendrimers were assembled with targeting ligands at peripheral ends. Increased expression of folate receptors are frequently observed in cancer cells of epithelial origin[54]. Herein, we used folate as a targeting ligand. Within G-4, the core SquareE strand of G-1 was fluorescently tagged with Cy5 for detection. One of the terminal end sequences (3WJ-c) was labeled with folate at 3'-end (custom ordered from Trilink) and then used to assemble G-4 dendrimers resulting in 16 folates distributed evenly across the G-4 dendrimer surface. Folate receptor positive KB cells were incubated with G-4 dendrimers at different concentrations and the incubation efficiencies were analyzed using flow cytometry (FIG. 33A). G-4 dendrimers with folate displayed increase in intracellular uptake with increasing RNA concentrations from 1 nM to 3 nM to 6 nM, compared to G-4 dendrimers without any folate. This is attributed to folate receptor mediated endocytosis. Confocal fluorescence microscopy (FIG. 33B) images further confirmed the internalization of G-4 dendrimers with folates as indicated by strong overlap of cytoplasma (green) and dendrimers (red). The results demonstrate that RNA dendrimers would be useful to deliver various payloads including radioligand, drug molecules, and RNAi modules into the cells.

Discussion

We demonstrated that RNA can serve as a new generation of building blocks to form homogenous supramolecular 3D dendrimers with defined size and shape. Our step-wise self assembly strategy utilizing a robust pRNA-3WJ motif is highly efficient and can generate homogeneous dendrimers under control with high yield and purity. Introduction of 2'-F RNA makes the dendrimers serum resistant and decoration of the dendrimers with targeting ligands results in high intracellular delivery to specific target cells.

Compared to small molecule based chemical polymers, RNA dendrimers can be made large enough (>10 nm) to avoid rapid renal excretion, yet small enough (65 nm for G-4 dendrimers) to enter cells via receptor-mediated endocytosis. The degradation of RNA can be timely controlled by adjusting the percent and location of chemically modified 2'-F nucleotides. Moreover, individual nucleotides within the RNA dendrimer can be labeled during chemical synthesis prior to dendrimer self-assembly, thus ensuring full utilization of void-spaces, which is an arduous challenge for small molecule based dendrimers. Compared to DNA counterparts, in addition to enhanced chemical stability after 2'-F modifications, RNA dendrimers are thermodynamically more stable[D15-16,D22,D37,D55-56] and will therefore not dissociate at ultra-low concentrations in vivo, and therapeutic RNA interference modules, such as siRNA and miRNA can be seamlessly integrated into the sequence design.

The ease of chemical synthesis of RNA strands, the simplicity of self-assembly without synthetic reactions, the ease of functionalization of modular units prior to assembly, and the multivalent nature of RNA dendrimers will help in high loading of desired functional modules, such as drugs, targeting, therapeutic, and imaging agents for myriad of applications in bioelectronics, biomimetic membranes, imaging, diagnostics and therapeutics.

All publications, patents, and patent applications mentioned in this specification are herein incorporated by reference to the same extent as if each individual publication, patent, or patent application was specifically and individually indicated to be incorporated by reference, including the references set forth in the following list:

REFERENCES

1. Hanahan D, Weinberg R A. The hallmarks of cancer. *Cell.* 100(1), 57-70 (2000).
2. Hanahan D, Weinberg R A. Hallmarks of cancer: the next generation. *Cell.* 144(5), 646-674 (2011).
3. Jemal A, Bray F, Center M M, et al. Global cancer statistics. *CA Cancer. J. Clin.* 61(2), 69-90 (2011).

4. http://www.cancer.org/cancer/cancerbasics/economic-impact-of-cancer.
5. Baskar R, Lee K A, Yeo R, et al. Cancer and radiation therapy: current advances and future directions. *Int. J. Med. Sci.* 9(3), 193-199 (2012).
6. Bloomer W D, Hellman S. Normal tissue responses to radiation therapy. *N. Engl. J. Med.* 293(2), 80-83 (1975).
7. Bentzen S M. Preventing or reducing late side effects of radiation therapy: radiobiology meets molecular pathology. *Nat. Rev. Cancer.* 6(9), 702-713 (2006).
8. Spencer R P, Radiophamaceuticals in therapy. In: *Radionuclides in Therapy.* Spencer R P, Seevers R H, and Friedman A M (Ed.), CRC Press, Inc., Boca Raton, Fla. (1987).
9. Peer D, Karp J M, Hong S, et al. Nanocarriers as an emerging platform for cancer therapy. *Nat. Nanotechnol.* 2(12), 751-760 (2007).
10. Davis M E, Chen Z G, Shin D M. Nanoparticle therapeutics: an emerging treatment modality for cancer. *Nat. Rev. Drug Discov.* 7(9), 771-782 (2008).
11. Brannon-Peppas L, Blanchette J O. Nanoparticle and targeted systems for cancer therapy. *Adv. Drug Deliv. Rev.* 56(11), 1649-1659 (2004).
12. Lee H, Lytton-Jean A K, Chen Y, et al. Molecularly self-assembled nucleic acid nanoparticles for targeted in vivo siRNA delivery. *Nat. Nanotechnol.* 7(6), 389-393 (2012).
13. Guo P. The emerging field of RNA nanotechnology. Nat. Nanotechnol. 5(12), 833-842 (2010).
14. Shu Y, Pi F, Sharma A, et al. Stable RNA nanoparticles as potential new generation drugs for cancer therapy. *Adv. Drug Deliv. Rev.* 66, 74-89 (2014).
15. Kairemo K, Erba P, Bergstrom K, et al. Nanoparticles in cancer. *Cur. Radiopharm.* 1(1), 30-36 (2008).
16. Cai W., Gao T., Hong H., Sun J. Applications of gold nanoparticles in cancer nanotechnology, *Nano. Sci. App.* 1, 17-32 (2008).
17. Zhang L, Chen H, Wang L, et al. Delivery of therapeutic radioisotopes using nanoparticle platforms: potential benefit in systemic radiation therapy. *Nano. Sci. App.* 3, 159-170 (2010).
18. Shu Y, Cinier M, Shu D, Guo P. Assembly of multifunctional phi29 pRNA nanoparticles for specific delivery of siRNA and other therapeutics to targeted cells. *Methods.* 54(2), 204-214 (2011).
19. Haque F, Shu D, Shu Y, et al. Ultrastable synergistic tetravalent RNA nanoparticles for targeting to cancers. *Nano Today.* 7(4), 245-257 (2012).
20. Shu Y, Haque F, Shu D, et al. Fabrication of 14 different RNA nanoparticles for specific tumor targeting without accumulation in normal organs. *RNA.* 19(6), 766-777 (2013).
21. Guo P, Zhang C, Chen C, et al. Inter-RNA interaction of phage phi29 pRNA to form a hexameric complex for viral DNA transportation. *Mol. Cell.* 2(1), 149-155 (1998).
22. Guo P, Haque F, Hallahan B, et al. Uniqueness, advantages, challenges, solutions, and perspectives in therapeutics applying RNA nanotechnology. *Nucleic. Acid Ther.* 22(4), 226-245 (2012).
23. Bindewald E, Afonin K, Jaeger L, et al. Multistrand RNA secondary structure prediction and nanostructure design including pseudoknots. *ACS Nano.* 5(12), 9542-9551 (2011).
24. Ye X, Hemida M, Zhang H M, et al. Current advances in Phi29 pRNA biology and its application in drug delivery. Wiley. *Interdiscip. Rev. RNA.* 3(4), 469-481 (2012).
25. Afonin K A, Danilov E O, Novikova I V, et al. TokenRNA: A new type of sequence-specific, label-free fluorescent biosensor for folded RNA molecules. *Chembiochem.* 9(12), 1902-1905 (2008).
26. Shu D, Moll W D, Deng Z, et al. Bottom-up assembly of RNA arrays and superstructures as potential parts in nanotechnology. *Nano Lett.* 4(9), 1717-1723 (2004).
27. Shu D, Shu Y, Haque F, et al. Thermodynamically stable RNA three-way junctions for constructing multifuntional nanoparticles for delivery of therapeutics. *Nat. Nanotechnol.* 6 (10), 658-667 (2011).
28. Abdelmawla S, Guo S, Zhang L, et al. Pharmacological characterization of chemically synthesized monomeric pRNA nanoparticles for systemic delivery. Mol. Ther. 19(7), 1312-1322 (2011).
29. Cerchia L, Giangrande P H, McNamara J O, et al. Cell-specific aptamers for targeted therapies. *Methods Mol. Biol.* 535, 59-78 (2009).
30. Guo P, Trottier M. Biological and biochemical properties of the small viral RNA (pRNA) essential for the packaging of the double-stranded DNA of phage f29. *Semin. Virol.* 5, 27-37 (1994).
31. Luo W, Guo P, Li H. Ultrastable pRNA 3WJ nanoparticles as potential 1-125 and C-131 carriers for targeted radiation therapy. Med. Phys. 41, 302(2014), 2014 *American Association of Medical Physicists Annual Meeting*, Austin, TX, 20 Jul.-24 Jul. 2014.
32. Rajendran J C. Therapeutic Radioisotopes, in *Nuclear Medicine Therapy.* Eary, J F, and Brenner W (Ed.), Informa Healthcare USA, Inc., New York, 2007.
33. Hoefnagel C A. Radionuclide cancer therapy, *Ann. Nucl. Med.* 12(2), 61-70 (1998).
34. Sofou S. Radionuclide carriers for targeting of cancer, *Int. J. Nanomed.,* 3(2), 181-199 (2008).
35. Hamoudeh M, Kamleh M A, Diab R, Fessi H. Radionuclides delivery systems for nuclear imaging and radiotherapy of cancer, *Adv. Drug Del. Rev.,* 60, 1329-1346 (2008).
36. Williams L E, DeNardo G L, Meredith R F. Targeted radionuclide therapy, *Med. Phys.* 35(7), 3062-3068 (2008).
37. Lyubchenko Y L, Shlyakhtenko L S. AFM for analysis of structure and dynamics of DNA and protein-DNA complexes. *Methods.* 47(3), 206-213 (2009).
38. Meigooni A S, Hayes J L, Zhang H, et al. Experimental and theoretical determination of dosimetric characteristics of IsoAid ADVANTAGE $^{125}$I brachytherapy source. *Med. Phys.* 29(9), 2152-2158 (2002).
39. Prestidge B R, Bice W S, Jurkovic I, et al., Cesium-131 permanent prostate brachytherapy: an initial report. *Int. J. Radiat. Oncol. Biol. Phys.* 63, S336-S337 (2005).
40. Ravi A, Keller B, Pignol J, Evaluation of the radiation safety of using Cs-131 seeds for permanent breast seed implantation, *Int. J. Radiat. Oncol. Biol. Phys.* 81, S720-S721 (2011).
41. Yan W, Trichter S, Sabbas A, et al. Cesium-131 brachytherapy for lung cancer: dosimetric, safety considerations and initial experience. *Int. J. Radiat. Oncol. Biol. Phys.* 78, S540-S541 (2010).
42. Rivard M, Melhus C S, Sioshansi S, et al, The impact of prescription depth, dose rate, plaque size, and source loading on the central axis using Pd-103, 1-125, and Cs-131. *Brachytherapy,* 7(4), 327-335 (2008).
43. Luo W, Molloy J, Aryal P, et al. Determination of prescription dose for Cs-131 permanent implants using the BED formalism including resensitization correction. *Med. Phys.* 41(2):024101 (2014).

44. Wooten C E, Randall M, Edwards J, et al. Implementation and early clinical results utilizing Cs-131 permanent interstitial implants for gynecologic malignancies. *Gynecol. Oncol.* pii: S0090-8258(14)00133-4 (2014).
45. Murphy M K, Piper R K, Greenwood L R, et al. Evaluation of the new cesium-131 seed for use in low-energy x-ray brachytherapy. *Med. Phys.* 31(6), 1529-1538 (2004).
46. Rosenbaum V, Riesner D. Temperature-gradient gel electrophoresis: thermodynamic analysis of nucleic acids and proteins in purified form and in cellular extracts. *Biophy. Chem.* 26(2-3), 235-246 (1987).
47. Binzel D W, Khisamutdinov E F, Guo P. Entropy-driven one-step formation of Phi29 pRNA 3WJ from three RNA fragments. *Biochemistry.* 53(14), 2221-2231 (2014).
48. Pieken W A, Olsen D B, Benseler F, et al. Kinetic characterization of ribonuclease-resistant 2'-modified hammerhead ribozymes. *Science.* 253(5017), 314-317 (1991).
49. Kawasaki A M, Casper M D, Freier S M, et al. Uniformly modified 2'-deoxy-2'-fluoro phosphorothioate oligonucleotides as nuclease-resistant antisense compounds with high affinity and specificity for RNA targets. *J. Med. Chem.* 36(7), 831-841 (1993).
50. Sabahi A, Guidry J, Inamati G B, et al. Hybridization of 2'-ribose modified mixed-sequence oligonucleotides: thermodynamic and kinetic studies. *Nucleic Acids Res.* 29(10), 2163-2170 (2001).
51. Liu J, Guo S, Cinier M, et al. Fabrication of stable and RNase-resistant RNA nanoparticles active in gearing the nanomotors for viral DNA packaging. *ACS Nano.* 5(1), 237 (2011).
52. Guo P. RNA Nanotechnology: Engineering, Assembly and Applications in Detection, Gene Delivery and Therapy. *J. Nano. Nanotech.* 5(12), 1964-1982 (2005).
53. Guo P, Haque F. RNA Nanotechnology and Therapeutics. CRC Press, Boca Raton, F L, 2013.
54. Khisamutdinov E F, Jasinski D L, Guo P. RNA as a Boiling-Resistant Anionic Polymer Material To Build Robust Structures with Defined Shape and Stoichiometry. *ACS Nano.* 8(5), 4771-4781 (2014).
55. Jasinski D L, Khisamutdinov E F, Lyubchenko Y L, et al. Physicochemically Tunable Polyfunctionalized RNA Square Architecture with Fluorogenic and Ribozymatic Properties. *ACS Nano.* 8(8), 7620-7629 (2014).
56. Khisamutdinov E F, Li H, Jasinski D L, et al. Enhancing immunomodulation on innate immunity by shape transition among RNA triangle, square and pentagon nanovehicles. *Nucleic Acids Res.* 42(15), 9996-10004 (2014).
57. Lee F T, Rigopoulos A, Hall C, et al. Specific localization, gamma camera imaging, and intracellular trafficking of radiolabelled chimeric anti-G(D3) ganglioside monoclonal antibody KM871 in SK-MEL-28 melanoma xenografts. *Cancer Res.* 61(11), 4474-4482 (2001).
58. Zinn K R, Chaudhurt T R, Krasnykh V N, et al. Gamma Camera Dual Imaging with a Somatostatin Receptor and Thymidine Kinase after Gene Transfer with a Bicistronic Adenovirus in Mice, Radiology, 223(2), 417-425 (2002).
59. Meng L J, Fu G, Roy E J, et al. An Ultrahigh Resolution SPECT System for I-125 Mouse Brain Imaging Studies, Nucl Instrum Methods Phys Res A. 600(1): 498-505 (2009).
G1. Tandon P, Farahani K. NCI Image-Guided Drug Delivery Summit. Cancer Res. 2011 Jan. 15; 71:314-7
G2. Bao G, Mitragotri S, Tong S. Multifunctional nanoparticles for drug delivery and molecular imaging. Annu. Rev. Biomed. Eng 2013; 15:253-82
G3. Bae Y H, Park K. Targeted drug delivery to tumors: myths, reality and possibility. J. Control Release 2011 Aug. 10; 153(3):198-205
G4. Terreno E, Uggeri F, Aime S. Image guided therapy: the advent of theranostic agents. J. Control Release 2012 Jul. 20; 161(2):328-37
G5. Lammers T, Rizzo L Y, Storm G, Kiessling F. Personalized nanomedicine. Clin. Cancer Res. 2012 Sep. 15; 18(18):4889-94
G6. Lammers T, Kiessling F, Hennink W E, Storm G. Nanotheranostics and image-guided drug delivery: current concepts and future directions. Mol Pharm. 2010 Dec. 6; 7(6):1899-912
G7. Lammers T, Kiessling F, Hennink W E, Storm G. Drug targeting to tumors: principles, pitfalls and (pre-) clinical progress. J. Control Release 2012 Jul. 20; 161(2):175-87
G8. Guo P. The emerging field of RNA nanotechnology. Nature Nanotechnology 2010 December; 5(12):833-42. PMCID:PMC3149862
G9. Shu D, Shu Y, Haque F, Abdelmawla S, Guo P. Thermodynamically stable RNA three-way junctions for constructing multifunctional nanoparticles for delivery of therapeutics. Nature Nanotechnology 2011; 6:658-67. PMCID:PMC3189281
G10. Haque F, Shu D, Shu Y, Shlyakhtenko L, Rychahou P, Evers M, Guo P. Ultrastable Synergistic Tetravalent RNA Nanoparticles For Targeting To Cancers. Nano Today 2012; 7:245-57. PMCID:PMC3458310
G11. Shu Y, Haque F, Shu D, Li W, Zhu Z, Kotb M, Lyubchenko Y, Guo P. Fabrication of 14 Different RNA Nanoparticles for Specific Tumor Targeting without Accumulation in Normal Organs. RNA 2013; 19:766-77. PMCID:PMC3683911
G12. Abdelmawla S, Guo S, Zhang L, Pulukuri S, Patankar P, Conley P, Trebley J, Guo P, Li Q X. Pharmacological characterization of chemically synthesized monomeric pRNA nanoparticles for systemic delivery. Molecular Therapy 2011; 19:1312-22. PMCID:PMC3129564
G13. Liu J, Guo S, Cinier M, Shlyakhtenko L, Shu Y, Chen C, Shen G, Guo P. Fabrication of stable and RNase-resistant RNA nanoparticles active in gearing the nanomotors for viral DNA packaging. ACS Nano 2010; 5:237-46. PMCID:PMC3026857
G14. Zhang H, Endrizzi J A, Shu Y, Haque F, Sauter C, Shlyakhtenko L S, Lyubchenko Y, Guo P, Chi Y I. Crystal Structure of 3WJ Core Revealing Divalent Ion-promoted Thermostability and Assembly of the Phi29 Hexameric Motor pRNA. RNA 2013 Aug. 20; 19:1226-37. PMCID: PMC3753930
G15. Shu Y, Shu D, Haque F, Guo P. Fabrication of pRNA nanoparticles to deliver therapeutic RNAs and bioactive compounds into tumor cells. Nat Protoc. 2013 September; 8(9):1635-59. NIHMSID: NIHMS526437.
G16. Shu D, Zhang L, Khisamutdinov E, Guo P. Programmable folding of fusion RNA complex driven by the 3WJ motif of phi29 motor pRNA. Nucleic Acids Res. 2013; Doi: 10.1093/nar/gkt885. PMCID:In Process
G17. Reif R, Haque F, Guo P. Fluorogenic RNA Nanoparticles for Monitoring RNA Folding and Degradation in Real Time in Living Cells. Nucleic Acid Ther. 2013; 22(6):428-37. PMCID:PMC3507523
G18. Feng L, Li S K, Liu H, Liu C Y, LaSance K, Haque F, Shu D, Guo P. Ocular delivery of pRNA nanoparticles: distribution and clearance after subconjunctival injection. Pharmaceutical Research 2013; In press. doi: 10.1007/s11095-013-1226-x. PMCID:In Process G19. Shu Y, Cinier M, Fox S R, Ben-Johnathan N, Guo P. Assembly of Therapeutic pRNA-siRNA Nanoparticles Using Bipartite Approach. Molecular Therapy 2011 Apr. 5; 19:1304-11. PMCID:PMC3129561

G20. Shu D, Moll W D, Deng Z, Mao C, Guo P. Bottom-up assembly of RNA arrays and superstructures as potential parts in nanotechnology. Nano Lett. 2004; 4:1717-23. PMCID:PMC2746825

G21. Guo S, Tschammer N, Mohammed S, Guo P. Specific delivery of therapeutic RNAs to cancer cells via the dimerization mechanism of phi29 motor pRNA. Hum Gene Ther. 2005; 16:1097-109

G22. Khaled A, Guo S, Li F, Guo P. Controllable Self-Assembly of Nanoparticles for Specific Delivery of Multiple Therapeutic Molecules to Cancer Cells Using RNA Nanotechnology. Nano Letters 2005 Sep. 14; 5:1797-808. PMCID:PMC2846701

G23. Guo S, Huang F, Guo P. Construction of folate-conjugated pRNA of bacteriophage phi29 DNA packaging motor for delivery of chimeric siRNA to nasopharyngeal carcinoma cells. Gene Ther 2006; 13(10): 814-20. PMCID:PMC2840388

G24. Guo P, Haque F, Hallahan B, Reif R, Li H. Uniqueness, advantages, challenges, solutions, and perspectives in therapeutics applying RNA nanotechnology. Nucleic Acid Ther. 2012 August; 22(4):226-45. PMCID:PMC3426230

G25. Freier S M, Kierzek R, Jaeger J A, Sugimoto N, Caruthers M H, Neilson T, Turner D H. Improved free-energy parameters for predictions of RNA duplex stability. Proc. Natl. Acad. Sci. U.S.A 1986 December; 83(24): 9373-7. PMCID:PMC387140

G26. Ehresmann C, Baudin F, Mougel M, Romby P, Ebel J-P, Ehresmann B. Probing the structure of RNAs in solution. Nucleic Acids Res. 1987; 15:9109-28

G27. Privalov P L, Filiminov V V. Thermodynamic analysis of transfer RNA unfolding. J. Mol. Biol. 1978; 122:447-64

G28. Pleij C W A, Rietveld K, Bosch L. A new principle of RNA folding based on pseudonotting. Nucleic Acids Res. 1985 Mar. 11; 13(5):1717-31

G29. Zuker M. On finding all suboptimal foldings of an RNA molecule. Science 1989; 244:48-52

G30. Studnicka G M, Rahn G M, Cummings I W, Salser W A. Computer method for predicting the secondary structure of single-stranded RNA. Nucleic Acids Res. 1978; 5:3365-87

G31. Reid B R. NMR studies on RNA structure and dynamics. Annu. Rev. Biochem. 1981; 50:969-96

G32. Guo P, Zhang C, Chen C, Trottier M, Garver K. Inter-RNA interaction of phage phi29 pRNA to form a hexameric complex for viral DNA transportation. Mol. Cell. 1998; 2:149-55

G33. Hendrix R W. Bacteriophage DNA packaging: RNA gears in a DNA transport machine (Minireview). Cell 1998; 94:147-50

G34. Ikawa Y, Tsuda K, Matsumura S, Inoue T. De novo synthesis and development of an RNA enzyme. Proc. Natl. Acad. Sci. U.S.A 2004 Sep. 21; 101(38):13750-5

G35. Matsumura S, Ohmori R, Saito H, Ikawa Y, Inoue T. Coordinated control of a designed trans-acting ligase ribozyme by a loop-receptor interaction. FEBS Lett. 2009 Sep. 3; 583(17):2819-26

G36. Leontis N B, Lescoute A, Westhof E. The building blocks and motifs of RNA architecture. Curr Opin Struct Biol 2006; 16:279-87

G37. Schroeder K T, McPhee S A, Ouellet J, Lilley D M. A structural database for k-turn motifs in RNA. RNA. 2010 August; 16(8):1463-8

G38. Li X, Horiya S, Harada K. An efficient thermally induced RNA conformational switch as a framework for the functionalization of RNA nanostructures. J. Am. Chem. Soc. 2006 Mar. 29; 128(12):4035-40

G39. Sugimoto N, Nakano S, Katoh M, Matsumura A, Nakamuta H, Ohmichi T, Yoneyama M, Sasaki M. Thermodynamic parameters to predict stability of RNA/DNA hybrid duplexes. Biochemistry 1995 Sep. 5; 34(35): 11211-6

G40. Searle M S, Williams D H. On the stability of nucleic acid structures in solution: enthalpy-entropy compensations, internal rotations and reversibility. Nucleic Acids Res. 1993 May 11; 21(9):2051-6

G41. Laurenti E, Barde I, Verp S, Offner S, Wilson A, Quenneville S, Wiznerowicz M, MacDonald H R, Trono D, Trumpp A. Inducible gene and shRNA expression in resident hematopoietic stem cells in vivo. Stem Cells 2010 August; 28(8):1390-8

G42. Hoeprich S, ZHou Q, Guo S, Qi G, Wang Y, Guo P. Bacterial virus phi29 pRNA as a hammerhead ribozyme escort to destroy hepatitis B virus. Gene Ther. 2003; 10:1258-67

G43. Chang K Y, Tinoco I Jr. Characterization of a "kissing" hairpin complex derived from the human immunodeficiency virus genome. Proc Natl Acad Sci U.S.A 1994; 91(18):8705-9

G44. Bindewald E, Hayes R, Yingling Y G, Kasprzak W, Shapiro B A. RNAJunction: a database of RNA junctions and kissing loops for three-dimensional structural analysis and nanodesign. Nucleic Acids Res. 2008 January; 36:D392-D397. PMCID:PMC2238914

G45. Wagner C, Ehresmann C, Ehresmann B, Brunel C. Mechanism of dimerization of bicoid mRNA: initiation and stabilization. J. Biol. Chem. 2004 Feb. 6; 279:4560-9

G46. Fire A, Xu S, Montgomery M K, Kostas S A, Driver S E, Mello C C. Potent and specific genetic interference by double-stranded RNA in *Caenorhabditis elegans*. Nature 1998 February; 391:806-11

G47. Aagaard L, Rossi J J. RNAi therapeutics: Principles, prospects and challenges. Advanced Drug Delivery Reviews 2007 Mar. 30; 59(2-3):75-86

G48. Kruger K, Grabowski P J, Zaug A J, Sands J, Gottschling D E, Cech T R. Self-splicing RNA: autoexcision and autocyclization of the ribosomal RNA intervening sequence of Tetrahymena. Cell 1982; 31:147-57

G49. Guerrier-Takada C, Gardiner K, Marsh T, Pace N, Altman S. The RNA moiety of ribonuclease P is the catalytic subunit of the enzyme. Cell 1983; 35:849-57

G50. Tucker B J, Breaker R R. Riboswitches as versatile gene control elements. Curr. Opin. Struct. Biol. 2005 June; 15:342-8

G51. Blount K F, Breaker R R. Riboswitches as antibacterial drug targets. Nat. Biotechnol. 2006; 24:1558-64

G52. Lee R C, Feinbaum R L, Ambros V. The *C. elegans* heterochronic gene lin-4 encodes small RNAs with antisense complementarity to lin-14. Cell 1993 Dec. 3; 75(5): 843-54

G53. Couzin J. Breakthrough of the year. Small RNAs make big splash. Science 2002 Dec. 20; 298(5602):2296-7

G54. Guo P, Erickson S, Anderson D. A small viral RNA is required for in vitro packaging of bacteriophage phi29 DNA. Science 1987; 236:690-4

G55. Shu D, Zhang H, Jin J, Guo P. Counting of six pRNAs of phi29 DNA-packaging motor with customized single molecule dual-view system. EMBO J. 2007; 26:527-37. PMCID:PMC1783441

G56. Helmling S, Moyroud E, Schroeder W, Roehl I, Kleinjung F, Stark S, Bahrenberg G, Gillen C, Klussmann S, Vonhoff S. A new class of Spiegelmers containing 2'-fluoro-nucleotides. Nucleosides Nucleotides Nucleic Acids 2003 May; 22:1035-8

G57. Luy B, Marino J P. Measurement and application of 1H-19F dipolar couplings in the structure determination of 2'-fluorolabeled RNA. J. Biomol. NMR 2001 May; 20(1):39-47

G58. Reif B, Wittmann V, Schwalbe H, Griesinger C, Worner K, Jahn Hofmann K, Engels J W, Bermel W. Structural comparison of oligoribonucleotides and their 2'-deoxy-2'-fluoro analogs by heteronuclear NMR spectroscopy. Helvetica Chimica Acta 1997; 80(6):1952-71

G59. Behlke M A. Chemical modification of siRNAs for in vivo use. Oligonucleotides. 2008 December; 18(4):305-19

G60. Behlke M A. Progress towards in vivo use of siRNAs. Mol Ther. 2006 April; 13:644-70

G61. Pyle A M, Cech T R. Ribozyme recognition of RNA by tertiary interactions with specific ribose 2'-OH groups. Nature 1991; 350:628-31

G62. Zaug A J, Grabowski P J, Cech T R. Autocatalytic cyclization of an excised intervening sequence RNA is a cleavage-ligation reaction. Nature 1983; 301:578-83

G63. Zappulla D C, Cech T R. Yeast telomerase RNA: a flexible scaffold for protein subunits. Proc. Natl. Acad. Sci. U.S.A 2004 Jul. 6; 101(27):10024-9

G64. Cech T R. RNA chemistry. Ribozyme self-replication? Nature 1989; 339:507-8

G65. Stark B C, Kole R, Bowman E J, Altman S. Ribonuclease P: an enzyme with an essential RNA component. Proc. Natl. Acad. Sci. U.S.A 1978 August; 75:3717-21

G66. Forster A C, Altman S. External guide sequences for an RNA enzyme. Science 1990 Aug. 17; 249(4970):783-6

G67. de Fougerolles A, Vornlocher H P, Maraganore J, Lieberman J. Interfering with disease: a progress report on siRNA-based therapeutics. Nat Rev Drug Discov 2007 June; 6(6):443-53

G68. Kim D H, Rossi J J. Strategies for silencing human disease using RNA interference. Nat Rev Genet 2007 March; 8(3):173-84

G69. Rozema D B, Lewis D L, Wakefield D H, Wong S C, Klein J J, Roesch P L, Bertin S L, Reppen T W, Chu Q, Blokhin A V, et al. Dynamic PolyConjugates for targeted in vivo delivery of siRNA to hepatocytes. Proceedings of the National Academy of Sciences 2007 Aug. 7; 104(32):12982-7

G70. Seth S, Johns R, Templin M V. Delivery and biodistribution of siRNA for cancer therapy: challenges and future prospects. Ther. Deliv. 2012 February; 3(2):245-61

G71. Li W, Szoka F. Lipid-based Nanoparticles for Nucleic Acid Delivery. Pharm. Res 2007 Mar. 15; 24:438-49

G72. Adams K E, Ke S, Kwon S, Liang F, Fan Z, Lu Y, Hirschi K, Mawad M E, Barry M A, Sevick-Muraca E M. Comparison of visible and near-infrared wavelength-excitable fluorescent dyes for molecular imaging of cancer. J. Biomed. Opt. 2007 March; 12:024017

G73. Miao Y, Shelton T, Quinn T P. Therapeutic efficacy of a 177Lu-labeled DOTA conjugated alpha-melanocyte-stimulating hormone peptide in a murine melanoma-bearing mouse model. Cancer Biother. Radiopharm. 2007 June; 22(3):333-41

G74. Miao Y, Benwell K, Quinn T P. 99mTc- and 111In-labeled alpha-melanocyte-stimulating hormone peptides as imaging probes for primary and pulmonary metastatic melanoma detection. J Nucl. Med. 2007 January; 48(1):73-80

G75. Wei L, Zhang X, Gallazzi F, Miao Y, Jin X, Brechbiel M W, Xu H, Clifford T, Welch M J, Lewis J S, et al. Melanoma imaging using (111)In-, (86)Y- and (68)Ga-labeled CHX-A"-Re(Arg11)CCMSH. Nucl. Med. Biol 2009 May; 36(4):345-54. PMCID:PMC2752876

G76. Kumar S R, Gallazzi F A, Ferdani R, Anderson C J, Quinn T P, Deutscher S L. In vitro and in vivo evaluation of (64)Cu-radiolabeled KCCYSL (SEQ ID NO: 32) peptides for targeting epidermal growth factor receptor-2 in breast carcinomas. Cancer Biother. Radiopharm. 2010 December; 25(6):693-703. PMCID:PMC3026654

G77. Gambini J P, Cabral P, Alonso O, Savio E, Figueroa S D, Zhang X, Ma L, Deutscher S L, Quinn T P. Evaluation of 99mTc-glucarate as a breast cancer imaging agent in a xenograft animal model. Nucl. Med. Biol 2011 February; 38(2):255-60

G78. Chen J, Cheng Z, Owen N K, Hoffman T J, Miao Y, Jurisson S S, Quinn T P. Evaluation of an (111)In-DOTA-rhenium cyclized alpha-MSH analog: a novel cyclic-peptide analog with improved tumor-targeting properties. J. Nucl. Med. 2001 December; 42(12):1847-55

G79. Zhang X, Yue Z, Lu B Y, Vazquez-Flores G J, Yuen J, Figueroa S D, Gallazzi F, Cutler C, Quinn T P, Lacy J L. Copper-62 labeled ReCCMSH peptide analogs for melanoma PET imaging. Curr. Radiopharm. 2012 October; 5(4):329-35

G80. Rockey W M, Huang L, Kloepping K C, Baumhover N J, Giangrande P H, Schultz M K. Synthesis and radiolabeling of chelator-RNA aptamer bioconjugates with copper-64 for targeted molecular imaging. Bioorg. Med. Chem. 2011 Jul. 1; 19(13):4080-90

G81. Xu W, Lu Y. A smart magnetic resonance imaging contrast agent responsive to adenosine based on a DNA aptamer-conjugated gadolinium complex. Chem. Commun.(Camb.) 2011 May 7; 47(17):4998-5000. PMCID:PMC3298773

G82. Parker N, Turk M J, Westrick E, Lewis J D, Low P S, Leamon C P. Folate receptor expression in carcinomas and normal tissues determined by a quantitative radioligand binding assay. Anal. Biochem. 2005 Mar. 15; 338(2):284-93

G83. Leamon C P. Preclinical antitumor activity of a novel folate-targeted dual drug conjugate. Mol Pharmacol. 2007; 4:659-67

G84. Reddy J A, Westrick E, Santhapuram H K R, Howard S J, Miller M L, Vetzel M, Vlahov I, Chari R V J, Goldmacher V S, Leamon C P. Folate Receptor-Specific Antitumor Activity of EC131, a Folate-Maytansinoid Conjugate. Cancer Research 2007 Jul. 1; 67:6376-82

G85. Shigdar S, Lin J, Yu Y, Pastuovic M, Wei M, Duan W. RNA aptamer against a cancer stem cell marker epithelial cell adhesion molecule. Cancer Sci. 2011 Feb. 1; 102:991-8

G86. Went P, Vasei M, Bubendorf L, Terracciano L, Tornillo L, Riede U, Kononen J, Simon R, Sauter G, Baeuerle P A. Frequent high-level expression of the immunotherapeutic target Ep-CAM in colon, stomach, prostate and lung cancers. Br. J. Cancer 2006 Jan. 16; 94(1):128-35. PMCID:PMC2361083

G87. Dalerba P, Dylla S J, Park I K, Liu R, Wang X, Cho R W, Hoey T, Gurney A, Huang E H, Simeone D M, et al.

Phenotypic characterization of human colorectal cancer stem cells. Proc. Natl. Acad. Sci. U.S.A 2007 Jun. 12; 104(24):10158-63

G88. Ellington A D, Szostak J W. In vitro selection of RNA molecules that bind specific ligands. Nature 1990; 346: 818-22

G89. Tuerk C, Gold L. Systematic evolution of ligands by exponential enrichment: RNA ligands to bacteriophage T4 DNA polymerase. Science 1990; 249:505-10

G90. Ritter U, mm-Welk C, Fuchs U, Bohle R M, Borkhardt A, Woessmann W. Design and evaluation of chemically synthesized siRNA targeting the NPM-ALK fusion site in anaplastic large cell lymphoma (ALCL). Oligonucleotides 2003; 13(5):365-73

G91. Rychahou P G, Jackson L N, Silva S R, Rajaraman S, Evers B M. Targeted molecular therapy of the PI3K pathway: therapeutic significance of PI3K subunit targeting in colorectal carcinoma. Ann. Surg. 2006 June; 243 (6):833-42. PMCID:PMC1570577

G92. Rychahou P G, Kang J, Gulhati P, Doan H Q, Chen L A, Xiao S Y, Chung D H, Evers B M. Akt2 overexpression plays a critical role in the establishment of colorectal cancer metastasis. Proc. Natl. Acad. Sci. U.S.A 2008 Dec. 23; 105(51):20315-20. PMCID:PMC2629319

G93. Rychahou P G, Murillo C A, Evers B M. Targeted RNA interference of PI3K pathway components sensitizes colon cancer cells to TNF-related apoptosis-inducing ligand (TRAIL). Surgery 2005 August; 138(2):391-7

G94. Bartel D P. MicroRNAs: target recognition and regulatory functions. Cell 2009 Jan. 23; 136(2):215-33

G95. Rossi S, Di Narzo A F, Mestdagh P, Jacobs B, Bosman F T, Gustavsson B, Majoie B, Roth A, Vandesompele J, Rigoutsos I, et al. microRNAs in colon cancer: a roadmap for discovery. FEBS Lett. 2012 Sep. 21; 586(19):3000-7

G96. Ye X, Hemida M, Zhang H M, Hanson P, Ye Q, Yang D. Current advances in Phi29 pRNA biology and its application in drug delivery. Wiley. Interdiscip. Rev. RNA. 2012 Feb. 23; 3(4):469-81

G97. Ye X, Liu Z, Hemida M G, Yang D. Targeted delivery of mutant tolerant anti-coxsackievirus artificial microRNAs using folate conjugated bacteriophage Phi29 pRNA. PLoS. One. 2011; 6(6):e21215

G98. Xiong B, Cheng Y, Ma L, Zhang C. MiR-21 regulates biological behavior through the PTEN/PI-3 K/Akt signaling pathway in human colorectal cancer cells. Int. J Oncol. 2013 January; 42(1):219-28

G99. Zuker M. Mfold web server for nucleic acid folding and hybridization prediction. Nucleic Acids Res. 2003 Jul. 1; 31(13):3406-15

G100. Chen A K, Behlke M A, Tsourkas A. Avoiding false-positive signals with nuclease-vulnerable molecular beacons in single living cells. Nucleic Acids Res 2007; 35(16):e105. PMCID:PMC2018645

G101. Chen A K, Behlke M A, Tsourkas A. Efficient cytosolic delivery of molecular beacon conjugates and flow cytometric analysis of target RNA. Nucleic Acids Res 2008 July; 36(12):e69. PMCID:PMC2475621

G102. Mhlanga M M, Vargas D Y, Fung C W, Kramer F R, Tyagi S. tRNA-linked molecular beacons for imaging mRNAs in the cytoplasm of living cells. Nucleic Acids Res 2005; 33(6):1902-12. PMCID:PMC1074395

G103. Rhee W J, Santangelo P J, Jo H, Bao G. Target accessibility and signal specificity in live-cell detection of BMP-4 mRNA using molecular beacons. Nucleic Acids Res 2008 March; 36(5):e30. PMCID:PMC2275124

G104. Kim J K, Choi K J, Lee M, Jo M H, Kim S. Molecular imaging of a cancer-targeting theragnostics probe using a nucleolin aptamer- and microRNA-221 molecular beacon-conjugated nanoparticle. Biomaterials 2012 January; 33(1):207-17

G105. Peng X H, Cao Z H, Xia J T, Carlson G W, Lewis M M, Wood W C, Yang L. Real-time detection of gene expression in cancer cells using molecular beacon imaging: new strategies for cancer research. Cancer Res 2005 Mar. 1; 65(5):1909-17

G106. Bryson J M, Fichter K M, Chu W J, Lee J H, Li J, Madsen L A, McLendon P M, Reineke T M. Polymer beacons for luminescence and magnetic resonance imaging of DNA delivery. Proc. Natl. Acad. Sci. U.S.A 2009 Oct. 6; 106(40):16913-8. PMCID:PMC2761363

G107. Qiu L, Wu C, You M, Han D, Chen T, Zhu G, Jiang J, Yu R, Tan W. A targeted, self-delivered, and photocontrolled molecular beacon for mRNA detection in living cells. J Am. Chem. Soc 2013 Sep. 4; 135(35):12952-5. PMCID:PMC3791631

G108. Liu T W, Akens M K, Chen J, Wise-Milestone L, Wilson B C, Zheng G. Imaging of specific activation of photodynamic molecular beacons in breast cancer vertebral metastases. Bioconjug. Chem. 2011 Jun. 15; 22(6): 1021-30

G109. Caravan P. Strategies for increasing the sensitivity of gadolinium based MRI contrast agents. Chem. Soc Rev. 2006 June; 35(6):512-23

G110. Galletto R, Maillard R, Jezewska M J, Bujalowski W. Global conformation of the *Escherichia coli* replication factor DnaC protein in absence and presence of nucleotide cofactors. Biochemistry 2004 Aug. 31; 43(34):10988-1001

G111. Tucci P, Agostini M, Grespi F, Markert E K, Terrinoni A, Vousden K H, Muller P A, Dotsch V, Kehrloesser S, Sayan B S, et al. Loss of p63 and its microRNA-205 target results in enhanced cell migration and metastasis in prostate cancer. Proc. Natl. Acad. Sci. U.S.A 2012 Sep. 18; 109(38):15312-7

G112. Hong J, Huang Y, Li J, Yi F, Zheng J, Huang H, Wei N, Shan Y, An M, Zhang H, et al. Comprehensive analysis of sequence-specific stability of siRNA. FASEB J. 2010 December; 24(12):4844-55

G113. Chen A K, Davydenko O, Behlke M A, Tsourkas A. Ratiometric bimolecular beacons for the sensitive detection of RNA in single living cells. Nucleic Acids Res 2010 August; 38(14):e148. PMCID:PMC2919734

G114. Deiters A, Garner R A, Lusic H, Govan J M, Dush M, Nascone-Yoder N M, Yoder J A. Photocaged morpholino oligomers for the light-regulation of gene function in zebrafish and *Xenopus* embryos. J Am. Chem. Soc 2010 Nov. 10; 132(44):15644-50. PMCID:PMC3001396

G115. Morrissey D V, Lockridge J A, Shaw L, Blanchard K, Jensen K, Breen W, Hartsough K, Machemer L, Radka S, Jadhav V, et al. Potent and persistent in vivo anti-HBV activity of chemically modified siRNAs. Nat. Biotechnol. 2005 August; 23:1002-7

G116. Judge A D, Sood V, Shaw J R, Fang D, McClintock K, MacLachlan I. Sequence-dependent stimulation of the mammalian innate immune response by synthetic siRNA. Nat Biotech 2005 April; 23(4):457-62

G117. Hornung V, Guenthner-Biller M, Bourquin C, Ablasser A, Schlee M, Uematsu S, Noronha A, Manoharan M, Akira S, de Fougerolles A, et al. Sequence-specific potent induction of IFN-[alpha] by short interfering RNA in plasmacytoid dendritic cells through TLR7. Nat Med 2005 March; 11(3):263-70

G118. Gunnery S, Mathews M B. RNA binding and modulation of PKR activity. Methods 1998 July; 15(3):189-98

G119. Kumar S R, Quinn T P, Deutscher S L. Evaluation of an 111In-radiolabeled peptide as a targeting and imaging agent for ErbB-2 receptor expressing breast carcinomas. Clin. Cancer Res. 2007 Oct. 15; 13(20):6070-9

G120. Calzada V, Zhang X, Fernandez M, az-Miqueli A, Iznaga-Escobar N, Deutscher S L, Balter H, Quinn T P, Cabral P. A potencial theranostic agent for EGF-R expression tumors: (177)Lu-DOTA-nimotuzumab. Curr. Radiopharm. 2012 October; 5(4):318-24

G121. Ishikawa F, Yasukawa M, Lyons B, Yoshida S, Miyamoto T, Yoshimoto G, Watanabe T, Akashi K, Shultz L D, Harada M. Development of functional human blood and immune systems in NOD/SCID/IL2 receptor {gamma} chain(null) mice. Blood 2005 Sep. 1; 106(5):1565-73

G122. Shapiro E M, Sharer K, Skrtic S, Koretsky A P. In vivo detection of single cells by MRI. Magn Reson. Med. 2006 February; 55(2):242-9

G123. Stratta P, Canavese C, Aime S. Gadolinium-enhanced magnetic resonance imaging, renal failure and nephrogenic systemic fibrosis/nephrogenic fibrosing dermopathy. Curr. Med. Chem. 2008; 15(12):1229-35

G124. Cheng Z, Thorek D L, Tsourkas A. Gadolinium-conjugated dendrimer nanoclusters as a tumor-targeted T1 magnetic resonance imaging contrast agent. Angew. Chem. Int. Ed Engl. 2010; 49(2):346-50. PMCID:PMC2862691

G125. Boswell C A, Eck P K, Regino C A, Bernardo M, Wong K J, Milenic D E, Choyke P L, Brechbiel M W. Synthesis, characterization, and biological evaluation of integrin alphavbeta3-targeted PAMAM dendrimers. Mol. Pharm. 2008 July; 5(4):527-39. PMCID:PMC2574599

G126. Kobayashi H, Brechbiel M W. Nano-sized MRI contrast agents with dendrimer cores. Adv. Drug Deliv. Rev. 2005 Dec. 14; 57(15):2271-86

G127. Langereis S, de Lussanet Q G, van Genderen M H, Meijer E W, Beets-Tan R G, Griffioen A W, van Engelshoven J M, Backes W H. Evaluation of Gd(III) DTPA-terminated poly(propylene imine) dendrimers as contrast agents for MR imaging. NMR Biomed. 2006 February; 19(1):133-41

G128. Langereis S, Dirksen A, Hackeng T M, van Genderen M H P, Meijer E W. Dendrimers and magnetic resonance imaging. New Journal of Chemistry 2007; 31(7):1152-60

G129. Rudovsky J, Botta M, Hermann P, Hardcastle K I, Lukes I, Aime S. PAMAM dendrimeric conjugates with a Gd-DOTA phosphinate derivative and their adducts with polyaminoacids: the interplay of global motion, internal rotation, and fast water exchange. Bioconjug. Chem. 2006 July; 17(4):975-87

G130. Swanson S D, Kukowska-Latallo J F, Patri A K, Chen C, Ge S, Cao Z, Kotlyar A, East A T, Baker J R. Targeted gadolinium-loaded dendrimer nanoparticles for tumor-specific magnetic resonance contrast enhancement. Int. J. Nanomedicine. 2008; 3(2):201-10. PMCID:PMC2527674

G131. Zhu W, Okollie B, Bhujwalla Z M, Artemov D. PAMAM dendrimer-based contrast agents for MR imaging of Her-2/neu receptors by a three-step pretargeting approach. Magn Reson. Med. 2008 April; 59(4):679-85. PMCID:PMC2947957

G132. Longmire M, Choyke P L, Kobayashi H. Dendrimer-based contrast agents for molecular imaging. Curr. Top. Med. Chem. 2008; 8(14):1180-6. PMCID:PMC3454535

G133. Menjoge A R, Kannan R M, Tomalia D A. Dendrimer-based drug and imaging conjugates: design considerations for nanomedical applications. Drug Discov. Today 2010 March; 15(5-6):171-85

G134. Neerman M F, Zhang W, Parrish A R, Simanek E E. In vitro and in vivo evaluation of a melamine dendrimer as a vehicle for drug delivery. Int. J. Pharm. 2004 Aug. 20; 281(1-2):129-32

G135. Malik N, Wiwattanapatapee R, Klopsch R, Lorenz K, Frey H, Weener J W, Meijer E W, Paulus W, Duncan R. Dendrimers: relationship between structure and biocompatibility in vitro, and preliminary studies on the biodistribution of 125I-labelled polyamidoamine dendrimers in vivo. J. Control Release 2000 Mar. 1; 65(1-2):133-48

G136. Nwe K, Bernardo M, Regino C A, Williams M, Brechbiel M W. Comparison of MRI properties between derivatized DTPA and DOTA gadolinium-dendrimer conjugates. Bioorg. Med. Chem. 2010 Aug. 15; 18(16):5925-31. PMCID:PMC2918719

G137. Caravan P, Ellison J J, McMurry T J, Lauffer R B. Gadolinium(III) Chelates as MRI Contrast Agents: Structure, Dynamics, and Applications. Chem. Rev. 1999 Sep. 8; 99(9):2293-352

G138. Hardy P A, Keeley D, Schorn G, Forman E, Ai Y, Venugopalan R, Zhang Z, Bradley L H. Convection enhanced delivery of different molecular weight tracers of gadolinium-tagged polylysine. J. Neurosci. Methods 2013 Sep. 30; 219(1):169-75

G139. Dan M, Scott D F, Hardy P A, Wydra R J, Hilt J Z, Yokel R A, Bae Y. Block copolymer cross-linked nano-assemblies improve particle stability and biocompatibility of superparamagnetic iron oxide nanoparticles. Pharm. Res. 2013 February; 30(2):552-61

G140. Wang S, Haque F, Rychahou P G, Evers B M, Guo P. Engineered Nanopore of Phi29 DNA-Packaging Motor for Real-Time Detection of Single Colon Cancer Specific Antibody in Serum. ACS Nano 2013 Oct. 23; DOI: 10.1021/nn404435v D1. Buhleier, E.; Wehner, W.; Vogtle, F. Cascade-Chain-Like and Nonskid-Chain-Like Syntheses of Molecular Cavity Topologies. *Synthesis-Stuttgart* 1978, (2), 155-158.

D2. Kukowska-Latallo, J. F.; Bielinska, A. U.; Johnson, J.; Spindler, R.; Tomalia, D. A.; Baker, J. R., Jr. Efficient transfer of genetic material into mammalian cells using Starburst polyamidoamine dendrimers. *Proc Natl Acad Sci USA* 1996, 93 (10), 4897-4902.

D3. Nilsen, T. W.; Grayzel, J.; Prensky, W. Dendritic nucleic acid structures. *J Theor. Biol* 1997, 187 (2), 273-284.

D4. Astruc, D. Electron-transfer processes in dendrimers and their implication in biology, catalysis, sensing and nanotechnology. *Nat. Chem.* 2012, 4 (4), 255-267.

D5. Nanjwade, B. K.; Bechra, H. M.; Derkar, G. K.; Manvi, F. V.; Nanjwade, V. K. Dendrimers: emerging polymers for drug-delivery systems. *Eur. J Pharm. Sci.* 2009, 38 (3), 185-196.

D6. Hong, C. A.; Eltoukhy, A. A.; Lee, H.; Langer, R.; Anderson, D. G.; Nam, Y. S. Dendrimeric siRNA for Efficient Gene Silencing. *Angew. Chem. Int. Ed Engl.* 2015, 54 (23), 6740-6744.

D7. Kobayashi, H.; Brechbiel, M. W. Nano-sized MRI contrast agents with dendrimer cores. *Adv. Drug Deliv. Rev.* 2005, 57 (15), 2271-2286.

D8. Kaminskas, L. M.; Boyd, B. J.; Porter, C. J. Dendrimer pharmacokinetics: the effect of size, structure and surface characteristics on ADME properties. *Nanomedicine (Lond)* 2011, 6 (6), 1063-1084.

D9. Li, Y.; Tseng, Y. D.; Kwon, S. Y.; D'Espaux, L.; Bunch, J. S.; McEuen, P. L.; Luo, D. Controlled assembly of dendrimer-like DNA. *Nat Mater.* 2004, 3 (1), 38-42.

D10. Meng, H. M.; Zhang, X.; Lv, Y.; Zhao, Z.; Wang, N. N.; Fu, T.; Fan, H.; Liang, H.; Qiu, L.; Zhu, G.; Tan, W. DNA dendrimer: an efficient nanocarrier of functional nucleic acids for intracellular molecular sensing. *ACS Nano* 2014, 8 (6), 6171-6181.

D11. Choi, Y.; Baker, J. R., Jr. Targeting cancer cells with DNA-assembled dendrimers: a mix and match strategy for cancer. *Cell Cycle* 2005, 4 (5), 669-671.

D12. Zhou, T.; Wang, Y.; Dong, Y.; Chen, C.; Liu, D.; Yang, Z. Tetrahedron DNA dendrimers and their encapsulation of gold nanoparticles. *Bioorg. Med. Chem.* 2014, 22 (16), 4391-4394.

D13. Zhou, T.; Chen, P.; Niu, L.; Jin, J.; Liang, D.; Li, Z.; Yang, Z.; Liu, D. pH-responsive size-tunable self-assembled DNA dendrimers. *Angew. Chem. Int. Ed Engl.* 2012, 51 (45), 11271-11274.

D14. Leontis N B; Lescoute A; Westhof E The building blocks and motifs of RNA architecture. *Curr Opin Struct Biol* 2006, 16, 279-287.

D15. Searle, M. S.; Williams, D. H. On the stability of nucleic acid structures in solution: enthalpy-entropy compensations, internal rotations and reversibility. *Nucleic Acids Res.* 1993, 21 (9), 2051-2056.

D16. Guo, P. The emerging field of RNA nanotechnology. *Nature Nanotechnology* 2010, 5 (12), 833-842.

D17. Guo, P.; Haque, F.; Hallahan, B.; Reif, R.; Li, H. Uniqueness, advantages, challenges, solutions, and perspectives in therapeutics applying RNA nanotechnology. *Nucleic Acid Ther.* 2012, 22 (4), 226-245.

D18. Shu, Y.; Pi, F.; Sharma, A.; Rajabi, M.; Haque, F.; Shu, D.; Leggas, M.; Evers, B. M.; Guo, P. Stable RNA nanoparticles as potential new generation drugs for cancer therapy. *Adv. Drug Deliv. Rev.* 2014, 66C, 74-89.

D19. Guo, P.; Haque, F. *RNA Nanotechnology and Therapeutics*; CRC Press: Boca Raton, F L, 2013.

D20. Shukla, G. C.; Haque, F.; Tor, Y.; Wilhelmsson, L. M.; Toulme, J. J.; Isambert, H.; Guo, P.; Rossi, J. J.; Tenenbaum, S. A.; Shapiro, B. A. A Boost for the Emerging Field of RNA Nanotechnology. *ACS Nano* 2011, 5 (5), 3405-3418.

D21. Leontis, N.; Sweeney, B.; Haque, F.; Guo, P. Conference Scene: Advances in RNA nanotechnology promise to transform medicine. *Nanomedicine* 2013, 8, 1051-1054.

D22. Shu, D.; Shu, Y.; Haque, F.; Abdelmawla, S.; Guo, P. Thermodynamically stable RNA three-way junctions for constructing multifuntional nanoparticles for delivery of therapeutics. *Nature Nanotechnology* 2011, 6, 658-667.

D23. Haque, F.; Shu, D.; Shu, Y.; Shlyakhtenko, L.; Rychahou, P.; Evers, M.; Guo, P. Ultrastable synergistic tetravalent RNA nanoparticles for targeting to cancers. *Nano Today* 2012, 7, 245-257.

D24. Shu, Y.; Haque, F.; Shu, D.; Li, W.; Zhu, Z.; Kotb, M.; Lyubchenko, Y.; Guo, P. Fabrication of 14 Different RNA Nanoparticles for Specific Tumor Targeting without Accumulation in Normal Organs. *RNA* 2013, 19, 766-777.

D25. Guo, P.; Zhang, C.; Chen, C.; Trottier, M.; Garver, K. Inter-RNA interaction of phage phi29 pRNA to form a hexameric complex for viral DNA transportation. *Mol. Cell.* 1998, 2, 149-155.

D26. Grabow, W. W.; Zakrevsky, P.; Afonin, K. A.; Chworos, A.; Shapiro, B. A.; Jaeger, L. Self-Assembling RNA Nanorings Based on RNAI/II Inverse Kissing Complexes. *Nano Lett.* 2011, 11 (2), 878-887.

D27. Afonin, K. A.; Viard, M.; Koyfman, A. Y.; Martins, A. N.; Kasprzak, W. K.; Panigaj, M.; Desai, R.; Santhanam, A.; Grabow, W. W.; Jaeger, L.; Heldman, E.; Reiser, J.; Chiu, W.; Freed, E. O.; Shapiro, B. A. Multifunctional RNA nanoparticles. *Nano Lett.* 2014, 14 (10), 5662-5671.

D28. Khisamutdinov, E. F.; Jasinski, D. L.; Guo, P. RNA as a boiling-resistant anionic polymer material to build robust structures with defined shape and stoichiometry. *ACS Nano.* 2014, 8, 4771-4781.

D29. Ohno, H.; Kobayashi, T.; Kabata, R.; Endo, K.; Iwasa, T.; Yoshimura, S. H.; Takeyasu, K.; Inoue, T.; Saito, H. Synthetic RNA-protein complex shaped like an equilateral triangle. *Nat. Nanotechnol.* 2011, 6 (2), 116-120.

D30. Jasinski, D.; Khisamutdinov, E. F.; Lyubchenko, Y. L.; Guo, P. Physicochemically Tunable Poly-Functionalized RNA Square Architecture with Fluorogenic and Ribozymatic Properties. *ACS Nano* 2014, 8, 7620-7629.

D31. Dibrov, S. M.; McLean, J.; Parsons, J.; Hermann, T. Self-assembling RNA square. *Proc. Natl. Acad. Sci. U.S.A* 2011, 108 (16), 6405-6408.

D32. Severcan I; Geary C; V. E.; C. A.; Jaeger L Square-shaped RNA particles from different RNA folds. *Nano Lett.* 2009, 9, 1270-1277.

D33. Khisamutdinov, E.; Li, H.; Jasinski, D.; Chen, J.; Fu, J.; Guo, P. Enhancing immunomodulation on innate immunity by shape transition among RNA triangle, square, and pentagon nanovehicles. *Nucleic Acids Res.* 2014, 42, 9996-10004.

D34. Afonin, K. A.; Bindewald, E.; Yaghoubian, A. J.; Voss, N.; Jacovetty, E.; Shapiro, B. A.; Jaeger, L. In vitro assembly of cubic RNA-based scaffolds designed in silico. *Nat. Nanotechnol.* 2010, 5 (9), 676-682.

D35. Geary, C.; Rothemund, P. W.; Andersen, E. S. A single-stranded architecture for cotranscriptional folding of RNA nanostructures. *Science* 2014, 345, 799-804.

D36. Guo, P.; Erickson, S.; Anderson, D. A small viral RNA is required for in vitro packaging of bacteriophage phi29 DNA. *Science* 1987, 236, 690-694.

D37. Binzel, D. W.; Khisamutdinov, E. F.; Guo, P. Entropy-driven one-step formation of Phi29 pRNA 3WJ from three RNA fragments. *Biochemistry* 2014, 53 (14), 2221-2231.

D38. Lee, T. J.; Haque, F.; Shu, D.; Yoo, J. Y.; Li, H.; Yokel, R. A.; Horbinski, C.; Kim, T. H.; Kim, S.-H.; Nakano, I.; Kaur, B.; Croce, C. M.; Guo, P. RNA nanoparticles as a vector for targeted siRNA delivery into glioblastoma mouse model. *Oncotarget* 2015, 6, 14766-14776.

D39. Rychahou, P.; Haque, F.; Shu, Y.; Zaytseva, Y.; Weiss, H. L.; Lee, E. Y.; Mustain, W.; Valentino, J.; Guo, P.; Evers, B. M. Delivery of RNA nanoparticles into colorectal cancer metastases following systemic administration. *ACS Nano* 2015, 9 (2), 1108-1116.

D40. Abdelmawla, S.; Guo, S.; Zhang, L.; Pulukuri, S.; Patankar, P.; Conley, P.; Trebley, J.; Guo, P.; Li, Q. X. Pharmacological characterization of chemically synthesized monomeric pRNA nanoparticles for systemic delivery. *Molecular Therapy* 2011, 19, 1312-1322.

D41. Cui, D.; Zhang, C.; Liu, B.; Shu, Y.; Du, T.; Shu, D.; Wang, K.; Dai, F.; Liu, Y.; Li, C.; Pan, F.; Yang, Y.; Ni, J.; Li, H.; Brand-Saberi, B.; Guo, P. Regression of gastric cancer by systemic injection of RNA nanoparticles carrying both ligand and siRNA. *Scientific reports* 2015, 5, 10726.

D42. Shu, D.; Li, H.; Shu, Y.; Xiong, G.; Carson, W. E.; Haque, F.; Xu, R.; Guo, P. Systemic delivery of anti-miRNA for suppression of triple negative breast cancer utilizing RNA nanotechnology. *ACS Nano* 2015, Accepted. DOI: 10.1021/acsnano.5b02471.

D43. Lee, T.; Yagati, A. K.; Pi, F.; Sharma, A.; Chio, J. W.; Guo, P. Construction of RNA-quantum dot chimera for nanoscale resistive biomemory application. *ACS Nano* 2015, In press.

D44. Zhang, H.; Endrizzi, J. A.; Shu, Y.; Haque, F.; Sauter, C.; Shlyakhtenko, L. S.; Lyubchenko, Y.; Guo, P.; Chi, Y. I. Crystal Structure of 3WJ Core Revealing Divalent Ion-promoted Thermostability and Assembly of the Phi29 Hexameric Motor pRNA. *RNA* 2013, 19, 1226-1237.

D45. Li, H.; Lee, T.; Dziubla, T.; Pi, F.; Guo, S.; Xu, J.; Li, C.; Haque, F.; Liang, X.; Guo, P. RNA as a stable polymer to build controllable and defined nanostructures for material and biomedical applications. *Nano Today* 2015, In press.

D46. Shu, Y.; Shu, D.; Haque, F.; Guo, P. Fabrication of pRNA nanoparticles to deliver therapeutic RNAs and bioactive compounds into tumor cells. *Nat Protoc.* 2013, 8 (9), 1635-1659.

D47. Lyubchenko, Y. L.; Shlyakhtenko, L. S.; Ando, T. Imaging of nucleic acids with atomic force microscopy. *Methods* 2011, 54, 274-283.

D48. Zuker, M. Mfold web server for nucleic acid folding and hybridization prediction. *Nucleic Acids Res.* 2003, 31 (13), 3406-3415.

D49. Behlke, M. A. Chemical modification of siRNAs for in vivo use. *Oligonucleotides.* 2008, 18 (4), 305-319.

D50. Krol, J.; Loedige, I.; Filipowicz, W. The widespread regulation of microRNA biogenesis, function and decay. *Nat Rev. Genet.* 2010, 11 (9), 597-610.

D51. Liu, J.; Guo, S.; Cinier, M.; Shlyakhtenko, L. S.; Shu, Y.; Chen, C.; Shen, G.; Guo, P. Fabrication of stable and RNase-resistant RNA nanoparticles active in gearing the nanomotors for viral DNA packaging. *ACS Nano* 2011, 5 (1), 237-246.

D52. Helmling, S.; Moyroud, E.; Schroeder, W.; Roehl, I.; Kleinjung, F.; Stark, S.; Bahrenberg, G.; Gillen, C.; Klussmann, S.; Vonhoff, S. A new class of Spiegelmers containing 2'-fluoro-nucleotides. *Nucleosides Nucleotides Nucleic Acids* 2003, 22, 1035-1038.

D53. Grodzinski, P.; Torchilin, V.; (Editors) *Advanced Drug Delivery Reviews: Cancer Nanotechnology*; Volume 66 ed.; Elsevier: 2014.

D54. Parker, N.; Turk, M. J.; Westrick, E.; Lewis, J. D.; Low, P. S.; Leamon, C. P. Folate receptor expression in carcinomas and normal tissues determined by a quantitative radioligand binding assay. *Anal. Biochem.* 2005, 338 (2), 284-293.

D55. Sugimoto, N.; Nakano, S.; Katoh, M.; Matsumura, A.; Nakamuta, H.; Ohmichi, T.; Yoneyama, M.; Sasaki, M. Thermodynamic parameters to predict stability of RNA/DNA hybrid duplexes. *Biochemistry* 1995, 34 (35), 11211-11216.

D56. Rauzan, B.; McMichael, E.; Cave, R.; Sevcik, L. R.; Ostrosky, K.; Whitman, E.; Stegemann, R.; Sinclair, A. L.; Serra, M. J.; Deckert, A. A. Kinetics and Thermodynamics of DNA, RNA, and Hybrid Duplex Formation. *Biochemistry* 2013, 52 (5), 765-772.

It will be understood that various details of the presently disclosed subject matter can be changed without departing from the scope of the subject matter disclosed herein. Furthermore, the foregoing description is for the purpose of illustration only, and not for the purpose of limitation.

---

We claim:

1. A method of diagnosing cancer in a subject, the method comprising administering to the subject an RNA dendrimer molecule, wherein the RNA dendrimer molecule comprises (a) a central core multi-branched RNA junction motif, wherein the central core motif comprises a plurality of branches, wherein a branch comprises at least one RNA oligonucleotide, and wherein the central core motif comprises at least one RNA oligonucleotide having at least 90% identity to SEQ ID NO: 12 (SquareE); and (b) an outer surface multi-branched RNA junction motif comprising at least one repeating multi-branched RNA junction motif unit, wherein the repeating unit comprises a plurality of branches, and wherein a branch comprises at least one RNA oligonucleotide, wherein the RNA dendrimer molecule comprises at least one imaging module, wherein the RNA dendrimer molecule comprises a folate receptor targeting module, wherein the cancer comprises a cancer that overexpresses folate receptor, and diagnosing the subject as having cancer if the RNA dendrimer molecule is detected in the subject.

2. The method of claim 1, wherein the RNA dendrimer molecule further comprises at least one targeting module, at least one therapeutic module, or a combination thereof.

3. The method of claim 1, wherein the plurality of branches comprising the central core multi-branched RNA junction motif comprises a three-branched RNA junction motif, or four-branched RNA junction motif, a six-branched RNA junction motif, or an eight-branched RNA junction motif.

4. The method of claim 1, wherein the plurality of branches comprising the repeating multi-branched RNA junction motif unit comprises a three-branched RNA junction motif, or a four-branched RNA junction motif, a six-branched RNA junction motif, and an eight-branched RNA junction motif.

5. The method of claim 3 or 4, wherein the three-branched RNA junction motif comprises an a3WJ RNA module having at least 90% identity to nucleotide sequence 5'-UUG CCA UGU GUA UGU GGG-3' (SEQ ID NO: 1); a b3WJ RNA module having at least 90% identity to nucleotide sequence 5'-CCC ACA UAC UUU GUU GAUCC-3' (SEQ ID NO: 2); or a c3WJ RNA module having at least 90% identity to nucleotide sequence 5'-GGA UCA AUC AUG GCA A-3' (SEQ ID NO: 3), or a combination thereof.

6. The method of claim 3 or 4, wherein the central core multi-branched RNA junction motif is a polygon shaped architecture comprising a three-branched RNA junction motif at each corner.

7. The method of claim 1, wherein the imaging module comprises a fluorescent dye, a radionuclide, a contrast agent, a reporter imaging molecule, a reference imaging molecule, or any combination thereof.

8. The method of claim 7, wherein the reference imaging module comprises a reference dye and a quencher.

9. The method of claim 7, wherein the contrast agent comprises at least one MRI contrast agent, at least one gadolinium contrast agent, or both.

10. The method of claim 2, wherein the targeting module comprises a cancer targeting module.

11. The method of claim 10, wherein the cancer targeting module is a ligand that binds to at least one cancer cell surface marker.

12. The method of claim 10, wherein the targeting module comprises a chemical ligand or RNA aptamer.

13. The method of claim 11, wherein the ligand comprises folate.

14. The method of claim 11, wherein the cell surface marker comprises a folate receptor.

15. The method of claim 11, wherein the ligand binds to an epithelial cell adhesion molecule (EpCAM).

16. The method of claim 11, wherein the cell surface marker comprises an epithelial cell adhesion molecule (EpCAM).

17. The method of claim 12, wherein the aptamer is an EpCAM RNA aptamer.

18. The method of claim 2, wherein the therapeutic module comprises a siRNA, a miRNA, an anti-mRNA, a ribozyme RNA, an antisense RNA, a chemotherapeutic drug, a cytotoxic drug, a riboswitch, or an endosome disrupting agent.

19. The method of claim 18, wherein the cytotoxic drug comprises doxorubicin, paclitaxel, paclitaxel derivatives and analogues, cytochalasin D, rapamycin, rapamycin derivatives and analogues, camptothecin, dexamethasone, and 5-fluorouracil, a quinazolinone derivative, metallic silver, tranilast, everolimus and/or related compounds.

20. The method of claim 1, wherein the RNA dendrimer molecule further comprises an oligonucleotide having at least 90% identity to nucleotide sequences of at least one of:

3WJ-a: UUG CCA UGU GUA UGU GGG (SEQ ID NO: 1)
3WJ-b: CCC ACA UAC UUU GUU GAU CC (SEQ ID NO: 2)
3WJ-c: GGA UCA AUC AUG GCA A (SEQ ID NO: 3)
3WJ-a_rev: GGG UGU AUG UGU ACC GUU (SEQ ID NO: 4)
3WJ-b_rev: CCU AGU UGU UUC AUA CAC CC (SEQ ID NO: 5)
3WJ-c_rev: AAC GGU ACU AAC UAG G (SEQ ID NO: 6)
3WJ-c-folate: GGA UCA AUC AUG GCA A—folate (SEQ ID NO: 7)
SquareA: GGG AGC CGU CAA UCA UGG CAA GUG UCC GCC AUA CUU UGU UGC ACG CAC (SEQ ID NO: 8)
SquareB: GGG AGC GUG CAA UCA UGG CAA GCG CAU CGC AUA CUU UGU UGC GAC CUA (SEQ ID NO: 9)
SquareC: GGG AGG UCG CAA UCA UGG CAA CGA UAG AGC AUA CUU UGU UGG CUG GAG (SEQ ID NO: 10)
SquareD: GGG ACC AGC CAA UCA UGG CAA UAU ACA CGC AUA CUU UGU UGA CGG CGG (SEQ ID NO: 11)
b-SquareA: GGC CCA CAU ACU UUG UUG AUC CAU GGU GCG UAG GGU CGU CAA UCA UGG CAA GUG UCC GCC AUA CUU UGU UGC ACU CCC UUG CUC AUC A (SEQ ID NO: 13)
b-SquareB: GGC CCA CAU ACU UUG UUG AUC CUG AUG AGC AAG GGA GUG CAA UCA UGG CAA GCG UAU CGC AUA CUU UGU UGA GAA CCC UAU GUG ACU U (SEQ ID NO: 14)
b-SquareC: GGC CCA CAU ACU UUG UUG AUC CAA GUC ACA UAG GGU UCG CAA UCA UGG CAA CGA UAG AGC AUA CUU UGU UGG AGU CCC UUA GAG UAG A (SEQ ID NO: 15)
b-SquareD: GGC CCA CAU ACU UUG UUG AUC CUC UAC UCU AAG GGA CUC CAA UCA UGG CAA UAU ACA CGC AUA CUU UGU UGA CGA CCC UAC GCA CCA U (SEQ ID NO: 16)
3WJ-a-b_rev: UUG CCA UGU GUA UGU GGG CCU AGU UGU UUC AUA CAC CC (SEQ ID NO: 17)

3WJ-c-b_rev: GGA UCA AUC AUG GCA A CCU AGU UGU UUC AUA CAC CC (SEQ ID NO: 18)

3WJ-b-a_rev: CCC ACA UAC UUU GUU GAU CC GGG UGU AUG UGU ACC GUU (SEQ ID NO: 19) or 3WJ-b-c_rev: CCC ACA UAC UUU GUU GAU CC AAC GGU ACU AAC UAG G (SEQ ID NO: 20).

21. The method of claim 1, wherein RNA dendrimer is administered as a composition comprising a therapeutically effective amount of the RNA dendrimer molecule.

22. The method of claim 1, wherein the central core motif further comprises an RNA oligonucleotide having at least 90% identity to at least one of SEQ ID NO: 8 (SquareA), SEQ ID NO: 9 (SquareB), SEQ ID NO: 10 (SquareC), SEQ ID NO: 11 (SquareD), SEQ ID NO: 13 (b-SquareA), SEQ ID NO: 14 (b-SquareB), SEQ ID NO: 15 (b-SquareC), or SEQ ID NO: 9 (b-SquareD).

23. The method of claim 21, wherein the composition further comprises a pharmaceutically acceptable carrier.

24. The method of claim 1, wherein the subject is a mammal or a non-mammal vertebrate.

25. The method of claim 1, wherein the subject is a human.

26. The method of claim 1, wherein the cancer is a colon cancer.

* * * * *